(12) United States Patent
Tomoo et al.

(10) Patent No.: US 8,293,781 B2
(45) Date of Patent: Oct. 23, 2012

(54) INDOLE DERIVATIVES HAVING CPLA$_2$ INHIBITING ACTIVITY AND APPLICATIONS AND PRODUCTION METHODS OF THE SAME

(75) Inventors: Toshiyuki Tomoo, Kawanishi (JP);
Takashi Nakatsuka, Tatebayashi (JP);
Yasuhiro Hayashi, Mishima-gun (JP);
Toyoko Katayama, Takatsuki (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 314 days.

(21) Appl. No.: 12/532,738

(22) PCT Filed: Mar. 28, 2008

(86) PCT No.: PCT/JP2008/056742
§ 371 (c)(1),
(2), (4) Date: Sep. 23, 2009

(87) PCT Pub. No.: WO2008/120818
PCT Pub. Date: Oct. 9, 2008

(65) Prior Publication Data
US 2010/0113777 A1    May 6, 2010

(30) Foreign Application Priority Data

Mar. 29, 2007 (JP) ................. 2007-088307
Jun. 13, 2007 (JP) ................. 2007-156198

(51) Int. Cl.
*A61K 31/402* (2006.01)
*C07D 209/04* (2006.01)
(52) U.S. Cl. .................... 514/415; 548/469
(58) Field of Classification Search ............ 548/469
See application file for complete search history.

(56) References Cited

U.S. PATENT DOCUMENTS

| 4,536,505 A | 8/1985 | Browne |
| 5,290,936 A | 3/1994 | Beheshti et al. |
| 5,744,488 A | 4/1998 | Cross et al. |
| 5,902,726 A | 5/1999 | Kliewer et al. |
| 5,994,554 A | 11/1999 | Kliewer et al. |

FOREIGN PATENT DOCUMENTS

| DE | 31 31 728 C2 | 3/1982 |
| DE | 3543982 A1 | 6/1986 |
| EP | 0126401 | 11/1984 |
| EP | 1 526 159 A1 | 4/2005 |
| GB | 216847 | 4/1924 |
| GB | 2168347 | 6/1986 |
| JP | 8-509003 | 9/1996 |
| JP | 11-349568 | 12/1999 |
| JP | 2005-515997 | 6/2005 |
| WO | 99/15129 A2 | 4/1999 |
| WO | 99/15129 A3 | 4/1999 |
| WO | WO 99/46259 | 9/1999 |
| WO | 01/72723 A1 | 10/2001 |
| WO | 03/000688 A1 | 1/2003 |
| WO | 03/014116 A1 | 2/2003 |
| WO | 03/048122 A2 | 6/2003 |
| WO | 03/048122 A3 | 6/2003 |
| WO | 2005/016339 A1 | 2/2005 |
| WO | 2006/077364 A1 | 7/2006 |
| WO | 2006/077366 A1 | 7/2006 |
| WO | 2006/128142 A2 | 11/2006 |

OTHER PUBLICATIONS

Chronic obstructive pulmonary disease [online] retrieved from the internet on Sep. 27, 2011 from URL; http://www.ncbi.nlm.nih.gov/pubmedhealth/PMH0001153/.*
Vippagunta, et al. Advanced Drug Delivery Reviews 48 (2001) 3-26.*
Nakamura, "Cyclooxygenase (COS)-2 selective inhibitors: aspirin, a due COX-1/COX-2 inhibitor to COS-2 Selective Inhibitors" Nippon Yakurigaku Zassi, Folia Pharmacol. Jpn., vol. 118, (2001), pp. 219-230. (English Abstract).
Molecular Medicine vol. 42, No. 10 (2005) pp. 1137-1142 (in Japanese).
Rolin et al., "Prostanoids as Pharmacological Targets in COPD and Asthma," European Journal of Pharmacology, vol. 533 (2006) pp. 89-100.
Terawaki et al., "Absence of Leukotriene B$_4$ Receptor 1 Confers Resistance to Airway Hyperresponsiveness and Th2-Type Immune Responses[1]," J. Immunol., vol. 175, (2005) pp. 4217-4225.
Suzuki et al., "Pharmacological Profile and Clinical Effects of Montelukast Sodium (Singulair® Chewable Tablet) an Antiasthmatic Agent," Nippon Yakurigaku Zassh, Folia Pharmacol. Jpn. vol. 120, (2002) pp. 343-352. (English Abstract).
Ishii et al., "Platelet-Activating Factor Receptor Develops Airway Hyperresponsiveness Independently of Airway Inflammation in a Murine Asthma Model," J. Immunol., vol. 172, (2004) pp. 7095-7102.
Kihara et al., "Dual Phase Regulation of Experimental Allergic Encephalomyelitis by Platelet-Activating Factor," J. Exp. Med., vol. 202, No. 6, (Sep. 19, 2005), pp. 853-863.

(Continued)

Primary Examiner — Shawquia Young
(74) Attorney, Agent, or Firm — Drinker Biddle & Reath LLP

(57) ABSTRACT

A compound, or its salt, or a solvate thereof having a cPLA$_2$ inhibiting activity having the formula (I):

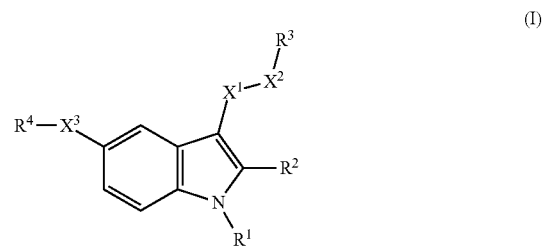

or a pharmaceutical composition, cPLA$_2$ inhibitor and inhibitors of various lipid mediator production containing the same as active ingredients.

30 Claims, No Drawings

OTHER PUBLICATIONS

Hikiji et al., "Absence of Platelet-Activating Factor Receptor Protects Mice from Osteoporosis Following Ovariectomy," J. Clin. Invest., vol. 114, No. 1, (Jul. 2004) pp. 85-93.

Nagase et al., "Platelet-Activating Factor Mediates Acid-Induced Lung Injury in Genetically Engineered Mice," J. Clin. Invest., (Oct. 1999), vol. 104, No. 8, pp. 1071-1076.

Malaviya et al., "Targeting Cytosolic Phospholipase $A_2$ by Arachidonly Trifluoromethyl Ketone Prevents Chronic Inflammation in Mice," Euro. J. of Pharm., vol. 539 (2006), pp. 195-204.

Nagase et al., "A Potent Inhibitor of Cytosolic Phospholipase $A_2$, Arachidonyl Trifluoromethyl Ketone, Attenuates LPS-induced Lung Injury in Mice," Am. J. Physiol Lung Cell Mol. Physiol, vol. 284, (2003) pp. L720-L726.

Bellido-Reyes et al., "Cytosolic Phospholipase $A_2$ Inhibition Attenuates Ischemia-Reperfusion Injury in an Isolated Rat Lung Model," Transplantation, vol. 81, No. 12, (Jun. 27, 2006) pp. 1700-1707.

Burke et al., "BMS-229724 is a Tight-Binding Inhibitor of Cytosolic Phospholipase $A_2$, That Acts at the Lipid/Water Interface and Possesses Anti-Inflammatory Activity in Skin Inflammation Models," J. Pharma. Exp. Therapeutics, (2002) vol. 298, No. 1, pp. 376-385.

Amandi-Burgermeister et al., "Suppression of Cytokine Synthesis, Integrin Expression and Chronic Inflammation by Inhibitors of Cytosolic Phospholipase $A_2$," Eur. J. of Pharm., (1997) vol. 326, pp. 237-250.

Shimizu et al., "Cytosolic Phospholipase $A_2$: Biochemical Properties and Physiological Roles," IUBMB Life, vol. 58(5-6), (May-Jun. 2006), pp. 328-333.

Lehr, Matthias, "Cytosolic Phospholipase $A_2$ as a Target for Drug Design," Drugs of the Future (2000), vol. 25. No. 8, pp. 823-832.

Lehr, Matthias, "Phospholipase $A_2$ Inhibitors in Inflammation," Expert Opin. Ter. Patents, (2001), vol. 11. No. 7, pp. 1123-1136.

Gopalsamy et al., "1,2,4-Oxadiazolidin-3,5-diones and 1,3,5-triazin-2,4,6-triones as Cytosolic Phospholipase $A_2$ α Inhibitors," Bioorganic & Medicinal Chemistry Letters, (2006), vol. 16, pp. 2978-2981.

Kokotos et al., "Novel 2-Oxoamide Inhibitors of Human Group IVA Phospholipase $A_2$," J. Med. Chem, (2002) vol. 45, pp. 2891-2893.

Stephens et al., "Differential Inhibition of Group IVA and Group VIA Phospholipase $A_2$ by 2-Oxoamides," J. Med. Chem. (2006) vol. 49, pp. 2821-2828.

Connolly et al., "Design and synthesis of a Novel and Potent Series of Inhibitors of Cytosolic Phospholipase $A_2$ Based on a 1,3-Disubstituted Propan-2-one Skeleton," J. Med. Chem. (2002) vol. 45, pp. 1348-1362.

Ludwig et al., "Design and Synthesis of 1-Indol-1-yl-propan-2-ones as Inhibitors of Human Cytosolic Phospholipase $A_2$ α.," J. Med. Chem. (2006) vol. 49, pp. 2611-2620.

McKew et al., "Inhibition of Cytosolic Phospholipase $A_2$ α: Hit to Lead Optimization," J. Med. Chem. (2006) vol. 49, pp. 135-158.

Hartwig et al., "Room-Temperature Palladium-Catalyzed Amination of Aryl Bromides and Chlorides and Extended Scope of Aromatic C-N Bond Formation with a Commercial Ligand," J. Org. Chem. (1999), vol. 64, pp. 5575-5580.

Old et al., "Efficient Palladium-Catalyzed N-Arylation of Indoles," Amer. Chem. Soc., Organic Letters, (2000), vol. 2, No. 10, pp. 1403-1406.

Arimura et al., "Prevention of Allergic Inflammation by a Novel Prostaglandin Receptor Antagonist, S-5751," J. Pharm. and Exper. Therapeutics, (2001) vol. 298, No. 2, pp. 411-419.

Hozawa et al., "Effects of a PAF Antagonist, Y-24180, on Bronchial Hyperresponsiveness in Patients with Asthma," Am. J. Respir. Crit. Care Med., (1995) vol. 152, pp. 1198-1202.

Theodorou et al., "Anaphylactic Colonic Hypersecretion in Cow's Milk Sensitized Guinea-Pigs Depends Upon Release of Interleukin-1, Prostaglandins and Mast Cell Degranulation," Aliment Pharmacol. Ther. (1994) vol. 8, pp. 301-307.

Santos et al., "Characterisation of Immune Mediator Release During the Immediate Response to Segmental Mucosal Challenge in the Jejunum of Patients with Food Allergy," Gut, (1999), vol. 45, pp. 553-558.

Ii et al., "Group IVA Phospholipase $A_2$-Associated Production of MMP-9 in Macrophages and Formation of Atherosclerotic Lesions," Biol. Pharm. Bull. (Mar. 2008), vol. 31, No. 3, pp. 363-368.

Rücker et al., "2D QSAR of PPARγ Agonist Binding and Transactivation," Bioorganic & Medicinal Chemistry (2006) vol. 14, pp. 5178-5195.

Lee et al., "Benzenesulfonamide Indole Inhibitors of Cytosolic Phospholipase $A_2$ α: Optimization of in vitro Potency and Rat Pharmacokinetics for Oral Efficacy," Bioorganic & Medicinal Chemistry, (2008) vol. 16, pp. 1345-1358.

Fritsche et al., "1-(2-Carboxyindol-5-yloxy)propan-2-ones as Inhibitors of Human Cytosolic Phospholipase $A_2$ α: Synthesis, Biological Activity, Metabolic Stability, and Solubility," Bioorganic & Medicinal Chemistry, (2008) vol. 16, pp. 3489-3500.

Hess et al., "1-(5-Carboxy- and 5-carbamoylindol-1-yl)propan-2-ones as Inhibitors of Human Cytosolic Phospholipase $A_2$ α: Bioisosteric Replacement of the Carboxylic Acid and Carboxamide Moiety," Bioorganic & Medicinal Chemistry, (2007), vol. 15, pp. 2883-2891.

Hegen et al., "Efficacy of Giripladib, A Novel Inhibitor of Cytosolic Phospholipase A2ALPHA, in Two Mouse Models of Rheumatoid Arthritis," Annu. Eur. Congr. Rheumatol (EULAR) (2008), Abstract THU0061.

Runarsson et al., "The Expression of Cytosolic Phospholipase $A_2$ and Biosynthesis of Leukotriene $B_4$ in Acute Myeloid Leukemia Cells," Eur. J. of Haematology (2007) vol. 79, No. 6, pp. 468-476.

Roger P. Dickinson, "Thromboxane Modulating Agents. 1. Design of 1-[(Arylsulfonyl)Amino] Alkylindole Derivatives as Dual Thromboxane Synthase Inhibitor/Thromboxane Receptor Antagonists," Bioorganic & Medicinal Chemistry Letters, 1995, pp. 3017-3022, vol. 5, No. 24, Elsevier Science Ltd.

Brad R. Henke et al., "Synthesis and Biological Activity of a Novel Series of Indole-Derived PPARγ Agonists," Bioorganic & Medicinal Chemistry Letters, 1999, pp. 3329-3334, vol. 9, No. 23, Elsevier Science Ltd.

Joachim Ludwig et al., "Design and Synthesis of 1-Indol-1-yl-propan-2-ones as Inhibitors of Human Cytosolic Phospholipase $A_2$α," J. Med. Chem, 2006, pp. 2611-2620, vol. 49, No. 8, American Chemical Society, Washington, DC.

International Search Report issued on Jun. 3, 2008 in International PCT Application No. PCT/JP2008/056742 filed Mar. 28, 2008.

Extended European Search Report dated Mar. 24, 2010 (includes the supplementary European Search Report and the European search opinion) from European Patent Application No. 08739849.1.

Yamasaki, Noritsugu et al., "Preparation and formulation of indole derivatives as hypoglycemics and phosphodiesterase 5 inhibitors"; XP-002572961 retrieved from STN database accession No. 1998:239201 abstract & WO 98/15530 A1 (Fujisawa Pharmaceutical Co., Ltd., Japan) Apr. 16, 1998, pp. 1-3.

\* cited by examiner

INDOLE DERIVATIVES HAVING CPLA$_2$ INHIBITING ACTIVITY AND APPLICATIONS AND PRODUCTION METHODS OF THE SAME

CROSS REFERENCE TO RELATED APPLICATIONS

This application is the National Stage of International Application No. PCT/JP2008/056742 filed Mar. 28, 2008, and claims benefit of Japanese Patent Application Nos. 2007-088307 filed Mar. 29, 2007 and 2007-156198 filed Jun. 13, 2007, which are herein incorporated by reference in their entirety.

TECHNICAL FIELD

The present invention relates to indole derivatives having a cPLA$_2$ (cytosolic phospholipase A$_2$) inhibiting activity, pharmacologically acceptable salts of the same or their solvates and cPLA$_2$ inhibitors etc. containing the same as active ingredients. Furthermore, the present invention relates to intermediates for the production of the derivatives and production methods of the same. The compounds of the present invention are compounds effective against diseases in various fields of treatment including inflammatory diseases and allergic diseases.

BACKGROUND ART

Phospholipase A$_2$(PLA$_2$) in general is an enzyme which specifically hydrolyzes the ester bonds at the sn-2 position of glycerophospholipids and produces fatty acids and lysophospholipids. At the present time, in mammals, the existence 10 types or more of PLA$_2$ has been found. They are classified based on their locality, molecular weight, substrate specificity, etc. to secretory type PLA$_2$ (sPLA$_2$), cytosolic PLA$_2$ (cPLA$_2$), Ca$^{2+}$ independent PLA$_2$ (iPLA$_2$) and other families, but among these, cPLA$_2$ plays a central role in the stimuli-induced production of lipid mediators, since it selectively releases arachidonic acid from the sn-2 position of the glycerophospholipids in the cytoplasm, adjusts the activity in the presence of a μM concentration of calcium ions or by phosphorylation by mitogen-activated protein kinase (MAP kinase).

It is known that arachidonic acid taken from PLA$_2$ produces as metabolites prostanoids, leukotrienes, platelet activating factors and other lipid mediators having various bioactivities.

The action of cyclooxygenase (COX) on arachidonic acid produces prostanoids. "Prostanoids" is the general name for prostaglandins (PG) and thromboxanes (TX). Prostaglandins include prostaglandin E$_2$ (PGE$_2$), prostaglandin D$_2$ (PGD$_2$), prostaglandin F$_{2\alpha}$ (PGF$_{2\alpha}$), prostaglandin I$_2$ (PGI$_2$), etc., while thromboxanes include thromboxane A$_2$ (TXA$_2$), thromboxane B$_2$ (TXB$_2$), etc. These prostanoids express various physiological actions through specific receptors.

5-lipoxygenase (5-LOX) acts on arachidonic acid to produce leukotrienes (LT). Leukotrienes include leukotriene B$_4$ (LTB$_4$), cysteinyl leukotriene (Cys-LT), etc. Cysteinyl leukotriene includes leukotriene C$_4$ (LTC$_4$), leukotriene D$_4$ (LTD$_4$), leukotriene E$_4$ (LTE$_4$), etc.

On the other hand, when the phospholipids of membranes are hydrolyzed by cPLA$_2$ and arachidonic acid is released, lysophospholipids are produced. Lysophospholipids are metabolized and produce platelet activating factors (PAF). It is known that the prostanoids produced from the COX route have various physiological activities and are involved in the conditions of various diseases.

It is known that PGE$_2$ has a fever-inducing action, pain increasing action, vasodilating action and other inflammatory actions. COX inhibitors are widely used as anti-inflammatory drugs and analgesics in inflammatory diseases such as rheumatoid arthritis, osteoarthritis or other arthritis. It is clear that PGE$_2$ is involved in swelling and pain or other conditions in inflammatory diseases (See Non-Patent Document 1).

It is known that PGD$_2$ has an airway smooth muscle contraction action, increased vascular permeability action, eosinophil chemotactic action, and other actions. In recent years, in studies of the DP receptor, that is a receptor of PGD$_2$, deficient mice it has been clarified that the allergic airway inflammation is remarkably ameliorated, the production of Th2 type cytokine is decreased at the airway inflammation site, etc., and therefore, the possibility of PGD$_2$, which is deeply involved in conditions of allergic airway inflammation including bronchial asthma through actions through its receptor (DP receptor), is suggested (See Non-Patent Document 2).

Further, DP receptor selective inhibitors suppress the airway inflammation and development of airway hyperreactivity in animal models of asthma (See Non-Patent Document 27).

PGE$_2$ and PGD$_2$ are induced, depending upon the inflammation of the allergic colitis induced by food and COX inhibitors exhibit a suppressive action, so it is clear that PGE$_2$ and PGD$_2$ are involved in food allergy and allergic colitis conditions (See Non-Patent Documents 29 and 30).

TXA$_2$ and TXB$_2$ have a platelet aggregation action, vascular smooth muscle contraction action, airway smooth muscle contraction action and other actions. TX synthesizing enzyme inhibitors and TXA$_2$ receptor antagonists suppress the development of airway hyperreactivity and asthmatic broncoconstrictions, and therefore, are used as drugs for treatment of asthma. It is shown that TXA$_2$ and TXB$_2$ contribute to conditions of bronchial asthma or other respiratory diseases (See Non-Patent Document 3).

It is known that the LT produced from the 5-LOX pathway also has various physiological activities and is involved in conditions of various diseases. LTB$_4$ is a powerful activating factor of white blood cells, promotes the exuding of neutrophils or other inflammatory cells to the inflammatory site and stimulates the release of superoxides and proteases damaging the tissue. In recent years, in mice deficient in the BLT1 receptor, a receptor of LTB$_4$, alleviation of allergic airway inflammation and airway hyperreactivity and suppression of the Th2 type immunoreaction have been reported, so the involvement of LTB$_4$ in bronchial asthma or other airway inflammatory conditions is suggested (See Non-Patent Document 4).

Further, Cys-LT (LTC$_4$/LTD$_4$/LTE$_4$) exhibits a bronchial smooth muscle contraction action and action in chemoattracting and activating eosinophils and other inflammatory cells. The Cys-LT1 receptor, a receptor of Cys-LT, antagonist exhibits efficacy in an animal asthma model. Further, in clinical studies as well, its pharmaceutical effect as a drug for treatment of bronchial asthma and allergic rhinitis has been confirmed, and therefore, it is known that Cys-LT is deeply involved in allergic airway inflammation (See Non-Patent Document 5). The PAF produced by metabolization of lysophospholipids exhibits a platelet activating action, bronchial smooth muscle contraction action and other physiological actions. From studies using PAF receptor deficient mice, the involvement of PAF in exacerbation of bronchial asthma, multiple sclerosis, osteoporosis, acute lung injury or other conditions has been suggested (See Non-Patent Documents 6, 7, 8 and 9).

Further, it is shown that a PAF receptor antagonist ameliorates airway hyperreactivity in bronchial asthma patients (See Non-Patent Document 28).

As described above, cPLA$_2$ is a major enzyme which acts on the phospholipids of the cell membrane and produces arachidonic acid and lysophospholipids, and therefore, plays an important role in the production of prostanoids, LT, PAF, and other lipid mediators. Therefore, if inhibiting the cPLA$_2$ enzyme so as to suppress the release of arachidonic acid and lysophospholipids, the production of prostanoids, LT, PAF and other lipid mediators positioned downstream of the metabolic cascade should be suppressed and, in turn, it is believed that treatment or prevention of various diseases initiated or exacerbated by production of these lipid mediators should become possible. As examples of such diseases, rheumatoid arthritis, osteoarthritis, dysmenorrhea, acute pain, bronchial asthma and other asthma, allergic rhinitis, chronic and acute airway inflammation, chronic obstructive pulmonary disease, acute lung injury, multiple sclerosis, cerebral ischemia/reperfusion injury, dermatitis, ulticaria, eczema, prurigo, pancreatitis, psoriasis, inflammatory colitis, food allergy, allergic colitis, osteoporosis, atherosclerosis, etc. may be mentioned.

Up to now, it has been reported that several types of cPLA$_2$ inhibitor exhibit efficacy in animal models such as asthma, acute lung injury, cerebral ischemia/reperfusion injury, arthritis, dermatitis and other animal models (See Non-Patent Documents 10, 11, 12, 13 and 14). Further, in cPLA$_2$α-deficient mice, alleviation of the disease is observed in asthma, arthritis, acute lung injury, pulmonary fibrosis, inflammatory bone resorption, multiple sclerosis, cerebral ischemia/reperfusion injury, atherosclerosis, and other models (See Non-Patent Documents 15 and 31). In these diseases, it is believed that cPLA$_2$ is involved in the onset or exacerbation of the disease, and therefore, inhibiting the cPLA$_2$ should enable treatment or prevention of these diseases.

cPLA$_2$ inhibitors have already been described in reviews (See Non-Patent Documents 16 and 17), and as described above, some of the inhibitors has been reported to have the efficacy in animal disease models. Further, recently, in addition to the cPLA$_2$ inhibitors described in the reviews referenced above, oxa(thia)zolidine derivatives (See Patent Documents 1 and 2), oxadiazolidinedione derivatives (See Non-Patent Document 18), triazinetrione derivatives (See Non-Patent Document 18), oxamide derivatives (See Non-Patent Documents 19 and 20), trifluorobutanone derivatives (See Patent Document 3 and Non-Patent Document 13), propanone derivatives (See Non-Patent Document 21), indolylpropanone derivatives (See Non-Patent Document 22), indole derivatives (See Patent Document 4 and Non-Patent Document 23), etc. are disclosed as novel cPLA$_2$ inhibitors. However, there has been no example of the above cPLA$_2$ inhibitors being commercialized as pharmaceuticals.

On the other hand, indole skeleton compounds similar, in structure, to the present invention compounds have been disclosed in the documents (See Patent Documents 5 and 6 and Non-Patent Document 24) etc., but there is no description of the compounds having an aromatic group directly at the nitrogen atom of 1-position as disclosed in the present invention and no disclosure relating to the cPLA$_2$ inhibiting activity.

Further, indole skeleton compounds similar in structure to the present invention compounds are disclosed in the documents (See Patent Document 7), but the substituents of the indole at 2-position and 3-position differ from the present invention. Further, the document does not relate to a pharmaceutical. Further, the documents (See Non-Patent Documents 25 and 26) etc. concerning the examples of production of indole skeleton compounds are known, but the substituents of the compounds differ from the present invention compounds.

Patent Document 1: WO 03/000668
Patent Document 2: WO 01/072723
Patent Document 3: WO 99/015129
Patent Document 4: WO 03/048122
Patent Document 5: WO 05/016339
Patent Document 6: U.S. Pat. No. 5,994,554
Patent Document 7: EP 1526159
Non-Patent Document 1: Nippon Yakurigaku Zasshi 118 (2001) 219
Non-Patent Document 2: Molecular Medicine 42 (2005) 1137
Non-Patent Document 3: Eur J Pharmacol 533 (2006) 89
Non-Patent Document 4: J Immunol 175 (2005) 4217
Non-Patent Document 5: Nippon Yakurigaku Zasshi 120 (2002) 343
Non-Patent Document 6: J Immunol 172 (2004) 7095
Non-Patent Document 7: J Exp Med 202 (2005) 853
Non-Patent Document 8: J Clin Invest 114 (2004) 85
Non-Patent Document 9: J Clin Invest 104 (1999) 1071
Non-Patent Document 10: Eur J Pharmacol 539 (2006) 195
Non-Patent Document 11: Am J Physiol Lung Cell Mol Physiol 284 (2003) L720
Non-Patent Document 12: Transplantation 81 (2006) 1700
Non-Patent Document 13: J Pharmacol Exp Ther 298 (2001) 376
Non-Patent Document 14: Eur J Pharmacol 326 (1997) 237
Non-Patent Document 15: IUBMB Life 58 (2006) 328
Non-Patent Document 16: Drugs Fut 25 (2000) 823
Non-Patent Document 17: Expert Opin Ther Patents 11 (2001) 1123
Non-Patent Document 18: Bioorg Med Chem Lett 16 (2006) 2978
Non-Patent Document 19: J Med Chem 45 (2002) 2891
Non-Patent Document 20: J Med Chem 49 (2006) 2821
Non-Patent Document 21: J Med Chem 45 (2002) 1348
Non-Patent Document 22: J Med Chem 49 (2006) 2611
Non-Patent Document 23: J Med Chem 49 (2006) 135
Non-Patent Document 24: Bioorg Med Chem Lett 9 (1999) 3329
Non-Patent Document 25: J Org Chem 64 (1999) 5575
Non-Patent Document 26: Org Lett 2 (2000) 1403
Non-Patent Document 27: J Pharmacol Exp Ther 298 (2001) 411
Non-Patent Document 28: Am J Respir Clit Care Med 152 (1995) 1198
Non-Patent Document 29: Aliment Pharmacol Ther 8 (1994) 301
Non-Patent Document 30: Gut 45 (1999) 553
Non-Patent Document 31: Biol Pharm Bull 31 (2008) 363

DISCLOSURE OF THE INVENTION

The object of the present invention is to provide new compounds having a cPLA$_2$ inhibiting activity and pharmaceutical compositions containing the aforementioned compound as active ingredients, cPLA$_2$ inhibitors, and inhibitors of production of various lipid mediators. Compounds inhibiting cPLA$_2$ suppress the release of arachidonic acid and lysophospholipids in the cells and further suppress the production of the metabolites, that is, various lipid mediators, to thereby exhibit effects against various allergic diseases and inflammatory diseases. Specifically, those compounds are useful as drugs for the prevention or treatment of diseases such as rheumatoid arthritis, osteoarthritis, dysmenorrhea, acute pain, bronchial asthma and other asthma, allergic rhinitis, chronic and acute airway inflammation, chronic obstructive pulmonary disease, acute lung injury, pulmonary fibrosis, multiple sclerosis, cerebral ischemia/reperfusion injury, dermatitis, ulticaria, eczema, prurigo, pancreatitis, psoriasis, inflammatory colitis, food allergy, allergic colitis, osteoporosis, atherosclerosis, etc.

Further, the object of the present invention is to provide production methods of the compounds and intermediates useful for production.

The inventors engaged in intensive research to develop compounds having superior $cPLA_2$ inhibitory activity and, as a result, found that compounds having indole skeleton shown as general formula (I) have an excellent $cPLA_2$ inhibitory activity and thereby completed the present invention.

That is, the present invention provides a compound having the formula (I):

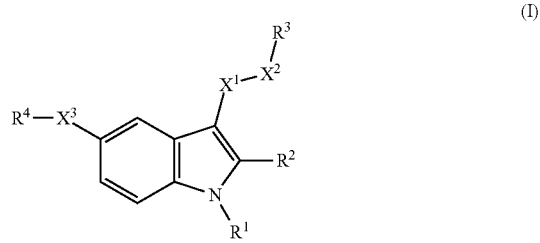

wherein $R^1$ indicates (1) a $C_6$ to $C_{14}$ aromatic hydrocarbon group, (2) a 5- to 10-membered aromatic heterocyclic group including one to four hetero atoms selected from nitrogen atoms, sulfur atoms, and oxygen atoms, other than carbon atoms or (3) a bicyclic or tricyclic condensed polycyclic group formed by the condensation of the above aromatic heterocyclic group and the above $C_6$ to $C_{14}$ aromatic hydrocarbon cyclic ring, where said groups (1) to (3) of $R^1$ may be optionally, substituted with one to five groups selected from (i) a halogen atom, (ii) a nitro, (iii) a cyano, (iv) a $C_1$ to $C_6$ alkyl unsubstituted or substituted with one to three groups selected from a halogen atom, a $C_1$ to $C_6$ alkoxy unsubstituted or substituted with one to three halogen atoms, a $C_1$ to $C_7$ acyloxy, a hydroxyl, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms, and a $C_6$ to $C_{14}$ aromatic hydrocarbon oxy unsubstituted or substituted with one to three halogen atoms, (v) a $C_2$ to $C_6$ alkenyl unsubstituted or substituted with one to three halogen atoms, (vi) a $C_2$ to $C_6$ alkynyl unsubstituted or substituted with one to three halogen atoms, (vii) a $C_3$ to $C_6$ cycloalkyl, (viii) a hydroxyl, (ix) a $C_1$ to $C_6$ alkoxy unsubstituted or substituted with one to three groups selected from a halogen atom, a $C_1$ to $C_6$ alkoxy unsubstituted or substituted with one to three halogen atoms, a $C_7$ to $C_{16}$ aralkyloxy, a hydroxyl, a mono- or di-$C_1$ to $C_6$ alkylamino, a carbamoyl, a mono- or di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (x) a $C_6$ to $C_{14}$ aromatic hydrocarbon oxy unsubstituted or substituted with one to three groups selected from a halogen atom, a $C_1$ to $C_6$ alkyl, a $C_1$ to $C_6$ alkoxy and a hydroxyl (xi) a 5- to 6-membered heterocyclic oxy unsubstituted or substituted with one to three halogen atoms, (xii) a $C_1$ to $C_5$ alkylenedioxy, (xiii) a $C_1$ to $C_6$ alkylthio unsubstituted or substituted with one to three groups selected from a halogen atom, a $C_1$ to $C_6$ alkoxy, a hydroxyl, a mono- or di-$C_1$ to $C_6$ alkylamino, a carbamoyl, a mono- or di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (xiv) a 5- to 6-membered heterocyclic thio unsubstituted or substituted with one to three halogen atoms, (xv) an amino, (xvi) a mono-$C_1$ to $C_6$ alkylamino, (xvii) a di-$C_1$ to $C_6$ alkylamino, (xviii) a 5- to 6-membered cyclic amino, (xix) a $C_1$ to $C_6$ acyl, (xx) a carboxyl, (xxi) a $C_1$ to $C_6$ alkoxycarbonyl, (xxii) a carbamoyl, (xxiii) a thiocarbamoyl, (xxiv) a mono-$C_1$ to $C_6$ alkylcarbamoyl, (xxv) a di-$C_1$ to $C_6$ alkylcarbamoyl, (xxvi) a 5- to 6-membered heterocyclic carbonyl unsubstituted or substituted with one to three halogen atoms, (xxvii) a sulfo, (xxviii) a $C_1$ to $C_6$ alkylsulfonyl, (xxix) a $C_1$ to $C_6$ acylamino unsubstituted or substituted with a $C_1$ to $C_6$ alkoxy, (xxx) a $C_1$ to $C_6$ alkoxycarbonylamino, (xxxi) an aminosulfonyl, (xxxii) a mono- or di-$C_1$ to $C_6$ alkylaminosulfonyl and (xxxiii) a 5- to 6-membered heterocyclic sulfonyl unsubstituted or substituted with one to three halogen atoms, $R^2$ indicates (1) a hydrogen atom, (2) a $C_1$ to $C_6$ alkyl, (3) a $C_3$ to $C_6$ cycloalkyl group or (4) a halogen atom, $R^3$ indicates (1) a $C_6$ to $C_{14}$ aromatic hydrocarbon group or (2) a 5- to 10-membered aromatic heterocyclic group including one to four hetero atoms selected from nitrogen atoms, sulfur atoms and oxygen atoms, other than carbon atoms, where the groups (1) to (2) of said $R^3$ may be optionally substituted with one to five groups selected from (i) a halogen atom, (ii) a $C_1$ to $C_6$ alkyl unsubstituted or substituted with one to three halogen atoms, (iii) a $C_3$ to $C_6$ cycloalkyl, (iv) a hydroxyl, (v) a $C_1$ to $C_6$ alkoxy unsubstituted or substituted with one to three halogen atoms, (vi) a $C_1$ to $C_5$ alkylenedioxy, (vii) a $C_1$ to $C_6$ alkylthio unsubstituted or substituted with one to three halogen atoms, (viii) an amino, (ix) a mono-$C_1$ to $C_6$ alkylamino and (x) a di-$C_1$ to $C_6$ alkylamino, $R^4$ indicates (1) —$CO_2R^5$ where $R^5$ indicates a hydrogen atom, a $C_1$ to $C_6$ alkyl or a $C_7$ to $C_{16}$ aralkyl, (2) —$COC(R^6)_3$ where $R^6$ indicates a halogen atom, (3) —$CONR^7R^8$ where $R^7$ and $R^8$ may be the same or different and indicate a hydrogen atom, a hydroxyl, a $C_1$ to $C_6$ alkyl, a $C_7$ to $C_{16}$ aralkyl, a $C_1$ to $C_6$ alkoxy, a $C_7$ to $C_{16}$ aralkyloxy, a cyano or a tetrazole, (4) —CHO, (5) —$CONHSC_2R^9$ where $R^9$ indicates a hydrogen atom, a $C_1$ to $C_6$ alkyl, a phenyl unsubstituted or substituted with one to three $C_1$ to $C_3$ alkyls or a $C_7$ to $C_{16}$ aralkyl, (6) a cyano, (7) a tetrazole, (8) an isoxazole, (9) an isothiazole or (10) a hydroxythiadiazole, $X^1$ indicates (1) a carbonyl group or (2) methylene, $X^2$ indicates (1) a straight-chain, branched or cyclic $C_1$ to $C_6$ alkylene or (2) a connecting bond, $X^3$ indicates (1) a straight-chain or branched $C_1$ to $C_6$ alkylene, (2) a straight-chain or branched $C_2$ to $C_6$ alkenylene or (3) a straight-chain or branched $C_2$ to $C_6$ alkynylene or its salt or their solvates.

The present invention further provides $cPLA_2$ inhibitors and inhibitors of production of various lipid mediators (arachidonic acid, prostanoids, prostaglandins, leukotrienes, prostaglandin $E_2$, prostaglandin $D_2$, thromboxane $A_2$ or $B_2$, cyteinyl leukotriene, leukotriene $B_4$, and platelet activating factors) containing compounds having the formula (I) or their salts or their solvates, as an active ingredient.

The present invention further provides pharmaceutical compositions containing compounds having the formula (I) or their pharmacologically acceptable salts or their solvates, as active ingredients. These pharmaceutical compositions are useful for the prevention or treatment of diseases involving cPLA$_2$. Here, "involving cPLA$_2$" has the four meanings of:

(1) Involvement of the increase in the amount of expression of cPLA$_2$ enzymes in the exacerbation of conditions,
(2) Involvement of the increase in activity of cPLA$_2$ enzymes in the exacerbation of conditions,
(3) Involvement of the increase in amount of lipid mediators produced based on the cPLA$_2$ enzymatic activity in the exacerbation of conditions and
(4) Involvement of the change in the balance of the amounts of lipid mediators produced based on cPLA$_2$ enzymatic activity in the exacerbation of conditions.

Diseases involving cPLA$_2$ include inflammatory diseases or allergic diseases and inflammatory respiratory diseases. Inflammatory respiratory diseases include asthma, allergic rhinitis, chronic and acute airway inflammation, chronic obstructive pulmonary disease, acute lung injury, and pulmonary fibrosis. Further, bronchial asthma or other asthma includes adult asthma and juvenile asthma (atopic, non-atopic), exercise-induced asthma, aspirin asthma, coughing asthma, occupational asthma, etc. The present invention compounds have actions inhibiting cPLA$_2$, actions suppressing the production of lipid mediators, and anti-inflammatory actions and exhibit effects against inflammatory diseases or allergic diseases. In particular, they are useful for the prevention and treatment of airway allergic inflammatory diseases such as bronchial asthma and allergic rhinitis.

Diseases involving cPLA$_2$ further include rheumatoid arthritis, osteoarthritis, dysmenorrheal, and acute pain. The present invention compounds suppress PGE$_2$ production, and therefore, are useful for the prevention or treatment of pain on diseases due to PGE$_2$ production such as rheumatoid arthritis, osteoarthritis, acute pain and dysmenorrhea.

The diseases involving cPLA$_2$, further, include multiple sclerosis, cerebral ischemia/reperfusion injury, dermatitis, ulticaria, eczema, prurigo, pancreatitis, psoriasis, inflammatory colitis, food allergy, allergic colitis, osteoporosis and atherosclerosis. The present invention compounds exhibit actions inhibiting cPLA$_2$ and actions suppressing the production of lipid mediators, exhibit effects in animal dermatitis models as well, and are useful for the prevention or treatment of these diseases.

The present invention further provides production methods of a compound having the formula (I) or its salts.

Specifically, it provides the following methods:

A production method for a compound having the formula (I):

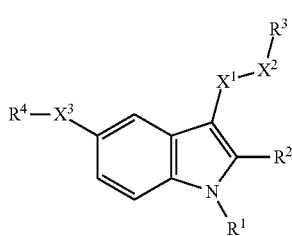
(I)

wherein R$^1$, R$^2$, R$^3$, R$^4$, X$^1$, X$^2$ and X$^3$ are as defined above or its salt by reacting a compound (II) having the formula (II):

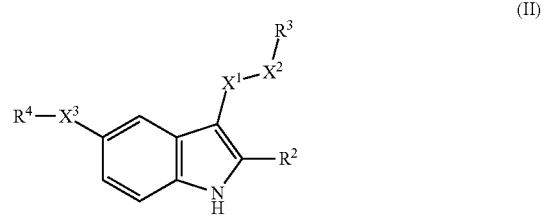
(II)

wherein R$^2$, R$^3$, R$^4$, X$^1$, X$^2$ and X$^3$ are as defined above or its salts with a compound having the formula (III):

R$^1$—Y$^1$ (III)

wherein R$^1$ is as defined above and Y$^1$ is a halogen atom or triflate or its salt and, if necessary, removing the protective groups and/or reducing the same, a production method for a compound having the formula (I):

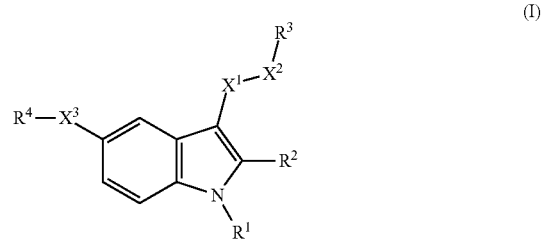
(I)

wherein R$^1$, R$^2$, R$^3$, R$^4$, X$^1$, X$^2$ and X$^3$ are as defined above or its salt by reacting a compound (IV) having the formula (IV):

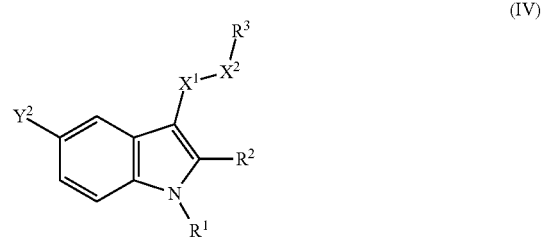
(IV)

wherein R$^1$, R$^2$, R$^3$, X$^1$ and X$^2$ are as defined above, and Y$^2$ is a halogen atom or its salt with a compound having the formula (V):

R$^4$—X$^3$—H (V)

wherein R$^4$ and X$^3$ are as defined above or its salt and, if necessary, removing the protective groups and/or reducing the same, and a production method of a compound having the formula (I):

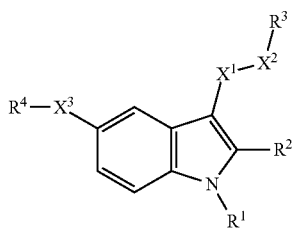

(I)

wherein $R^1$, $R^2$, $R^3$, $R^4$, $X^1$, $X^2$ and $X^3$ are as defined above or its salt by reacting a compound (VI) having the formula (VI):

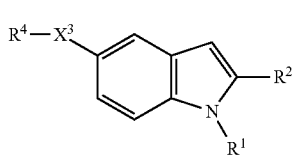

(VI)

wherein $R^1$, $R^2$, $R^4$ and $X^3$ are as defined above or its salt with a compound having the formula (VII)

$$R^3-X^2-Z \qquad (VII)$$

wherein $R^3$ and $X^2$ are as defined above and Z is a halocarbonyl group or (1H-1,2,3-benzotriazol-1-yl)carbonyl group or a compound having the formula (VIII)

(VIII)

wherein $R^{3a}$ indicates a 5- to 10-membered aromatic heterocyclic group including one to four hetero atoms selected from nitrogen atoms, sulfur atoms and oxygen atoms, other than carbon atoms, and may be optionally substituted with one to five groups selected from (i) a halogen atom, (ii) a $C_1$ to $C_6$ alkyl unsubstituted or substituted with one to three halogen atoms, (iii) a $C_3$ to $C_6$ cycloalkyl, (iv) a hydroxyl, (v) a $C_1$ to $C_6$ alkoxy unsubstituted or substituted with one to three halogen atoms, (vi) a $C_1$ to $C_5$ alkylenedioxy, (vii) a $C_1$ to $C_6$ alkylthio unsubstituted or substituted with one to three halogen atoms, (viii) an amino, (ix) a mono-$C_1$ to $C_6$ alkylamino and (x) a di-$C_1$ to $C_6$ alkylamino or its salt and, if necessary, removing the protective groups and/or reducing the same.

The present invention further provides indole derivatives having the formulae (II), (IV) and (VI) useful as intermediates for production of the compound having the formula (I) or its salt or their solvates.

When the compounds having the formulae (I) to (VIII) or their salts have asymmetric carbons in their structures, both optical active isomers and their mixtures are included in the scope of the present invention. When there are two or more asymmetric carbons, their diastereomer mixtures are also included in the scope of the present invention. Further, when compounds having the formulae (I) to (VIII) or their salts have double bonds in their structures, their cis forms, trans forms and their mixtures are also included in the scope of the present invention.

The compound having the formula (I) or its salts may form solvates by contact or recrystallization with water, methanol, ethanol, 1-propanol, 2-propanol, formic acid, ethyl formate, acetic acid, methyl acetate, ethyl acetate, propyl acetate, n-butyl acetate, isobutyl acetate or other solvents or mixed these solvents. Their solvates are also included in the scope of the present invention.

The compound having the formula (I) of the present invention inhibits the $cPLA_2$ to suppress the release of arachidonic acid and lysophospholipids in the cells and further suppress the production of their metabolized products, that is, various lipid mediators, to exhibit an effect against various allergic diseases and inflammatory diseases. Specifically, it is useful as a medicine for the prevention or treatment of diseases such as rheumatoid arthritis, osteoarthritis, dysmenorrhea, acute pain, bronchial asthma or other asthma, allergic rhinitis, chronic and acute airway inflammation, chronic obstructive pulmonary disease, acute lung injury, pulmonary fibrosis, multiple sclerosis, cerebral ischemia/reperfusion injury, dermatitis, ulticaria, eczema, prurigo, pancreatitis, psoriasis, inflammatory colitis, food allergy, allergic colitis, osteoporosis, atherosclerosis, etc. Bronchial asthma or other asthma includes adult asthma and juvenile asthma (atopic and non-atopic), exercise-induced asthma, aspirin asthma, coughing asthma, occupational asthma, etc. Further, the compounds having the formulae (II), (IV) and (VI) are important, as intermediates, when producing the compound having the formula (I). By going through these compounds, it is possible to easily produce the final target compound of the present invention shown in formula (I).

BEST MODE FOR CARRYING OUT THE INVENTION

In the Description, the terms "alkyl", "alkenyl", "alkynyl" and "alkoxy" include both straight-chain or branched groups.

I. Explanation of Compounds Having Formula (I)

In the above formula (I), as examples of the "$C_6$ to $C_{14}$ aromatic hydrocarbon group" of $R^1$, a monocyclic or polycyclic aromatic hydrocarbon group, more specifically, a 6- to 14-membered monocyclic or polycyclic aromatic hydrocarbon group of phenyl, biphenyl, naphthyl, indenyl, anthryl, phenanthryl, etc. (preferably phenyl, biphenyl, naphthyl, etc., particularly preferably phenyl) etc. may be mentioned.

Further, as the "a 5- to 10-membered aromatic heterocyclic group including one to four hetero atoms selected from nitrogen atoms, sulfur atoms and oxygen atoms, other than carbon atoms", expressed by $R^1$, for example, a monocyclic group preferably including, other than carbon atoms, one or more (e.g., 1 to 4, preferably 1 to 3) of one or two types of hetero atoms selected from nitrogen atoms, sulfur atoms and oxygen atoms, or their condensed aromatic heterocyclic groups, more specifically, thienyl, furyl, pyrrolyl, imidazolyl, pyrazolyl, triazolyl, tetrazolyl, thiazolyl, isothiazolyl, oxazolyl, isoxazolyl, pyridyl, pyrazinyl, pyrimidinyl, pyridazinyl, naphthylidinyl, purinyl, etc. may be mentioned. In particular, a 5- to 6-membered aromatic heterocyclic group is preferable, specifically, pyridyl, pyrimidinyl and thienyl, particularly pyridyl is preferable.

Further, as the "a bicyclic or tricyclic condensed polycyclic group formed by condensation of the above aromatic heterocyclic group and the above $C_6$ to $C_{14}$ aromatic hydrocarbon cyclic ring" expressed by $R^1$, benzothienyl, benzofuryl, indolyl, isoindolyl, benzimidazolyl, benzopyrazolyl, benzotriazolyl, benzothiazolyl, benzoisothiazolyl, benzooxazolyl, benzoisoxazolyl, benzodioxolyl, quinolyl, isoquinolyl, quinoxalinyl, phthalazinyl (preferably, benzothienyl, benzofuryl, benzodioxolyl and quinolyl) etc. may be mentioned.

Next, the substituent groups (i) to (xxxiii) of the groups expressed by $R^1$ in the formula (I) will be shown as specific examples.

(i) a halogen atom (e.g., fluorine, chlorine, bromine and iodine may be mentioned)

(ii) a nitro (iii) a cyano (iv) a $C_1$ to $C_6$ alkyl unsubstituted or substituted with one to three groups selected from a halogen atom, a $C_1$ to $C_6$ alkoxy unsubstituted or substituted with one to three halogen atoms, a $C_1$ to $C_7$ acyloxy, a hydroxyl, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms (as the halogen atom, fluorine, chlorine, bromine and iodine may be mentioned, as the $C_1$ to $C_6$ alkoxy, methoxy, ethoxy, n-propoxy, i-propoxy, n-butoxy, i-butoxy, s-butoxy, t-butoxy, n-pentyloxy and n-hexyloxy, etc. may be mentioned, as the $C_1$ to $C_7$ acyloxy, acetoxy, pivaloyloxy and benzoyloxy, etc. may be mentioned, as the 5- to 6-membered heterocyclic, pyridine, pyrimidine, piperidine, pyrrolidine and morpholine, etc. may be mentioned, as the 5- to 6-membered heterocyclic oxy, a (pyridin-2-yl)oxy, (pyridin-3-yl)oxy and (pyrimidin-2-yl)oxy, etc. may be mentioned, as the $C_6$ to $C_{14}$ aromatic hydrocarbon, phenyl, 1-naphthyl and 2-naphthyl, etc. may be mentioned, as the $C_6$ to $C_{14}$ aromatic hydrocarbon oxy, phenoxy, 1-naphthoxy and 2-naphthoxy, etc. may be mentioned, as the $C_1$ to $C_6$ alkyl, methyl, ethyl, n-propyl, i-propyl, n-butyl, i-butyl, s-butyl, t-butyl, n-pentyl, n-hexyl, etc. may be mentioned. As specific examples, methyl, ethyl, n-propyl, i-propyl, n-butyl, i-butyl, s-butyl, t-butyl, n-pentyl, n-hexyl, fluoromethyl, difluoromethyl, trifluoromethyl, chloromethyl, dichloromethyl, trichloromethyl, 2,2,2-trifluoroethyl, 2,2,2-trichloroethyl, methoxymethyl, ethoxymethyl, 2-methoxyethyl, 2-ethoxyethyl, hydroxymethyl, 1-hydroxyethyl, 2-hydroxyethyl, acetoxymethyl, 1-acetoxyethyl, 2-acetoxyethyl, 1-pivaloyloxyethyl, 2-benzoyloxyethyl, (pyridin-2-yl)methyl, (pyridin-4-yl)methyl, (pyridin-3-yl)methyl, (pyrimidin-2-yl)methyl, 2-(pyridin-2-yl)ethyl, 2-(pyridin-4-yl)ethyl, (pyrrolidin-1-yl)methyl, piperidinomethyl, morpholinomethyl, (pyridin-2-yl)oxymethyl, (5-fluoropyridin-2-yl)oxymethyl, phenylmethyl, 4-fluorophenylmethyl, 2-(4-fluorophenyl)ethyl, phenoxymethyl, 2-phenoxyethyl, (4-fluorophenoxy)methyl, (4-chlorophenoxy)methyl and 1-naphthoxymethyl, etc. (preferably methyl, ethyl, n-propyl, difluoromethyl, trifluoromethyl, methoxymethyl, 2-methoxyethyl, hydroxymethyl, 1-hydroxyethyl, 2-hydroxyethyl, acetoxymethyl, 1-acetoxyethyl, 2-acetoxyethyl, (pyridin-2-yl)methyl, (pyridin-4-yl)methyl, phenoxymethyl and (4-fluorophenoxy)methyl etc.) may be mentioned)

(v) a $C_2$ to $C_6$ alkenyl unsubstituted or substituted with one to three halogen atoms (as the halogen atom, fluorine, chlorine, bromine and iodine may be mentioned, as the $C_2$ to $C_6$ alkenyl, for example, vinyl, allyl, isopropenyl, 2-buten-1-yl, 4-penten-1-yl, 5-hexen-1-yl, etc. may be mentioned)

(vi) a $C_2$ to $C_6$ alkynyl unsubstituted or substituted with one to three halogen atoms (as the halogen atom, fluorine, chlorine, bromine and iodine may be mentioned, as the $C_2$ to $C_6$ alkynyl, for example, ethynyl, 2-propynyl, 2-butyn-1-yl, 4-pentyn-1-yl, 5-hexyn-1-yl, etc. may be mentioned)

(vii) a $C_3$ to $C_6$ cycloalkyl (e.g., cyclopropyl, cyclobutyl, cyclopentyl, cyclohexyl etc. may be mentioned)

(viii) a hydroxyl (ix) a $C_1$ to $C_6$ alkoxy unsubstituted or substituted with one to three groups selected from a halogen atom, a $C_1$ to $C_6$ alkoxy unsubstituted or substituted with one to three halogen atoms, a $C_7$ to $C_{16}$ aralkyloxy, a hydroxyl, a mono- or di-$C_1$ to $C_6$ alkylamino, a Carbamoyl, a mono- or a di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms (as a halogen atom, fluorine, chlorine, bromine and iodine may be mentioned, as the $C_1$ to $C_6$ alkoxy, methoxy, ethoxy, n-propoxy, i-propoxy, n-butoxy, i-butoxy, s-butoxy, t-butoxy, n-pentoxy and n-hexoxy, etc. may be mentioned, as the $C_7$ to $C_{16}$ aralkyloxy, benzyloxy, 2-phenylethoxy, 3-phenylpropoxy, etc. (preferably benzyloxy etc.) may be mentioned, as the mono- or di-$C_1$ to $C_6$ alkylamino, N-methylamino, N,N-dimethylamino and N,N-diethylamino, etc. may be mentioned, as the mono- or di-$C_1$ to $C_6$ alkylcarbamoyl, N-methylcarbamoyl, N,N-dimethylcarbamoyl and N,N-diethylcarbamoyl, etc. may be mentioned, as the mono- or di-$C_7$ to $C_{16}$ aralkylcarbamoyl, N-benzylcarbamoyl and N,N-dibenzylcarbamoyl, etc. may be mentioned, as the $C_1$ to $C_6$ alkoxycarbonyl, methoxycarbonyl, ethoxycarbonyl, t-butoxycarbonyl, etc. may be mentioned, as the $C_1$ to $C_6$ acyloxy, acetoxy, pivaloyloxy and benzoyloxy, etc. may be mentioned, as the 5- to 6-membered heterocyclic, pyridine, pyrimidine, piperidine, pyrrolidine, morpholine and tetrahydropyranyl, etc. may be mentioned, as the 5- to 6-membered heterocyclic oxy, (pyridin-2-yl)oxy, (pyridin-3-yl)oxy and (pyrimidin-2-yl)oxy, etc. may be mentioned, as the $C_6$ to $C_{14}$ aromatic hydrocarbon, phenyl, 1-naphthyl and 2-naphthyl, etc. may be mentioned, and as the $C_6$ to $C_{14}$ aromatic hydrocarbon oxy, phenoxy, 1-naphthoxy and 2-naphthoxy, etc. may be mentioned. As specific examples, methoxy, ethoxy, n-propoxy, i-propoxy, n-butoxy, i-butoxy, s-butoxy, t-butoxy, n-pentoxy, n-hexoxy, fluoromethoxy, difluoromethoxy, trifluoromethoxy, chloromethoxy, dichloromethoxy, trichloromethoxy, 2-methoxyethoxy, 2-ethoxyethoxy, 3-methoxypropoxy, 2-hydroxyethoxy, 3-hydroxypropoxy, 2-(N,N-dimethylamino)ethoxy, 2-(carbamoyl)ethoxy, 2-(N,N-dimethylcarbamoyl)ethoxy, 2-(N,N-dibenzylcarbamoyl)ethoxy, 2-carboxyethoxy, 2-(methoxycarbonyl)ethoxy, 2-(ethoxycarbonyl)ethoxy, 2-(acetoxycarbonyl)ethoxy, (pyridin-2-yl)methyloxy, (pyridin-3-yl)methyloxy, (pyridin-4-yl)methyloxy, 2-(pyridin-2-yl)ethoxy, 2-(pyridin-3-yl)ethoxy, 2-(pyridin-4-yl)ethoxy, 3-(pyridin-2-yl)propoxy, 3-(pyridin-3-yl)propoxy, 3-(pyridin-4-yl)propoxy, 2-(pyrrolidin-1-yl)ethoxy, 2-piperidinoethoxy, 2-morpholinoethoxy, (tetrahydro-2H-pyran-2-yl)methoxy, 2-[(pyridin-2-yl)oxy]ethoxy, benzyloxy, 4-fluorobenzyloxy, 1-naphthylmethyloxy, phenetyloxy, 2-(phenoxy)ethoxy and 3-(phenoxy)propoxy, etc. (preferably, methoxy, ethoxy, n-propoxy, i-propoxy, difluoromethoxy, trifluoromethoxy, 2-methoxyethoxy, 3-methoxypropoxy, 2-hydroxyethoxy, 3-hydroxypropoxy, (pyridin-2-yl)methyloxy, (pyridin-3-yl)methyloxy, 2-(pyridin-2-yl)ethoxy, 2-(pyridin-3-yl)ethoxy, 2-(pyridin-4-yl)ethoxy, 3-(pyridin-3-yl)propoxy, 3-(pyridin-4-yl)propoxy, 2-(pyrrolidin-1-yl)ethoxy, (tetrahydro-2H-pyran-2-yl)methoxy and benzyloxy, etc.) may be mentioned)

(x) a $C_6$ to $C_{14}$ aromatic hydrocarbon oxy unsubstituted or substituted with one to three groups selected from a halogen atom, a $C_1$ to $C_6$ alkyl, a $C_1$ to $C_6$ alkoxy and a hydroxyl (e.g., phenoxy, 4-fluorophenoxy, 4-methylphenoxy, 4-methoxyphenoxy, 4-hydroxyphenoxy, etc. may be mentioned)

(xi) a 5- to 6-membered heterocyclic oxy unsubstituted or substituted with one to three halogen atoms (e.g., (tetrahydro-2H-pyran-2-yl)oxy, (tetrahydro-4H-pyran-4-yl)oxy, etc. may be mentioned)

(xii) a $C_1$ to $C_5$ alkylenedioxy (e.g., methylenedioxy, ethylenedioxy, etc. may be mentioned)

(xiii) a $C_1$ to $C_6$ alkylthio unsubstituted or substituted with one to three groups selected from a halogen atom, a $C_1$ to $C_6$ alkoxy, a hydroxyl, a mono- or di-$C_1$ to $C_6$ alkylamino, a carbamoyl, a mono- or di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms, and a $C_6$ to $C_{14}$ aromatic hydrocarbon oxy unsubstituted or substituted with one to three halogen atoms (as the halogen atom, fluorine, chlorine, bromine and iodine may be mentioned, as the $C_1$ to $C_6$ alkoxy, methoxy, ethoxy, n-propoxy, i-propoxy, n-butoxy, i-butoxy, s-butoxy, t-butoxy, n-pentoxy and n-hexoxy etc. may be mentioned, as the mono- or di-$C_1$ to $C_6$ alkylamino, N-methylamino, N,N-dimethylamino and N,N-diethylamino etc. may be mentioned, as the mono- or di-$C_1$ to $C_6$ alkylcarbamoyl, N-methylcarbamoyl, N,N-dimethylcarbamoyl and N,N-diethylcarbamoyl etc. may be mentioned, as the mono- or di-$C_7$ to $C_{16}$ aralkylcarbamoyl, N-benzylcarbamoyl and N,N-dibenzylcarbamoyl, etc. may be mentioned, as the $C_1$ to $C_6$ alkoxycarbonyl, methoxycarbonyl, ethoxycarbonyl and t-butoxycarbonyl, etc. may be mentioned, as the $C_1$ to $C_6$ acyloxy, acetoxy, pivaloyloxy and benzoyloxy, etc. may be mentioned, as the 5- to 6-membered heterocyclic, pyridine, pyrimidine, piperidine, pyrrolidine, morpholine and tetrahydropyranyl, etc. may be mentioned, as the 5- to 6-membered heterocyclic oxy, (pyridin-2-yl)oxy, (pyridin-3-yl)oxy and (pyrimidin-2-yl)oxy, etc. may be mentioned, as the $C_6$ to $C_{14}$ aromatic hydrocarbon, phenyl, 1-naphthyl, 2-naphthyl, etc. may be mentioned, as the $C_6$ to $C_{14}$ aromatic hydrocarbon oxy, phenoxy, 1-naphthoxy, 2-naphthoxy, etc. may be mentioned, as the $C_1$ to $C_6$ alkylthio, methylthio, ethylthio, n-propylthio, propylthio, n-butylthio, i-butylthio, s-butylthio, t-butylthio, n-pentylthio and n-hexylthio, etc. may be mentioned. As specific examples, methylthio, ethylthio, n-propylthio, i-propylthio, n-butylthio, i-butylthio, s-butylthio, t-butylthio, n-pentylthio, n-hexylthio, fluoromethylthio, difluoromethylthio, trifluoromethylthio, chloromethylthio, dichloromethylthio, trichloromethylthio, 2-methoxyethylthio, 2-ethoxyethylthio, 3-methoxypropylthio, 2-hydroxyethylthio, 3-hydroxypropylthio, 2-(N,N-dimethylamino)ethylthio, 2-(carbamoyl)ethylthio, 2-(N,N-dimethylcarbamoyl)ethylthio, 2-(N,N-dibenzylcarbamoyl)ethylthio, 2-carboxyethylthio, 2-(methoxycarbonyl)ethylthio, 2-(ethoxycarbonyl)ethylthio, 2-(acetoxycarbonyl)ethylthio, (pyridin-2-yl)methylthio, (pyridin-3-yl)methylthio, (pyridin-4-yl)methylthio, 2-(pyridin-2-yl)ethylthio, 2-(pyridin-3-yl)ethylthio, 2-(pyridin-4-yl)ethylthio, 3-(pyridin-2-yl)propylthio, 3-(pyridin-3-yl)propylthio, 3-(pyridin-4-yl)propylthio, 2-(pyrrolidin-1-yl)ethylthio, 2-piperidinoethylthio, 2-morpholinoethylthio, (tetrahydro-2H-pyran-2-yl)methylthio, 2-[(pyridin-2-yl)oxy]ethylthio, benzylthio, 4-fluorobenzylthio, 1-naphthylmethylthio, phenetylthio, 2-(phenoxy)ethylthio and 3-(phenoxy)propylthio, etc. (preferably, methylthio, ethylthio, n-propylthio, i-propylthio, difluoromethylthio, trifluoromethylthio, 2-methoxyethylthio, 3-methoxypropylthio, 2-hydroxyethylthio, 3-hydroxypropylthio, (pyridin-2-yl)methylthio, (pyridin-3-yl)methylthio, 2-(pyridin-2-yl)ethylthio, 2-(pyridin-3-yl)ethylthio, 2-(pyridin-4-yl)ethylthio, 3-(pyridin-3-yl)propylthio, 3-(pyridin-4-yl)propylthio, 2-(pyrrolidin-1-yl)ethylthio, (tetrahydro-2H-pyran-2-yl)methylthio and benzylthio, etc.) may be mentioned)

(xiv) a 5- to 6-membered heterocyclic thio unsubstituted or substituted with one to three halogen atoms (e.g., (tetrahydro-2H-pyran-2-yl)thio, (tetrahydro-4H-pyran-4-yl)thio, etc. may be mentioned)

(xv) an amino (xvi) a mono-$C_1$ to $C_6$ alkylamino (e.g., N-methylamino etc. may be mentioned)

(xvii) a di-$C_1$ to $C_6$ alkylamino (e.g., N,N-dimethylamino etc. may be mentioned)

(xviii) a 5- to 6-membered cyclic amino (e.g., piperidino, piperazino, etc. may be mentioned)

(xix) a $C_1$ to $C_6$ acyl (e.g., acetyl, propanoyl, butyryl, isobutyryl, pivaloyl, etc. may be mentioned)

(xx) a carboxyl (xxi) a $C_1$ to $C_6$ alkoxycarbonyl (e.g., methoxycarbonyl, ethoxycarbonyl, etc. may be mentioned)

(xxii) a carbamoyl (xxiii) a thiocarbamoyl (xxiv) a mono-$C_1$ to $C_6$ alkylcarbamoyl (e.g., N-methylcarbamoyl, N-ethylcarbamoyl, etc. may be mentioned)

(xxv) a di-$C_1$ to $C_6$ alkylcarbamoyl (e.g., N,N-dimethylcarbamoyl, N,N-diethylcarbamoyl, etc. may be mentioned)

(xxvi) a 5- to 6-membered heterocyclic carbonyl unsubstituted or substituted with one to three halogen atoms (e.g., (pyrrolidin-1-yl)carbonyl, piperidinocarbonyl, morpholinocarbonyl, etc. may be mentioned)

(xxvii) a sulfo (xxviii) a $C_1$ to $C_6$ alkylsulfonyl (e.g., methylsulfonyl etc. may be mentioned)

(xxix) a $C_1$ to $C_6$ acylamino unsubstituted or substituted with a $C_1$ to $C_6$ alkoxy (e.g., methoxyacetylamino group etc. may be mentioned)

(xxx) a $C_1$ to $C_6$ alkoxycarbonylamino (e.g., methoxycarbonylamino, ethoxycarbonylamino, etc. may be mentioned)

(xxxi) an aminosulfonyl (xxxii) a mono- or di-$C_1$ to $C_6$ alkylaminosulfonyl (e.g., N-methylaminosulfonyl, N,N-dimethylaminosulfonyl, etc. may be mentioned)

(xxxiii) a 5- to 6-membered heterocyclic sulfonyl unsubstituted or substituted with one to three halogen atoms (e.g., (pyrrolidin-1-yl)sulfonyl, piperidinosulfonyl, morpholinosulfonyl, etc. may be mentioned)

In the substituent groups expressed by the above-mentioned $R^1$, (i) a halogen atom, (ii) a nitro, (iii) a cyano, (iv) a $C_1$ to $C_6$ alkyl unsubstituted or substituted with one to three groups selected from a halogen atom, a $C_1$ to $C_6$ alkoxy unsubstituted or substituted with one to three halogen atoms, a $C_1$ to $C_7$ acyloxy, a hydroxyl, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (v) a $C_2$ to $C_6$ alkenyl unsubstituted or substituted with one to three halogen atoms, (vi) a $C_2$ to $C_6$ alkynyl unsubstituted or substituted with one to three halogen atoms, (vii) a $C_3$ to $C_6$ cycloalkyl, (viii) a hydroxyl, (ix) a $C_1$ to $C_6$ alkoxy unsubstituted or substituted with one to three groups selected from a halogen atom, a $C_1$ to $C_6$ alkoxy unsubstituted or substituted with one to three halogen atoms, a $C_7$ to $C_{16}$ aralkyloxy, a hydroxyl, a mono- or di-$C_1$ to $C_6$ alkylamino, a carbamoyl, a mono- or di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (x) a $C_6$ to $C_{14}$ aromatic hydrocarbon oxy unsubstituted or substituted with one to three groups selected from a halogen atom, a $C_1$ to $C_6$ alkyl, a $C_1$ to $C_6$ alkoxy and a hydroxyl, (xi) a 5- to 6-membered heterocyclic oxy unsubstituted or substituted with one to three halogen atoms, (xii) a $C_1$ to $C_5$ alkylenedioxy, (xv) an amino, (xvi) a mono-$C_1$ to $C_6$ alkylamino, (xvii) a di-$C_1$ to $C_6$ alkylamino, (xviii) a 5- to 6-membered cyclic amino, (xix) a $C_1$ to $C_6$ acyl, (xx) a carboxyl, (xxi) a $C_1$ to $C_6$ alkoxycarbonyl, (xxii) a carbamoyl, (xxiv) a mono-$C_1$ to $C_6$ alkylcarbamoyl, (xxv) a di-$C_1$ to $C_6$ alkylcarbamoyl, (xxvi) a 5- to 6-membered heterocyclic carbonyl unsubstituted or substituted with one to three halogen atoms, (xxvii) a sulfo, (xxviii) a $C_1$ to $C_6$ alkylsulfonyl, (xxix) a $C_1$ to $C_6$ acylamino unsubstituted or substituted with $C_1$ to $C_6$ alkoxy, (xxx) a $C_1$ to $C_6$ alkoxycarbonylamino, (xxxi) an aminosulfonyl, (xxxii) a mono- or di-$C_1$ to $C_6$ alkylaminosulfonyl and (xxxiii) a 5- to 6-membered heterocyclic sulfonyl unsubstituted or substituted with one to three halogen atoms are particularly preferred.

As the "$C_1$ to $C_6$ alkyl" expressed by $R^2$, methyl, ethyl, etc. (preferably methyl) may be mentioned, as the "$C_3$ to $C_6$ cycloalkyl", cyclopropyl and cyclobutyl (preferably cyclopropyl) may be mentioned, as the "halogen atom", fluorine, chlorine and bromine (preferably fluorine) may be mentioned.

As examples of the "$C_6$ to $C_{14}$ aromatic hydrocarbon group" and "5- to 10-membered aromatic heterocyclic group including one to four hetero atoms selected from nitrogen atoms, sulfur atoms and oxygen atoms, other than carbon atoms" expressed by $R^3$, ones the same as the examples of the "$C_6$ to $C_{14}$ aromatic hydrocarbon group" and "5- to 10-membered aromatic heterocyclic group including one to four hetero atoms selected from nitrogen atoms, sulfur atoms, and oxygen atoms, other than carbon atoms" expressed by the above $R^1$ may be mentioned As the "$C_6$ to $C_{14}$ aromatic hydrocarbon group" expressed by $R^3$, phenyl is particularly preferred. As the "5- to 10-membered aromatic heterocyclic group including one to four hetero atoms selected from nitrogen atoms, sulfur atoms and oxygen atoms, other than carbon atoms", a 5- to 6-membered aromatic heterocyclic group, particularly pyridyl is preferred.

Next, the substituent groups (i) to (x) of the "$C_6$ to $C_{14}$ aromatic hydrocarbon group" and "5- to 10-membered aromatic heterocyclic group including one to four hetero atoms selected from nitrogen atoms, sulfur atoms and oxygen atoms, other than carbon atoms" expressed by $R^3$ in the formula (I) will be shown together with specific examples.

(i) a halogen atom (e.g., fluorine, chlorine, bromine and iodine may be mentioned)

(ii) a $C_1$ to $C_6$ alkyl unsubstituted or substituted with one to three halogen atoms (as the halogen atom, fluorine, chlorine, bromine and iodine may be mentioned, as the $C_1$ to $C_6$ alkyl, for example, methyl, ethyl, n-propyl, i-propyl, n-butyl, i-butyl, s-butyl, t-butyl, n-pentyl, n-hexyl, etc. may be mentioned)

(iii) a $C_3$ to $C_6$ cycloalkyl (e.g., cyclopropyl, cyclobutyl, cyclopentyl, cyclohexyl, etc. may be mentioned)

(iv) a hydroxyl (v) a $C_1$ to $C_6$ alkoxy unsubstituted or substituted with one to three halogen atoms (as the halogen atom, fluorine, chlorine, bromine and iodine may be mentioned, as the $C_1$ to $C_6$ alkoxy, for example, methoxy, ethoxy, n-propoxy, i-propoxy, n-butoxy, i-butoxy, s-butoxy, t-butoxy, n-pentoxy, n-hexoxy, etc. may be mentioned)

(vi) a $C_1$ to $C_5$ alkylenedioxy (e.g., methylenedioxy, ethylenedioxy, etc. may be mentioned)

(vii) a $C_1$ to $C_6$ alkylthio unsubstituted or substituted with one to three halogen atoms (as the halogen atom, fluorine, chlorine, bromine and iodine may be mentioned, as the $C_1$ to $C_6$ alkylthio, for example, methylthio, ethylthio, n-propylthio, i-propylthio, n-butylthio, i-butylthio, s-butylthio, t-butylthio, n-pentylthio, n-hexylthio, etc. may be mentioned)

(viii) an amino (ix) a mono-$C_1$ to $C_6$ alkylamino (e.g., N-methylamino etc. may be mentioned)

(x) a di-$C_1$ to $C_6$ alkylamino (e.g., N,N-dimethylamino etc. may be mentioned)

As the $C_1$ to $C_6$ alkyl expressed by $R^5$ in the group —$CO_2R^5$ expressed by $R^4$, methyl, ethyl, n-propyl, t-butyl, n-pentyl, etc., preferably $C_1$ to $C_4$ alkyl (e.g., methyl, ethyl, t-butyl, etc.) may be mentioned, as the $C_7$ to $C_{16}$ aralkyl, benzyl, phenylethyl, phenylpropyl, etc., preferably $C_7$ to $C_8$ aralkyl (benzyl etc.) may be mentioned.

As the halogen atom expressed by $R^6$ in the group —COC($R^6$)$_3$ expressed by $R^4$, fluorine, chlorine, bromine and iodine, preferably fluorine, chlorine and bromine may be mentioned.

As the $C_1$ to $C_6$ alkyl expressed by the $R^7$ and $R^8$ in the group —$CONR^7R^8$ expressed by $R^4$, methyl, ethyl, n-propyl, i-propyl, n-butyl, i-butyl, s-butyl, t-butyl, n-pentyl, n-hexyl, etc., preferably, $C_1$ to $C_4$ alkyl (methyl, ethyl, n-propyl, n-butyl, t-butyl, etc.) may be mentioned, as the $C_7$ to $C_{16}$ aralkyl, benzyl, 2-phenylethyl, 3-phenylpropyl, etc., preferably, $C_7$ to $C_8$ aralkyl (benzyl, 2-phenylethyl, etc.) may be mentioned, as the $C_1$ to $C_6$ alkoxy, methoxy, ethoxy, n-propoxy, i-propoxy, n-butoxy, i-butoxy, s-butoxy, t-butoxy, n-pentoxy, n-hexoxy, etc., preferably $C_1$ to $C_4$ alkoxy (methoxy, ethoxy, n-propoxy, n-butoxy, t-butoxy, etc.) may be mentioned, as the $C_7$ to $C_{16}$ aralkyloxy, benzyloxy, 2-phenylethoxy, 3-phenylpropoxy, etc., preferably $C_7$ to $C_8$ aralkyloxy(benzyloxy, 2-phenylethoxy, etc.) may be mentioned, as the group, —$CONR^7R^8$ expressed by $R^4$, where one of $R^7$ and $R^8$ is a hydrogen atom is preferable.

As the $C_1$ to $C_6$ alkyl expressed by $R^9$ in the group —$CONHSC_2R^9$ expressed by $R^4$, methyl, ethyl, n-propyl, propyl, n-butyl, i-butyl, s-butyl, t-butyl, n-pentyl, n-hexyl, etc., preferably $C_1$ to $C_4$ alkyl (methyl, ethyl, n-propyl, n-butyl, t-butyl, etc.) may be mentioned, as the phenyl unsubstituted or substituted with one to three $C_1$ to $C_3$ alkyls, phenyl, p-tolyl, m-tolyl, o-tolyl, p-ethylphenyl, p-(n-propyl)phenyl, etc., preferably phenyl, p-tolyl, etc. may be mentioned, as the $C_7$ to $C_{16}$ aralkyl, benzyl, 2-phenylethyl, 3-phenylpropyl, etc. preferably $C_7$ to $C_8$ aralkyl (benzyl, 2-phenylethyl, etc.) may be mentioned.

As the group expressed by $R^4$, the group —$CO_2R^5$ is particularly preferable, while as the group expressed by $R^5$, a hydrogen atom is particularly preferable.

$X^1$ is a carbonyl group or methylene group, while a methylene group is particularly preferable.

As specific examples of the straight-chain, branched or cyclic $C_1$ to $C_6$ alkylene expressed by $X^2$, methylene, 1,2-ethylene, 1,3-trimethylene, cyclopropylene, etc. may be mentioned.

As the $X^2$, a straight-chain $C_1$ to $C_6$ alkylene (particularly a methylene group) or a connecting bond is preferable.

As specific examples of (1) the straight-chain or branched $C_1$ to $C_6$ alkylene expressed by $X^3$, methylene, 1,2-ethylene, 1,3-trimethylene, etc. may be mentioned, as specific examples of (2) the straight-chain or branched $C_2$ to $C_6$ alkenylene, trans-ethenylene, cis-ethenylene, propenylene, etc. may be mentioned, as specific examples of (3) the straight-chain or branched $C_2$ to $C_6$ alkynylene, ethynylene, propynylene, etc. may be mentioned.

As $X^3$, straight-chain $C_1$ to $C_6$ alkylene (particularly 1,2-ethylene) and straight-chain $C_2$ to $C_6$ alkenylene (particularly trans-ethenylene) is preferable.

As preferable examples of the compound having the formula (I), the following may be mentioned 1. A compound where $R^1$ is (1) a $C_6$ to $C_{14}$ aromatic hydrocarbon group or (2) a 5- to 6-membered aromatic heterocyclic group including one to four hetero atoms selected from nitrogen atoms, sulfur atoms and oxygen atoms, other than carbon atoms.
2. A compound where the aromatic hydrocarbon group or aromatic heterocyclic group of $R^1$ is unsubstituted or is substituted with one to three groups selected from (i) a halogen atom, (ii) a nitro, (iii) a cyano, (iv) a $C_1$ to $C_6$ alkyl unsubstituted or substituted with one to three groups selected from a halogen atom, a $C_1$ to $C_6$ alkoxy unsubstituted or substituted with one to three halogen atoms, a $C_1$ to $C_7$ acyloxy, a hydroxyl, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (v) a $C_2$ to $C_6$ alkenyl unsubstituted or substituted with one to three halogen atoms, (vi) a $C_2$ to $C_6$ alkynyl unsubstituted or substituted with one to three halogen atoms, (vii) a $C_3$ to $C_6$ cycloalkyl, (viii) a hydroxyl, (ix) a $C_1$ to $C_6$ alkoxy unsubstituted or substituted with one to three groups selected from a halogen atom, a $C_1$ to $C_6$ alkoxy unsubstituted or substituted with one to three halogen atoms, a $C_7$ to $C_{16}$ aralkyloxy, a hydroxyl, a mono- or di-$C_1$ to $C_6$ alkylamino, a carbamoyl, a mono- or di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (x) a $C_6$ to $C_{14}$ aromatic hydrocarbon oxy unsubstituted or substituted with one to three groups selected from a halogen atom, a $C_1$ to $C_6$ alkyl, a $C_1$ to $C_6$ alkoxy and a hydroxyl, (xi) a 5- to 6-membered heterocyclic oxy unsubstituted or substituted with one to three halogen atoms, (xii) a $C_1$ to $C_5$ alkylenedioxy, (xv) an amino, (xvi) a mono-$C_1$ to $C_6$ alkylamino, (xvii) a di-$C_1$ to $C_6$ alkylamino, (xviii) a 5- to 6-membered cyclic amino, (xix) a $C_1$ to $C_6$ acyl, (xx) a carboxyl, (xxi) a $C_1$ to $C_6$ alkoxycarbonyl, (xxii) a carbamoyl, (xxiv) a mono-$C_1$ to $C_6$ alkylcarbamoyl, (xxv) a di-$C_1$ to $C_6$ alkylcarbamoyl, (xxvi) a 5- to 6-membered heterocyclic carbonyl unsubstituted or substituted with one to three halogen atoms, (xxvii) a sulfo, (xxviii) a $C_1$ to $C_6$ alkylsulfonyl, (xxix) a $C_1$ to $C_6$ acylamino unsubstituted or substituted with $C_1$ to $C_6$ alkoxy, (xxx) a $C_1$ to $C_6$ alkoxycarbonylamino, (xxxi) an aminosulfonyl, (xxxii) a mono- or di-$C_1$ to $C_6$ alkylaminosulfonyl and (xxxiii) a 5- to 6-membered heterocyclic sulfonyl unsubstituted or substituted with one to three halogen atoms.
3. A compound where $R^2$ is (1) a hydrogen atom or (2) a $C_1$ to $C_6$ alkyl.
4. A compound where $R^3$ indicates (1) a $C_6$ to $C_{14}$ aromatic hydrocarbon group or (2) a 5- to 6-membered aromatic heterocyclic group including one to four hetero atoms selected from nitrogen atoms, sulfur atoms and oxygen atoms, other than carbon atoms,
    where the groups (1) to (2) of the above $R^3$ may be substituted with one to three groups selected from (i) a halogen atom, (ii) a $C_1$ to $C_6$ alkyl unsubstituted or substituted with one to three halogen atoms, (iii) a hydroxyl and (iv) a $C_1$ to $C_6$ alkoxy unsubstituted or substituted with one to three halogen atoms.
5. A compound where $R^4$ is (1) —$CO_2R^5$ where $R^5$ indicates a hydrogen atom, a $C_1$ to $C_4$ alkyl or a $C_7$ to $C_8$ aralkyl, (2) —$COC(R^6)_3$ where $R^6$ indicates a fluorine atom, a chlorine atom or a bromine atom, (3) —$CONR^7R^8$ where one of $R^7$ and $R^8$ is a hydrogen atom and the other is a hydrogen atom, a hydroxyl, a $C_1$ to $C_4$ alkyl, a $C_7$ to $C_8$ aralkyl, a $C_1$ to $C_4$ alkoxy, a $C_7$ to $C_8$ aralkyloxy, a cyano or a tetrazole, (4) —CHO, (6) a cyano or (7) a tetrazole.
6. A compound where $R^4$ is shown by —$CO_2R^5$ where $R^5$ is a hydrogen atom, a $C_1$ to $C_4$ alkyl or a $C_7$ to $C_8$ aralkyl.
7. A compound where $X^2$ is (1) a straight-chain $C_1$ to $C_6$ alkylene or (2) a connecting bond.
8. A compound where $X^3$ is (1) a straight-chain $C_1$ to $C_6$ alkylene or (2) a straight-chain $C_2$ to $C_6$ alkenylene.
9. A compound where $R^1$ is a phenyl group, 2-pyridyl group, 3-pyridyl group or 4-pyridyl group unsubstituted or substituted with one to three groups selected from the following group of substituent groups (a):
    Group of substituent groups (a): (i) a halogen atom, (iv) a $C_1$ to $C_6$ alkyl which may be substituted with one to three groups selected from one to three halogen atoms, $C_1$ to $C_6$ alkoxy, $C_1$ to $C_7$ acyloxy, hydroxyl, 5- to 6-membered heterocyclic which may be substituted, 5- to 6-membered heterocyclic oxy which may be substituted, $C_6$ to $C_{14}$ aromatic hydrocarbon which may be substituted, and $C_6$ to $C_{14}$ aromatic hydrocarbon oxy which may be substituted, (viii) a hydroxyl, (ix) a $C_1$ to $C_6$ alkoxy which may be substituted with one to three groups selected from one to three halogen atoms, $C_1$ to $C_6$ alkoxy, $C_7$ to $C_{16}$ aralkyloxy, hydroxyl, mono- or di-$C_1$ to $C_6$ alkylamino, carbamoyl, mono- or di-$C_1$ to $C_6$ alkylcarbamoyl, mono- or di-$C_7$ to $C_{16}$ aralkylcarbamoyl, carboxyl, $C_1$ to $C_6$ alkoxycarbonyl, $C_1$ to $C_6$ acyloxy, 5- to 6-membered heterocyclic which may be substituted, 5- to 6-membered heterocyclic oxy which may be substituted, $C_6$ to $C_{14}$ aromatic hydrocarbon which may be substituted and $C_6$ to $C_{14}$ aromatic hydrocarbon oxy which may be substituted and (x) a $C_6$ to $C_{14}$ aromatic hydrocarbon oxy which may be substituted with one to three groups selected from a halogen atom, a $C_1$ to $C_6$ alkyl, a $C_1$ to $C_6$ alkoxy and a hydroxyl.

When the compound having the formula (I) has an amine or other basic group as a substituent group, a salt with an inorganic acid (e.g., hydrochloric acid, hydrobromic acid, sulfuric acid, nitric acid, phosphoric acid, periodic acid, etc.) or a salt with an organic acid (e.g., formic acid, acetic acid, butyric acid, oxalic acid, malonic acid, propionic acid, valeric acid, succinic acid, fumaric acid, maleic acid, tartaric acid, citric acid, malic acid, benzoic acid, methanesulfonic acid, ethanesulfonic acid, benzenesulfonic acid, p-toluenesulfonic acid, etc.) may also be formed. When the compound having the formula (I) has a carboxylic acid or other acidic group as a substituent group, a salt with an inorganic base (e.g., lithium, sodium, potassium, calcium, magnesium, or other alkali metals or alkaline earth metals, zinc or ammonia, etc.) or a salt with an organic base (e.g., triethanolamine, 2-aminoethanol, piperadine, N,N'-dibenzylethylenediamine, L-arginine, 2-amino-2-(hydroxymethyl) propane-1,3-diol, etc.) may also be formed.

The compound having the formula (I) or its salt may also be made a solvate with water, methanol, ethanol, 1-propanol, 2-propanol, formic acid, ethyl formate, acetic acid, methyl acetate, ethyl acetate, propyl acetate, n-butyl acetate, isobutyl acetate or another solvent, or a non-solvate. When forming a solvate, it may be coordinated with any number of solvent molecules.

As particular preferable specific examples of the indole derivatives shown by the general formula (I) or their salts provided by the present invention, the following may be illustrated:

3-[1-phenyl-3-(2-phenylethyl)-1H-indol-5-yl]propanoic acid,
3-{1-[4-(benzyloxy)phenyl]-3-(2-phenylethyl)-1H-indol-5-yl}propanoic acid,
3-[1-(4-hydroxyphenyl)-3-(2-phenylethyl)-1H-indol-5-yl]propanoic acid,
3-[1-(4-fluorophenyl)-3-(2-phenylethyl)-1H-indol-5-yl]propanoic acid,
3-{1-[4-(difluoromethoxy)phenyl]-3-(2-phenylethyl)-1H-indol-5-yl}propanoic acid,
3-{3-(2-phenylethyl)-1-[4-(trifluoromethoxy)phenyl]-1H-indol-5-yl}propanoic acid,
3-{1-[4-(methoxymethyl)phenyl]-3-(2-phenylethyl)-1H-indol-5-yl}propanoic acid,
3-{1-[4-(2-hydroxyethoxy)phenyl]-3-(2-phenylethyl)-1H-indol-5-yl}propanoic acid,
3-[1-(4-phenoxyphenyl)-3-(2-phenylethyl)-1H-indol-5-yl]propanoic acid,
(2E)-3-[1-(4-phenoxyphenyl)-3-(2-phenylethyl)-1H-indol-5-yl]propenoic acid,
sodium 3-[1-(4-phenoxyphenyl)-3-(2-phenylethyl)-1H-indol-5-yl]propanoate,
3-[1-(4-phenoxyphenyl)-3-(2-phenylethyl)-1H-indol-5-yl]propanoic acid 2-amino-2-(hydroxymethyl)propane-1,3-diol salt, and
3-[1-(4-phenoxyphenyl)-3-(2-phenylethyl)-1H-indol-5-yl]propanoic acid L-arginine salt II. Regarding Production Methods of Compound Having Formula (I) or its Salts The production method of a compound having the formula (I) or its salt or their solvates will now be explained. The compound having the formula (I) or its salt may be produced by any of the three production methods (A), (B) and (C) explained below.

Production Method (A)

The compound having the formula (I) or its salt may be produced by, for example, reacting the compound (II) having the formula (II):

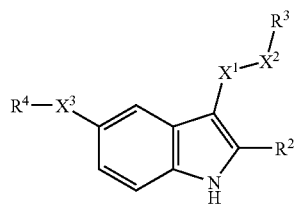

(II)

wherein $R^2$, $R^3$, $R^4$, $X^1$, $X^2$ and $X^3$ are as defined above or its salt with the compound having the formula (III):

— (III)

wherein $R^1$ is as defined above and $Y^1$ is a halogen atom or triflate or its salt and, if necessary, removing the protective groups (see Protective Groups in Organic Synthesis $3^{rd}$ Edition, Theodora W. Greene, Peter G. M. Wuts (John Wiley & Sons)) and/or reducing the same (e.g., a usual hydrogenation reaction using a palladium-carbon catalyst, or a Raney nickel catalyst, etc. (see 4th Edition Jikken Kagaku Koza (Experimental Chemistry Course) 26, the Chemical Society of Japan edited, 251-266 (Maruzen))).

As $Y^1$, a halogen atom (e.g., fluorine, chlorine, bromine, iodine, etc.) and a triflate, etc. may be used.

This reaction may be performed according to a known method (see e.g., J. Org. Chem., 64, 5575-5580 (1999) and Org. Lett., 2 (10) 1403-1406 (2000), or J. Am. Chem. Soc., 124, 11684-11688 (2002), J. Org. Chem., 70, 5164-5173 (2005), Synthesis, 5, 839-842 (2006) and J. Am. Chem. Soc., 128, 8742-8743 (2006), etc.) usually in the presence of a palladium catalyst or copper catalyst. As the palladium catalyst, for example, palladium acetate, bis(dibenzylideneacetone)palladium, etc. may be used. As the copper catalyst, for example, copper iodide (I), copper acetate (I), etc. may be used.

Further, this reaction may be performed using a phosphorus compound, as a ligand, when using a normal palladium catalyst and using an organic compound when using a copper catalyst. As the ligand of the phosphorus compound, for example, tri-tert-butylphosphine, 2-(di-tert-butylphosphino)biphenyl, 2-(dicyclohexylphosphino)biphenyl, etc. may be used, while as the ligand of the organic compound, for example, ethylenediamine, N,N'-dimethylethylenediamine, trans-1,2-cyclohexanediamine, trans-N,N'-dimethyl-1,2-cyclohexanediamine, poly(ethyleneglycol), β-diketones (for example, 2-acetylcyclohexanone, 2-propionylcyclohexanone, etc.), amino acids (e.g., L-proline etc.), etc. may be used.

Further, this reaction may be performed usually in the presence of a base. As the base, for example, sodium carbonate, sodium hydrogen carbonate, potassium carbonate, potassium hydrogen carbonate, cesium carbonate, or other alkali metal carbonates, trisodium phosphate, disodium hydrogen phosphate, sodium dihydrogen phosphate, tripotassium phosphate, dipotassium hydrogen phosphate, potassium dihydrogen phosphate, or other alkali metal phosphates, sodium tert-butoxide or other alkali metal alkoxides etc. may be used.

Further, this reaction may sometimes be performed in the copresence of a metal salt. As the metal salt, for example, potassium bromide, sodium bromide, lithium iodide, sodium iodide, potassium iodide, etc. may be mentioned.

Further, when this reaction is performed according to a known method (see e.g., Eur. J. Org. Chem., 2147-2151 (2007) etc.) using copper acetate (I) as a catalyst, it need not be performed in the copresence of a ligand, base, metal salt, etc.

Furthermore, this reaction may be usually performed in the presence of a solvent. As the solvent, for example, dioxane, tetrahydrofuran, 1,2-dimethoxyethane, diethyleneglycol dimethyl ether, poly(ethyleneglycol), or other ether, benzene, toluene, xylene or other aromatic hydrocarbon, acetonitrile or other nitrile, N,N-dimethylformamide, N,N-dimethylacetamide, N-methyl-2-pyrrolidone or other amide, dimethylsulfoxide or other sulfoxide, 1,3-dimethyl-3,4,5,6-tetrahydro-2 (1H)-pyrimidone or other urea, ethyl acetate, n-butyl acetate, or other acetic acid esters etc. may be used, as a sole solvent or mixed solvent.

Further, the starting compound (III) can be used a commercial product or a known compound. As such a starting compound (III), for example, bromobenzene, iodobenzene, 4-bromoanisole, 4-benzyloxybromobenzene, p-(methoxymethyl)bromobenzene, ethyleneglycol mono(4-bromophenyl) ether, p-bromofluorobenzene, 1-bromo-4-(difluoromethoxy)benzene, 1-bromo-4-(trifluoromethoxy)benzene, 4-chlorodiphenyl ether, 4-bromodiphenyl ether, 4-iododiphenyl ether, 2-benzyloxy-5-bromopyridine and phenyltriflate, etc. may be mentioned.

In this reaction, it is preferable to use the compound (III) in an amount of about 1 to about 5 moles, preferably about 1 to about 3 moles, based upon 1 mole of the compound (II) or its salt. The reaction temperature is about 60° C. to about 160° C., preferably about 60° C. to about 120° C., while the reaction time is preferably about 3 hours to about 48 hours.

Production Method (B)

The compound having the formula (I) or its salt may be produced by reacting, for example, the compound (IV) having the formula (IV):

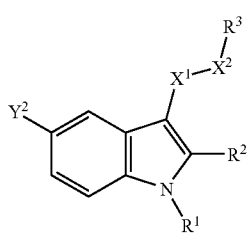

(IV)

wherein, $R^1$, $R^2$, $R^3$, $X^1$ and $X^2$ are as defined above, while $Y^2$ is a halogen atom or its salt with a compound having the formula (V):

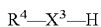

(V)

wherein $R^4$ and $X^3$ are as defined above or its salt and, if necessary, removing the protective groups (see Protective Groups in Organic Synthesis 3$^{rd}$ Edition, Theodora W. Greene, Peter G. M. Wuts (John Wiley & Sons)) and/or reducing the same (see 4th Edition Jikken Kagaku Koza (Experimental Chemistry Course) 26, the Chemical Society of Japan edited, (Maruzen)). This reaction may be used, when the compound having the formula (V) is an acrylic acid ester or propynic acid ester.

The reaction can obtain the compound (I) from the compound (IV) by, for example, following a generally used Heck reaction or other known method (see Advanced Organic Chemistry 3$^{rd}$ Edition, Part B, Francis A. Carey, Richard J. Sundberg, 418-419 (Plenum Press) etc.) and reacting an acrylic acid ester having the formula (V) (e.g., methyl acrylate, ethyl acrylate, etc.) in triethylamine or another basic solvent in the presence of a palladium catalyst (e.g., palladium acetate etc.), phospholigand (e.g., tris(2-methylphenyl)phosphine etc.) or the like under heating and reflux, then, if necessary, removing the protective groups (see Protective Groups in Organic Synthesis 3$^{rd}$ Edition, Theodora W. Greene, Peter G. M. Wuts (John Wiley & Sons)) and/or reducing it (e.g., a usual hydrogenation reaction using a palladium-carbon catalyst or a Raney nickel catalyst, etc. (see 4th Edition Jikken Kagaku Koza (Experimental Chemistry Course) 26, the Chemical Society of Japan edited, 251-266 (Maruzen)).

Further, it can also obtain the compound (I) from the compound (IV) by following a known method (see J. Med. Chem., 39 (16) 3179-3187 (1996), Tetrahedron Lett., 50, 4467-4470 (1975), etc.) and, for example, reacting a propynic acid ester having the formula (V) (e.g., methyl propynate, ethyl propynate, etc.) in diethylamine or other basic solvent in the presence of a palladium catalyst (e.g., dichlorobis(triphenylphosphine) palladium (II) etc.) and a copper halide (e.g., copper (I) iodide etc.), under heating, then, if necessary, removing the protective groups (see Protective Groups in Organic Synthesis 3$^{rd}$ Edition, Theodora W. Greene, Peter G. M. Wuts (John Wiley & Sons)) and/or reducing the same (see 4th Edition Jikken Kagaku Koza (Experimental Chemistry Course) 26, the Chemical Society of Japan edited, (Maruzen)).

Further, the starting compound (V) can be used a commercially available product or a known compound.

The compound (V) is preferably used in an amount of about 1 to about 5 moles, preferably about 1 to about 3 moles, based upon 1 mol of the reaction compound (IV) or its salts. The reaction temperature is preferably about 60° C. to about 120° C., while the reaction time is preferably about 3 hours to about 48 hours.

Production Method (C)

The compound having the formula (I) or its salt may be produced by, for example, reacting the compound (VI) having the formula (VI):

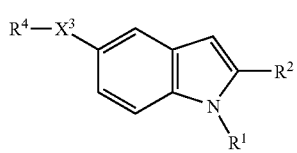

(VI)

wherein $R^1$, $R^2$, $R^4$, and $X^3$ are as defined above or its salt with a compound having the formula (VII):

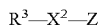

(VII)

wherein $R^3$ and $X^2$ are as defined above and Z is a halocarbonyl group or (1H-1,2,3-benzotriazol-1-yl)carbonyl group or the formula (VIII):

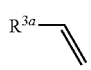

(VIII)

wherein $R^{3a}$ is a 5- to 10-membered aromatic heterocyclic group including one to four hetero atoms selected from nitrogen atoms, sulfur atoms and oxygen atoms, other than carbon atoms, and may be optionally substituted with one to five groups selected from (i) a halogen atom, (ii) a $C_1$ to $C_6$ alkyl unsubstituted or substituted with one to three halogen atoms, (iii) a $C_3$ to $C_6$ cycloalkyl, (iv) a hydroxyl, (v) a $C_1$ to $C_6$ alkoxy unsubstituted or substituted with one to three halogen atoms, (vi) a $C_1$ to $C_5$ alkylenedioxy, (vii) a $C_1$ to $C_6$ alkylthio unsubstituted or substituted with one to three halogen atoms, (viii) an amino, (ix) a mono-$C_1$ to $C_6$ alkylamino and (x) a di-$C_1$ to $C_6$ alkylamino or their salts and, if necessary, removing the protective groups (see Protective Groups in Organic Synthesis $3^{rd}$ Edition, Theodora W. Greene, Peter G. M. Wuts (John Wiley & Sons)) and/or reducing the same (see 4th Edition Jikken Kagaku Koza (Experimental Chemistry Course) 26, the Chemical Society of Japan edited, (Maruzen)).

As the group expressed by Z, chlorocarbonyl, bromocarbonyl or another halocarbonyl group, (1H-1,2,3-benzotriazol-1-yl)carbonyl group, etc. may be used.

This reaction can obtain the compound (I) by, for example, following the generally used Friedel-Crafts reaction or other known method (see March's Advanced Organic Chemistry $5^{th}$ Edition, Michael B. Smith, Jerry March, 712-714 (John Wiley & Sons)) and reacting the starting compound in methylene chloride, chloroform or another solvent in the presence of a Lewis acid catalyst (e.g., aluminum chloride, titanium tetrachloride, etc.), or the like, then, if necessary, removing the protective groups (see Protective Groups in Organic Synthesis $3^{rd}$ Edition, Theodora W. Greene, Peter G. M. Wuts (John Wiley & Sons)) and/or reducing it (e.g., the usual hydrogenation reaction using a palladium-carbon catalyst, Raney nickel catalyst, etc. (see 4th Edition Jikken Kagaku Koza (Experimental Chemistry Course) 26, the Chemical Society of Japan edited, 251-266 (Maruzen)).

Further, the starting compound (VII) may be used a commercially available product or known compound. For example, benzoyl chloride, phenylacetyl chloride, 1-phenylacetyl-1H-1,2,3-benzotriazole, etc. may be mentioned.

Further, the starting compound (VIII) may be a commercially available product or known compound. For example, 2-vinylpyridine, 3-vinylpyridine, etc. may be mentioned.

In the reaction, the compound (VII) or the compound (VIII) is preferably used in an amount of about 1 to about 5 moles, preferably about 1 to about 3 moles, based upon 1 mole of the compound (VI) or its salts. The reaction temperature is preferably room temperature to about 60° C., while the reaction time is preferably about 3 hours to about 48 hours.

The compound (I) of the present invention produced by the method of the above (A), (B) or (C) may be purified by a known means, for example, solvent extraction, liquid conversion, redissolution, salting out, crystallization, precipitation, recrystallization, chromatography, etc. When the compound (I) of the present invention or its salt is a optical active isomer, and including another optical isomer, it can be divided into the enanthiomers by general optical dividing means.

Further, when it is possible to use a reaction for removing the protective groups in the case where the compound (I) of the present invention produced by the method of (A), (B) or (C) has protective groups, a reduction reaction in the case of having a carbonyl group, a hydrogenation reaction or other reduction reaction in the case where $X^3$ forms a double bond (—CH═CH—) or there is otherwise a double bond, a reduction reaction in the case of having a nitro group, (i) an esterification reaction, (ii) an amidation reaction, and (iii) an acid chloride forming reaction in the case of having a carboxylic acid, a trifluoromethyl forming reaction in the case of having an acid chloride, (i) a hydrolysis reaction (see 4th Edition Jikken Kagaku Koza (Experimental Chemistry Course) 22, the Chemical Society of Japan edited, 7-11 (Maruzen)) and (ii) a reaction for conversion to a carboxylate by addition of a solid (e.g., pellets or flakes) base (e.g., lithium hydroxide, sodium hydroxide, potassium hydroxide, etc.) in a solvent (e.g., ethanol, 2-propanol, etc.) in the case of having an ester group, (i) an alkylation reaction, (ii) an acylation reaction and (iii) a sulfonylation reaction in the case of having an amino group or hydroxyl group, (i) an alkylation reaction, (ii) an acylation reaction, (iii) a sulfonylation reaction, (iv) a dehydration reaction and (v) a reduction reaction in the case of having a primary or secondary amide group, an addition reaction in the case of having a cyano group, etc. so as to enable conversion to functional groups by one step to five steps by an ordinary method, it is possible to produce the compound (I) converted in functional groups by the above condensation reaction, then, if necessary, conversion of the functional groups.

When the compound (I) of the present invention produced by the above has an amine or other basic group as a substituent group, it may be dissolved in water or a suitable organic solvent (e.g., methanol, ethanol, 1-propanol, 2-propanol, diethyl ether, tetrahydrofuran, ethyl acetate, butyl acetate, acetonitrile, methylene chloride, chloroform, benzene, toluene, etc.) and treated with an inorganic acid (e.g., hydrochloric acid, hydrobromic acid, sulfuric acid, nitric acid, phosphoric acid, periodic acid, etc.) or an organic acid (e.g., formic acid, acetic acid, butyric acid, oxalic acid, malonic acid, propionic acid, valeric acid, succinic acid, fumaric acid, maleic acid, tartaric acid, citric acid, malic acid, benzoic acid, methanesulfonic acid, ethanesulfonic acid, benzenesulfonic acid, p-toluenesulfonic acid, etc.) so as to obtain a suitable salt. When the compound (I) has a carboxylic acid or other acidic group as a substituent group, it may be dissolved in water or a suitable solvent (e.g., methanol, ethanol, 1-propanol, 2-propanol, diethyl ether, tetrahydrofuran, ethyl acetate, butyl acetate, acetonitrile, methylene chloride, chloroform, benzene, toluene, etc.) and treated with an inorganic base (e.g., lithium hydroxide, sodium hydroxide, potassium hydroxide, calcium hydroxide, magnesium hydroxide, or other hydroxide of an alkali metal or alkaline earth metal, zinc hydroxide or ammonia, etc.) or an organic base (e.g., triethanolamine, 2-aminoethanol, piperazine, N,N'-dibenzylethylenediamine, L-arginine, 2-amino-2-(hydroxymethyl)propane-1,3-diol, etc.) or organic metals (e.g., zinc acetate etc.) so as to obtain the corresponding salt.

The compound (I) of the present invention produced by the above method or its salt may be brought into contact with water, methanol, ethanol, 1-propanol, 2-propanol, formic acid, ethyl formate, acetic acid, methyl acetate, ethyl acetate, propyl acetate, n-butyl acetate, isobutyl acetate, or other solvents or mixed solvents including the same or may be recrystallized using these solvents so as to form solvates.

III. Explanation of Production Methods of Materials for Production of Compound Having Formula (I) or its Salts or Solvates The production methods of the starting compounds (II), (IV) and (VI) used for the production of the compound (I) or its salt or their solvates will be explained.

The starting compound (II) may be synthesized by the method of, for example, the following flows:

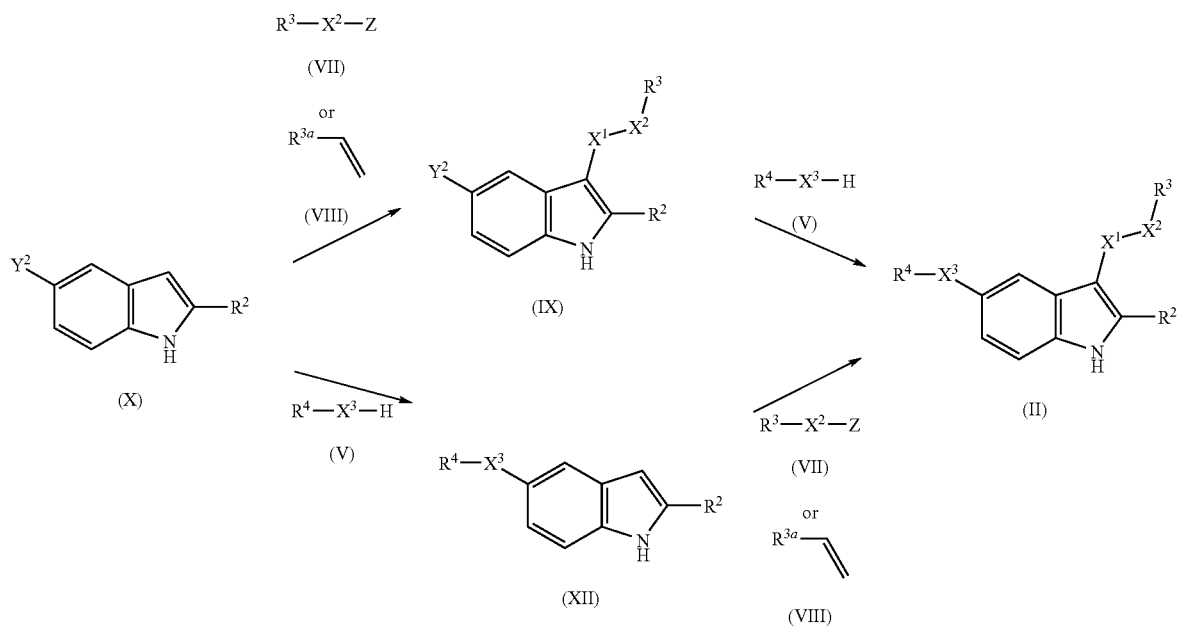

wherein $R^2$, $R^3$, $R^{3a}$, $R^4$, $X^1$, $X^2$ and $X^3$ are as defined above, $Y^2$ is a halogen atom and Z is a halocarbonyl group or (1H-1,2,3-benzotriazol-1-yl)carbonyl group.

As the group expressed by $Y^2$, a halogen atom (e.g., fluorine, chlorine, bromine, iodine, etc.), while as the group expressed by Z, chlorocarbonyl, bromocarbonyl or another halocarbonyl group or a (1H-1,2,3-benzotriazol-1-yl)carbonyl group may be used.

First, from the compound (X), for example, a generally used Friedel-Crafts reaction or other known method may be followed to react the compound (VII) in methylene chloride, chloroform or another solvent in the presence of a Lewis acid catalyst (e.g., aluminum chloride, titanium tetrachloride, etc.) or the like and, if necessary, to remove the protective groups (see Protective Groups in Organic Synthesis $3^{rd}$ Edition, Theodora W. Greene, Peter G. M. Wuts (John Wiley & Sons)) and/or reduce the same (as the reducing agent, for example, sodium borohydride, triethylsilane, lithium aluminum hydride, etc. may be mentioned (see 4th Edition Jikken Kagaku Koza (Experimental Chemistry Course) 26, the Chemical Society of Japan edited, 185-251 (Maruzen)) to obtain the compound (IX).

Further, the starting compounds (VII) and (X) described above can be used commercially available products or known compounds. As such a starting compound (VII), for example, benzoyl chloride, benzoyl bromide, phenylacetyl chloride, phenylacetyl bromide, 2-phenylpropionyl chloride, 3-phenylpropionyl chloride, 1-phenylacetyl-1H-1,2,3-benzotriazole, 1-(3-phenylpropionyl)-1H-1,2,3-benzotriazole etc. may be mentioned, while as the starting compound (X), for example, 5-bromoindole, 5-chloroindole, 5-bromo-2-methylindole, 5-chloro-2-methylindole, etc. may be mentioned.

Further, from the compound (X), a known method (see J. Am. Chem. Soc., 79, 3554-3559 (1957) etc.) may be followed to react the compound (VIII) in acetic acid or another solvent and, if necessary, remove the protective groups and/or reduce the same so as to obtain the compound (IX). As such a starting compound (VIII), for example, 2-vinylpyridine, 3-vinylpyridine, 4-vinylpyridine, etc. may be mentioned, while, as the starting compound (X), for example, 5-bromoindole, 5-chloroindole, 5-bromo-2-methylindole, 5-chloro-2-methylindole, etc. may be mentioned.

Next, from the compound (IX) thus obtained, for example, a generally used Heck reaction or other known method (see Advanced Organic Chemistry $3^{rd}$ Edition, Part B, Francis A. Carey, Richard J. Sundberg, 418-419 (Plenum Press) etc.) may be followed to react the compound (V) in triethylamine or another basic solvent or mixed solvent of triethylamine and toluene or the like in the presence of a palladium catalyst (e.g., palladium acetate etc.), phospholigand (e.g., tris(2-methylphenyl)phosphine etc.) or the like under heating and refluxing and, if necessary, remove the protective groups (see Protective Groups in Organic Synthesis $3^{rd}$ Edition, Theodora W. Greene, Peter G. M. Wuts (John Wiley & Sons)) and/or reduce it (e.g., a usual hydrogenation reaction using palladium-carbon catalyst or Raney nickel catalyst etc. (see 4th Edition Jikken Kagaku Koza (Experimental Chemistry Course) 26, the Chemical Society of Japan edited, 251-266 (Maruzen)) to obtain the compound (II).

The starting compound (V) described above can be used a commercially available product or a known compound. As such a starting compound (V), for example, an acrylic acid ester (e.g., methyl acrylate, ethyl acrylate and benzyl acrylate, etc.) etc. may be mentioned.

Further, from the compound (IX), a known method (see J. Med. Chem., 39 (16) 3179-3187 (1996) and Tetrahedron Lett., 50, 4467-4470 (1975) etc.) may be followed to react the compound (V), for example, in diethylamine or other basic solvent in the presence of a palladium catalyst (e.g., dichlorobis(triphenylphosphine)palladium (II) etc.) and copper halide (e.g., copper (I) iodide etc.) and, if necessary, remove the protective groups (see Protective Groups in Organic Synthesis $3^{rd}$ Edition, Theodora W. Greene, Peter G. M. Wuts (John Wiley & Sons)) and/or reduce the same (e.g., a usual hydrogenation reaction using a palladium-carbon catalyst or Raney nickel catalyst etc. (see 4th Edition Jikken Kagaku Koza (Experimental Chemistry Course) 26, the Chemical Society of Japan edited, 251-266 (Maruzen)) to obtain the compound (II).

As the starting compound (V), propynic acid esters (e.g., methyl propynate, ethyl propynate, etc.) etc. may be mentioned.

Further, the starting compound (II) may be obtained by changing the order of the above reactions and proceeding from the compound (X) through the compound (XII) or its salt.

The starting compound (IV) may be, for example, synthesized by the method shown in the following flows:

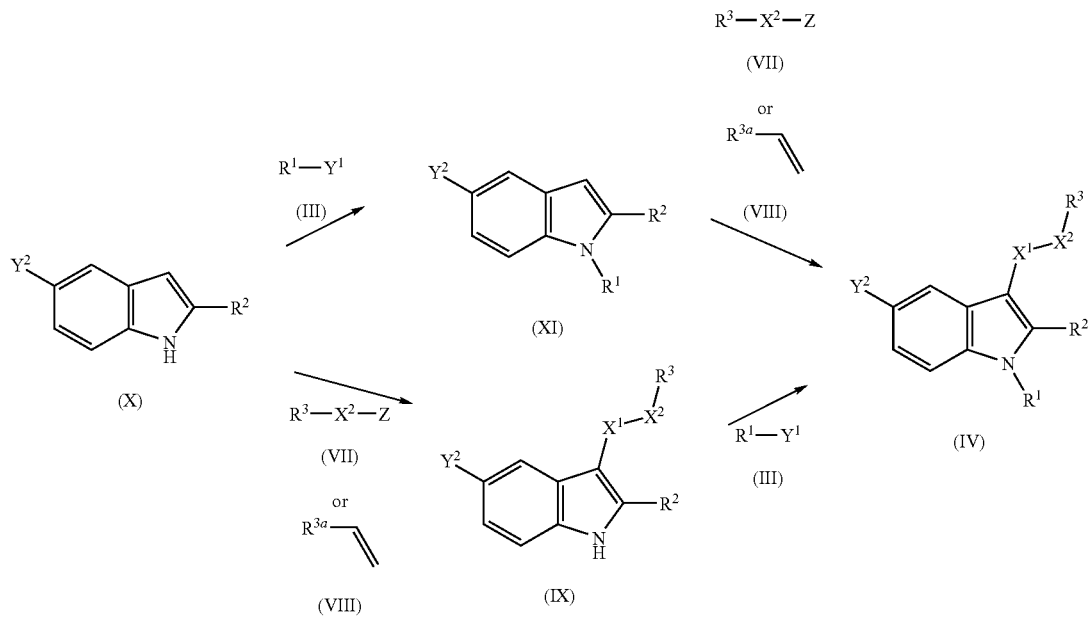

wherein $R^1$, $R^2$, $R^3$, $R^{3a}$, $X^1$ and $X^2$ are as defined above, $Y^1$ is a halogen atom or a triflate, $Y^2$ is a halogen atom, and Z is a halocarbonyl group or a (1H-1,2,3-benzotriazol-1-yl)carbonyl group.

As the group expressed by $Y^1$, a halogen atom (e.g., fluorine, chlorine, bromine, iodine, etc.) or a triflate, as the group expressed by $Y^2$, a halogen atom (e.g., fluorine, chlorine, bromine, iodine, etc.), as the group expressed by Z, chlorocarbonyl, bromocarbonyl or another halocarbonyl group, (1H-1,2,3-benzotriazol-1-yl)carbonyl group, etc. may be used.

First, the compound (X) or its salt may be reacted according to a known method (see J. Heterocycl. Chem., 24, 811 (1987) etc.) in the presence of a copper catalyst (e.g., copper (II) acetate, copper (I) bromide, etc.), alkali metal carbonate (e.g., potassium carbonate, sodium carbonate, etc.) and alkali metal hydroxide (e.g., potassium hydroxide, sodium hydroxide, etc.) or the like with a compound (III) or its salt and remove the protective groups and reduce the same, if necessary, to obtain the compound (XI). The starting compounds (X) and (III) described above may be used commercially available products or known compounds. As such a starting compound (III), for example, bromobenzene, iodobenzene, 4-bromoanisole, 4-bromodiphenyl ether, 4-iododiphenyl ether and phenyltriflate, etc. may be mentioned, while as the starting compound (X), for example, 5-bromoindole, 5-chloroindole, 5-bromo-2-methylindole, 5-chloro-2-methylindole, etc. may be mentioned.

Next, from the compound (XI) obtained above, for example, a generally used Friedel-Crafts reaction or other known method may be followed to react a compound (VII) or its salt in methylene chloride, chloroform or another solvent in the presence of a Lewis acid catalyst (e.g., aluminum chloride, titanium tetrachloride, etc.) or the like, then remove the protective groups and/or reduce it, if necessary, to thereby obtain the compound (IV). As such a starting compound (VII), for example, benzoyl chloride, benzoyl bromide, phenylacetyl chloride, phenylacetyl bromide, 2-phenylpropionyl chloride, 3-phenylpropionyl chloride, 1-phenylacetyl-1H-1, 2,3-benzotriazole, 1-(3-phenylpropionyl)-1H-1,2,3-benzotriazole, etc. may be mentioned.

Further, from the compound (XI), a known method (see J. Am. Chem. Soc., 79, 3554-3559 (1957) etc.) may be followed to react the compound (VIII) in acetic acid or another solvent and remove the protective groups and/or reduce it, if necessary, to thereby obtain the compound (IV). As such a starting compound (VIII), for example, 2-vinylpyridine, 3-vinylpyridine, 4-vinylpyridine, etc. may be mentioned.

Further, the starting compound (IV) may be obtained by changing the order of the above reactions and proceeding from the compound (X) through the above-mentioned compound (IX) or its salt.

The starting compound (VI) may, for example, be synthesized by the method shown by the following flows:

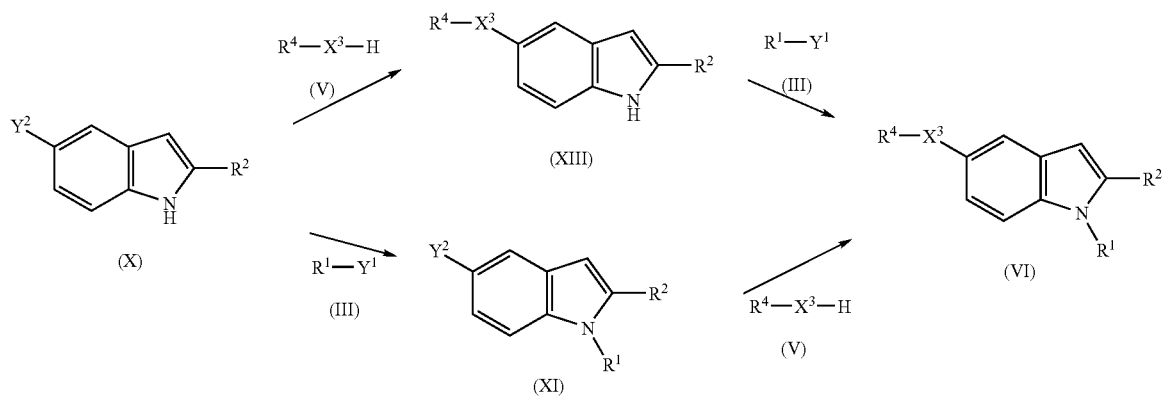

wherein $R^1$, $R^2$, $R^4$ and $X^3$ are as defined above, $Y^1$ is a halogen atom or a triflate and $Y^2$ is a halogen atom.

As the groups expressed by $Y^1$, a halogen atom (e.g., fluorine, chlorine, bromine, iodine, etc.) or a triflate, while as the groups expressed by $Y^2$, a halogen atom (e.g., fluorine, chlorine, bromine, iodine, etc.) may be used.

From the above-mentioned compound (X), for example, a generally used Heck reaction or other known methods (see Advanced Organic Chemistry 3$^{rd}$ Edition, Part B, Francis A. Carey, Richard J. Sundberg, 418-419 (Plenum Press)) may be followed to react a compound (V) in triethylamine or another basic solvent in the presence of a palladium catalyst (e.g., palladium acetate etc.), phospholigand (e.g., tris(2-methylphenyl)phosphine etc.), or the like under heating and reflux and remove the protective groups and/or reduce it, if necessary to thereby obtain the compound (XIII).

The starting compounds (V) and (X) described above may be used commercially available products or known compounds. As such a starting compound (V), for example, acrylic acid esters (e.g., methyl acrylate, ethyl acrylate and benzyl acrylate, etc.) etc. may be mentioned, while as the starting compound (X), for example, 5-bromoindole, 5-chloroindole, 5-bromo-2-methylindole, 5-chloro-2-methylindole, etc. may be mentioned.

Further, from the compound (X), a known method (see J. Med. Chem., 39, 16, 3179 (1996) and Tetrahedron Lett., 50, 4467 (1975) etc.) may be followed to, for example, react the compound (V) in diethylamine or another basic solvent in the presence of palladium catalyst (e.g., dichlorobis(triphenylphosphine)palladium (II) etc.), copper halides (e.g., copper (I) iodide etc.), or the like under heating and reflux and remove the protective groups and/or reduce it, if necessary, to thereby obtain the compound (XIII).

The starting compounds (V) and (X) described above may be used commercial products or known compounds. As such a starting compound (V), for example, a propynic acid ester (for example, methyl propynate, ethyl propynate, etc.) etc. may be mentioned, while as the starting compound (X), for example, 5-bromoindole, 5-chloroindole, 5-bromo-2-methylindole, 5-chloro-2-methylindole, etc. may be mentioned.

The compound (VI) may be obtained by reacting the compound (XIII) or its salt according to a known method (see J. Heterocycl. Chem., 24, 811 (1987) etc.) in the presence of a copper catalyst (e.g., copper (II) acetate, copper (I) bromide, etc.), alkali metal carbonate (e.g., potassium carbonate, sodium carbonate, etc.) and alkali metal hydroxide (e.g., potassium hydroxide, sodium hydroxide, etc.) or the like with the compound (III) or its salt and removing the protective groups and/or reducing it, if necessary.

As the compound (III), for example, bromobenzene, iodobenzene, 4-bromoanisole, 4-bromodiphenyl ether, 4-iododiphenyl ether and phenyltriflate, etc. may be mentioned.

Further, the starting compound (VI) may be obtained by changing the order of the reactions and proceeding from the compound (X) through the above-mentioned compound (XI) or its salt.

The present invention compounds have a $cPLA_2$ inhibiting activity and an action inhibiting the production of arachidonic acid, lysophospholipids, prostanoids, prostaglandins, leukotrienes, $PGE_2$, $PGD_2$, $TXA_2/B_2$, $LTB_4$, cysteinyl leukotriene ($LTC_4$, $LTD_4$, $LTE_4$), and PAF based on the same and can be used for the prevention or treatment of diseases in which these lipid mediators are involved in onset and exacerbation.

Specifically, they may be used as drugs for the prevention or treatment of rheumatoid arthritis, osteoarthritis, dysmenorrhea, acute pain, asthma including bronchial asthma, allergic rhinitis, chronic and acute airway inflammation, chronic obstructive pulmonary disease, acute lung injury, pulmonary fibrosis, multiple sclerosis, cerebral ischemia/reperfusion injury, dermatitis, ulticaria, eczema, prurigo, pancreatitis, psoriasis, inflammatory colitis, food allergy, allergic colitis, osteoporosis, atherosclerosis, or the like. Here, bronchial asthma or other asthma include adult asthma and juvenile asthma (atopic and nonatopic), exercise-induced asthma, aspirin asthma, coughing asthma, occupational asthma, etc.

When the present invention compounds are administered to humans for the purpose of treatment or prevention of the above diseases, they can be administered orally as dispersions, granules, tablets, capsules, pills, liquids, etc. or parenterally as injections, suppositories, transdermal absorbents, inhalants, etc. Further, together with the active amounts of the compounds, it is possible to mix pharmaceutical additives suitable for the form of the preparation such as excipients, binders, humectants, decay agents and lubricants as needed to obtain the pharmaceutical preparations. Further, in the case of injections, the injection is sterilized, together with a suitable vehicle, to obtain the final preparation.

The clinical dosage of the present invention compounds differs, depending on the condition and severity of the disease, route of administration, age and weight of the patient, or presence of any complications and, further, differs depending on the preparation as well. In the end, the dosage is left to the judgment of the physician, but in the case of oral administration to an adult, it is administered, as an active ingredient, in an amount of usually 0.1 to 1000 mg/day, preferably 0.1 to 500 mg/day, more preferably 1 to 100 mg/day, while in the case of parenteral administration, it is administered in an amount of ¹/₁₀ to ½ of the case of usual oral administration. This may be administered at one time or divided among several doses. The amounts of these dosages can be suitably adjusted in accordance with the age, condition, etc. of the patient.

Further, the present invention compound (I) or its salts or their solvates have low toxicity. In experiments administering the compound of Example 231 of the present invention to rats once a day over two weeks repeatedly orally, the nontoxic amount was 180 mg/kg/day.

EXAMPLES

Reference Examples, Examples and Experiment Examples will now be used to specifically explain the present invention, but the present invention is not limited to these Examples. The fractions including the target substances in the Examples and Reference Examples were detected by observation of TLC (thin layer chromatography). In TLC observation, as the TLC plate, a Merck 60F$_{254}$ was used, while as the detection method, a UV detector was used. For the MS, the ESI method (electrospray ionization method) or FAB method (fast atom bombardment ionization method) was used for detection of the cations.

Note that the chemical structures and identification data of the following Examples and Reference Examples are summarized in the Tables given later. The compounds of the Examples and Reference Examples correspond to the Example numbers and Reference Example numbers in the Tables.

Reference Example 1

5-bromo-1-phenyl-1H-indole

A mixture of 5-bromoindole (10 g), potassium carbonate (27 g), copper (I) bromide (0.73 g) and iodobenzene (135 g) was heated to 100° C., then was removed once from the oil bath, sodium hydroxide (1.58 g) and copper (II) acetate (50 mg) were added and the mixture was stirred at 140° C. for 9 hours. From the reaction solution, the insolubles were filtered off, the filtrate was distilled off in vacuo, and the residue obtained was purified by silica gel column chromatography (hexane:ethyl acetate=19:1 to 3:2) to afford the above-identified compound (4.6 g).

Reference Example 2

5-bromo-2-methyl-1-phenyl-1H-indole

The same reaction was performed as in Reference Example 1 except for using, instead of the 5-bromoindole, 5-bromo-2-methylindole to afford the above-identified compound (4.2 g).

Reference Example 3

5-bromo-3-phenylacetyl-1H-indole

A suspension of aluminum chloride (5.4 g) in methylene chloride (150 ml) was cooled to 0° C., phenylacetyl chloride (4.4 ml) was added, then 5-bromoindole (5.0 g) in a methylene chloride (200 ml) solution was added dropwise, then the mixture was stirred at room temperature over night. The reaction mixture was poured into ice water, and the mixture was extracted with methylene chloride and the organic layer was successively washed with 1 mol/l aqueous sodium hydroxide solution, water and brine and dried over anhydrous sodium sulfate. The solvent was distilled off in vacuo and the residue obtained was made to recrystallize from ethyl acetate to thereby afford the above-identified compound (2.9 g). Further, the above-identified compound was obtained by the following method.

To 5-bromoindole (160 g), 1-phenylacetyl-1H-1,2,3-benzotriazole (193.62 g) and methylene chloride (2120 ml) were added, the mixture was stirred under ice cooling while adding a solution of titanium(IV) chloride (179 ml) in a methylene chloride solution (450 ml) and the mixture was stirred at room temperature for 1.5 hours. To the reaction solution, methanol (220 ml) and water (1126 ml) were added, the mixture was stirred at room temperature for 21 hours and in an ice water bath for 3 hours, then the precipitated crystals were obtained by filtration to afford the above-identified compound (163.0 g).

Reference Example 4

5-bromo-3-(2-phenylethyl)-1H-indole

A suspension of the compound obtained at Reference Example 3 (20.5 g) in methanol (200 ml) was stirred under ice cooling, while adding sodium borohydride (25 g), and the mixture was stirred at room temperature for 15 hours. To the reaction solution, 1 mol/l hydrochloric acid (300 ml) was added, the mixture was extracted with methylene chloride and the organic layer was successively washed with water and brine and dried over anhydrous sodium sulfate.

The solvent was distilled off in vacuo, the oily substance obtained was dissolved in methylene chloride (1000 ml), the mixture was cooled to −78° C., a solution of 1 mol/l tin(II) chloride/methylene chloride (70 ml) was added, then triethylsilane (11.2 ml) was added and the mixture was stirred as is for 45 minutes. The reaction solution was slowly poured into water (1000 ml), then the organic layer was separated and successively washed with 5% aqueous sodium hydrogen carbonate solution, water and brine and dried over anhydrous sodium sulfate. The solvent was distilled off in vacuo and the residue obtained was purified by silica gel column chromatography (hexane:ethyl acetate=9:1 to 3:7) to afford the above-identified compound (16.1 g).

Further, the above-identified compound was also obtained by the following method.

Lithium aluminum hydride (22 mg) was suspended in diethyl ether (3.0 ml), the compound obtained at Reference Example 3 (60 mg) was added, and the mixture was stirred at room temperature for 1 hour. To the reaction solution, water (2.0 ml) and methanol (1.0 ml) were added, the mixture was extracted with diethyl ether and ethyl acetate, and the organic layer was successively washed with water and brine and dried over anhydrous sodium sulfate. The solvent was distilled off in vacuo, and the residue obtained was purified by silica gel column chromatography (hexane:ethyl acetate=19:1 to 13:7) to afford the above-identified compound (43 mg).

Furthermore, the above-identified compound was also obtained by the following method.

Lithium aluminum hydride (52.2 g) was suspended in cyclopentyl methyl ether (1450 ml), the compound obtained at Reference Example 3 (145.0 g) was added and the mixture was stirred at room temperature for 20 minutes. To the reaction solution, water (52.2 ml), 10% aqueous sodium hydroxide solution (52.2 ml) and water (156.6 ml) were successively added, the mixture was dried over anhydrous magnesium sulfate (52.2 g), then filtered. The solvent was distilled off from the filtrate in vacuo to afford the above-identified compound (142.3 g).

Reference Example 5

5-bromo-3-(2-pyridin-2-ylethyl)-1H-indole

To 5-bromoindole (5.9 g) in acetic acid (10 ml) solution, 2-vinylpyridine (3.6 ml) was added and the mixture was heated and refluxed for 15 hours. The reaction solution was cooled, then was diluted with ethyl acetate, the aqueous layer was made alkaline with 4N-aqueous sodium hydroxide solution and the mixture was extracted with ethyl acetate. The organic layer was dried with anhydrous sodium sulfate, the solvent was distilled off in vacuo, and the residue obtained was purified by silica gel column chromatography (hexane:ethyl acetate=1:1 to 17:33) to afford the above-identified compound (5.6 g).

Reference Example 6

1-bromo-4-[(difluoromethoxy)methyl]benzene

To a solution of 4-bromobenzyl alcohol (5.6 g) in acetonitrile (15 ml), sodium sulfate (0.28 g) was added. While warmed to 45° C., 2,2-difluoro-2-(fluorosulfonyl)acetic acid (1.78 g) was slowly dropwise added, and the mixture was heated and refluxed at 45° C. for 4 hours. The reaction solution was poured into water, the mixture was extracted with diethyl ether and the organic layer was washed with water and dried over anhydrous sodium sulfate. The solvent was distilled off in vacuo and the residue obtained was purified with silica gel column chromatography (hexane:ethyl acetate=19:1 to 17:3) to afford the above-identified compound (0.88 g).

Reference Example 7

5-bromo-3-(3-phenylpropanoyl)-1H-indole

To a solution of 5-bromoindole (1.0 g) in methylene chloride (10 ml), 1-(3-phenylpropanoyl)-1H-1,2,3-benzotriazole (1.28 g) was added. While stirring under ice cooling, a solution of titanium(IV) chloride (1.11 ml) in methylene chloride (5.0 ml) was added and the mixture was stirred at room temperature for 5 days. To the reaction solution, ice water (50 ml) was added, the mixture was stirred for a while, then the organic layer was separated and successively washed with water and brine and dried over anhydrous sodium sulfate. The solvent was distilled off in vacuo and the residue obtained was purified by silica gel column chromatography (methylene chloride:methanol=19:1 to 4:1) to afford the above-identified compound (1.22 g).

Reference Example 8

5-bromo-3-(3-phenylpropyl)-1H-indole

The compound obtained at Reference Example 7 (0.10 g) was suspended in diethyl ether (5.0 ml), lithium aluminum hydride (35 mg) was added and the mixture was stirred at room temperature for 20 minutes. To the reaction solution, methanol (2.0 ml) and water (5.0 ml) were added, the mixture was extracted with diethyl ether and ethyl acetate, and the organic layer was successively washed with water and brine and dried over anhydrous sodium sulfate. The solvent was distilled off in vacuo and the residue obtained was purified by silica gel column chromatography (hexane:ethyl acetate=9:1 to 1:1) to afford the above-identified compound (95 mg).

Example 1

3-benzoyl-5-bromo-1-phenyl-1H-indole

To a suspension of aluminum chloride (1.95 g) in methylene chloride (30 ml) was added benzoyl chloride (0.84 ml), and the mixture was stirred at room temperature for 1 hour, a solution of the compound obtained at Reference Example 1 (0.66 g) in methylene chloride (10 ml) was dropwise added, then the mixture was stirred at room temperature for 3 hours. The reaction mixture was poured into ice water, the mixture was extracted with methylene chloride and the organic layer was successively washed with saturated aqueous sodium hydrogen carbonate solution and brine and dried over anhydrous sodium sulfate. The solvent was distilled off in vacuo and the residue obtained was purified by silica gel column chromatography (hexane:ethyl acetate=9:1 to 1:1) to afford the above-identified compound (0.39 g).

Example 2

Methyl (2E)-3-(3-benzoyl-1-phenyl-1H-indol-5-yl)-2-propenoate

To a solution of the compound obtained at Example 1 (44 mg) in triethylamine (1.0 ml), methyl acrylate (0.031 ml), palladium acetate (1.5 mg) and tris(2-methylphenyl)phosphine (4.0 mg) were added and the mixture was heated and stirred in a sealed tube at 120° C. for 6 hours. The insolubles were filtered off, the filtrate was distilled off in vacuo, and the residue obtained was purified by silica gel column chromatography (hexane:ethyl acetate=17:3 to 1:1) to afford the above-identified compound (36 mg).

Example 3

(2E)-3-(3-benzoyl-1-phenyl-1H-indol-5-yl)-2-propenoic acid

To a solution of the compound obtained at Example 2 (35 mg) in tetrahydrofuran (2.0 ml)-methanol (0.15 ml) mixed solvent was added 1 mol/l aqueous sodium hydroxide solution (0.20 ml), and the mixture was stirred at room temperature for 27 hours. To the reaction mixture, 1 mol/l hydrochloric acid (0.20 ml) was added, the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=99:1 to 87:13) to afford the above-identified compound (35 mg).

Example 4

3-(3-benzoyl-1-phenyl-1H-indol-5-yl)propanoic acid

To a solution of the compound obtained at Example 3 (16 mg) in methanol (2.0 ml) was added 10% palladium carbon (7.0 mg), and the mixture was stirred under a hydrogen atmosphere at room temperature for 3 hours. The insolubles were filtered off, the filtrate was distilled off in vacuo, and the residue obtained was purified by silica gel column chromatography (methylene chloride:methanol=99:1 to 17:3) to afford the above-identified compound (8.5 mg).

Example 5

3-benzyl-5-bromo-1-phenyl-1H-indole

A solution of the compound obtained at Example 1 (50 mg) in methanol (0.5 ml) was stirred under ice cooling, while adding sodium borohydride (45 mg) and the mixture was stirred at room temperature for 6 hours. To the reaction mixture, 1 mol/l hydrochloric acid (1.0 ml) was added, the mixture was extracted with methylene chloride and the organic layer was successively washed with water and brine and dried over anhydrous sodium sulfate.

The oil substance obtained by distilling off the solvent in vacuo was dissolved in methylene chloride (1.0 ml), the mixture was cooled to −78° C., tin (II) chloride (0.017 ml) then triethyl silane (0.015 ml) were added, and the mixture was stirred for 1 hour. The reaction mixture was slowly poured into water, then the mixture was extracted with methylene chloride and the organic layer was successively washed with water, 5% aqueous sodium hydrogen carbonate solution and brine and dried over anhydrous sodium sulfate. The solvent was distilled off in vacuo and the residue obtained was purified by silica gel column chromatography (hexane:ethyl acetate=9:1 to 3:2) to obtain the above-identified compound (29 mg).

Example 6

Methyl (2E)-3-(3-benzyl-1-phenyl-1H-indol-5-yl)-2-propenoate

The same reaction was performed as in Example 2 except for using, instead of the compound obtained at Example 1, the compound obtained at Example 5 to afford the above-identified compound (24 mg).

Example 7

(2E)-3-(3-benzyl-1-phenyl-1H-indol-5-yl)-2-propenoic acid

The same reaction was performed as in Example 3 except for using, instead of the compound obtained at Example 2, the compound obtained at Example 6 to afford the above-identified compound (23 mg).

Example 8

3-(3-benzyl-1-phenyl-1H-indol-5-yl)propanoic acid

The same reaction was performed as in Example 4 except for using, instead of the compound obtained at Example 3, the compound obtained at Example 7 to afford the above-identified compound (6.3 mg).

Example 9

5-bromo-1-phenyl-3-phenylacetyl-1H-indole

The same reaction was performed as in Example 1 except for using, instead of benzoyl chloride, phenylacetyl chloride to afford the above-identified compound (90 mg).

Example 10

Methyl (2E)-3-[1-phenyl-3-(phenylacetyl)-1H-indol-5-yl]-2-propenoate

The same reaction was performed as in Example 2 except for using, instead of the compound obtained at Example 1, the compound obtained at Example 9 to afford the above-identified compound (27 mg).

Example 11

(2E)-3-[1-phenyl-3-(phenylacetyl)-1H-indol-5-yl]-2-propenoic acid

The same reaction was performed as in Example 3 except for using, instead of the compound obtained at Example 2, the compound obtained at Example 10 to afford the above-identified compound (12 mg).

Example 12

3-[1-phenyl-3-(phenylacetyl)-1H-indol-5-yl]propanoic acid

The same reaction was performed as in Example 4 except for using, instead of the compound obtained at Example 3, the compound obtained at Example 11 to afford the above-identified compound (1.9 mg).

Example 13

5-bromo-1-phenyl-3-(2-phenylethyl)-1H-indole

The same reaction was performed as in Example 5 except for using, instead of the compound obtained at Example 1, the compound obtained at Example 9 to afford the above-identified compound (39 mg).

Example 14

Methyl (2E)-3-[1-phenyl-3-(2-phenylethyl)-1H-indol-5-yl]-2-propenoate

The same reaction was performed as in Example 2 except for using, instead of the compound obtained at Example 1, the compound obtained at Example 13 to afford the above-identified compound (24 mg).

Example 15

(2E)-3-[1-phenyl-3-(2-phenylethyl)-1H-indol-5-yl]-2-propenoic acid

The same reaction was performed as in Example 3 except for using, instead of the compound obtained at Example 2, the compound obtained at Example 14 to afford the above-identified compound (21 mg).

Example 16

3-[1-phenyl-3-(2-phenylethyl)-1H-indol-5-yl]propanoic acid

The same reaction was performed as in Example 4 except for using, instead of the compound obtained at Example 3, the compound obtained at Example 15 to afford the above-identified compound (7.5 mg).

Example 17

3-[1-phenyl-3-(2-phenylethyl)-1H-indol-5-yl]propanoic acid 2-amino-2-(hydroxymethyl)propane-1,3-diol salt (1:1)

To a solution of the compound obtained at Example 16 (76 mg) in tetrahydrofuran (2.0 ml) was added 1.7 mol/l aqueous tris(hydroxymethyl)aminomethane solution (0.12 ml), the mixture was stirred for a while, then the solvent was distilled off to afford the above-identified compound (100 mg).

Example 18

N-cyano-3-[1-phenyl-3-(2-phenylethyl)-1H-indol-5-yl]propanamide

To a solution of the compound obtained at Example 16 (81 mg) in N,N-dimethylformamide (3.0 ml) were added cyanamide (14 mg), triethylamine (0.22 ml) and 25% n-propyl phosphonic acid anhydride/ethyl acetate solution (0.46 ml) and the mixture was heated and stirred at 60° C. for 24 hours. The reaction mixture was poured into water, the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=99:1 to 17:3) to afford the above-identified compound (19 mg).

Example 19

3-[1-phenyl-3-(2-phenylethyl)-1H-indol-5-yl]-N-tetrazolylpropanamide

The same reaction was performed as in Example 18 except for using, instead of the cyanamide, 5-amino-1H-tetrazole monohydrate to afford the above-identified compound (39 mg).

Example 20

N-benzyloxy-3-[1-phenyl-3-(2-phenylethyl)-1H-indol-5-yl]propanamide

The same reaction was performed as in Example 18 except for using, instead of the cyanamide, O-benzylhydroxylamine hydrochloride to afford the above-identified compound (162 mg).

Example 21

N-hydroxy-3-[1-phenyl-3-(2-phenylethyl)-1H-indol-5-yl]propanamide

The same reaction was performed as in Example 4 except for using, instead of the compound obtained at Example 3, the compound obtained at Example 20 to afford the above-identified compound (65 mg).

Example 22

3-[1-phenyl-3-(2-phenylethyl)-1H-indol-5-yl]propanamide

The compound obtained at Example 16 (322 mg) was dissolved in tetrahydrofuran (6.0 ml), the mixture was cooled to 0° C., carbonyl diimide (212 mg) was added, and the mixture was stirred at room temperature for 4 hours. Thereafter, 28% ammonia water (0.17 ml) was added and the mixture was stirred at room temperature at 1 hour. To the reaction mixture, 1 mol/l hydrochloric acid was added, the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=99:1 to 9:1) to afford the above-identified compound (290 mg).

Example 23

5-(2-cyanoethyl)-1-phenyl-3-(2-phenylethyl)-1H-indole

The compound obtained at Example 22 (290 mg) was dissolved in benzene (20 ml), thionyl chloride (0.18 ml) was added and the mixture was heated and refluxed for 20 hours. The solvent was distilled off in vacuo, and the residue obtained was purified by silica gel column chromatography (hexane:ethyl acetate=9:1 to 1:1) to afford the above-identified compound (100 mg).

Example 24

1-phenyl-3-(2-phenylethyl)-5-[2-(1H-tetrazol-5-yl)ethyl]-1H-indole

The compound obtained at Example 23 (80 mg), sodium azide (32 mg) and zinc(II) bromide (102 mg) were dissolved in N,N-dimethylformamide (2.0 ml)-water (1.0 ml) and the mixture was heated and refluxed at 120° C. for 3 days. To the reaction mixture was added 1 mol/l hydrochloric acid, and the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=99:1 to 22:3) to afford the above-identified compound (26 mg).

Example 25

Methyl (2E)-3-(1-phenyl-1H-indol-5-yl)-2-propenoate

The compound obtained at Reference Example 1 (1.1 g), palladium acetate (83 mg), tris(2-methylphenyl)phosphine (225 mg), triethylamine (33 ml) and methyl acrylate (1.08 ml) were mixed and heated to stir in a sealed tube at 120° C. for 5 hours. The insolubles were filtered off, the filtrate was distilled off in vacuo and the residue obtained was purified by silica gel column chromatography (hexane:ethyl acetate=9:1 to 1:1) to afford the above-identified compound (1.05 g).

Example 26

(2E)-3-[1-phenyl-3-(2-phenylpropanoyl)-1H-indol-5-yl]-2-propenoic acid

Step 1

2-phenylpropionic acid (75 mg) was dissolved in thionyl chloride (3.0 ml) and the mixture was heated and refluxed at 80° C. for 2.5 hours. After the reaction, the solvent was distilled off in vacuo, the residue obtained was dissolved in methylene chloride (5.0 ml), aluminum chloride (82 mg) was added under ice cooling, then a solution of the compound obtained Example 25 (100 mg) in methylene chloride (5.0 ml) was dropwise added, then the mixture was stirred at room temperature over night. The reaction solution was poured into ice water, the mixture was extracted with methylene chloride and the organic layer was washed with water and potassium carbonate and dried over anhydrous sodium sulfate. The solvent was distilled off in vacuo and the residue obtained was purified by silica gel column chromatography (hexane:ethyl acetate=9:1 to 1:1) to afford methyl (2E)-3-[1-phenyl-3-(2-phenylpropanoyl)-1H-indol-5-yl]-2-propenoate (59 mg).

Step 2

The same reaction was performed as in Example 3 except for using, instead of the compound obtained at Example 2, the compound obtained above to afford the above-identified compound (20 mg).

Example 27

3-[1-phenyl-3-(2-phenylpropanoyl)-1H-indol-5-yl]propanoic acid 2-amino-2-(hydroxymethyl)propane-1,3-diol salt (1:1)

Step 1

The same reaction was performed as in Example 4 except for using, instead of the compound obtained at Example 3, the compound obtained at Example 26 to afford 3-[1-phenyl-3-(2-phenylpropanoyl)-1H-indol-5-yl]propanoic acid (5.4 mg).

Step 2

The same operation was performed as in Example 17 except for using, instead of the compound obtained at Example 16, the compound obtained above to afford the above-identified compound (7.0 mg).

Example 28

3-[1-phenyl-3-(2-phenylpropyl)-1H-indol-5-yl]propanoic acid 2-amino-2-(hydroxymethyl)propane-1,3-diol salt (1:1)

Step 1

The compound obtained at Step 1 of Example 26 (90 mg), 85% potassium hydroxide (0.17 g), hydrazine monohydrate (0.26 ml) and ethylene glycol (2.0 ml) were mixed and the mixture was heated and stirred at 120° C. for 2 hours and at 210° C. for 5 hours. The reaction mixture was cooled, then 1 mol/l hydrochloric acid was added, the mixture was extracted with methylene chloride and the organic layer was washed with brine and dried over anhydrous sodium sulfate. The solvent was distilled off in vacuo and the residue obtained was purified by silica gel column chromatography (methylene chloride:methanol=99:1 to 22:3) to afford 3-[1-phenyl-3-(2-phenylpropyl)-1H-indol-5-yl]propanoic acid (35 mg).

Step 2

The same operation was performed as in Example 17 except for using, instead of the compound obtained at Example 16, the compound obtained above to afford the above-identified compound (46 mg).

Example 29

3-[1-phenyl-3-(2-phenylpropyl)-1H-indol-5-yl]propanamide

The same operation was performed as in Example 22 except for using, instead of the compound obtained at Example 16, the compound obtained at Step 1 of Example 28 to afford the above-identified compound (46 mg).

Example 30

5-bromo-1-phenyl-3-(2-phenylpropanoyl)-1H-indole

The same reaction was performed as in Example 1 except for using, instead of benzoyl chloride, 2-phenylpropionyl chloride to afford the above-identified compound (175 mg).

Example 31

5-bromo-1-phenyl-3-(2-phenylpropyl)-1H-indole

The same reaction was performed as in Example 5 except for using, instead of the compound obtained at Example 1, the compound obtained at Example 30 to afford the above-identified compound (82 mg).

Example 32

Methyl (2E)-3-[1-phenyl-3-(2-phenylpropyl)-1H-indol-5-yl]-2-propenoate

The same reaction was performed as in Example 2 except for using, instead of the compound obtained at Example 1, the compound obtained at Example 31 to afford the above-identified compound (57 mg).

Example 33

(2E)-3-[1-phenyl-3-(2-phenylpropyl)-1H-indol-5-yl]-2-propenoic acid

The same reaction was performed as in Example 3 except for using, instead of the compound obtained at Example 2, the compound obtained at Example 32 to afford the above-identified compound (57 mg).

Example 34

Methyl (2E)-3-[1-phenyl-3-(2-phenylbutanoyl)-1H-indol-5-yl]-2-propenoate

The same reaction was performed as in Example 1 except for using, instead of benzoyl chloride, 2-phenylbutyryl chloride, and using instead of the compound obtained at Reference Example 1, the compound obtained at Example 25 to afford the above-identified compound (173 mg).

Example 35

(2E)-3-[1-phenyl-3-(2-phenylbutanoyl)-1H-indol-5-yl]-2-propenoic acid

The same reaction was performed as in Example 3 except for using, instead of the compound obtained at Example 2, the compound obtained at Example 34 to afford the above-identified compound (77 mg).

Example 36

3-[1-phenyl-3-(2-phenylbutanoyl)-1H-indol-5-yl]propanoic acid 2-amino-2-(hydroxymethyl)propane-1,3-diol salt (1:1)

The same reaction and operation were performed as in Example 27 except for using, instead of the compound obtained at Example 26, the compound obtained at Example 35 to afford the above-identified compound (47 mg).

Example 37

3-[1-phenyl-3-(2-phenylbutyl)-1H-indol-5-yl]propanoic acid 2-amino-2-(hydroxymethyl)propane-1,3-diol salt (1:1)

The same reaction and operation were performed as in Example 28 except for using, instead of the compound obtained at Step 1 of Example 26, the compound obtained at Example 34 to afford the above-identified compound (47 mg).

Example 38

Methyl (2E)-3-{1-phenyl-3-[(1-phenylcyclopropyl)carbonyl]-1H-indol-5-yl}-2-propenoate The same reaction was performed as in step 1 of Example 26 except for using, instead of 2-phenylpropionic acid, 1-phenyl-1-cyclopropanecarboxylic acid to afford the above-identified compound (145 mg).

Example 39

(2E)-3-{1-phenyl-3-[(1-phenylcyclopropyl)carbonyl]-1H-indol-5-yl}-2-propenoic acid The same reaction was performed as in Example 3 except for using, instead of the compound obtained at Example 2, the compound obtained at Example 38 to afford the above-identified compound (66 mg).

Example 40

3-{1-phenyl-3-[(1-phenylcyclopropyl)carbonyl]-1H-indol-5-yl}propanoic acid

The same reaction was performed as in Example 4 except for using, instead of the compound obtained at Example 3, the compound obtained at Example 39 to afford the above-identified compound (12 mg).

Example 41

3-{1-phenyl-3-[(1-phenylcyclopropyl)methyl]-1H-indol-5-yl}propanoic acid 2-amino-2-(hydroxymethyl)propane-1,3-diol salt (1:1)

The same reaction and operation were performed as in Example 28 except for using, instead of the compound obtained at Step 1 of Example 26, the compound obtained at Example 38 to afford the above-identified compound (17 mg).

Example 42

5-bromo-2-methyl-1-phenyl-3-phenylacetyl-1H-indole

The same reaction was performed as in Example 1 except for using, instead of benzoyl chloride, phenylacetyl chloride, and using, instead of the compound obtained at Reference Example 1, the compound obtained at Reference Example 2 to afford the above-identified compound (67 mg).

Example 43

Methyl (2E)-3-[2-methyl-1-phenyl-3-(phenylacetyl)-1H-indol-5-yl]-2-propenoate

The same reaction was performed as in Example 2 except for using, instead of the compound obtained at Example 1, the compound obtained at Example 42 to afford the above-identified compound (57 mg).

Example 44

(2E)-3-[2-methyl-1-phenyl-3-(phenylacetyl)-1H-indol-5-yl]-2-propenoic acid

The same reaction was performed as in Example 3 except for using, instead of the compound obtained at Example 2, the compound obtained at Example 43 to afford the above-identified compound (55 mg).

Example 45

3-[2-methyl-1-phenyl-3-(phenylacetyl)-1H-indol-5-yl]propanoic acid

The same reaction was performed as in Example 4 except for using, instead of the compound obtained at Example 3, the compound obtained at Example 44 to afford the above-identified compound (36 mg).

Example 46

5-bromo-2-methyl-1-phenyl-3-(2-phenylethyl)-1H-indole

The same reaction was performed as in Example 5 except for using, instead of the compound obtained at Example 1, the compound obtained at Example 42 to afford the above-identified compound (0.62 g).

Example 47

Methyl (2E)-3-[2-methyl-1-phenyl-3-(2-phenylethyl)-1H-indol-5-yl]-2-propenoate

The same reaction was performed as in Example 2 except for using, instead of the compound obtained at Example 1, the compound obtained at Example 46 to afford the above-identified compound (87 mg).

Example 48

3-[2-methyl-1-phenyl-3-(2-phenylethyl)-1H-indol-5-yl]propanoic acid

Step 1
The same reaction was performed as in Example 3 except for using, instead of the compound obtained at Example 2, the compound obtained at Example 47 to afford (2E)-3-[2-methyl-1-phenyl-3-(2-phenylethyl)-1H-indol-5-yl]-2-propenoic acid (68 mg).

Step 2
The same reaction was performed as in Example 4 except for using, instead of the compound obtained at Example 3, the compound obtained above to afford the above-identified compound (29 mg).

Example 49

Methyl (2E)-3-[3-(1-naphthoyl)-1-phenyl-1H-indol-5-yl]-2-propenoate

The same reaction was performed as in Example 34 except for using, instead of 2-phenylbutyryl chloride, 1-naphthoyl chloride to afford the above-identified compound (118 mg).

Example 50

(2E)-3-[3-(1-naphthoyl)-1-phenyl-1H-indol-5-yl]-2-propenoic acid

The same reaction was performed as in Example 3 except for using, instead of the compound obtained at Example 2, the compound obtained at Example 49 to afford the above-identified compound (106 mg).

Example 51

3-[3-(1-naphthylmethyl)-1-phenyl-1H-indol-5-yl]propanoic acid

The same reaction was performed as in Step 1 of Example 28 except for using, instead of the compound obtained at Step 1 of Example 26, the compound obtained at Example 50 to afford the above-identified compound (5.0 mg).

Example 52

Methyl (2E)-3-[3-(2-naphthoyl)-1-phenyl-1H-indol-5-yl]-2-propenoate

The same reaction was performed as in Example 34 except for using, instead of 2-phenylbutyryl chloride, 2-naphthoyl chloride to afford the above-identified compound (90 mg).

Example 53

(2E)-3-[3-(2-naphthoyl)-1-phenyl-1H-indol-5-yl]-2-propenoic acid

The same reaction was performed as in Example 3 except for using, instead of the compound obtained at Example 2, the compound obtained at Example 52 to afford the above-identified compound (79 mg).

Example 54

3-[3-(2-naphthylmethyl)-1-phenyl-1H-indol-5-yl]propanoic acid

The same reaction was performed as in Step 1 of Example 28 except for using, instead of the compound obtained at Step 1 of Example 26, the compound obtained at Example 53 to afford the above-identified compound (29 mg).

Example 55

Methyl (2E)-3-{3-[(4-chlorophenyl)acetyl]-1-phenyl-1H-indol-5-yl}-2-propenoate

The same reaction was performed as in Example 34 except for using, instead of 2-phenylbutyryl chloride, 4-chlorophenylacetyl chloride to afford the above-identified compound (93 mg).

Example 56

(2E)-3-{3-[(4-chlorophenyl)acetyl]-1-phenyl-1H-indol-5-yl}-2-propenoic acid

The same reaction was performed as in Example 3 except for using, instead of the compound obtained at Example 2, the compound obtained at Example 55 to afford the above-identified compound (19 mg).

Example 57

3-{3-[(4-chlorophenyl)acetyl]-1-phenyl-1H-indol-5-yl}propanoic acid

The same reaction was performed as in Example 4 except for using, instead of the compound obtained at Example 3, the compound obtained at Example 56 to afford the above-identified compound (13 mg).

Example 58

3-{3-[2-(4-chlorophenyl)ethyl]-1-phenyl-1H-indol-5-yl}propanoic acid 2-amino-2-(hydroxymethyl)propane-1,3-diol salt (1:1)

The same reaction was performed as in Example 28 except for using, instead of the compound obtained at Step 1 of Example 26, the compound obtained at Example 55 to afford the above-identified compound (35 mg).

Example 59

Methyl (2E)-3-{3-[(4-fluorophenyl)acetyl]-1-phenyl-1H-indol-5-yl}-2-propenoate

The same reaction was performed as in Example 34 except for using, instead of 2-phenylbutyryl chloride, 4-fluorophenylacetyl chloride to afford the above-identified compound (143 mg).

Example 60

(2E)-3-{3-[(4-fluorophenyl)acetyl]-1-phenyl-1H-indol-5-yl}-2-propenoic acid

The same reaction was performed as in Example 3 except for using, instead of the compound obtained at Example 2, the compound obtained at Example 59 to afford the above-identified compound (13 mg).

Example 61

3-{3-[(4-fluorophenyl)acetyl]-1-phenyl-1H-indol-5-yl}propanoic acid

The same reaction was performed as in Example 4 except for using, instead of the compound obtained at Example 3, the compound obtained at Example 60 to afford the above-identified compound (12 mg).

Example 62

3-{3-[2-(4-fluorophenyl)ethyl]-1-phenyl-1H-indol-5-yl}propanoic acid 2-amino-2-(hydroxymethyl)propane-1,3-diol salt (1:1)

The same reaction was performed as in Example 28 except for using, instead of the compound obtained at Step 1 of Example 26, the compound obtained at Example 60 to afford the above-identified compound (16 mg).

Example 63

Methyl (2E)-3-{3-[(4-methoxyphenyl)acetyl]-1-phenyl-1H-indol-5-yl}-2-propenoate

The same reaction was performed as in Example 34 except for using, instead of 2-phenylbutyryl chloride, 4-methoxyphenylacetyl chloride to afford the above-identified compound (109 mg).

Example 64

(2E)-3-{3-[(4-methoxyphenyl)acetyl]-1-phenyl-1H-indol-5-yl}-2-propenoic acid

The same reaction was performed as in Example 3 except for using, instead of the compound obtained at Example 2, the compound obtained at Example 63 to afford the above-identified compound (70 mg).

Example 65

3-{3-[(4-methoxyphenyl)acetyl]-1-phenyl-1H-indol-5-yl}propanoic acid

The same reaction was performed as in Example 4 except for using, instead of the compound obtained at Example 3, the compound obtained at Example 64 to afford the above-identified compound (5.0 mg).

Example 66

3-{3-[2-(4-methoxyphenyl)ethyl]-1-phenyl-1H-indol-5-yl}propanoic acid 2-amino-2-(hydroxymethyl)propane-1,3-diol salt (1:1)

The same reaction was performed as in Example 28 except for using, instead of the compound obtained at Step 1 of Example 26, the compound obtained at Example 64 to afford the above-identified compound (13 mg).

Example 67

Methyl (2E)-3-{3-[(3-methoxyphenyl)acetyl]-1-phenyl-1H-indol-5-yl}-2-propenoate

The same reaction was performed as in Example 34 except for using, instead of 2-phenylbutyryl chloride, 3-methoxyphenylacetyl chloride to afford the above-identified compound (82 mg).

Example 68

3-{3-[2-(3-methoxyphenyl)ethyl]-1-phenyl-1H-indol-5-yl}propanoic acid 2-amino-2-(hydroxymethyl)propane-1,3-diol salt (1:1)

The same reaction was performed as in Example 28 except for using, instead of the compound obtained at Step 1 of Example 26, the compound obtained at Example 67 to afford the above-identified compound (30 mg).

Example 69

Methyl (2E)-3-{3-[(3,4-dimethoxyphenyl)acetyl]-1-phenyl-1H-indol-5-yl}-2-propenoate The same reaction was performed as in Example 34 except for using, instead of 2-phenylbutyryl chloride, (3,4-dimethoxyphenyl)acetyl chloride to afford the above-identified compound (100 mg).

Example 70

3-{3-[2-(3,4-dimethoxyphenyl)ethyl]-1-phenyl-1H-indol-5-yl}propanoic acid 2-amino-2-(hydroxymethyl)propane-1,3-diol salt (1:1)

The same reaction was performed as in Example 28 except for using, instead of the compound obtained at Step 1 of Example 26, the compound obtained at Example 69 to afford the above-identified compound (16 mg).

Example 71

Methyl (2E)-3-[3-(2-phenylethyl)-1H-indol-5-yl]-2-propenoate

The same reaction was performed as in Example 2 except for using, instead of the compound obtained at Example 1, the compound obtained at the Reference Example 4 to afford the above-identified compound (1.7 g).

Example 72

Methyl 3-[3-(2-phenylethyl)-1H-indol-5-yl]propanoate

The same reaction was performed as in Example 4 except for using, instead of the compound obtained at Example 3, the compound obtained at Example 71 to afford the above-identified compound (1.0 g).

Example 73

Methyl (2E)-3-[1-(4-methoxyphenyl)-3-(2-phenylethyl)-1H-indol-5-yl]-2-propenoate To a solution of the compound obtained at Example 71 (50 mg) in dimethoxyethane (1.0 ml) were added 4-bromoanisole (0.022 ml), palladium acetate (3.6 mg), 2-(di-tert-butylphosphino)biphenyl (9.7 mg) and tripotassium phosphate (48 mg), and the mixture heated and stirred in a pressure resistant sealed vessel at 80° C. for 15 hours. The reaction solution was cooled, then the insolubles were filtered off, the filtrate was distilled off in vacuo, and the residue obtained was purified by silica gel column chromatography (hexane:ethyl acetate=9:1 to 1:1) to afford the above-identified compound (26 mg).

Example 74

(2E)-3-[1-(4-methoxyphenyl)-3-(2-phenylethyl)-1H-indol-5-yl]-2-propenoic acid

The same reaction was performed as in Example 3 except for using, instead of the compound obtained at Example 2, the compound obtained at Example 73 to afford the above-identified compound (21 mg).

Example 75

Methyl 3-[1-(4-methoxyphenyl)-3-(2-phenylethyl)-1H-indol-5-yl]propanoate

To a solution of the compound obtained at Example 72 (57 mg) in dimethoxyethane (1.2 ml) were added 4-bromoanisole (0.048 ml), palladium acetate (10 mg), 2-(di-tert-butylphosphino)biphenyl (24 mg) and tripotassium phosphate (113 mg), and the mixture was heated and stirred in a pressure resistant sealed vessel at 100° C. over night and at 120° C. for 15 hours. The reaction mixture was cooled, then the insolubles were filtered off, the filtrate was distilled off in vacuo and the residue obtained was purified by silica gel column chromatography (hexane:ethyl acetate=9:1 to 1:1) to afford the above-identified compound (55 mg).

Example 76

3-[1-(4-methoxyphenyl)-3-(2-phenylethyl)-1H-indol-5-yl]propanoic acid

The same reaction was performed as in Example 3 except for using, instead of the compound obtained at Example 2, the compound obtained at Example 75 to afford the above-identified compound (63 mg).

Example 77

3-[1-(4-methoxyphenyl)-3-(2-phenylethyl)-1H-indol-5-yl]propanoic acid 2-amino-2-(hydroxymethyl)propane-1,3-diol salt (1:1)

The same operation was performed as in Example 17 except for using, instead of the compound obtained at Example 16, the compound obtained at Example 76 to afford the above-identified compound (83 mg).

Example 78

Ethyl 4-{5-[2-(methoxycarbonyl)ethyl]-3-(2-phenylethyl)-1H-indol-1-yl}benzoate

The same reaction was performed as in Example 75 except for using, instead of the 4-bromoanisole, ethyl p-bromobenzoate to afford the above-identified compound (52 mg).

Example 79

4-[5-(2-carboxyethyl)-3-(2-phenylethyl)-1H-indol-1-yl]benzoic acid

The same reaction was performed as in Example 3 except for using, instead of the compound obtained at Example 2, the compound obtained at Example 78 to afford the above-identified compound (16 mg).

Example 80

Methyl 3-[1-(4-cyanophenyl)-3-(2-phenylethyl)-1H-indol-5-yl]propanoate

The same reaction was performed as in Example 75 except for using, instead of 4-bromoanisole, 4-bromobenzonitrile to afford the above-identified compound (38 mg).

Example 81

3-[1-(4-cyanophenyl)-3-(2-phenylethyl)-1H-indol-5-yl]propanoic acid

The same reaction was performed as in Example 3 except for using, instead of the compound obtained at Example 2, the compound obtained at Example 80 to afford the above-identified compound (31 mg).

Example 82

Methyl 3-[1-(4-nitrophenyl)-3-(2-phenylethyl)-1H-indol-5-yl]propanoate

The same reaction was performed as in Example 75 except for using, instead of 4-bromoanisole, p-bromonitrobenzene to afford the above-identified compound (68 mg).

Example 83

3-[1-(4-nitrophenyl)-3-(2-phenylethyl)-1H-indol-5-yl]propanoic acid

The same reaction was performed as in Example 3 except for using, instead of the compound obtained at Example 2, the compound obtained at Example 82 to afford the above-identified compound (8.6 mg).

Example 84

Methyl 3-{1-[4-(dimethylamino)phenyl]-3-(2-phenylethyl)-1H-indol-5-yl}propanoate The same reaction was performed as in Example 75 except for using, instead of the 4-bromoanisole, 4-bromo-N,N-dimethylaniline to afford the above-identified compound (216 mg).

Example 85

3-{1-[4-(dimethylamino)phenyl]-3-(2-phenylethyl)-1H-indol-5-yl}propanoic acid

The same reaction was performed as in Example 3 except for using, instead of the compound obtained at Example 2, the compound obtained at Example 84 to afford the above-identified compound (200 mg).

Example 86

3-{1-[4-(dimethylamino)phenyl]-3-(2-phenylethyl)-1H-indol-5-yl}propanoic acid 2-amino-2-(hydroxymethyl)propane-1,3-diol salt (1:1)

The same operation was performed as in Example 17 except for using, instead of the compound obtained at Example 16, the compound obtained at Example 85 to afford the above-identified compound (272 mg).

Example 87

Methyl 3-{1-[4-(diethylamino)phenyl]-3-(2-phenylethyl)-1H-indol-5-yl}propanoate

The same reaction was performed as in Example 75 except for using, instead of 4-bromoanisole, 4-bromo-N,N-diethylaniline to afford the above-identified compound (138 mg).

Example 88

3-{1-[4-(diethylamino)phenyl]-3-(2-phenylethyl)-1H-indol-5-yl}propanoic acid

The same reaction was performed as in Example 3 except for using, instead of the compound obtained at Example 2, the compound obtained at Example 87 to afford the above-identified compound (109 mg).

Example 89

Methyl 3-[1-(4-aminophenyl)-3-(2-phenylethyl)-1H-indol-5-yl]propanoate

The same reaction was performed as in Example 4 except for using, instead of the compound obtained at Example 3, the compound obtained at Example 82 to afford the above-identified compound (12 mg).

Example 90

Methyl 3-{1-[4-(acetylamino)phenyl]-3-(2-phenylethyl)-1H-indol-5-yl}propanoate

To a solution of the compound obtained at Example 89 (11 mg) in pyridine (1.0 ml) were added N,N-dimethylaminopyridine (0.34 mg) and acetyl chloride (0.0024 ml), and the mixture was stirred at room temperature for 12 hours. To the reaction mixture was added methanol to quench the reaction, the mixture was dissolved in methylene chloride, then the organic layer was successively washed with dilute hydrochloric acid and brine and dried over anhydrous sodium sulfate. The solvent was distilled off in vacuo and the residue obtained was purified by silica gel column chromatography (hexane: ethyl acetate=19:1 to 1:1) to afford the above-identified compound (9.6 mg).

Example 91

3-{1-[4-(acetylamino)phenyl]-3-(2-phenylethyl)-1H-indol-5-yl}propanoic acid 2-amino-2-(hydroxymethyl)propane-1,3-diol salt (1:1)

Step 1
The same reaction was performed as in Example 3 except for using, instead of the compound obtained at Example 2, the compound obtained at Example 90 to afford 3-{1-[4-(acetylamino)phenyl]-3-(2-phenylethyl)-1H-indol-5-yl}propanoic acid (5.2 mg).
Step 2
The same reaction was performed as in Example 17 except for using, instead of the compound obtained at Example 16, the compound obtained above to afford the above-identified compound (7.7 mg).

Example 92

Methyl 3-[1-{4-[(2,2-dimethylpropanoyl)amino]phenyl}-3-(2-phenylethyl)-1H-indol-5-yl]propanoate The same reaction was performed as in Example 90 except for using, instead of acetyl chloride, pivaloyl chloride to afford the above-identified compound (12 mg).

Example 93

3-[1-{4-[(2,2-dimethylpropanoyl)amino]phenyl}-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 92 to afford the above-identified compound (14.5 mg).

Example 94

Methyl 3-[1-(4-methylphenyl)-3-(2-phenylethyl)-1H-indol-5-yl]propanoate

The same reaction was performed as in Example 75 except for using, instead of 4-bromoanisole, 4-bromotoluene to afford the above-identified compound (83 mg).

Example 95

3-[1-(4-methylphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 94 to afford the above-identified compound (96 mg).

Example 96

Methyl 3-[1-(3-methylphenyl)-3-(2-phenylethyl)-1H-indol-5-yl]propanoate

The same reaction was performed as in Example 75 except for using, instead of 4-bromoanisole, 3-bromotoluene to afford the above-identified compound (49 mg).

Example 97

3-[1-(3-methylphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 96 to afford the above-identified compound (53 mg).

Example 98

Methyl 3-[1-(2-methylphenyl)-3-(2-phenylethyl)-1H-indol-5-yl]propanoate

The same reaction was performed as in Example 75 except for using, instead of 4-bromoanisole, 2-bromotoluene to afford the above-identified compound (49 mg).

Example 99

3-[1-(2-methylphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 98 to afford the above-identified compound (53 mg).

Example 100

Methyl 3-[1-(3,4-dimethylphenyl)-3-(2-phenylethyl)-1H-indol-5-yl]propanoate

The same reaction was performed as in Example 75 except for using, instead of 4-bromoanisole, 4-bromo-o-xylene to afford the above-identified compound (132 mg).

Example 101

3-[1-(3,4-dimethylphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 100 to afford the above-identified compound (148 mg).

Example 102

Methyl 3-[1-(4-tert-butylphenyl)-3-(2-phenylethyl)-1H-indol-5-yl]propanoate

The same reaction was performed as in Example 75 except for using, instead of 4-bromoanisole, 1-bromo-4-tert-butylbenzene to afford the above-identified compound (49 mg).

Example 103

3-[1-(4-tert-butylphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 102 to afford the above-identified compound (27 mg).

Example 104

Methyl 3-[1-(4-chlorophenyl)-3-(2-phenylethyl)-1H-indol-5-yl]propanoate

The same reaction was performed as in Example 75 except for using, instead of 4-bromoanisole, p-bromochlorobenzene to afford the above-identified compound (50 mg).

Example 105

3-[1-(4-chlorophenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 104 to afford the above-identified compound (48 mg).

Example 106

Methyl 3-[1-(3-methoxyphenyl)-3-(2-phenylethyl)-1H-indol-5-yl]propanoate

The same reaction was performed as in Example 75 except for using, instead of 4-bromoanisole, 3-bromoanisole to afford the above-identified compound (38 mg).

Example 107

3-[1-(3-methoxyphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 106 to afford the above-identified compound (48 mg).

Example 108

Methyl 3-[1-(2-methoxyphenyl)-3-(2-phenylethyl)-1H-indol-5-yl]propanoate

The same reaction was performed as in Example 75 except for using, instead of 4-bromoanisole, 2-bromoanisole to afford the above-identified compound (46 mg).

Example 109

3-[1-(2-methoxyphenyl)-3-(2-phenylethyl)-1H-indol-5-yl]propanoic acid 2-amino-2-(hydroxymethyl)propane-1,3-diol salt (1:1)

The same reaction was performed as in Example 91 except for using, instead of the compound obtained at Example 90, the compound obtained at Example 108 to afford the above-identified compound (50 mg).

Example 110

Methyl 3-[1-(4-ethoxyphenyl)-3-(2-phenylethyl)-1H-indol-5-yl]propanoate

The same reaction was performed as in Example 75 except for using, instead of 4-bromoanisole, 4-bromophenetol to afford the above-identified compound (64 mg).

Example 111

3-[1-(4-ethoxyphenyl)-3-(2-phenylethyl)-1H-indol-5-yl]propanoic acid

The same reaction was performed as in Example 3 except for using, instead of the compound obtained at Example 2, the compound obtained at Example 110 to afford the above-identified compound (52 mg).

Example 112

3-[1-(4-ethoxyphenyl)-3-(2-phenylethyl)-1H-indol-5-yl]propanoic acid 2-amino-2-(hydroxymethyl)propane-1,3-diol salt (1:1)

The same reaction was performed as in Example 17 except for using, instead of the compound obtained at Example 16, the compound obtained at Example 111 to afford the above-identified compound (67 mg).

Example 113

1,1,1-trifluoro-4-[1-phenyl-3-(2-phenylethyl)-1H-indol-5-yl]butan-2-one

To a solution of the compound obtained at Example 16 (97 mg) in methylene chloride (1.5 ml) was added oxalyl chloride (0.055 ml), and the mixture was stirred at room temperature for 1 hour. From the reaction solution, the solvent was distilled off in vacuo, the residue obtained was dissolved in toluene (2.0 ml), trifluoroacetic acid anhydride (0.11 ml) and pyridine (0.055 ml) were added under ice cooling and the mixture was stirred at room temperature for 2 hours. To the reaction mixture was added water, and the mixture was extracted with ethyl acetate, and the organic layer was successively washed with water, saturated aqueous sodium hydrogen carbonate solution, and brine and dried over anhydrous sodium sulfate. The solvent was distilled off in vacuo, and the residue obtained was purified by silica gel column chromatography (hexane:ethyl acetate=19:1 to 2:3) to afford the above-identified compound (89 mg).

Example 114

4-[1-(4-ethoxyphenyl)-3-(2-phenylethyl)-1H-indol-5-yl]-1,1,1-trifluorobutan-2-one The same reaction was performed as in Example 113 except for using, instead of the compound obtained at Example 16, the compound obtained at Example 111 to afford the above-identified compound (50 mg).

Example 115

N-cyano-3-[1-(4-ethoxyphenyl)-3-(2-phenylethyl)-1H-indol-5-yl]propanamide

The same reaction was performed as in Example 18 except for using, instead of the compound obtained at Example 16, the compound obtained at Example 111 to afford the above-identified compound (19 mg).

Example 116

3-[1-(4-ethoxyphenyl)-3-(2-phenylethyl)-1H-indol-5-yl]-N-methoxy-N-methylpropanamide The compound obtained at Example 111 (87 mg) was dissolved in N,N-dimethylformamide (3.0 ml), N,O-dimethylhydroxylamine hydrochloride (27 mg), 1-hydroxybenzotriazole (43 mg) and 1-ethyl-3-(3-dimethylaminopropyl)carbodiimide hydrochloride (60 mg) were added, the mixture was cooled to 0° C., triethylamine (0.039 ml) was added and the mixture was stirred at room temperature for 12 hours. To the reaction mixture was added ethyl acetate, then the organic layer was successively washed with 1 mol/l hydrochloric acid, water, saturated aqueous sodium hydrogen carbonate solution, and brine and dried over anhydrous sodium sulfate. The solvent was distilled off in vacuo and the residue obtained was purified by silica gel column chromatography (hexane:ethyl acetate=9:1 to 1:1) to afford the above-identified compound (72 mg).

Example 117

3-[1-(4-ethoxyphenyl)-3-(2-phenylethyl)-1H-indol-5-yl]propanol

A solution of the compound obtained at Example 116 (60 mg) in tetrahydrofuran (2.0 ml) was cooled to 0° C., lithium aluminum hydride (15 mg) was added and the mixture was stirred at room temperature for 7 hours. To the reaction mixture were added water and 1 mol/l hydrochloric acid, and the mixture was extracted with ethyl acetate and the organic layer was washed with brine and dried over anhydrous sodium sulfate. The solvent was distilled off in vacuo, and the residue obtained was purified by silica gel column chromatography (hexane:ethyl acetate=9:1 to 1:1) to afford the above-identified compound (25 mg).

Example 118

Methyl 3-[3-(2-phenylethyl)-1-(4-propoxyphenyl)-1H-indol-5-yl]propanoate

The same reaction was performed as in Example 75 except for using, instead of 4-bromoanisole, 4-bromo-n-propoxybenzene to afford the above-identified compound (168 mg).

Example 119

3-[3-(2-phenylethyl)-1-(4-propoxyphenyl)-1H-indol-5-yl]propanoic acid

The same reaction was performed as in Example 3 except for using, instead of the compound obtained at Example 2, the compound obtained at Example 118 to afford the above-identified compound (146 mg).

Example 120

Methyl 3-[1-(4-isopropoxyphenyl)-3-(2-phenylethyl)-1H-indol-5-yl]propanoate

The same reaction was performed as in Example 75 except for using, instead of 4-bromoanisole, 4-bromo-isopropoxybenzene to afford the above-identified compound (39 mg).

Example 121

3-[1-(4-isopropoxyphenyl)-3-(2-phenylethyl)-1H-indol-5-yl]propanoic acid

The same reaction was performed as in Example 3 except for using, instead of the compound obtained at Example 2, the compound obtained at Example 120 to afford the above-identified compound (31 mg).

Example 122

Methyl 3-{1-[4-(benzyloxy)phenyl]-3-(2-phenylethyl)-1H-indol-5-yl}propanoate

The same reaction was performed as in Example 75 except for using, instead of 4-bromoanisole, 4-(benzyloxy)bromobenzene to afford the above-identified compound (122 mg).

Example 123

3-{1-[4-(benzyloxy)phenyl]-3-(2-phenylethyl)-1H-indol-5-yl}propanoic acid

The same reaction was performed as in Example 3 except for using, instead of the compound obtained at Example 2, the compound obtained at Example 122 to afford the above-identified compound (14 mg).

Example 124

3-{1-[4-(benzyloxy)phenyl]-3-(2-phenylethyl)-1H-indol-5-yl}propanoic acid 2-amino-2-(hydroxymethyl)propane-1,3-diol salt (1:1)

The same reaction was performed as in Example 17 except for using, instead of the compound obtained at Example 16, the compound obtained at Example 123 to afford the above-identified compound (17.5 mg).

Example 125

Methyl 3-[1-(4-hydroxyphenyl)-3-(2-phenylethyl)-1H-indol-5-yl]propanoate

The same reaction was performed as in Example 4 except for using, instead of the compound obtained at Example 3, the compound obtained at Example 122 to afford the above-identified compound (67 mg).

Example 126

3-[1-(4-hydroxyphenyl)-3-(2-phenylethyl)-1H-indol-5-yl]propanoic acid

The same reaction was performed as in Example 3 except for using, instead of the compound obtained at Example 2, the compound obtained at Example 125 to afford the above-identified compound (34 mg).

Example 127

Methyl 3-[3-(2-phenylethyl)-1-(3-pyridinyl)-1H-indol-5-yl]propanoate

The same reaction was performed as in Example 75 except for using, instead of 4-bromoanisole, 3-bromopyridine to afford the above-identified compound (52 mg).

Example 128

3-[3-(2-phenylethyl)-1-(3-pyridinyl)-1H-indol-5-yl]propanoic acid hydrochloride

Step 1

The same reaction was performed as in Example 3 except for using, instead of the compound obtained at Example 2, the compound obtained at Example 127 to afford 3-[3-(2-phenylethyl)-1-(3-pyridinyl)-1H-indol-5-yl]propanoic acid (49 mg).

Step 2

The compound obtained above (49 mg) was dissolved in ethanol (1.0 ml), saturated hydrochloric acid/methanol solution (0.1 ml) was added and the mixture was diluted with diethyl ether. The precipitated crystal was collected by filtration to afford the above-identified compound (54 mg).

Example 129

Methyl 3-[1-(6-methoxy-3-pyridinyl)-3-(2-phenylethyl)-1H-indol-5-yl]propanoate

The same reaction was performed as in Example 75 except for using, instead of 4-bromoanisole, 5-bromo-2-methoxypyridine to afford the above-identified compound (121 mg).

Example 130

3-[1-(6-methoxy-3-pyridinyl)-3-(2-phenylethyl)-1H-indol-5-yl]propanoic acid

The same reaction was performed as in Example 3 except for using, instead of the compound obtained at Example 2, the compound obtained at Example 129 to afford the above-identified compound (79 mg).

Example 131

Methyl 3-[3-(2-phenylethyl)-1-(2-pyridinyl)-1H-indol-5-yl]propanoate

The same reaction was performed as in Example 75 except for using, instead of 4-bromoanisole, 2-bromopyridine to afford the above-identified compound (33 mg).

Example 132

3-[3-(2-phenylethyl)-1-(2-pyridinyl)-1H-indol-5-yl]propanoic acid hydrochloride

Step 1

The same reaction was performed as in Example 3 except for using, instead of the compound obtained at Example 2, the compound obtained at Example 131 to afford 3-[3-(2-phenylethyl)-1-(2-pyridinyl)-1H-indol-5-yl]propanoic acid (31 mg).

Step 2

The compound obtained above (31 mg) was dissolved in methylene chloride (1.0 ml), 4N-hydrochloric acid/1,4-dioxane solution (0.010 ml) was added and the mixture was diluted with hexane. The precipitated crystal was collected by filtration to afford the above-identified compound (4.3 mg).

Example 133

Methyl 3-[1-(5-nitro-2-pyridinyl)-3-(2-phenylethyl)-1H-indol-5-yl]propanoate

The same reaction was performed as in Example 75 except for using, instead of 4-bromoanisole, 2-bromo-5-nitropyridine to afford the above-identified compound (94 mg).

Example 134

3-[1-(5-nitro-2-pyridinyl)-3-(2-phenylethyl)-1H-indol-5-yl]propanoic acid hydrochloride The same reaction was performed as in Example 132 except for using, instead of the compound obtained at Example 131, the compound obtained at Example 133 to afford the above-identified compound (9.7 mg).

Example 135

3-[1-(5-amino-2-pyridinyl)-3-(2-phenylethyl)-1H-indol-5-yl]propanoic acid

The same reaction was performed as in Example 4 except for using, instead of the compound obtained at Example 3, the compound obtained at Example 134 and making the reaction solvent ethyl acetate to afford the above-identified compound (1.8 mg).

Example 136

Methyl 3-[1-(5-amino-2-pyridinyl)-3-(2-phenyl-ethyl)-1H-indol-5-yl]propanoate

The same reaction was performed as in Example 4 except for using, instead of the compound obtained at Example 3, the compound obtained at Example 133 and making the reaction solvent an ethyl acetate-methanol mixed solvent to afford the above-identified compound (60 mg).

Example 137

Methyl 3-{1-[5-(dimethylamino)-2-pyridinyl]-3-(2-phenylethyl)-1H-indol-5-yl}propanoate To a solution of the compound obtained at Example 136 (29 mg) in N,N-dimethylformamide (1.0 ml) were added formic acid (0.014 ml) and 37% aqueous formaldehyde solution (0.030 ml), and the mixture was stirred at 100° C. for 8 hours. To the reaction mixture were added water and 1 mol/l aqueous sodium hydroxide solution, and the mixture was extracted with ethyl acetate and the organic layer was washed with water and brine and dried over anhydrous sodium sulfate. The solvent was distilled off in vacuo, and the residue obtained was purified by silica gel column chromatography (hexane:ethyl acetate=9:1 to 1:1) to afford the above-identified compound (9.0 mg).

Example 138

3-{1-[5-(dimethylamino)-2-pyridinyl]-3-(2-phenyl-ethyl)-1H-indol-5-yl}propanoic acid hydrochloride The same reaction was performed as in Example 132 except for using, instead of the compound obtained at Example 131, the compound obtained at Example 137 to afford the above-identified compound (3.0 mg).

Example 139

Methyl 3-{1-[5-(acetylamino)-2-pyridinyl]-3-(2-phenylethyl)-1H-indol-5-yl}propanoate To a solution of the compound obtained at Example 136 (33 mg) in pyridine (2.0 ml) was added anhydrous acetic acid (1.0 ml), and the mixture was stirred at room temperature for 62 hours. The reaction solution was distilled off in vacuo and the residue obtained was purified by silica gel chromatography (hexane:ethyl acetate=1:1) to afford the above-identified compound (21 mg).

Example 140

3-{1-[5-(acetylamino)-2-pyridinyl]-3-(2-phenyl-ethyl)-1H-indol-5-yl}propanoic acid The same reaction was performed as in Example 3 except for using, instead of the compound obtained at Example 2, the compound obtained at Example 139 to afford the above-identified compound (13 mg).

Example 141

Ethyl (2E)-3-[3-(2-phenylethyl)-1H-indol-5-yl]-2-propenoate

To a solution of the compound obtained at Reference Example 4 (10.6 g) in triethylamine (320 ml) were added ethyl acrylate (11.5 ml), palladium acetate (0.8 g) and tris(2-methylphenyl)phosphine (2.2 g), and the mixture was stirred at 105° C. for 6 hours. The insolubles were filtered off, the filtrate was distilled off in vacuo and the residue obtained was purified by silica gel column chromatography (hexane:ethyl acetate=4:1 to 1:9) to obtain the above-identified compound (11.2 g).

Further, the above-identified compound was also obtained by the following method.

To the compound obtained at Reference Example 4 (100.48 g) were added ethyl acrylate (108.6 ml), palladium acetate (892 mg), tris(2-methylphenyl)phosphine (3.04 g), triethylamine (283 ml) and toluene (722 ml), and the mixture was heated and stirred at 115° C. for 3 hours. Using silica gel (100.5 g), the insolubles were filtered off, the filtrate was distilled off in vacuo, ethyl acetate (110 ml) and hexane (1100 ml) were added to the residue obtained, the mixture was heated and stirred at 70° C. for 10 minutes, then the mixture was stirred at room temperature for 16 hours and further at 0 to 5° C. for 2 hours and the precipitated crystal was obtained by filtration to afford the above-identified compound (73.36 g).

Example 142

Ethyl 3-[3-(2-phenylethyl)-1H-indol-5-yl]propanoate

To a solution of the compound obtained at Example 141 (10 g) in ethyl acetate (100 ml)/ethanol (150 ml) mixed solvent was added 10% palladium carbon (3.0 g), and the mixture was stirred under a hydrogen atmosphere at a room temperature for 3 days. The insolubles were filtered off, the filtrate was distilled off in vacuo and the residue obtained was purified by silica gel column chromatography (hexane:ethyl acetate=4:1 to 2:3) to afford the above-identified compound (8.7 g).

Further, the above-identified compound was also obtained by the following method.

The compound obtained at Example 141 (102.23 g) was dissolved in ethanol (300 ml) and ethyl acetate (300 ml), Raney nickel (51 ml)/ethanol (300 ml) was added and the mixture was stirred under a hydrogen atmosphere (ordinary pressure) at room temperature for 6 hours. From the reaction solution, the insolubles were filtered off, then the solvent was distilled off from the filtrate to afford the above-identified compound (101.00 g).

Example 143

Ethyl (2E)-3-{1-[4-(benzyloxy)phenyl]-3-(2-phenyl-ethyl)-1H-indol-5-yl}-2-propenoate To a solution of the compound obtained at Example 141 (2.0 g) in n-butyl acetate (60 ml) were added 4-(benzyloxy)bromobenzene (3.3 g), palladium acetate (0.14 g), 2-(di-tert-butylphosphino)biphenyl (0.38 g) and tripotassium phosphate (5.3 g), and the mixture was heated and refluxed at 110° C. for 3 hours. The reaction solution was cooled, then the insolubles were filtered off, the filtrate was distilled off in vacuo and the residue obtained was purified by silica gel column chromatography (hexane:ethyl acetate=9:1 to 1:1) to afford the above-identified compound (1.4 g).

Example 144

(2E)-3-{1-[4-(benzyloxy)phenyl]-3-(2-phenylethyl)-1H-indol-5-yl}-2-propenoic acid To a solution of the compound obtained at Example 143 (0.58 g) in tetrahydrofuran (4.0 ml)-ethanol (4.0 ml) mixed solvent was added 1 mol/l aqueous sodium hydroxide solution (1.6 ml), and the mixture was stirred at room temperature over night. To the reaction mixture, 1 mol/l hydrochloric acid (3.0 ml) was added, the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=99:1 to 47:3) to afford the above-identified compound (0.49 g).

Example 145

Ethyl 3-{1-[2-(benzyloxy)phenyl]-3-(2-phenylethyl)-1H-indol-5-yl}propanoate

To a solution of the compound obtained at Example 142 (80 mg) in dimethoxyethane (4.0 ml) were added 2-(benzyloxy)bromobenzene (130 mg), palladium acetate (5.6 mg), 2-(di-tert-butylphosphino)biphenyl (15 mg) and tripotassium phosphate (212 mg), and the mixture was heated and refluxed at 110° C. over night. The reaction mixture was cooled, then the insolubles were filtered off, the filtrate was distilled off in vacuo and the residue obtained was purified by silica gel column chromatography (hexane:ethyl acetate=9:1 to 1:1) to afford the above-identified compound (80 mg).

Example 146

Ethyl 3-[1-(2-hydroxyphenyl)-3-(2-phenylethyl)-1H-indol-5-yl]propanoate

To a solution of the compound obtained at Example 145 (16 mg) in ethyl acetate (2.0 ml)-ethanol (2.0 ml) solution was added 10% palladium carbon (30 mg), and the mixture was stirred under a hydrogen atmosphere at room temperature over night. The insolubles were filtered off, the filtrate was distilled off in vacuo and the residue obtained was purified by silica gel column chromatography (hexane:ethyl acetate=9:1 to 3:2) to afford the above-identified compound (66 mg).

Example 147

3-[1-(2-hydroxyphenyl)-3-(2-phenylethyl)-1H-indol-5-yl]propanoic acid

To a solution of the compound obtained at Example 146 (64 mg) in tetrahydrofuran (2.0 ml)-ethanol (1.5 ml) mixed solvent was added 1 mol/l aqueous sodium hydroxide solution (0.35 ml), and the mixture was stirred at room temperature over night. To the reaction mixture was added 1 mol/l hydrochloric acid (0.40 ml), and the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=19:1 to 4:1) to afford the above-identified compound (57 mg).

Example 148

Ethyl 3-[1-(2-nitrophenyl)-3-(2-phenylethyl)-1H-indol-5-yl]propanoate

To a solution of the compound obtained at Example 142 (48 mg) in n-butyl acetate (3.0 ml) were added 2-bromonitrobenzene (60 mg), palladium acetate (4.0 mg), 2-(di-tert-butylphosphino)biphenyl (11 mg) and tripotassium phosphate (127 mg), and the mixture was heated and refluxed at 110° C. over night. The reaction mixture was cooled, then the insolubles were filtered off, the filtrate was distilled off in vacuo and the residue obtained was purified by silica gel column chromatography (hexane:ethyl acetate=9:1 to 3:2) to afford the above-identified compound (66 mg).

Example 149

3-[1-(2-nitrophenyl)-3-(2-phenylethyl)-1H-indol-5-yl]propanoic acid

The same reaction was performed as in Example 144 except for using, instead of the compound obtained at Example 143, the compound obtained at Example 148 to afford the above-identified compound (12 mg).

Example 150

Ethyl 3-[1-(2-aminophenyl)-3-(2-phenylethyl)-1H-indol-5-yl]propanoate

The same reaction was performed as in Example 146 except for using, instead of the compound obtained at Example 145, the compound obtained at Example 148 to afford the above-identified compound (34 mg).

Example 151

3-[1-(2-aminophen 1)-3-(2-phenylethyl)-1H-indol-5-yl]propanoic acid

The same reaction was performed as in Example 144 except for using, instead of the compound obtained at Example 143, the compound obtained at Example 150 to afford the above-identified compound (18 mg).

Example 152

Ethyl 3-{1-[2-(acetylamino)phenyl]-3-(2-phenylethyl)-1H-indol-5-yl}propanoate

The same reaction was performed as in Example 139 except for using, instead of the compound obtained at Example 136, the compound obtained at Example 150 to afford the above-identified compound (15 mg).

Example 153

3-{1-[2-(acetylamino)phenyl]-3-(2-phenylethyl)-1H-indol-5-yl}propanoic acid

The same reaction was performed as in Example 144 except for using, instead of the compound obtained at Example 143, the compound obtained at Example 152 to afford the above-identified compound (15 mg).

Example 154

Ethyl 3-{1-[3-(benzyloxy)phenyl]-3-(2-phenylethyl)-1H-indol-5-yl}propanoate

The same reaction was performed as in Example 148 except for using, instead of 2-bromonitrobenzene, 3-(benzyloxy)bromobenzene to afford the above-identified compound (112 mg).

Example 155

3-{1-[3-(benzyloxy)phenyl]-3-(2-phenylethyl)-1H-indol-5-yl}propanoic acid 2-amino-2-(hydroxymethyl)propane-1,3-diol salt (1:1)

Step 1

The same reaction was performed as in Example 144 except for using, instead of the compound obtained at Example 143, the compound obtained at Example 154 to afford 3-{1-[3-(benzyloxy)phenyl]-3-(2-phenylethyl)-1H-indol-5-yl}propanoic acid (16 mg).

Step 2

To a solution of the compound obtained above (16 mg) in tetrahydrofuran (1.0 ml) was added 0.1 mol/l aqueous tris (hydroxymethyl)aminoethane solution (0.34 ml), and the mixture was stirred for a while, then the solvent was distilled off to afford the above-identified compound (20 mg).

Example 156

Ethyl 3-[1-(3-hydroxyphenyl)-3-(2-phenylethyl)-1H-indol-5-yl]propanoate

The same reaction was performed as in Example 146 except for using, instead of the compound obtained at Example 145, the compound obtained at Example 154 to afford the above-identified compound (86 mg).

Example 157

3-[1-(3-hydroxyphenyl)-3-(2-phenylethyl)-1H-indol-5-yl]propanoic acid

The same reaction was performed as in Example 144 except for using, instead of the compound obtained at Example 143, the compound obtained at Example 156 to afford the above-identified compound (54 mg).

Example 158

Ethyl 3-[1-(3-ethoxyphenyl)-3-(2-phenylethyl)-1H-indol-5-yl]propanoate

To a solution of the compound obtained at Example 156 (65 mg) in acetone (5.0 ml) were added potassium carbonate (33 mg) and ethyl iodide (0.62 ml), and the mixture was heated and refluxed at 60° C. over night. The insolubles were filtered off, the filtrate was distilled off in vacuo, and the residue obtained was purified by silica gel column chromatography (hexane:ethyl acetate=9:1 to 3:2) to afford the above-identified compound (58 mg).

Example 159

3-[1-(3-ethoxyphenyl)-3-(2-phenylethyl)-1H-indol-5-yl]propanoic acid

The same reaction was performed as in Example 144 except for using, instead of the compound obtained at Example 143, the compound obtained at Example 158 to afford the above-identified compound (56 mg).

Example 160

Ethyl 3-[3-(2-phenylethyl)-1-(3-propoxyphenyl)-1H-indol-5-yl]propanoate

The same reaction was performed as in Example 158 except for using, instead of ethyl iodide, n-propyl iodide to afford the above-identified compound (58 mg).

Example 161

3-[3-(2-phenylethyl)-1-(3-propoxyphenyl)-1H-indol-5-yl]propanoic acid

The same reaction was performed as in Example 144 except for using, instead of the compound obtained at Example 143, the compound obtained at Example 160 to afford the above-identified compound (50 mg).

Example 162

Ethyl 3-[1-(3-isopropoxyphenyl)-3-(2-phenylethyl)-1H-indol-5-yl]propanoate

The same reaction was performed as in Example 158 except for using, instead of ethyl iodide, isopropyl iodide to afford the above-identified compound (60 mg).

Example 163

3-[1-(3-isopropoxyphenyl)-3-(2-phenylethyl)-1H-indol-5-yl]propanoic acid

The same reaction was performed as in Example 144 except for using, instead of the compound obtained at Example 143, the compound obtained at Example 162 to afford the above-identified compound (46 mg).

Example 164

Ethyl 3-[1-(3-nitrophenyl)-3-(2-phenylethyl)-1H-indol-5-yl]propanoate

The same reaction was performed as in Example 148 except for using, instead of 2-bromonitrobenzene, 3-bromonitrobenzene to afford the above-identified compound (75 mg).

Example 165

3-[1-(3-nitrophenyl)-3-(2-phenylethyl)-1H-indol-5-yl]propanoic acid

The same reaction was performed as in Example 144 except for using, instead of the compound obtained at Example 143, the compound obtained at Example 164 to afford the above-identified compound (23 mg).

Example 166

Ethyl 3-[1-(3-aminophenyl)-3-(2-phenylethyl)-1H-indol-5-yl]propanoate

The same reaction was performed as in Example 146 except for using, instead of the compound obtained at Example 145, the compound obtained at Example 164 to afford the above-identified compound (63 mg).

Example 167

3-[1-(3-aminophenyl)-3-(2-phenylethyl)-1H-indol-5-yl]propanoic acid

The same reaction was performed as in Example 144 except for using, instead of the compound obtained at Example 143, the compound obtained at Example 166 to afford the above-identified compound (25 mg).

Example 168

Ethyl 3-{1-[3-(acetylamino)phenyl]-3-(2-phenylethyl)-1H-indol-5-yl}propanoate

The same reaction was performed as in Example 139 except for using, instead of the compound obtained at Example 136, the compound obtained at Example 166 to afford the above-identified compound (20 mg).

Example 169

3-{1-[3-(acetylamino)phenyl]-3-(2-phenylethyl)-1H-indol-5-yl}propanoic acid

The same reaction was performed as in Example 144 except for using, instead of the compound obtained at Example 143, the compound obtained at Example 168 to afford the above-identified compound (17 mg).

Example 170

Ethyl 3-[1-{3-[(2,2-dimethylpropanoyl)amino]phenyl}-3-(2-phenylethyl)-1H-indol-5-yl]propanoate To a solution of the compound obtained at Example 166 (23 mg) in pyridine (1.0 ml) were added N,N-dimethylaminopyridine (2.7 mg) and pivaloyl chloride (0.028 ml), and the mixture was stirred at room temperature for 14 hours. To the reaction mixture was added methanol to quench the reaction, the mixture was dissolved in methylene chloride, then the organic layer was washed with dilute hydrochloric acid and brine and dried over anhydrous sodium sulfate. The solvent was distilled off in vacuo, and the residue obtained was purified by silica gel column chromatography (hexane:ethyl acetate=9:1 to 3:2) to afford the above-identified compound (27 mg).

Example 171

3-[1-{3-[(2,2-dimethylpropanoyl)amino]phenyl}-3-(2-phenylethyl)-1H-indol-5-yl]propanoic acid The same reaction was performed as in Example 144 except for using, instead of the compound obtained at Example 143, the compound obtained at Example 170 to afford the above-identified compound (23 mg).

Example 172

Ethyl 3-[1-(3-cyanophenyl)-3-(2-phenylethyl)-1H-indol-5-yl]propanoate

The same reaction was performed as in Example 148 except for using, instead of 2-bromonitrobenzene, m-bromobenzonitrile to afford the above-identified compound (60 mg).

Example 173

3-[1-(3-cyanophenyl)-3-(2-phenylethyl)-1H-indol-5-yl]propanoic acid

The same reaction was performed as in Example 144 except for using, instead of the compound obtained at Example 143, the compound obtained at Example 172 to afford the above-identified compound (0.21 mg).

Example 174

Ethyl 3-[1-(3-formylphenyl)-3-(2-phenylethyl)-1H-indol-5-yl]propanoate

The same reaction was performed as in Example 148 except for using, instead of 2-bromonitrobenzene, 3-bromobenzaldehyde to afford the above-identified compound (56 mg).

Example 175

3-[1-(3-formylphenyl)-3-(2-phenylethyl)-1H-indol-5-yl]propanoic acid

The same reaction was performed as in Example 144 except for using, instead of the compound obtained at Example 143, the compound obtained at Example 174 to afford the above-identified compound (17 mg).

Example 176

Ethyl 3-{5-[2-(ethoxycarbonyl)ethyl]-3-(2-phenylethyl)-1H-indol-1-yl}benzoate

The same reaction was performed as in Example 148 except for using, instead of 2-bromonitrobenzene, ethyl 3-bromobenzoate to afford the above-identified compound (94 mg).

Example 177

3-[5-(2-carboxyethyl)-3-(2-phenylethyl)-1H-indol-1-yl]benzoic acid

The same reaction was performed as in Example 144 except for using, instead of the compound obtained at Example 143, the compound obtained at Example 176 to afford the above-identified compound (33 mg).

Example 178

Ethyl 3-{1-[3-(dimethylamino)phenyl]-3-(2-phenylethyl)-1H-indol-5-yl}propanoate

The same reaction was performed as in Example 148 except for using, instead of 2-bromonitrobenzene, 3-bromo-N,N-dimethylaniline to afford the above-identified compound (76 mg).

Example 179

3-{1-[3-(dimethylamino)phenyl]-3-(2-phenylethyl)-1H-indol-5-yl}propanoic acid

The same reaction was performed as in Example 144 except for using, instead of the compound obtained at Example 143, the compound obtained at Example 178 to afford the above-identified compound (58 mg).

Example 180

Ethyl 3-[1-(3-chlorophenyl)-3-(2-phenylethyl)-1H-indol-5-yl]propanoate

The same reaction was performed as in Example 148 except for using, instead of 2-bromonitrobenzene, 3-bromochlorobenzene to afford the above-identified compound (50 mg).

Example 181

3-[1-(3-chlorophenyl)-3-(2-phenylethyl)-1H-indol-5-yl]propanoic acid

The same reaction was performed as in Example 144 except for using, instead of the compound obtained at Example 143, the compound obtained at Example 180 to afford the above-identified compound (33 mg).

Example 182

Ethyl 3-[1-(3-fluorophenyl)-3-(2-phenylethyl)-1H-indol-5-yl]propanoate

The same reaction was performed as in Example 148 except for using, instead of 2-bromonitrobenzene, 3-bromofluorobenzene to afford the above-identified compound (17 mg).

Example 183

3-[1-(3-fluorophenyl)-3-(2-phenylethyl)-1H-indol-5-yl]propanoic acid

The same reaction was performed as in Example 144 except for using, instead of the compound obtained at Example 143, the compound obtained at Example 182 to afford the above-identified compound (6.4 mg).

Example 184

Ethyl 3-{1-[3-(difluoromethoxy)phenyl]-3-(2-phenylethyl)-1H-indol-5-yl}propanoate The same reaction was performed as in Example 148 except for using, instead of 2-bromonitrobenzene, 3-(difluoromethoxy) bromobenzene to afford the above-identified compound (86 mg).

Example 185

3-{1-[3-(difluoromethoxy)phenyl]-3-(2-phenylethyl)-1H-indol-5-yl}propanoic acid

The same reaction was performed as in Example 144 except for using, instead of the compound obtained at Example 143, the compound obtained at Example 184 to afford the above-identified compound (69 mg).

Example 186

Ethyl 3-[1-(4-fluorophenyl)-3-(2-phenylethyl)-1H-indol-5-yl]propanoate

The same reaction was performed as in Example 148 except for using, instead of 2-bromonitrobenzene, p-bromofluorobenzene to afford the above-identified compound (415 mg).

Example 187

3-[1-(4-fluorophenyl)-3-(2-phenylethyl)-1H-indol-5-yl]propanoic acid

The same reaction was performed as in Example 144 except for using, instead of the compound obtained at Example 143, the compound obtained at Example 186 to afford the above-identified compound (327 mg).

Example 188

Ethyl 3-{1-[4-(difluoromethoxy)phenyl]-3-(2-phenylethyl)-1H-indol-5-yl}propanoate The same reaction was performed as in Example 148 except for using, instead of 2-bromonitrobenzene, 1-bromo-4-(difluoromethoxy)benzene to afford the above-identified compound (244 mg).

Example 189

3-{1-[4-(difluoromethoxy)phenyl]-3-(2-phenylethyl)-1H-indol-5-yl}propanoic acid

The same reaction was performed as in Example 144 except for using, instead of the compound obtained at Example 143, the compound obtained at Example 188 to afford the above-identified compound (224 mg).

Example 190

3-{1-[4-(difluoromethoxy)phenyl]-3-(2-phenylethyl)-1H-indol-5-yl}propanoic acid 2-amino-2-(hydroxymethyl)propane-1,3-diol salt (1:1)

To a solution of the compound obtained at Example 189 (77 mg) in ethanol (2.0 ml) were added tris(hydroxymethyl)aminoethane (22 mg) and water (2.0 ml), and the mixture was stirred for a while, then the solvent was distilled off and the residue was recrystallized from ethanol to afford the above-identified compound (96 mg).

Example 191

Ethyl 3-{3-(2-phenylethyl)-1-[4-(trifluoromethoxy)phenyl]-1H-indol-5-yl}propanoate The same reaction was performed as in Example 148 except for using, instead of 2-bromonitrobenzene, 1-bromo-4-(trifluoromethoxy)benzene to afford the above-identified compound (110 mg).

Example 192

3-{3-(2-phenylethyl)-1-[4-(trifluoromethoxy)phenyl]-1H-indol-5-yl}propanoic acid The same reaction was performed as in Example 144 except for using, instead of the compound obtained at Example 143, the compound obtained at Example 191 to afford the above-identified compound (43 mg).

Example 193

3-{3-(2-phenylethyl)-1-[4-(trifluoromethoxy)phenyl]-1H-indol-5-yl}propanoic acid 2-amino-2-(hydroxymethyl)propane-1,3-diol salt (1:1)

The same reaction was performed as in Example 190 except for using, instead of the compound obtained at Example 189, the compound obtained at Example 192 to afford the above-identified compound (54 mg).

Example 194

Ethyl 3-[1-(4-nitrophenyl)-3-(2-phenylethyl)-1H-indol-5-yl]propanoate

The same reaction was performed as in Example 148 except for using, instead of 2-bromonitrobenzene, 4-bromonitrobenzene to afford the above-identified compound (1.1 g).

Example 195

Ethyl 3-[1-(4-aminophenyl)-3-(2-phenylethyl)-1H-indol-5-yl]propanoate

The same reaction was performed as in Example 146 except for using, instead of the compound obtained at Example 145, the compound obtained at Example 194 to afford the above-identified compound (428 mg).

Example 196

3-[1-(4-aminophenyl)-3-(2-phenylethyl)-1H-indol-5-yl]propanoic acid

The same reaction was performed as in Example 144 except for using, instead of the compound obtained at Example 143, the compound obtained at Example 195 to afford the above-identified compound (60 mg).

Example 197

3-[1-{4-[(methoxyacetyl)amino]phenyl}-3-(2-phenylethyl)-1H-indol-5-yl]propanoic acid Step 1
To a solution of the compound obtained at Example 195 (106 mg) in N,N-dimethylformamide (2.0 ml) were added methoxyacetic acid (0.040 ml), triethylamine (0.30 ml) and 25% n-propyl phosphonic acid anhydride/ethyl, acetate solution (0.60 ml), and the mixture was stirred at room temperature over night. The reaction mixture was poured into water, then the mixture was extracted with ethyl acetate, the organic layer was successively washed with water and brine and dried over anhydrous sodium sulfate and the solvent was distilled off in vacuo to afford a crude product of ethyl 3-[1-{4-[(methoxyacetyl)amino]phenyl}-3-(2-phenylethyl)-1H-indol-5-yl]propanoate (127 mg).

Step 2
The same reaction was performed as in Example 144 except for using, instead of the compound obtained at Example 143, the compound obtained above to afford the above-identified compound (106 mg).

Example 198

Ethyl 3-{1-[6-(benzyloxy)pyridin-3-yl]-3-(2-phenylethyl)-1H-indol-5-yl}propanoate The same reaction was performed as in Example 148 except for using, instead of 2-bromonitrobenzene, 2-benzyloxy-5-bromopyridine to afford the above-identified compound (178 mg).

Example 199

3-{1-[6-(benzyloxy)pyridin-3-yl]-3-(2-phenylethyl)-1H-indol-5-yl}propanoic acid

The same reaction was performed as in Example 144 except for using, instead of the compound obtained at Example 143, the compound obtained at Example 198 to afford the above-identified compound (6.4 mg).

Example 200

Ethyl 3-{1-[4-(2-methoxyethyl)phenyl]-3-(2-phenylethyl)-1H-indol-5-yl}propanoate The same reaction was performed as in Example 148 except for using, instead of 2-bromonitrobenzene, 1-bromo-4-(2-methoxyethyl)benzene to afford the above-identified compound (53 mg).

Example 201

3-{1-[4-(2-methoxyethyl)phenyl]-3-(2-phenylethyl)-1H-indol-5-yl}propanoic acid

The same reaction was performed as in Example 144 except for using, instead of the compound obtained at Example 143, the compound obtained at Example 200 to afford the above-identified compound (43 mg).

Example 202

Ethyl 3-{1-[4-(2-methoxyethoxy)phenyl]-3-(2-phenylethyl)-1H-indol-5-yl}propanoate The same reaction was performed as in Example 148 except for using, instead of 2-bromonitrobenzene, 1-bromo-4-(2-methoxyethoxy)benzene to afford the above-identified compound (69 mg).

Example 203

3-{1-[4-(2-methoxyethoxy)phenyl]-3-(2-phenylethyl)-1H-indol-5-yl}propanoic acid

The same reaction was performed as in Example 144 except for using, instead of the compound obtained at

Example 204

Ethyl 3-{3-(2-phenylethyl)-1-[5-(trifluoromethyl)pyridin-2-yl]-1H-indol-5-yl}propanoate The same reaction was performed as in Example 148 except for using, instead of 2-bromonitrobenzene, 2-bromo-5-(trifluoromethyl)pyridine to afford the above-identified compound (93 mg).

Example 205

3-{3-(2-phenylethyl)-1-[5-(trifluoromethyl)pyridin-2-yl]-1H-indol-5-yl}propanoic acid The same reaction was performed as in Example 144 except for using, instead of the compound obtained at Example 143, the compound obtained at Example 204 to afford the above-identified compound (17 mg).

Example 206

Ethyl 3-{3-(2-phenylethyl)-1-[4-(trifluoromethyl)phenyl]-1H-indol-5-yl}propanoate The same reaction was performed as in Example 148 except for using, instead of 2-bromonitrobenzene, 4-bromobenzotrifluoride to afford the above-identified compound (72 mg).

Example 207

3-{3-(2-phenylethyl)-1-[4-(trifluoromethyl)phenyl]-1H-indol-5-yl}propanoic acid

The same reaction was performed as in Example 144 except for using, instead of the compound obtained at Example 143, the compound obtained at Example 206 to afford the above-identified compound (55 mg).

Example 208

Ethyl 3-{1-[4-(2-hydroxyethyl)phenyl]-3-(2-phenylethyl)-1H-indol-5-yl}propanoate The same reaction was performed as in Example 148 except for using, instead of 2-bromonitrobenzene, 4-bromophenetyl alcohol to afford the above-identified compound (22 mg).

Example 209

3-{1-[4-(2-hydroxyethyl)phenyl]-3-(2-phenylethyl)-1H-indol-5-yl}propanoic acid

The same reaction was performed as in Example 144 except for using, instead of the compound obtained at Example 143, the compound obtained at Example 208 to afford the above-identified compound (18 mg).

Example 210

Ethyl 3-[1-(3,4-dimethoxyphenyl)-3-(2-phenylethyl)-1H-indol-5-yl]propanoate

The same reaction was performed as in Example 148 except for using, instead of 2-bromonitrobenzene, 3,4-dimethoxybromobenzene to afford the above-identified compound (65 mg).

Example 211

3-[1-(3,4-dimethoxyphenyl)-3-(2-phenylethyl)-1H-indol-5-yl]propanoic acid

The same reaction was performed as in Example 144 except for using, instead of the compound obtained at Example 143, the compound obtained at Example 210 to afford the above-identified compound (18 mg).

Example 212

Ethyl 3-{3-(2-phenylethyl)-1-[4-(tetrahydro-2H-pyran-2-yloxy)phenyl]-1H-indol-5-yl}propanoate The same reaction was performed as in Example 148 except for using, instead of 2-bromonitrobenzene, 2-(4-bromophenoxy)tetrahydro-2H-pyrane to afford the above-identified compound (121 mg).

Example 213

3-{3-(2-phenylethyl)-1-[4-(tetrahydro-2H-pyran-2-yloxy)phenyl]-1H-indol-5-yl}propanoic acid The same reaction was performed as in Example 144 except for using, instead of the compound obtained at Example 143, the compound obtained at Example 212 to afford the above-identified compound (29 mg).

Example 214

3-{3-(2-phenylethyl)-1-[4-(tetrahydro-2H-pyran-2-yloxy)phenyl]-1H-indol-5-yl}propanoic acid 2-amino-2-(hydroxymethyl)propane-1,3-diol salt (1:1)

The same reaction was performed as in Example 190 except for using, instead of the compound obtained at Example 189, the compound obtained at Example 213 to afford the above-identified compound (89 mg).

Example 215

Ethyl 3-{1-[4-(methoxymethyl)phenyl]-3-(2-phenylethyl)-1H-indol-5-yl}propanoate

The same reaction was performed as in Example 148 except for using, instead of 2-bromonitrobenzene, p-(methoxymethyl)bromobenzene to afford the above-identified compound (36 mg).

Example 216

3-{1-[4-(methoxymethyl)phenyl]-3-(2-phenylethyl)-1H-indol-5-yl}propanoic acid

The same reaction was performed as in Example 144 except for using, instead of the compound obtained at Example 143, the compound obtained at Example 215 to afford the above-identified compound (27 mg).

Example 217

3-{1-[4-(methoxymethyl)phenyl]-3-(2-phenylethyl)-1H-indol-5-yl}propanoic acid 2-amino-2-(hydroxymethyl)propane-1,3-diol salt (1:1)

The same reaction was performed as in Example 190 except for using, instead of the compound obtained at Example 189, the compound obtained at Example 216 to afford the above-identified compound (49 mg).

Example 218

Ethyl 3-{1-[4-(acetoxymethyl)phenyl]-3-(2-phenylethyl)-1H-indol-5-yl}propanoate

The same reaction was performed as in Example 148 except for using, instead of 2-bromonitrobenzene, 4-bromobenzyl acetate to afford the above-identified compound (93 mg).

Example 219

3-{1-[4-(hydroxymethyl)phenyl]-3-(2-phenylethyl)-1H-indol-5-yl}propanoic acid

The same reaction was performed as in Example 144 except for using, instead of the compound obtained at Example 143, the compound obtained at Example 218 to afford the above-identified compound (27 mg).

Example 220

3-{1-[4-(hydroxymethyl)phenyl]-3-(2-phenylethyl)-1H-indol-5-yl}propanoic acid 2-amino-2-(hydroxymethyl)propane-1,3-diol salt (1:1)

The same reaction was performed as in Example 190 except for using, instead of the compound obtained at Example 189, the compound obtained at Example 219 to afford the above-identified compound (76 mg).

Example 221

Ethyl 3-{3-(2-phenylethyl)-1-[4-(2-pyrrolidin-1-ylethoxy)phenyl]-1H-indol-5-yl}propanoate The same reaction was performed as in Example 148 except for using, instead of 2-bromonitrobenzene, 1-[2-(4-bromophenoxy)ethyl]pyrrolidine to afford the above-identified compound (172 mg).

Example 222

3-{3-(2-phenylethyl)-1-[4-(2-pyrrolidin-1-ylethoxy)phenyl]-1H-indol-5-yl}propanoic acid The same reaction was performed as in Example 144 except for using, instead of the compound obtained at Example 143, the compound obtained at Example 221 to afford the above-identified compound (125 mg).

Example 223

3-{3-(2-phenylethyl)-1-[4-(2-pyrrolidin-1-ylethoxy)phenyl]-1H-indol-5-yl}propanoic acid hydrochloride The compound obtained at Example 222 (125 mg) was dissolved in 1,4-dioxane (2.0 ml), the 4N-hydrochloric acid/1,4-dioxane solution (0.065 ml) was added, then the mixture was stirred for a while. The solvent was distilled off in vacuo to afford the above-identified compound (134 mg).

Example 224

Ethyl 3-{3-(2-phenylethyl)-1-[4-(tetrahydro-2H-pyran-4-yloxy)phenyl]-1H-indol-5-yl}propanoate The same reaction was performed as in Example 148 except for using, instead of 2-bromonitrobenzene, 1-bromo-4-(tetrahydro-4-pyranoxy)benzene to afford the above-identified compound (163 mg).

Example 225

3-{3-(2-phenylethyl)-1-[4-(tetrahydro-2H-pyran-4-yloxy)phenyl]-1H-indol-5-yl}propanoic acid The same reaction was performed as in Example 144 except for using, instead of the compound obtained at Example 143, the compound obtained at Example 224 to afford the above-identified compound (134 mg).

Example 226

3-{3-(2-phenylethyl)-1-[4-(tetrahydro-2H-pyran-4-yloxy)phenyl]-1H-indol-5-yl}propanoic acid 2-amino-2-(hydroxymethyl)propane-1,3-diol salt (1:1)

The same reaction was performed as in Example 190 except for using, instead of the compound obtained at Example 189, the compound obtained at Example 225 to afford the above-identified compound (128 mg).

Example 227

Ethyl 3-{1-[4-(2-hydroxyethoxy)phenyl]-3-(2-phenylethyl)-1H-indol-5-yl}propanoate The same reaction was performed as in Example 148 except for using, instead of 2-bromonitrobenzene, ethylene glycol mono(4-bromophenyl)ether to afford the above-identified compound (358 mg).

Example 228

3-{1-[4-(2-hydroxyethoxy)phenyl]-3-(2-phenylethyl)-1H-indol-5-yl}propanoic acid

The same reaction was performed as in Example 144 except for using, instead of the compound obtained at Example 143, the compound obtained at Example 227 to afford the above-identified compound (307 mg).

Example 229

3-{1-[4-(2-hydroxyethoxy)phenyl]-3-(2-phenylethyl)-1H-indol-5-yl}propanoic acid 2-amino-2-(hydroxymethyl)propane-1,3-diol salt (1:1)

The same reaction was performed as in Example 190 except for using, instead of the compound obtained at Example 189, the compound obtained at Example 228 to afford the above-identified compound (240 mg).

Example 230

Ethyl 3-[1-(4-phenoxyphenyl)-3-(2-phenylethyl)-1H-indol-5-yl]propanoate

The same reaction was performed as in Example 148 except for using, instead of the 2-bromonitrobenzene, 4-bromodiphenyl ether. That is, to a solution of the compound obtained at Example 142 (60 mg) in n-butyl acetate (4.5 ml) were added 4-bromodiphenyl ether (93 mg), palladium acetate (4.3 mg), 2-(di-tert-butylphosphino)biphenyl (11.4 mg) and tripotassium phosphate (161 mg), and the mixture was heated and stirred at 120° C. for 24 hours. The reaction mixture was cooled to room temperature, then the insolubles were filtered off, the filtrate was distilled off in vacuo and the residue obtained was purified by silica gel column chromatography (hexane:ethyl acetate=9:1 to 3:2) to afford the above-identified compound (77 mg).

Further, the above-identified compound was also obtained by the following method.

To a solution of the compound obtained at Example 142 (3.58 g) in N,N-dimethylformamide (11 ml) were added 4-bromodiphenyl ether (5.55 g), copper(I) iodide (212 mg), N,N'-dimethylethylenediamine (393 mg), tripotassium phosphate (4.96 g) and sodium iodide (3.34 g), and the mixture was heated and stirred at 110° C. for 5 hours. The reaction mixture was cooled to room temperature, then toluene (18 ml) was added, the precipitated insolubles were filtered off, saturated aqueous potassium hydrogen sulfate solution (10 ml), water (5.0 ml), and 2N-hydrochloric acid (10 ml) were added to the filtrate and the mixture was washed with brine and dried with anhydrous magnesium sulfate. The solvent was distilled off in vacuo and the residue obtained was purified by silica gel column chromatography (hexane:ethyl acetate=9:1 to 3:2) to afford the above-identified compound (4.64 g).

Example 231

3-[1-(4-phenoxyphenyl)-3-(2-phenylethyl)-1H-indol-5-yl]propanoic acid 2-amino-2-(hydroxymethyl)propane-1,3-diol salt (1:1)

Step 1

The same reaction was performed as in Example 144 except for using, instead of the compound obtained at Example 143, the compound obtained at Example 230. That is, to a solution of the compound obtained at Example 230 (77 mg) in tetrahydrofuran (4.0 ml)-ethanol (3.0 ml) mixed solvent was added 1 mol/l aqueous sodium hydroxide solution (0.32 ml), and the mixture was stirred at room temperature over night. To the reaction mixture was added 1 mol/l hydrochloric acid (0.40 ml), and the mixture was extracted with ethyl acetate and the organic layer was successively washed with water and brine, and dried over anhydrous sodium sulfate. The solvent was distilled off in vacuo and the residue obtained was purified by silica gel column chromatography (methylene chloride:methanol=99:1 to 17:3) to afford 3-[1-(4-phenoxyphenyl)-3-(2-phenylethyl)-1H-indol-5-yl]propanoic acid (43 mg).

Step 2

The same reaction was performed as in Example 190 except for using, instead of the compound obtained at Example 189, the compound obtained above. That is, the compound obtained at the above Step 1 (43 mg) was dissolved in an ethanol (2.0 ml)/water (1.0 ml) mixed solvent, tris (hydroxymethyl)aminoethane (11.3 mg) was added, the resultant solution was stirred for a while, then the solvent was distilled off in vacuo to afford the above-identified compound (54 mg).

Example 232

Ethyl 3-[1-(2,3-dihydro-1,4-benzodioxin-6-yl)-3-(2-phenylethyl)-1H-indol-5-yl]propanoate The same reaction was performed as in Example 148 except for using, instead of 2-bromonitrobenzene, 6-bromo-1,4-benzodioxane to afford the above-identified compound (63 mg).

Example 233

3-[1-(2,3-dihydro-1,4-benzodioxin-6-yl)-3-(2-phenylethyl)-1H-indol-5-yl]propanoic acid 2-amino-2-(hydroxymethyl)propane-1,3-diol salt (1:1)

Step 1

The same reaction was performed as in Example 144 except for using, instead Of the compound obtained at Example 143, the compound obtained at Example 232 to afford 3-[1-(2,3-dihydro-1,4-benzodioxin-6-yl)-3-(2-phenylethyl)-1H-indol-5-yl]propanoic acid (10 mg).

Step 2

The same reaction was performed as in Example 190 except for using, instead of the compound obtained at Example 189, the compound obtained above to afford the above-identified compound (13 mg).

Example 234

Ethyl 3-{3-(2-phenylethyl)-1-[4-(pyridin-2-ylmethyl)phenyl]-1H-indol-5-yl}propanoate The same reaction was performed as in Example 148 except for using, instead of 2-bromonitrobenzene, 2-(p-chlorobenzyl)pyridine to afford the above-identified compound (137 mg).

Example 235

3-{3-(2-phenylethyl)-1-[4-(pyridin-2-ylmethyl)phenyl]-1H-indol-5-yl}propanoic acid hydrochloride Step 1

The same reaction was performed as in Example 144 except for using, instead of the compound obtained at Example 143, the compound obtained at Example 234 to afford 3-[3-(2-phenylethyl)-1-[4-(pyridin-2-ylmethyl)phenyl]-1H-indol-5-yl]propanoic acid (23 mg).

Step 2

The compound obtained above (49 mg) was dissolved in tetrahydrofuran (1.0 ml), 4N-hydrochloric acid/1,4-dioxane solution (0.015 ml) was added, then the solvent was distilled off in vacuo. The residue was redissolved in methylene chloride (1.0 ml) and diluted with diethyl ether, then the precipitated crystal was collected by filtration to afford the above-identified compound (14 mg).

Example 236

Ethyl 3-{3-(2-phenylethyl)-1-[4-(pyridin-4-ylmethyl)phenyl]-1H-indol-5-yl}propanoate The same reaction was performed as in Example 148 except for using, instead of 2-bromonitrobenzene, 4-(p-chlorobenzyl)pyridine to afford the above-identified compound (83 mg).

Example 237

3-{3-(2-phenylethyl)-1-[4-(pyridin-4-ylmethyl)phenyl]-1H-indol-5-yl}propanoic acid hydrochloride Step 1
The same reaction was performed as in Example 144 except for using, instead of the compound obtained at Example 143, the compound obtained at Example 236 to afford 3-{3-(2-phenylethyl)-1-[4-(pyridin-4-ylmethyl)phenyl]-1H-indol-5-yl}propanoic acid (10 mg).
Step 2
The compound obtained above (10 mg) was dissolved in tetrahydrofuran (1.0 ml), 4N-hydrochloric acid/1,4-dioxane solution (0.008 ml) was added and the solvent was distilled off in vacuo to afford the above-identified compound (11 mg).

Example 238

Ethyl (2E)-3-[1-(4-hydroxyphenyl)-3-(2-phenylethyl)-1H-indol-5-yl]-2-propenoate

A solution of the compound obtained at Example 143 (164 mg) in methylene chloride (3.0 ml) was cooled to −78° C., 1 mol/l boron tribromide/methylene chloride (0.070 ml) solution was added, and the mixture was stirred for 40 minutes. To the reaction mixture were added water and methylene chloride, and the organic layer was successively washed with saturated aqueous sodium hydrogen carbonate solution, water and brine and dried over anhydrous sodium sulfate. The solvent was distilled off in vacuo and the residue obtained was purified by silica gel column chromatography (hexane:ethyl acetate=9:1 to 1:1) to afford the above-identified compound (101 mg).

Example 239

(2E)-3-[1-(4-hydroxyphenyl)-3-(2-phenylethyl)-1H-indol-5-yl]-2-propenoic acid

The same reaction was performed as in Example 144 except for using, instead of the compound obtained at Example 143, the compound obtained at Example 238 to afford the above-identified compound (71 mg).

Example 240

Ethyl 3-{1-[4-(benzyloxy)phenyl]-3-(2-phenylethyl)-1H-indol-5-yl}propanoate

The same reaction was performed as in Example 143 except for using, instead of the compound obtained at Example 141, the compound obtained at Example 142 to afford the above-identified compound (3.6 g).

Example 241

Ethyl 3-[1-(4-hydroxyphenyl)-3-(2-phenylethyl)-1H-indol-5-yl]propanoate

The same reaction was performed as in Example 146 except for using, instead of the compound obtained at Example 145, the compound obtained at Example 240 to afford the above-identified compound (1.3 g).

Example 242

Ethyl 3-{3-(2-phenylethyl)-1-[4-(tetrahydro-2H-pyran-2-ylmethoxy)phenyl]-1H-indol-5-yl}propanoate The compound obtained at Example 241 (57 mg), tetrahydropyran-2-methanol (0.016 ml), and triphenylphosphine (37 mg) were dissolved in tetrahydrofuran (3.0 ml), the mixture was cooled to 5° C., 40% diethylazodicarboxylate/toluene solution (0.026 ml) was added and the mixture was stirred at room temperature for 20 hours. The solvent was distilled off in vacuo and the residue obtained was purified by silica gel column chromatography (hexane:ethyl acetate=23:2 to 3:2) to afford the above-identified compound (50 mg).

Example 243

3-{3-(2-phenylethyl)-1-[4-(tetrahydro-2H-pyran-2-ylmethoxy)phenyl]-1H-indol-5-yl}propanoic acid 2-amino-2-(hydroxymethyl)propane-1,3-diol salt (1:1)

Step 1
The same reaction was performed as in Example 144 except for using, instead of the compound obtained at Example 143, the compound obtained at Example 242 to afford 3-{3-(2-phenylethyl)-1-[4-(tetrahydro-2H-pyran-2-ylmethoxy)phenyl]-1H-indol-5-yl}propanoic acid (51 mg).
Step 2
The same reaction was performed as in Example 190 except for using, instead of the compound obtained at Example 189, the compound obtained above to afford the above-identified compound (64 mg).

Example 244

Ethyl 3-{3-(2-phenylethyl)-1-[4-(pyridin-2-ylmethoxy)phenyl]-1H-indol-5-yl}propanoate The same reaction was performed as in Example 242 except for using, instead of tetrahydropyran-2-methanol, 2-pyridinemethanol to afford the above-identified compound (87 mg).

Example 245

3-{3-(2-phenylethyl)-1-[4-(pyridin-2-ylmethoxy)phenyl]-1H-indol-5-yl}propanoic acid The same reaction was performed as in Example 144 except for using, instead of the compound obtained at Example 143, the compound obtained at Example 244 to afford the above-identified compound (66 mg).

Example 246

3-{3-(2-phenylethyl)-1-[4-(pyridin-2-ylmethoxy)phenyl]-1H-indol-5-yl}propanoic acid hydrochloride The compound obtained at Example 245 (59 mg) was dissolved in methylene chloride (2.0 ml), a 4N-hydrochloric acid/1,4-dioxane solution (0.035 ml) was added and the mixture was diluted with diethyl ether. The precipitated crystal was collected by filtration to afford the above-identified compound (48 mg).

Example 247

Ethyl 3-{3-(2-phenylethyl)-1-[4-(pyridin-3-ylmethoxy)phenyl]-1H-indol-5-yl}propanoate The same reaction was performed as in Example 242 except for using, instead of tetrahydropyran-2-methanol, 3-pyridinemethanol to afford the above-identified compound (187 mg).

Example 248

3-{3-(2-phenylethyl)-1-[4-(pyridin-3-ylmethoxy)phenyl]-1H-indol-5-yl}propanoic acid The same reaction was performed as in Example 144 except for using, instead of the compound obtained at Example 143, the compound obtained at Example 247 to afford the above-identified compound (91 mg).

Example 249

3-{3-(2-phenylethyl)-1-[4-(pyridin-3-ylmethoxy)phenyl]-1H-indol-5-yl}propanoic acid hydrochloride The same reaction was performed as in Example 246 except for using, instead of the compound obtained at Example 245, the compound obtained at Example 248 to afford the above-identified compound (98 mg).

Example 250

Ethyl 3-{3-(2-phenylethyl)-1-[4-(2-pyridin-2-ylethoxy)phenyl]-1H-indol-5-yl}propanoate The same reaction was performed as in Example 242 except for using, instead of tetrahydropyran-2-methanol, 2-(2-hydroxyethyl)pyridine to afford the above-identified compound (111 mg).

Example 251

3-{3-(2-phenylethyl)-1-[4-(2-pyridin-2-ylethoxy)phenyl]-1H-indol-5-yl}propanoic acid The same reaction was performed as in Example 144 except for using, instead of the compound obtained at Example 143, the compound obtained at Example 250 to afford the above-identified compound (62 mg).

Example 252

Ethyl 3-{3-(2-phenylethyl)-1-[4-(2-pyridin-3-ylethoxy)phenyl]-1H-indol-5-yl}propanoate The same reaction was performed as in Example 242 except for using, instead of tetrahydropyran-2-methanol, 3-(2-hydroxyethyl)pyridine to afford the above-identified compound (155 mg).

Example 253

3-{3-(2-phenylethyl)-1-[4-(2-pyridin-3-ylethoxy)phenyl]-1H-indol-5-yl}propanoic acid The same reaction was performed as in Example 144 except for using, instead of the compound obtained at Example 143, the compound obtained at Example 252 to afford the above-identified compound (90 mg).

Example 254

Ethyl 3-{3-(2-phenylethyl)-1-[4-(2-pyridin-4-ylethoxy)phenyl]-1H-indol-5-yl}propanoate The same reaction was performed as in Example 242 except for using, instead of tetrahydropyran-2-methanol, 4-(2-hydroxyethyl)pyridine to afford the above-identified compound (96 mg).

Example 255

3-{3-(2-phenylethyl)-1-[4-(2-pyridin-4-ylethoxy)phenyl]-1H-indol-5-yl}propanoic acid The same reaction was performed as in Example 144 except for using, instead of the compound obtained at Example 143, the compound obtained at Example 254 to afford the above-identified compound (16 mg).

Example 256

Ethyl 3-{3-(2-phenylethyl)-1-[4-(3-pyridin-3-ylpropoxy)phenyl]-1H-indol-5-yl}propanoate The same reaction was performed as in Example 242 except for using, instead of tetrahydropyran-2-methanol, the 3-pyridinepropanol to afford the above-identified compound (74 mg).

Example 257

3-{3-(2-phenylethyl)-1-[4-(3-pyridin-3-ylpropoxy)phenyl]-1H-indol-5-yl}propanoic acid The same reaction was performed as in Example 144 except for using, instead of the compound obtained at Example 143, the compound obtained at Example 256 to afford the above-identified compound (40 mg).

Example 258

3-{3-(2-phenylethyl)-1-[4-(3-pyridin-3-ylpropoxy)phenyl]-1H-indol-5-yl}propanoic acid hydrochloride The same reaction was performed as in Example 246 except for using, instead of the compound obtained at

Example 259

Ethyl 3-{3-(2-phenylethyl)-1-[4-(3-pyridin-4-ylpropoxy)phenyl]-1H-indol-5-yl}propanoate The same reaction was performed as in Example 242 except for using, instead of tetrahydropyran-2-methanol, 4-pyridinepropanol to afford the above-identified compound (70 mg).

Example 260

3-{3-(2-phenylethyl)-1-[4-(3-pyridin-4-ylpropoxy)phenyl]-1H-indol-5-yl}propanoic acid The same reaction was performed as in Example 144 except for using, instead of the compound obtained at Example 143, the compound obtained at Example 259 to afford the above-identified compound (51 mg).

Example 261

5-bromo-1-phenyl-3-(2-pyridin-2-ylethyl)-1H-indole

A mixture of the compound obtained at Reference Example 5 (301 mg), iodobenzene (1.45 ml), potassium carbonate (550 mg), potassium hydroxide (66 mg), copper(II) acetate (18 mg) and copper(I) bromide (14 mg) was stirred at 150° C. over night. From the reaction mixture, the insolubles were filtered off, the filtrate was distilled off in vacuo and the residue obtained was purified by basic silica gel column chromatography (hexane:ethyl acetate=9:1 to 3:2) to afford the above-identified compound (313 mg).

Example 262

Ethyl (2E)-3-[1-phenyl-3-(2-pyridin-2-ylethyl)-1H-indol-5-yl]-2-propenoate

The same reaction was performed as in Example 141 except for using, instead of the Reference Example 4, the compound obtained at Example 261 to afford the above-identified compound (254 mg).

Example 263

(2E)-3-[1-phenyl-3-(2-pyridin-2-ylethyl)-1H-indol-5-yl]-2-propenoic acid

The same reaction was performed as in Example 144 except for using, instead of the compound obtained at Example 143, the compound obtained at Example 262 to afford the above-identified compound (100 mg).

Example 264

3-[1-phenyl-3-(2-pyridin-2-ylethyl)-1H-indol-5-yl]propanoic acid

The same reaction was performed as in Example 4 except for using, instead of the compound obtained at Example 3, the compound obtained at Example 263 to afford the above-identified compound (23 mg).

Example 265

1-[4-(benzyloxy)phenyl]-5-bromo-3-(2-pyridin-2-ylethyl)-1H-indole

The same reaction was performed as in Example 261 except for using, instead of iodobenzene, 4-benzyloxyiodobenzene to afford the above-identified compound (426 mg).

Example 266

Ethyl (2E)-3-{1-[4-(benzyloxy)phenyl]-3-(2-pyridin-2-ylethyl)-1H-indol-5-yl}-2-propenoate The same reaction was performed as in Example 141 except for using, instead of the Reference Example 4, the compound obtained at Example 265 to afford the above-identified compound (112 mg).

Example 267

(2E)-3-{1-[4-(benzyloxy)phenyl]-3-(2-pyridin-2-ylethyl)-1H-indol-5-yl}-2-propenoic acid The same reaction was performed as in Example 144 except for using, instead of the compound obtained at Example 143, the compound obtained at Example 266 to afford the above-identified compound (81 mg).

Example 268

3-{1-[4-(benzyloxy)phenyl]-3-(2-pyridin-2-ylethyl)-1H-indol-5-yl}propanoic acid

The same reaction was performed as in Example 4 except for using, instead of the compound obtained at Example 3, the compound obtained at Example 267 to afford the above-identified compound (41 mg).

Example 269

3-[1-(4-hydroxyphenyl)-3-(2-pyridin-2-ylethyl)-1H-indol-5-yl]propanoic acid hydrochloride Step 1
The same reaction was performed as in Example 4 except for using, instead of the compound obtained at Example 3, the compound obtained at Example 267 to obtain 3-[1-(4-hydroxyphenyl)-3-(2-pyridin-2-ylethyl)-1H-indol-5-yl]propanoic acid (48 rug).

Step 2
The compound obtained above (10 mg) was dissolved in tetrahydrofuran (2.0 ml), 4N-hydrochloric acid/1,4-dioxane solution (0.015 ml) was added and the solvent was distilled off in vacuo to afford the above-identified compound (21 mg).

Example 270

Ethyl (2E)-3-[1-(4-hydroxyphenyl)-3-(2-pyridin-2-ylethyl)-1H-indol-5-yl]-2-propenoate The same reaction was performed as in Example 238 except for using, instead of the compound obtained at Example 143, the compound obtained at Example 266 to afford the above-identified compound (123 mg).

Example 271

(2E)-3-[1-(4-hydroxyphenyl)-3-(2-pyridin-2-yl-ethyl)-1H-indol-5-yl]-2-propenoic acid The same reaction was performed as in Example 144 except for using, instead of the compound obtained at Example 143, the compound obtained at Example 270 to afford the above-identified compound (6.0 mg).

Example 272

Ethyl (2E)-3-[3-(2-pyridin-2-ylethyl)-1H-indol-5-yl]-2-propenoate

The same reaction was performed as in Example 141 except for using, instead of the Reference Example 4, the Reference Example 5 to afford the above-identified compound (2.3 g).

Example 273

Ethyl 3-[3-(2-pyridin-2-ylethyl)-1H-indol-5-yl]propanoate

The same reaction was performed as in Example 142 except for using, instead of the compound obtained at Example 141, the compound obtained at Example 272 to afford the above-identified compound (1.3 g).

Example 274

Ethyl 3-[1-(4-phenoxyphenyl)-3-(2-pyridin-2-yl-ethyl)-1H-indol-5-yl]propanoate

To a solution of the compound obtained at Example 273 (40 mg) in n-butyl acetate (4.0 ml) were added 4-bromodiphenyl ether (62 mg), palladium acetate (5.4 mg), 2-(di-tert-butylphosphino)biphenyl (14 mg) and tripotassium phosphate (102 mg), and the mixture was heated and refluxed at 120° C. for 24 hours. The reaction mixture was cooled, then the insolubles were filtered off, the filtrate was distilled off in vacuo and the residue obtained was purified by silica gel column chromatography (hexane:ethyl acetate=9:1 to 1:1) to afford the above-identified compound (43 mg).

Example 275

3-[1-(4-phenoxyphenyl)-3-(2-pyridin-2-ylethyl)-1H-indol-5-yl]propanoic acid hydrochloride Step 1

The same reaction was performed as in Example 144 except for using, instead of the compound obtained at Example 143, the compound obtained at Example 274 to afford 3-[1-(4-phenoxyphenyl)-3-(2-pyridin-2-ylethyl)-1H-indol-5-yl]propanoic acid (40 mg).

Step 2

The compound obtained above (40 mg) was dissolved in tetrahydrofuran (1.0 ml), 4N-hydrochloric acid/1,4-dioxane solution (0.025 ml) was added, and the solvent was distilled off in vacuo to afford the above-identified compound (43 mg).

Example 276

Ethyl 3-{1-[4-(difluoromethoxy)phenyl]-3-(2-pyridin-2-ylethyl)-1H-indol-5-yl}propanoate The same reaction was performed as in Example 274 except for using, instead of 4-bromodiphenyl ether, 4-(difluoromethoxy)bromobenzene to afford the above-identified compound (42 mg).

Example 277

3-{1-[4-(difluoromethoxy)phenyl]-3-(2-pyridin-2-ylethyl)-1H-indol-5-yl}propanoic acid hydrochloride The same reaction was performed as in Example 275 except for using, instead of the compound obtained at Example 274, the compound obtained at Example 276 to afford the above-identified compound (29 mg).

Example 278

Ethyl 3-{1-[4-(2-hydroxyethoxy)phenyl]-3-(2-pyridin-2-ylethyl)-1H-indol-5-yl}propanoate The same reaction was performed as in Example 274 except for using, instead of 4-bromodiphenyl ether, ethylene glycol mono(4-bromophenyl)ether to afford the above-identified compound (71 mg).

Example 279

3-{1-[4-(2-hydroxyethoxy)phenyl]-3-(2-pyridin-2-ylethyl)-1H-indol-5-yl}propanoic acid hydrochloride The same reaction was performed as in Example 275 except for using, instead of the compound obtained at Example 274, the compound obtained at Example 278 to afford the above-identified compound (69 mg).

Example 280

Ethyl 3-{1-[3-(benzyloxy)phenyl]-3-(2-pyridin-2-ylethyl)-1H-indol-5-yl}propanoate The same reaction was performed as in Example 274 except for using, instead of 4-bromodiphenyl ether, 3-(benzyloxy)bromobenzene to afford the above-identified compound (101 mg).

Example 281

3-{1-[3-(benzyloxy)phenyl]-3-(2-pyridin-2-ylethyl)-1H-indol-5-yl}propanoic acid hydrochloride Step 1

The same reaction was performed as in Example 144 except for using, instead of the compound obtained at Example 143, the compound obtained at Example 280 to afford 3-{1-[3-(benzyloxy)phenyl]-3-(2-pyridin-2-ylethyl)-1H-indol-5-yl}propanoic acid (106 mg).

Step 2

The compound obtained above (15 mg) was dissolved in methylene chloride (1.0 ml), 4N-hydrochloric acid/1,4-diox-

Example 282

3-[1-(3-hydroxyphenyl)-3-(2-pyridin-2-ylethyl)-1H-indol-5-yl]propanoic acid hydrochloride Step 1
The same reaction was performed as in Example 4 except for using, instead of the compound obtained at Example 3, the compound obtained at Step 1 of Example 281 to afford 3-[1-(3-hydroxyphenyl)-3-(2-pyridin-2-ylethyl)-1H-indol-5-yl]propanoic acid (28 mg).
Step 2
The compound obtained above (28 mg) was dissolved in methylene chloride (2.0 ml), 4N-hydrochloric acid/1,4-dioxane solution (0.020 ml) was added, and the solvent was distilled off in vacuo to afford the above-identified compound (31 mg).

Example 283

N-benzyloxy-3-[1-(4-hydroxyphenyl)-3-(2-phenylethyl)-1H-indol-5-yl]propanamide

To a solution of the compound obtained at Example 126 (111 mg) in N,N-dimethylformamide (5.0 ml) were added O-benzylhydroxylamine hydrochloride (70 mg), triethylamine (0.29 ml), and 50% n-propylphosphonic acid anhydride/ethyl acetate solution (0.31 ml), and the mixture was heated and stirred at room temperature for 26 hours. The reaction mixture was poured into water, the mixture was extracted with ethyl acetate and the organic layer was successively washed with water and brine and dried over anhydrous sodium sulfate. The solvent was distilled off in vacuo, and the residue obtained was purified by silica gel column chromatography (hexane:ethyl acetate=4:1 to 3:2) to afford the above-identified compound (70 mg).

Example 284

N-hydroxy-3-[1-(4-hydroxyphenyl)-3-(2-phenylethyl)-1H-indol-5-yl]propanamide

The same reaction was performed as in Example 4 except for using, instead of the compound obtained at Example 3, the compound obtained at Example 283 to afford the above-identified compound (39 mg).

Example 285

N-benzyloxy-3-{1-[4-(difluoromethoxy)phenyl]-3-(2-phenylethyl)-1H-indol-5-yl}propanamide The same reaction was performed as in Example 283 except for using, instead of the compound obtained at Example 126, the compound obtained at Example 189 to afford the above-identified compound (134 mg).

Example 286

3-{1-[4-(difluoromethoxy)phenyl]-3-(2-phenylethyl)-1H-indol-5-yl}-N-hydroxypropanamide The same reaction was performed as in Example 4 except for using, instead of the compound obtained at Example 3, the compound obtained at Example 285 to afford the above-identified compound (64 mg).

Example 287

Ethyl 3-{1-[4-(benzyloxy)-3,5-difluorophenyl]-3-(2-phenylethyl)-1H-indol-5-yl}propanoate The same reaction was performed as in Example 148 except for using, instead of 2-bromonitrobenzene, 4-(benzyloxy)-3,5-difluorobromobenzene to afford the above-identified compound (128 mg).

Example 288

3-{1-[4-(benzyloxy)-3,5-difluorophenyl]-3-(2-phenylethyl)-1H-indol-5-yl}propanoic acid 2-amino-2-(hydroxymethyl)propane-1,3-diol salt (1:1)

Step 1
The same reaction was performed as in Example 144 except for using, instead of the compound obtained at Example 143, the compound obtained at Example 287 to afford 3-{1-[4-(benzyloxy)-3,5-difluorophenyl]-3-(2-phenylethyl)-1H-indol-5-yl}propanoic acid (111 mg).
Step 2
The same reaction was performed as in Example 190 except for using, instead of the compound obtained at Example 189, the compound obtained above to afford the above-identified compound (126 mg).

Example 289

3-[1-(3,5-difluoro-4-hydroxyphenyl)-3-(2-phenylethyl)-1H-indol-5-yl]propanoic acid The same reaction was performed as in Example 4 except for using, instead of the compound obtained at Example 3, the compound obtained at Example 288 to afford the above-identified compound (35 mg).

Example 290

Ethyl 3-[1-{4-[(4-fluorophenoxy)methyl]phenyl}-3-(2-phenylethyl)-1H-indol-5-yl]propanoate The same reaction was performed as in Example 148 except for using, instead of 2-bromonitrobenzene, (4-bromobenzyl) (4-fluorophenyl)ether to afford the above-identified compound (115 mg).

Example 291

3-[1-{4-[(4-fluorophenoxy)methyl]phenyl}-3-(2-phenylethyl)-1H-indol-5-yl]propanoic acid 2-amino-2-(hydroxymethyl)propane-1,3-diol salt (1:1)

Step 1
The same reaction was performed as in Example 144 except for using, instead of the compound obtained at Example 143, the compound obtained at Example 290 to afford 3-[1-{4-[(4-fluorophenoxy)methyl]phenyl}-3-(2-phenylethyl)-1H-indol-5-yl]propanoic acid (95 mg).
Step 2
The same reaction was performed as in Example 190 except for using, instead of the compound obtained at Example 189, the compound obtained above to afford the above-identified compound (113 mg).

Example 292

Ethyl 3-[1-{4-[(difluoromethoxy)methyl]phenyl}-3-(2-phenylethyl)-1H-indol-5-yl]propanoate The same reaction was performed as in Example 148 except for using, instead of 2-bromonitrobenzene, the compound obtained at Reference Example 6 to afford the above-identified compound (102 mg).

Example 293

3-[1-{4-[(difluoromethoxy)methyl]phenyl}-3-(2-phenylethyl)-1H-indol-5-yl]propanoic acid The same reaction was performed as in Example 144 except for using, instead of the compound obtained at Example 143, the compound obtained at Example 292 to afford the above-identified compound (95 mg).

Example 294

Ethyl 3-{1-[4-(1-acetoxyethyl)phenyl]-3-(2-phenylethyl)-1H-indol-5-yl}propanoate The same reaction was performed as in Example 148 except for using, instead of 2-bromonitrobenzene, ethyl 1-(4-bromophenyl)acetate to afford the above-identified compound (136 mg).

Example 295

3-{1-[4-(1-hydroxyethyl)phenyl]-3-(2-phenylethyl)-1H-indol-5-yl}propanoic acid 2-amino-2-(hydroxymethyl)propane-1,3-diol salt (1:1)

Step 1
The same reaction was performed as in Example 144 except for using, instead of the compound obtained at Example 143, the compound obtained at Example 294 to afford 3-{1-[4-(1-hydroxyethyl)phenyl]-3-(2-phenylethyl)-1H-indol-5-yl}propanoic acid (134 mg).

Step 2
The same reaction was performed as in Example 190 except for using, instead of the compound obtained at Example 189, the compound obtained above to afford the above-identified compound (95 mg).

Example 296

Ethyl 3-{1-[4-(benzyloxy)-3,5-difluorophenyl]-3-(2-pyridin-2-ylethyl)-1H-indol-5-yl}propanoate The same reaction was performed as in Example 274 except for using, instead of 4-bromodiphenyl ether, 4-(benzyloxy)-3,5-difluorobromobenzene to afford the above-identified compound (106 mg).

Example 297

3-{1-[4-(benzyloxy)-3,5-difluorophenyl]-3-(2-pyridin-2-ylethyl)-1H-indol-5-yl}propanoic acid The same reaction was performed as in Example 144 except for using, instead of the compound obtained at Example 143, the compound obtained at Example 296 to afford the above-identified compound (85 mg).

Example 298

3-[1-(3,5-difluoro-4-hydroxyphenyl)-3-(2-pyridin-2-ylethyl)-1H-indol-5-yl]propanoic acid hydrochloride Step 1
The same reaction was performed as in Example 4 except for using, instead of the compound obtained at Example 3, the compound obtained at Example 297 to afford 3-[1-(3,5-difluoro-4-hydroxyphenyl)-3-(2-pyridin-2-ylethyl)-1H-indol-5-yl]propanoic acid (42 mg).

Step 2
The compound obtained above (42 mg) was dissolved in tetrahydrofuran (1.0 ml)-acetonitrile (1.0 ml) mixed solvent, a 4N-hydrochloric acid/1,4-dioxane solution (0.025 ml) was added and the solvent was distilled off in vacuo to afford the above-identified compound (46 mg).

Example 299

Ethyl 3-[1-{4-[(4-fluorophenoxy)methyl]phenyl}-3-(2-pyridin-2-ylethyl)-1H-indol-5-yl]propanoate The same reaction was performed as in Example 274 except for using, instead of 4-bromodiphenyl ether, (4-bromobenzyl) (4-fluorophenyl)ether to afford the above-identified compound (27 mg).

Example 300

3-[1-{4-[(4-fluorophenoxy)methyl]phenyl}-3-(2-pyridin-2-ylethyl)-1H-indol-5-yl]propanoic acid hydrochloride Step 1
The same reaction was performed as in Example 144 except for using, instead of the compound obtained at Example 143, the compound obtained at Example 299 to afford 3-[1-{4-[(4-fluorophenoxy)methyl]phenyl}-3-(2-pyridin-2-ylethyl)-1H-indol-5-yl]propanoic acid (18 mg).

Step 2
The compound obtained above (18 mg) was dissolved in methylene chloride (1.0 ml), 4N-hydrochloric acid/1,4-dioxane solution (0.010 ml) was added, and the solvent was distilled off in vacuo to afford the above-identified compound (20 mg).

Example 301

Ethyl 3-[1-{4-[(difluoromethoxy)methyl]phenyl}-3-(2-pyridin-2-ylethyl)-1H-indol-5-yl]propanoate The same reaction was performed as in Example 274 except for using, instead of 4-bromodiphenyl ether, the compound obtained at Reference Example 6 to afford the above-identified compound (78 mg).

Example 302

3-[1-{4-[(difluoromethoxy)methyl]phenyl}-3-(2-pyridin-2-ylethyl)-1H-indol-5-yl]propanoic acid hydrochloride Step 1
The same reaction was performed as in Example 144 except for using, instead of the compound obtained at Example 143, the compound obtained at Example 301 to afford 3-[1-{4-[(difluoromethoxy)methyl]phenyl}-3-(2-pyridin-2-ylethyl)-1H-indol-5-yl]propanoic acid (71 mg).

Step 2
The compound obtained above (71 mg) was dissolved in methylene chloride (2.0 ml), 4N-hydrochloric acid/1,4-dioxane solution (0.040 ml) was added, and the solvent was distilled off in vacuo to afford the above-identified compound (77 mg).

Example 303

Ethyl 3-{1-[4-(1-acetoxyethyl)phenyl]-3-(2-pyridin-2-ylethyl)-1H-indol-5-yl}propanoate The same reaction was performed as in Example 274 except for using, instead of 4-bromodiphenyl ether, ethyl 1-(4-bromophenyl)acetate to afford the above-identified compound (123 mg).

Example 304

3-{1-[4-(1-hydroxyethyl)phenyl]-3-(2-pyridin-2-ylethyl)-1H-indol-5-yl}propanoic acid hydrochloride Step 1
The same reaction was performed as in Example 144 except for using, instead of the compound obtained at Example 143, the compound obtained at Example 301 to afford 3-{1-[4-(1-hydroxyethyl)phenyl]-3-(2-pyridin-2-ylethyl)-1H-indol-5-yl}propanoic acid (99 mg).
Step 2
The compound obtained above (99 mg) was dissolved in methylene chloride (3.0 ml), 4N-hydrochloric acid/1,4-dioxane solution (0.060 ml) was added, and the solvent was distilled off in vacuo to afford the above-identified compound (108 mg).

Example 305

Ethyl 3-{3-(2-phenylethyl)-1-[4-(pyrrolidin-1-ylmethyl)phenyl]-1H-indol-5-yl}propanoate The same reaction was performed as in Example 148 except for using, instead of 2-bromonitrobenzene, 1-(4-bromobenzyl)pyrrolidine to afford the above-identified compound (72 mg).

Example 306

3-{3-(2-phenylethyl)-1-[4-(pyrrolidin-1-ylmethyl)phenyl]-1H-indol-5-yl}propanoic acid The same reaction was performed as in Example 144 except for using, instead of the compound obtained at Example 143, the compound obtained at Example 305 to afford the above-identified compound (50 mg).

Example 307

Ethyl 3-{1-[4-(morpholin-4-ylmethyl)phenyl]-3-(2-phenylethyl)-1H-indol-5-yl}propanoate The same reaction was performed as in Example 148 except for using, instead of 2-bromonitrobenzene, 4-(4-bromobenzyl)morpholine to afford the above-identified compound (123 mg).

Example 308

3-{1-[4-(morpholin-4-ylmethyl)phenyl]-3-(2-phenylethyl)-1H-indol-5-yl}propanoic acid The same reaction was performed as in Example 144 except for using, instead of the compound obtained at Example 143, the compound obtained at Example 307 to afford the above-identified compound (71 mg).

Example 309

Ethyl 3-[1-{4-[(dimethylamino)carbonyl]phenyl}-3-(2-phenylethyl)-1H-indol-5-yl]propanoate The same reaction was performed as in Example 148 except for using, instead of 2-bromonitrobenzene, 4-bromodimethylbenzamide to afford the above-identified compound (54 mg).

Example 310

3-[1-{4-[(dimethylamino)carbonyl]phenyl}-3-(2-phenylethyl)-1H-indol-5-yl]propanoic acid The same reaction was performed as in Example 144 except for using, instead of the compound obtained at Example 143, the compound obtained at Example 309 to afford the above-identified compound (28 mg).

Example 311

Ethyl 3-{1-[4-(morpholin-4-ylcarbonyl)phenyl]-3-(2-phenylethyl)-1H-indol-5-yl}propanoate The same reaction was performed as in Example 148 except for using, instead of 2-bromonitrobenzene, (4-bromophenyl)morpholin-4-ylmethanone to afford the above-identified compound (112 mg).

Example 312

3-{1-[4-(morpholin-4-ylcarbonyl)phenyl]-3-(2-phenylethyl)-1H-indol-5-yl}propanoic acid The same reaction was performed as in Example 144 except for using, instead of the compound obtained at Example 143, the compound obtained at Example 311 to afford the above-identified compound (43 mg).

Example 313

Ethyl 3-{1-[3-(dimethylcarbamoyl)phenyl]-3-(2-phenylethyl)-1H-indol-5-yl}propanoate The same reaction was performed as in Example 148 except for using, instead of 2-bromonitrobenzene, 3-bromo-N,N-dimethylbenzamide to afford the above-identified compound (54 mg).

Example 314

3-{1-[3-(dimethylcarbamoyl)phenyl]-3-(2-phenylethyl)-1H-indol-5-yl}propanoic acid The same reaction was performed as in Example 144 except for using, instead of the compound obtained at Example 143, the compound obtained at Example 313 to afford the above-identified compound (28 mg).

Example 315

Ethyl 3-{1-[3-(morpholin-4-ylcarbonyl)phenyl]-3-(2-phenylethyl)-1H-indol-5-yl}propanoate The same reaction was performed as in Example 148 except for using, instead of 2-bromonitrobenzene, (3-bromophenyl)morpholin-4-ylmethanone to afford the above-identified compound (67 mg).

Example 316

3-{1-[3-(morpholin-4-ylcarbonyl)phenyl]-3-(2-phenylethyl)-1H-indol-5-yl}propanoic acid The same reaction was performed as in Example 144 except for using, instead of the compound obtained at Example 143, the compound obtained at Example 315 to afford the above-identified compound (40 mg).

Example 317

Ethyl 3-[1-{4-[(dimethylamino)sulfonyl]phenyl}-3-(2-phenylethyl)-1H-indol-5-yl]propanoate The same reaction was performed as in Example 148 except for using, instead of 2-bromonitrobenzene, 4-bromo-N,N-dimethylbenzenesulfonamide to afford the above-identified compound (98 mg).

Example 318

3-[1-{4-[(dimethylamino)sulfonyl]phenyl}-3-(2-phenylethyl)-1H-indol-5-yl]propanoic acid The same reaction was performed as in Example 144 except for using, instead of the compound obtained at Example 143, the compound obtained at Example 317 to afford the above-identified compound (82 mg).

Example 319

Ethyl 3-{1-[4-(morpholin-4-ylsulfonyl)phenyl]-3-(2-phenylethyl)-1H-indol-5-yl}propanoate The same reaction was performed as in Example 148 except for using, instead of 2-bromonitrobenzene, 4-(4-bromobenzenesulfonyl)morpholine to afford the above-identified compound (85 mg).

Example 320

3-{1-[4-(morpholin-4-ylsulfonyl)phenyl]-3-(2-phenylethyl)-1H-indol-5-yl}propanoic acid The same reaction was performed as in Example 144 except for using, instead of the compound obtained at Example 143, the compound obtained at Example 319 to afford the above-identified compound (77 mg).

Example 321

Ethyl 3-[1-{3-[(dimethylamino)sulfonyl]phenyl}-3-(2-phenylethyl)-1H-indol-5-yl]propanoate The same reaction was performed as in Example 148 except for using, instead of 2-bromonitrobenzene, 3-bromo-N,N-dimethylbenzenesulfonamide to afford the above-identified compound (89 mg).

Example 322

3-[1-{3-[(dimethylamino)sulfonyl]phenyl}-3-(2-phenylethyl)-1H-indol-5-yl]propanoic acid The same reaction was performed as in Example 144 except for using, instead of the compound obtained at Example 143, the compound obtained at Example 321 to afford the above-identified compound (71 mg).

Example 323

Ethyl 3-{1-[3-(morpholin-4-ylsulfonyl)phenyl]-3-(2-phenylethyl)-1H-indol-5-yl}propanoate The same reaction was performed as in Example 148 except for using, instead of 2-bromonitrobenzene, 4-(3-bromobenzenesulfonyl)morpholine to afford the above-identified compound (80 mg).

Example 324

3-{1-[3-(morpholin-4-ylsulfonyl)phenyl]-3-(2-phenylethyl)-1H-indol-5-yl}propanoic acid The same reaction was performed as in Example 144 except for using, instead of the compound obtained at Example 143, the compound obtained at Example 323 to afford the above-identified compound (71 mg).

Example 325

Ethyl 3-{1-[4-(methylsulfonyl)phenyl]-3-(2-phenylethyl)-1H-indol-5-yl}propanoate The same reaction was performed as in Example 148 except for using, instead of 2-bromonitrobenzene, 1-bromo-4-(methylsulfonyl)benzene to afford the above-identified compound (110 mg).

Example 326

3-{1-[4-(methylsulfonyl)phenyl]-3-(2-phenylethyl)-1H-indol-5-yl}propanoic acid

The same reaction was performed as in Example 144 except for using, instead of the compound obtained at Example 143, the compound obtained at Example 325 to afford the above-identified compound (87 mg).

Example 327

Ethyl 3-{1-[4-(3-hydroxypropoxy)phenyl]-3-(2-phenylethyl)-1H-indol-5-yl}propanoate The compound obtained at Example 241 (130 mg), 3-bromopropanol (0.031 ml), and potassium carbonate (52 mg)

were dissolved in N,N-dimethylformamide (4.0 ml) and the mixture was heated and stirred at 110° C. for 10 hours. The reaction mixture was diluted with ethyl acetate, washed with water and dried over anhydrous sodium sulfate. The solvent was distilled off in vacuo and the residue obtained was purified by silica gel column chromatography (hexane:ethyl acetate=3:2 to 2:3) to afford the above-identified compound (90 mg).

Example 328

3-{1-[4-(3-hydroxypropoxy)phenyl]-3-(2-phenylethyl)-1H-indol-5-yl}propanoic acid 2-amino-2-(hydroxymethyl)propane-1,3-diol salt (1:1)

Step 1
The same reaction was performed as in Example 144 except for using, instead of the compound obtained at Example 143, the compound obtained at Example 327 to afford 3-{1-[4-(3-hydroxypropoxy)phenyl]-3-(2-phenylethyl)-1H-indol-5-yl}propanoic acid (84 mg).
Step 2
The same reaction was performed as in Example 190 except for using, instead of the compound obtained at Example 189, the compound obtained above to afford the above-identified compound (98 mg).

Example 329

4-{1-[4-(difluoromethoxy)phenyl]-3-(2-phenylethyl)-1H-indol-5-yl}-1,1,1-trifluorobutan-2-one To a solution of the compound obtained in Example 189 (129 mg) in methylene chloride (2.5 ml) was added oxalyl chloride (0.067 ml), and the mixture was stirred at room temperature for 2 hours. From the reaction mixture, the solvent was distilled off in vacuo, the residue obtained was dissolved in toluene (3.0 ml), trifluoroacetic acid anhydride (0.13 ml) and pyridine (0.058 ml) were added under ice cooling and the mixture was stirred at room temperature over night. To the reaction mixture was added 1N-hydrochloric acid (0.1 ml), the mixture was extracted with ethyl acetate and the organic layer was successively washed with water, saturated aqueous sodium hydrogen carbonate solution and brine and dried over anhydrous sodium sulfate. The solvent was distilled off in vacuo and the residue obtained was purified by silica gel column chromatography (methylene chloride: methanol=99:1 to 23:2) to afford the above-identified compound (50 mg).

Example 330

1,1,1-trifluoro-4-[1-(4-phenoxyphenyl)-3-(2-phenylethyl)-1H-indol-5-yl]butan-2-one To a solution of the compound obtained at Step 1 of Example 231 (102 mg) in methylene chloride (2.0 ml) was added oxalyl chloride (0.050 ml), and the mixture was stirred at room temperature for 2 hours. From the reaction mixture, the solvent was distilled off in vacuo, the residue obtained was dissolved in toluene (2.5 ml), trifluoroacetic acid anhydride (0.095 ml) and pyridine (0.046 ml) were added under ice cooling and the mixture was stirred at room temperature over night. To the reaction mixture was added 1N-hydrochloric acid (0.1 ml), and the mixture was extracted with ethyl acetate and the organic layer was successively washed with water, saturated aqueous sodium hydrogen carbonate solution and brine and dried over anhydrous sodium sulfate. The solvent was distilled off in vacuo and the residue obtained was purified by silica gel column chromatography (methylene chloride:methanol=25:0 to 23:2) to afford the above-identified compound (33 mg).

Example 331

N-(methylsulfonyl)-3-[1-(4-phenoxyphenyl)-3-(2-phenylethyl)-1H-indol-5-yl]propanamide To a solution of the compound (100 mg) obtained at Step 1 of Example 231 in N,N-dimethylformamide (1.0 ml) was added 1,1-carbonyldimidazole (39 mg), and the mixture was stirred at room temperature for 1 hour. To the reaction mixture were added methanesulfonamide (23 mg) and 1,8-diazabicyclo[5.4.0]-7-undecene (0.036 ml), and the mixture stirred at room temperature over night. To the reaction mixture was added 2N-hydrochloric acid (0.1 ml), and the mixture was extracted with ethyl acetate, the organic layer was successively washed with water, saturated aqueous sodium hydrogen carbonate solution and brine, and dried over anhydrous sodium sulfate. The solvent was distilled off in vacuo and the residue obtained was purified by silica gel column chromatography (hexane:ethyl acetate=9:1 to 1:1) to afford the above-identified compound (86 mg).

Example 332

3-{1-[4-(difluoromethoxy)phenyl]-3-(2-phenylethyl)-1H-indol-5-yl}-N-(phenylsulfonyl)propanamide To a solution of the compound obtained at Example 189 (109 mg) in tetrahydrofuran (1.5 ml) was added benzenesulfonyl isocyanate (0.035 ml), and the mixture was stirred at room temperature for 10 minutes, then, to the reaction mixture was added triethylamine (0.035 ml), and the mixture was stirred at room temperature for 12 hours. To the reaction mixture was added 2N-hydrochloric acid (0.1 ml), and the mixture was extracted with ethyl acetate and the organic layer was successively washed with water, saturated aqueous sodium hydrogen carbonate solution and brine, and dried over anhydrous sodium sulfate. The solvent was distilled off in vacuo and the residue obtained was purified by silica gel column chromatography (hexane:ethyl acetate=2:0 to 1:1) to afford the above-identified compound (75 mg).

Example 333

N-[(4-methylphenyl)sulfonyl]-3-[(1-(4-phenoxyphenyl)-3-(2-phenylethyl)-1H-indol-5-yl]propanamide To a solution of the compound obtained at Step 1 of Example 231 (74 mg) in methylene chloride (1.0 ml) were added 4-dimethylaminopyridine (26 mg) and p-toluenesulfonamide (36 mg). The mixture was ice cooled, N,N-dicyclohexylcarbodiimide (43 mg) was added and the mixture was stirred at room temperature over night. To the reaction mixture was added 2N-hydrochloric acid (0.1 ml), and the mixture was extracted with ethyl acetate and the organic layer was successively washed with water, saturated aqueous sodium hydrogen carbonate solution, and brine and dried over anhydrous sodium sulfate. The solvent was distilled off in vacuo and the residue obtained was purified by silica gel column chromatography (hexane:ethyl acetate=9:1 to 9:11) to afford the above-identified compound (68 mg).

Example 334

3-[1-(4-methylthiophenyl)-3-(2-phenylethyl)-1H-indol-5-yl]propanoic acid

Step 1
The same reaction was performed as in Example 148 except for using, instead of 2-bromonitrobenzene, 4-bromothioanisole so as to afford ethyl 3-[1-(4-methylthiophenyl)-3-(2-phenylethyl)-1H-indol-5-yl]propanoate (46 mg).
Step 2
The same reaction was performed as in Example 144 except for using, instead of the compound obtained in Example 143, the compound obtained at Step 1 to afford the above-identified compound (28 mg).

Example 335

3-[1-(4-benzylthiophenyl)-3-(2-phenylethyl)-1H-indol-5-yl]propanoic acid

Step 1
The same reaction was performed as in Example 148 except for using, instead of 2-bromonitrobenzene, benzyl 4-bromophenyl sulfide to afford ethyl 3-[1-(4-benzylthiophenyl)-3-(2-phenylethyl)-1H-indol-5-yl]propanoate (275 mg).
Step 2
The same reaction was performed as in Example 144 except for using, instead of the compound obtained at Example 143, the compound obtained at Step 1 to afford the above-identified compound (171 mg).

Example 336

Ethyl (2E)-3-[3-(3-phenylpropyl)-1H-indol-5-yl]-2-propenoate

The same reaction was performed as in Example 141 except for using, instead of the compound obtained at Reference Example 4, the compound obtained at Reference Example 8 to afford the above-identified compound (93 mg).

Example 337

Ethyl 3-[3-(3-phenylpropyl)-1H-indol-5-yl]-2-propanoate

To a solution of the compound obtained in Example 336 (92 mg) in ethanol (4.0 ml) was added a suspension of Raney nickel (10 mg) in ethanol (4.0 ml), and the mixture was stirred in a hydrogen atmosphere at room temperature for 2.5 hours. The insolubles were filtered off, the filtrate was distilled off in vacuo and the residue obtained was purified by silica gel column chromatography (hexane:ethyl acetate=9:1 to 3:2) to afford the above-identified compound (88 mg).

Example 338

Ethyl 3-{1-[4-(benzyloxy)phenyl]-3-(3-phenylpropyl)-1H-indol-5-yl}propanoate

To a solution of the compound obtained in Example 337 (86 mg) in n-butyl acetate (8.0 ml) were added 4-(benzyloxy) bromobenzene (135 mg), palladium acetate (11 mg), 2-(di-tert-butylphosphino)biphenyl (31 mg) and tripotassium phosphate (217 mg), and the mixture was heated and refluxed at 115° C. for 12 hours. The reaction mixture was cooled, then the insolubles were filtered off, the filtrate was distilled off in vacuo, and the residue obtained was purified by silica gel column chromatography (hexane:ethyl acetate=19:1 to 3:2) to afford the above-identified compound (42 mg).

Example 339

3-{1-[4-(benzyloxy)phenyl]-3-(3-phenylpropyl)-1H-indol-5-yl}propanoic acid

The same reaction was performed as in Example 144 except for using, instead of the compound obtained at Example 143, the compound obtained at Example 338 to afford the above-identified compound (26 mg).

Example 340

3-[1-(4-hydroxyphenyl)-3-(3-phenylpropyl)-1H-indol-5-yl]propanoic acid

To a solution of the compound obtained in Example 339 (15 mg) in methanol (2.0 ml)-ethyl acetate (1.5 ml) mixed solvent was added 10% palladium carbon (2.0 mg), and the mixture was stirred in a hydrogen atmosphere at room temperature for 48 hours. The insolubles were filtered off, the filtrate was distilled off in vacuo and the residue obtained was purified by silica gel column chromatography (methylene chloride:methanol=99:1 to 9:1) to afford the above-identified compound (8.0 mg).

Example 341

Ethyl 3-[1-{4-[2-(benzyloxy)ethoxy]phenyl}-3-(2-phenylethyl)-1H-indol-5-yl]propanoate To a solution of the compound obtained at Example 142 (446 mg) in n-butyl acetate (30 ml) were added 4-[2-(benzyloxy)ethoxy]bromobenzene (852 mg), palladium acetate (62 mg), 2-(di-tert-butylphosphino)biphenyl (166 mg) and tripotassium phosphate (1.18 g), and the mixture was heated and refluxed at 120° C. for 20 hours. The reaction mixture was cooled, then the insolubles were filtered off, the filtrate was distilled off in vacuo and the residue obtained was purified by silica gel column chromatography (hexane:ethyl acetate=19:1 to 7:13) to afford the above-identified compound (760 mg).

Example 342

3-[1-{4-[2-(benzyloxy)ethoxy]phenyl}-3-(2-phenylethyl)-1H-indol-5-yl]propanoic acid The same reaction was performed as in Example 144 except for using, instead of the compound obtained at Example 143, the compound obtained at Example 341 to afford the above-identified compound (83 mg).

Example 343

Ethyl (2E)-3-[1-{4-[2-(benzyloxy)ethoxy]phenyl}-3-(2-phenylethyl)-1H-indol-5-yl]propenoate To a solution of the compound obtained at Example 141 (446 mg) in n-butyl acetate (45 ml) were added 4-[2-(benzyloxy)ethoxy]bromobenzene (1.07 g), palladium acetate (63 mg), 2-(di-tert-butylphosphino)biphenyl (167 mg) and tripotassium phosphate (1.2 g), and the mixture was heated and refluxed at 120° C. over night. The reaction mixture was cooled, then the insolubles were filtered off, the filtrate was distilled off in vacuo, and the residue obtained was purified by silica gel column chromatography (hexane:ethyl acetate=19:1 to 2:3) to afford the above-identified compound (277 mg).

Example 344

Ethyl (2E)-3-{1-[4-(2-hydroxyethoxy)phenyl]-3-(2-phenylethyl)-1H-indol-5-yl}propenoate To a solution of the compound obtained at Example 343 (277 mg) in methylene chloride (5.0 ml), 1 mol/l boron tribromide/methylene chloride solution (1.0 ml) was added, and the mixture was stirred at −78° C. for 30 minutes. The reaction solution was raised to room temperature, then water was added to the reaction mixture, the mixture was extracted with methylene chloride and the organic layer was successively washed with saturated aqueous sodium hydrogen carbonate solution and brine and dried over anhydrous sodium sulfate. The solvent was distilled off in vacuo and the residue obtained was purified by silica gel column chromatography (hexane:ethyl acetate=19:1 to 2:3) to afford the above-identified compound (170 mg).

Example 345

(2E)-3-{1-[4-(2-hydroxyethoxy)phenyl]-3-(2-phenylethyl)-1H-indol-5-yl}propenoic acid To a solution of the compound obtained at Example 344 (160 mg) in tetrahydrofuran (20 ml)-ethanol (6.0 ml) mixed solvent was added 1 mol/l aqueous sodium hydroxide solution (1.4 ml), and the mixture was stirred at 45° C. for 5 hours. Further, 2 mol/l aqueous sodium hydroxide solution (0.1 ml) was added, the mixture was stirred at 40° C. for 12 hours, then 1 mol/l aqueous sodium hydroxide solution (0.45 ml) was added and the mixture was stirred at 55° C. for 6 hours. To the reaction mixture, 1 mol/l hydrochloric acid (3.0 ml) was added, and the mixture was extracted with ethyl acetate and the organic layer was successively washed with water and brine and dried over anhydrous sodium sulfate. The solvent was distilled off in vacuo and the residue obtained was purified by silica gel column chromatography (methylene chloride:methanol=99:1 to 17:3) to afford the above-identified compound (68 mg).

Example 346

Ethyl (2E)-3-{1-[4-(difluoromethoxy)phenyl]-3-(2-phenylethyl)-1H-indol-5-yl}propenoate To a solution of the compound obtained at Example 141 (200 mg) in n-butyl acetate (15 ml) were added 1-bromo-4-(difluoromethoxy)benzene (281 mg), palladium acetate (28 mg), 2-(di-tert-butylphosphino)biphenyl (75 mg) and tripotassium phosphate (535 mg), and the mixture was heated and stirred at 120° C. for 12 hours. The reaction mixture was cooled to room temperature, then the insolubles were filtered off, the filtrate was distilled off in vacuo and the residue obtained was purified by silica gel column chromatography (hexane:ethyl acetate=19:1 to 9:11) to afford the above-identified compound (227 mg).

Example 347

(2E)-3-{1-[4-(difluoromethoxy)phenyl]-3-(2-phenylethyl)-1H-indol-5-yl}propenoic acid To a solution of the compound obtained at Example 346 (227 mg) in tetrahydrofuran (8.0 ml)-ethanol (6.0 ml) mixed solvent was added 1 mol/l aqueous sodium hydroxide solution (0.98 ml), and the mixture was stirred at room temperature over night. Further, 2 mol/l aqueous sodium hydroxide solution (0.5 ml) was added and the mixture was stirred at room temperature for a further 1 day. To the reaction mixture was added 2 mol/l hydrochloric acid (1.5 ml), and the mixture was extracted with ethyl acetate and the organic layer was successively washed with water and brine, and dried over anhydrous sodium sulfate. The solvent was distilled off in vacuo and the residue obtained was purified by silica gel column chromatography (methylene chloride:methanol=99:1 to 9:1) to afford the above-identified compound (72 mg).

Example 348

Ethyl (2E)-3-[1-(4-phenoxyphenyl)-3-(2-phenylethyl)-1H-indol-5-yl]propenoate

To a solution of the compound obtained at Example 141 (200 mg) in n-butyl acetate (15 ml) were added 4-bromodiphenyl ether (312 mg), palladium acetate (28 mg), 2-(di-tert-butylphosphino)biphenyl (75 mg) and tripotassium phosphate (535 mg), and the mixture was heated and stirred at 120° C. for 18 hours, palladium acetate (10 mg) was added and the mixture was heated and stirred at 120° C. for 6 hours. The reaction mixture was cooled to room temperature, then the insolubles were filtered off, the filtrate was distilled off in vacuo and the residue obtained was purified by silica gel column chromatography (hexane:ethyl acetate=19:1 to 9:11) to afford the above-identified compound (227 mg).

Example 349

(2E)-3-[1-(4-phenoxyphenyl)-3-(2-phenylethyl)-1H-indol-5-yl]propenoic acid

To a solution of the compound obtained at Example 348 (227 mg) in tetrahydrofuran (8.0 ml)-ethanol (6.0 ml) mixed solvent was added 1 mol/l aqueous sodium hydroxide solution (0.93 ml), and the mixture was stirred at room temperature over night. Further, 2 mol/l sodium hydroxide aqueous solution (0.5 ml) was added and the mixture was stirred at room temperature for a further 1 day. To the reaction mixture was added 2 mol/l hydrochloric acid (1.5 ml), and the mixture was extracted with ethyl acetate and the organic layer was successively washed with water and brine, and dried over anhydrous sodium sulfate. The solvent was distilled off in vacuo and the residue obtained was purified by silica gel column chromatography (methylene chloride:methanol=99:1 to 9:1) to afford the above-identified compound (71 mg).

Example 350

3-[1-(4-phenoxyphenyl)-3-(2-phenylethyl)-1H-indol-5-yl]propanoic acid

The compound obtained at Step 1 of Example 231 (0.96 g) was dissolved in ethyl acetate (1.0 ml), n-heptane (4.5 ml) was added, the mixture was raised to 85° C., then the solution was allowed to cool and was stirred at room temperature over night. The precipitated crystals were obtained by filtration to afford the above-identified compound (0.79 g).

Example 351

Sodium 3-[1-(4-phenoxyphenyl)-3-(2-phenylethyl)-1H-indol-5-yl]propanoate (1:1)

The compound obtained at Example 350 (100 mg) was dissolved in ethanol (5.0 ml), 1 mol/l aqueous sodium hydroxide solution (0.217 ml) was added and the mixture was stirred for a while at room temperature. The solvent was distilled off in vacuo, ethyl acetate (5.0 ml) was added to the residue, the mixture was raised to 77° C., then the mixture was stirred at room temperature for 2 days. The precipitated solid was obtained by filtration to obtain the above-identified compound (75 mg).

Example 352

Zinc 3-[1-(4-phenoxyphenyl)-3-(2-phenylethyl)-1H-indol-5-yl]propanoate (1:2)

A mixture of the compound obtained at Example 350 (100 mg) and zinc acetate dihydrate (23.8 mg) was dissolved in toluene (2.0 ml), n-hexane (0.5 ml) was added, the mixture was raised to 70° C., the solution was allowed to cool and stirred at room temperature over night. The precipitated crystal was obtained by filtration to afford the above-identified compound (100 mg).

Example 353

3-[1-(4-phenoxyphenyl)-3-(2-phenylethyl)-1H-indol-5-yl]propanoic acid piperazine salt (2:1)

The compound obtained at Example 350 (462 mg) was dissolved in ethanol (20 ml), piperazine (43 mg) was added, and the mixture was stirred at room temperature for 3 days. The precipitated crystal was obtained by filtration to afford the above-identified compound (445 mg).

Example 354

3-[1-(4-phenoxyphenyl)-3-(2-phenylethyl)-1H-indol-5-yl]propanoic acid N,N'-dibenzylethylenediamine salt (2:1)

A mixture of the compound obtained at Example 350 (100 mg) and N,N'-dibenzylethylenediamine (26.0 mg) was dissolved in toluene (1.0 ml), n-hexane (1.0 ml) was added, the mixture was raised to 70° C., the solution was allowed to cool and was stirred at room temperature over night. The precipitated crystal was obtained by filtration to afford the above-identified compound (86 mg).

Example 355

3-[1-(4-phenoxyphenyl)-3-(2-phenylethyl)-1H-indol-5-yl]propanoic acid L-arginine salt (1:1)

To a mixture of the compound obtained at Example 350 (100 mg) and L-arginine (37.7 mg) was added a mixed solvent of acetonitrile (2.0 ml)/water (3.0 ml), and the mixture was raised to 80° C., then the solution was allowed to cool and stirred at room temperature for 2 hours. The precipitated crystal was obtained by filtration to afford the above-identified compound (117 mg).

Example 356

3-[1-(4-phenoxyphenyl)-3-(2-phenylethyl)-1H-indol-5-yl]propanoic acid 2-amino-2-(hydroxymethyl)propane-1,3-diol salt (1:1)

Step 1

To a solution of the compound obtained at Example 142 (15.30 g) in toluene (76 ml) were added 4-iododiphenyl ether (28.18 g), copper(I) iodide (1.944 g), N,N'-dimethylethylenediamine (3.420 g) and tripotassium phosphate (21.186 g), and the mixture was heated and stirred at 92° C. for 5 hours. The reaction mixture was allowed to cool, then silica gel (15.3 g) was used to filter off the insolubles and the solvent was distilled off from the filtrate in vacuo to afford a crude product of ethyl 3-[1-(4-phenoxyphenyl)-3-(2-phenylethyl)-1H-indol-5-yl]propanoate.

Step 2

The compound obtained at Step 1 above was dissolved in 2-propanol (153 ml), and the mixture was warmed to 65° C., then flake shaped sodium hydroxide (2.855 g) was added, and the mixture was stirred at 65° C. for 2 hours, then the solid precipitating in the reaction mixture was collected by filtration to afford sodium 3-[1-(4-phenoxyphenyl)-3-(2-phenylethyl)-1H-indol-5-yl]propanoate as a powder.

Step 3

To the compound obtained at Step 2 above were added ethyl acetate (68 ml) and 1 mol/l hydrochloric acid (68 ml), and the mixture was stirred at room temperature for a while, then the organic layer was separated, washed with brine (29 ml) and dried over anhydrous magnesium sulfate. The solvent was distilled off in vacuo to afford 3-[1-(4-phenoxyphenyl)-3-(2-phenylethyl)-1H-indol-5-yl]propanoic acid.

Step 4

The compound obtained at Step 3 above was dissolved in ethanol (200 ml), tris(hydroxymethyl)aminomethane (5.76 g) was added, then the mixture was warmed to 60° C., then allowed to cool and stirred at room temperature over night. Further, the mixture was cooled and stirred for 2 hours in an ice water bath, then the precipitated crystal was obtained by filtration to afford the above-identified compound (24.21 g).

Experimental Example 1

Measurement of cPLA$_2$ Inhibitory Activity of Test Compounds

The cPLA$_2$ inhibitory activity was measured based on the method described in the document [See H. Naraba et al., J. Immunol. 160, 2974-2982 (1998)] and modified in the following way.

A DMSO solution of the present invitation compounds was diluted to 2.5 times the final concentration with the assay buffer (4 mM CaCl$_2$, 2 mM dithiothreitol, 150 mM NaCl, 50 mM HEPES buffer solution (pH7.5)) containing 0.55 mg/ml BSA. To 20 µl of this, cPLA$_2$ crudely purified from the cytoplasm fraction of U937 was added in an amount of 10 µl after dilution by an assay buffer solution containing 0.55 mg/ml BSA. A liposome prepared by ultrasonically treating L-α-1-palmitoyl-2-[14C]arachidonyl-phosphatidyl choline (made by PerkinElmer) and adjusted by the assay buffer solution to a concentration of phosphatidyl choline of 10 µM was added and stirred in by an amount of 20 µl and the mixture was reacted at 37° C. for 60 minutes. The [$^{14}$C]-arachidonic acid released due to the reaction was extracted based on the method described in the documents [see V. P. Dole et al., J. Biol. Chem. 235, 2595 (1960)], was added to Lumaplate® (made by PerkinElmer), dried, then measured by Topcount® (made by PerkinElmer). Except for not adding the present invention compounds, the same procedure was performed as the above to obtain the enzyme control. Except for not adding the invention compounds and not adding the enzyme, the same procedure was followed as above to obtain a negative control. The inhibiting activity was expressed as a percent (%) of the value minus the negative control with respect to the value of the enzyme control minus the negative control. From this, the 50% inhibiting concentration (IC$_{50}$, µM) was calculated. The results are shown in the following Table 1.

TABLE 1

| Ex. No. | IC$_{50}$ (µM) |
|---|---|
| 3 | 0.494 |
| 4 | 0.146 |
| 7 | 1.040 |
| 8 | 0.182 |
| 11 | 1.913 |
| 12 | 0.261 |
| 15 | 0.316 |
| 16 | 0.075 |
| 17 | 0.038 |
| 18 | 0.976 |
| 19 | 10.848 |
| 21 | 15.779 |
| 22 | >100 |
| 24 | 12.758 |
| 26 | 3.398 |
| 27 | 0.385 |
| 28 | 0.258 |
| 29 | 21.317 |
| 33 | 0.662 |
| 35 | 5.808 |
| 36 | 0.330 |
| 37 | 1.450 |
| 39 | 10.839 |
| 40 | 2.297 |
| 41 | 0.634 |
| 44 | 0.421 |
| 45 | 0.225 |
| 48 | 0.126 |
| 50 | 6.990 |
| 51 | 0.704 |
| 53 | 5.517 |
| 54 | 6.117 |
| 56 | 6.401 |
| 57 | 1.387 |
| 58 | 1.157 |
| 60 | 5.724 |
| 61 | 0.653 |
| 62 | 0.565 |
| 64 | 19.573 |
| 65 | 1.913 |
| 66 | 0.718 |
| 68 | 1.000 |
| 70 | 1.356 |
| 74 | 0.157 |
| 77 | 0.026 |
| 79 | 0.180 |
| 81 | 0.058 |
| 83 | 0.101 |
| 85 | 0.077 |
| 86 | 0.024 |
| 88 | 0.142 |
| 91 | 0.207 |
| 93 | 0.112 |
| 95 | 0.077 |
| 97 | 0.099 |
| 99 | 0.288 |
| 101 | 0.096 |
| 103 | 0.419 |

TABLE 1-continued

| Ex. No. | IC$_{50}$ (µM) |
|---|---|
| 105 | 0.036 |
| 107 | 0.195 |
| 109 | 0.224 |
| 112 | 0.015 |
| 113 | 1.152 |
| 114 | 0.740 |
| 115 | 0.061 |
| 116 | 2.165 |
| 117 | 0.527 |
| 119 | 0.007 |
| 121 | 0.007 |
| 124 | 0.008 |
| 126 | 0.011 |
| 128 | 0.250 |
| 130 | 0.113 |
| 132 | 0.225 |
| 134 | 0.211 |
| 135 | 0.277 |
| 138 | 0.034 |
| 140 | 0.117 |
| 144 | 0.042 |
| 147 | 0.779 |
| 149 | 0.278 |
| 151 | 0.185 |
| 153 | 7.961 |
| 155 | 0.208 |
| 157 | 0.186 |
| 159 | 0.515 |
| 161 | 0.813 |
| 163 | 1.749 |
| 165 | 0.154 |
| 167 | 0.049 |
| 169 | 0.205 |
| 171 | 0.210 |
| 173 | 0.259 |
| 175 | 0.143 |
| 177 | 2.525 |
| 179 | 0.182 |
| 181 | 0.138 |
| 183 | 0.070 |
| 185 | 0.278 |
| 187 | 0.058 |
| 189 | 0.043 |
| 190 | 0.028 |
| 193 | 0.141 |
| 196 | 0.066 |
| 197 | 0.157 |
| 199 | 0.986 |
| 201 | 0.219 |
| 203 | 0.010 |
| 205 | 0.133 |
| 207 | 0.064 |
| 209 | 0.244 |
| 211 | 0.790 |
| 213 | 0.015 |
| 214 | 0.005 |
| 216 | 0.086 |
| 217 | 0.047 |
| 219 | 0.147 |
| 220 | 0.146 |
| 222 | 0.049 |
| 223 | 0.057 |
| 225 | 0.008 |
| 226 | 0.008 |
| 228 | 0.004 |
| 229 | 0.014 |
| 231 | 0.020 |
| 233 | 0.082 |
| 235 | 0.122 |
| 237 | 0.193 |
| 239 | 0.054 |
| 243 | 0.004 |
| 245 | 0.010 |
| 246 | 0.007 |
| 248 | 0.007 |
| 249 | 0.026 |
| 251 | 0.009 |
| 253 | 0.014 |

TABLE 1-continued

| Ex. No. | IC$_{50}$ (µM) |
|---|---|
| 255 | 0.012 |
| 257 | 0.007 |
| 258 | 0.002 |
| 260 | 0.008 |
| 263 | 1.442 |
| 264 | 0.338 |
| 267 | 0.110 |
| 268 | 0.019 |
| 269 | 0.077 |
| 271 | 0.357 |
| 275 | 0.012 |
| 277 | 0.098 |
| 279 | 0.245 |
| 281 | 0.278 |
| 282 | 0.582 |
| 284 | >3.0 |
| 286 | >3.0 |
| 288 | 0.264 |
| 289 | 0.182 |
| 291 | 0.083 |
| 293 | 0.191 |
| 295 | 0.755 |
| 297 | 0.442 |
| 298 | 0.923 |
| 300 | 0.381 |
| 302 | 0.764 |
| 304 | >3.0 |
| 306 | 0.871 |
| 308 | 0.149 |
| 310 | 0.354 |
| 312 | 0.404 |
| 314 | >3.0 |
| 316 | >3.0 |
| 318 | 0.271 |
| 320 | 0.258 |
| 322 | 1.911 |
| 324 | 1.634 |
| 326 | 0.486 |
| 328 | 0.057 |
| 329 | 0.318 |
| 330 | 0.726 |
| 331 | >3.0 |
| 332 | >3.0 |
| 333 | >3.0 |
| 334 | 0.011 |
| 335 | 0.009 |
| 339 | 0.460 |
| 340 | 0.568 |
| 342 | 0.002 |

Experimental Example 2

Evaluation of Activity of Test Compounds in Inhibiting PGE$_2$ Production

For evaluation of the PGE$_2$ production inhibiting activity, the lipopolysaccharide (LPS)-induced PGE$_2$ production system using mouse peritoneal exudate cells with reference to the method of Kim et al. (see Kim, Y K et al., Biol Pharm Bull 25: 472, 2002) was used. That is, 2 ml of thioglycolate solution (made by Sigma, Brewer's Thioglycorate medium) per mice were intraperitoneally administered to 8-week old female C3H/HeN mice (Charles River Japan). After 4 days, a phosphate buffer saline (PBS) 5 ml was used to wash the abdominal cavity and the infiltrating cells were recovered. The recovered cells were suspended in a predetermined concentration in an RPMI1640 medium (Nacalai Tesque) containing 10% bovine fetal serum (BioWhittaker) and 10 µg/ml gentamycin (Invitrogen).

The infiltrating cell suspension 100 µl containing 2×10$^5$ cells per well was inoculated in a 96-well culture plate, then the test compound solution or solvent 50 µl was added. Under conditions of 5% CO$_2$ and 37° C., this was precultured for 15 minutes, then LPS (made by Sigma: L-4524) solution 50 µl (final concentration of LPS of 10 µg/ml) was added, and the mixture was cultured for a further 6 hours. After the end of the culture, the culture supernatant was recovered and the PGE$_2$ concentration in the supernatant was measured using an EIA kit (made by Amersham). Based on the measurement value, the test compound concentration suppressing 50% of the PGE$_2$ production at the time of non-addition of a compound (IC$_{50}$ value) was calculated. The IC$_{50}$ values of typical compounds are shown in Table 2.

TABLE 2

| Example No. (test compound) | IC$_{50}$ value (µM) |
|---|---|
| 17 | 1.32 |
| 48 | 2.49 |
| 114 | 2.22 |
| 115 | 0.30 |
| 124 | 0.13 |
| 126 | 0.54 |
| 128 | 6.43 |
| 138 | 0.58 |
| 147 | 1.24 |
| 157 | 2.25 |
| 187 | 0.28 |
| 190 | 0.85 |
| 193 | 0.18 |
| 217 | 1.70 |
| 229 | 0.80 |
| 231 | 0.50 |

Experimental Example 3

Evaluation of Activity of Test Substance in Inhibiting PGD$_2$ Production

To evaluate the PGD$_2$ production inhibiting activity, the antigen-induced PGD$_2$ production system using rat mast cell like cell line RBL-2H3 sensitized by a dinitrophenol (DNP) specific IgE with reference to the method of Yamashita et al. (see Yamashita, M. et al., Br J Pharmacol 129: 367, 2000) was used. That is, rat mast cell like cell line RBL-2H3 cells were suspended in a Dulbecco's modified Eagle's medium (Nacalai Tesque) containing 10% bovine fetal serum (BioWhittaker) and 10 µg/ml gentamycin (Invitrogen). The infiltrating cell suspension 200 µl containing 1×10$^5$ cells per well was inoculated to 96-well culture plate and cultured over night under conditions of 5% CO$_2$ and 37° C. The culture supernatant was removed, then the suspension was cultured for 2 hours in the presence of an anti-DNP-IgE antibody (1 µg/ml) for 2 hours to sensitize it. After the sensitization, the supernatant was removed and the test compound solution or solvent was added. The resultant product was precultured for 30 minutes, then 10 µg/ml of antigen (DNP-human serum albumin conjugate) was added to elicite PGD$_2$ production.

30 minutes after antigen stimulus, the culture supernatant was recovered and the amount of PGD$_2$ in the supernatant was measured using an EIA kit (made by Cayman). Based on the measurement value, the test compound concentration (IC$_{50}$ value) suppressing the amount of PGD$_2$ production at the time of nonaddition of the compound by 50% was calculated. The IC$_{50}$ values of typical compounds are shown in Table 3.

TABLE 3

| Example No. (test compound) | IC$_{50}$ value (μM) |
|---|---|
| 126 | 1.21 |
| 187 | 0.43 |
| 190 | 1.11 |
| 193 | 0.82 |
| 217 | 1.12 |
| 229 | 0.89 |
| 231 | 0.76 |

Experimental Example 4

Evaluation of Activity of Test Substance in Inhibiting LTB$_4$ and Cys-LTs

For the evaluation by LTB$_4$ and Cys-LTs production inhibiting activity, the calcium ionophore-induced LTB$_4$ and Cys-LTs production system using the rat mast cell like cell line RBL-2H3 with reference to the method of Ishiwara et al. (see Ishiwara M. et al., J Pharmacol Exp Ther 307: 583, 2003) was used. That is, rat mast cell like cell line RBL-2H3 cells were suspended in Dulbecco's modified Eagle's medium (Nacalai Tesque) containing 10% bovine fetal serum (BioWhittaker) and 10 μg/ml gentamycin (Invitrogen). The infiltrating cell suspension 200 μl containing 1×10$^5$ cells per well was inoculated to 96-well culture plate and cultured over night under conditions of 5% CO$_2$ and 37° C. The culture supernatant was removed, then the test compound solution or solvent 50 μl was added. After 30 minutes preculture, calcium ionophore (A23187) was added to a final concentration of 5 μM to induce leukotriene production.

One hour after calcium ionophore stimulus, the culture supernatant was recovered and the amounts of LTB$_4$ and Cys-LTs in the supernatant were measured using an EIA kit (made by Amersham). Based on the measurement values, the test compound concentrations suppressing 50% of the mediator production at the time of non-addition of a compound (IC$_{50}$ value) were calculated. The IC$_{50}$ values of the LTB$_4$ and Cys-LTs productions of typical compounds are shown in Table 4 and Table 5.

TABLE 4

| Example No. (test compound) | IC$_{50}$ value (μM) |
|---|---|
| 126 | 0.77 |
| 187 | 0.26 |
| 190 | 0.38 |
| 193 | 0.63 |
| 217 | 0.50 |
| 229 | 0.02 |
| 231 | 0.18 |

TABLE 5

| Example No. (test compound) | IC$_{50}$ value (μM) |
|---|---|
| 126 | 4.17 |
| 187 | 0.89 |
| 190 | 1.06 |
| 193 | 1.38 |
| 217 | 1.26 |
| 229 | 0.40 |
| 231 | 0.30 |

Experimental Example 5

Evaluation of Activity of Test Substance in Inhibiting TXB$_2$ Production

For evaluation of the TXB$_2$ production inhibiting activity, the calcium ionophore-induced TXB$_2$ production system using whole blood with reference to the method of Alanko (see Alanko J., Prostaglandins 45: 193, 1993) was used. That is, heparin blood taken from Hartley guinea pigs was diluted 2-fold by an RPMI1640 medium (Nakalai Tesque) containing 10 μg/ml gentamycin (Invitrogen). The entire blood after dilution was inoculated in a 96-well culture plate in amounts of 200 μl per well, then the test compound solution or solvent was added. After 30 minutes preculture, calcium ionophore (A23187) was added to a final concentration of 5 μM to induce TXB$_2$ production. 15 minutes after stimulus, the supernatant was recovered by centrifugal separation and the amount of TXB$_2$ in the supernatant was measured using an EIA kit (Amersham).

Based on the measurement value, the test compound concentration suppressing 50% of the TXB$_2$ production at the time of non-addition of a compound (IC$_{50}$ value) was calculated. The IC$_{50}$ values of typical compounds are shown in Table 6.

TABLE 6

| Example No. (test compound) | IC$_{50}$ value (μM) |
|---|---|
| 126 | 1.53 |
| 187 | 5.14 |
| 190 | 1.37 |
| 193 | 1.31 |
| 217 | 2.02 |
| 229 | 0.58 |
| 231 | 0.54 |

Experimental Example 6

Effects of Test Compounds in TPA-Induced Mouse Dermatitis Model

Phorbol ester (TPA) was applied to the ear to elicit acute inflammation having ear edema as a main symptom. In the present test model, it is known that arachidonic acid metabolites, constituting various lipid mediators, are involved in inflammation. By this Experiment, it is possible to evaluate the anti-inflammatory action in vivo of anti-inflammatory drugs acting on the arachidonic acid cascade.

The Experiment was performed with reference to the method of Chang et al. (see Chang J., Eur J Pharmacol 142: 197, 1987). That is, the ear of female C57BL/6 mice (Charles River Japan) were painted with 20 μl of TPA in an acetone solution (concentration 50 μg/ml) to induce dermatitis at the ear. The ear thicknesses before application of TPA and 6 hours after application of TPA were measured using a dial gauge and the increase in ear thickness caused by inflammation was calculated. The test compound or the 0.5% hydroxypropyl cellulose solution as vehicle was administered orally to the mice 30 minutes before application of TPA. Note that the number of mice used in the test was made six per group.

Based on the measurement value, the action of each test compound in suppressing the increase in ear thickness due to application of TPA was evaluated. The rate of suppression of the increase in ear thickness of typical compounds is shown in Table 7.

TABLE 7

| Example No. (test compound) | Dosage (mg/kg) | Suppression rate of increase in ear thickness (%) |
|---|---|---|
| 126 | 50 | 27.6 |
| 187 | 50 | 25.4 |
| 190 | 50 | 27.6 |
| 193 | 50 | 19.4 |
| 217 | 50 | 22.8 |
| 229 | 50 | 23.9 |
| 231 | 50 | 30.4 |

Experimental Example 7

Effects of Test Compounds in Guinea Pig Antigen Induced Bronchial Asthma Model

Hartley male guinea pigs (Kyudo Co., Ltd.) were sensitized by inhaling the aerosolized 1% OVA-containing physiological saline solution for consecutive 8 days. One week after the final sensitization, antigen antibody reaction was elicited by inhaling the aerosolized 2% OVA-containing physiological saline solution. 24 hours and 1 hour before antigen challenge, metyrapone (10 mg/kg, 1.0 ml/kg) was injected to the hind limb peripheral vein. 30 minutes before antigen challenge, pyrilamine maleate (10 mg/kg, 1.0 ml/kg) was administered intraperitoneally. The test compound (5 mg/kg and 20 mg/kg, 5.0 ml/kg) was administered once a day from the day after the final sensitization to the day before challenge. On the day of challenge, it was administered orally 1 hour before challenge and 8 hours after challenge. Note that the number of mice used in the test was made eight per group.

The airway resistance (sRaw) was measured using a total respiratory function analysis system (Pulmos-I, made by M.I.P.S.) before antigen challenge, 1 minute after finishing the antigen challenge, and 2, 4, 5, 6, 7, 8, and 22 to 24 hours after antigen challenge. The immediate asthmatic response (IAR) was evaluated by calculating the rates of change based on the measurement values before challenge and 1 minute after challenge and finding the value obtained by subtracting the rate of change of each compound administered groups from the rate of change of the vehicle administered group with the control inhibition rate as a percent (%) with respect to the value of the vehicle administered group. The late asthmatic response (LAR) was evaluated by calculating the AUC from the rate of change 4 to 8 hours after inducement based on the measurement values and finding the value obtained by subtratcting the AUC of each compound administered group from the AUC of the vehicle administered group with the control inhibition rate as a percent (%) with respect to the value of the vehicle administered group. The rates of suppression of typical compounds with respect to the increases in airway resistances in immediate asthmatic response (IAR) and late asthmatic response (LAR) are shown in Table 8.

TABLE 8

Airway Resistance

| Example No. (test compound) | Dosage (mg/kg) | IAR suppression rate (%) | LAR suppression rate (%) |
|---|---|---|---|
| 190 | 5 | 2 | 46 |
| 190 | 20 | 2 | 42 |
| 229 | 5 | 15 | 22 |
| 229 | 20 | 33 | 37 |
| 231 | 5 | 21 | 45 |
| 231 | 20 | 59 | 78 |

The airway hyperreactivity was measured 22 to 24 hours after inducement. Physiological saline solution and acetyl choline in 0.0625, 0.125, 0.25, 0.5, 1, and 2 mg/ml amounts in physiological saline solutions were successively nebulized and made to be inhaled by guinea pigs 1 minute at a time each, then the sRaw was measured by a total respiratory function analysis system (Pulmos-I, made by M.I.P.S.) The results of evaluation of typical compounds are shown in Table 9 for different acetyl choline concentrations ($PC_{100}Ach$, mg/ml) inducing 100% airway resistance.

TABLE 9

Airway Hyperreactivity

| Example No. (test compound) | Dosage (mg/kg) | $PC_{100}ACh$ (mg/mL) |
|---|---|---|
| Saline | — | 1.80 |
| Vehicle | — | 0.39 |
| 190 | 5 | 0.57 |
| 190 | 20 | 0.50 |
| 229 | 5 | 0.47 |
| 229 | 20 | 0.74 |
| 231 | 5 | 1.02 |
| 231 | 20 | 1.09 |

The number of cells in a bronchial alveolar lavage fluid was counted after measurement of the airway hyperreactivity. Each guinea pig was exsanguinated under anesthesia, its chest was opened, a cannular was inserted into the trachea, then physiological saline was injected into and sucked out from the lungs to recover the bronchial alveolar lavage fluid (BALF). The BALF was centrifugally separated, the obtained precipitate (pellets) was suspended in physiological saline and the total number of cells per 1 μl was calculated by an automatic blood cell counting system (Sysmex F-820). The total number of cells was calculated, then the sample was again centrifugally separated and the obtained pellets were hemolyzed, diluted, centrifuged, and dried, then stained by May-Greenwald's-Giemsa dye. Using a microscope, the ratios of the macrophages, eosinophil granulocytes, neutrophils, and lymphocytes to the total blood cell count (total number of cells) were found and the ratios used to calculate the numbers of cells per μl. The inhibiting rate was found as a percent (%) of the value of the number of cells of the control vehicle administered group minus the number of cells of each compound administered group with respect to the value of the number of cells of the vehicle administered group minus the number of cells of the negative control saline inhalation group. The inhibiting rates of typical compounds against the infiltrating cells are shown in Table 10.

TABLE 10

Inhibitory Rate of Infiltrating Cells in BALF

| Example No. (test compound) | Dosage (mg/kg) | Total number of cells (%) | Macrophages (%) | Eosinophils (%) | Neutrophils (%) | Lymphocytes (%) |
|---|---|---|---|---|---|---|
| 190 | 5 | 33 | 66 | 41 | 0 | 30 |
| 190 | 20 | 62 | 76 | 76 | 37 | 42 |
| 229 | 5 | 30 | 58 | 51 | 0 | 11 |
| 229 | 20 | 35 | 46 | 46 | 16 | 12 |
| 231 | 5 | 58 | 80 | 58 | 38 | 45 |
| 231 | 20 | 72 | 85 | 69 | 64 | 55 |

The structures and physical data of the compounds according to the Reference Examples and Examples of the present invention are shown as follows.

TABLE 11

| Ref. Ex. No | Structure | ¹H-NMR | MS(ESI) [M + H]⁺ |
|---|---|---|---|
| 1 | 5-bromo-1-phenyl-1H-indole | 1H NMR (400 MHz, CHLOROFORM-d) δ ppm 6.63 (d, J = 3.6 Hz, 1 H) 7.26-7.43 (m, 4 H) 7.46-7.56 (m, 4 H) 7.82 (d, J = 2.0 Hz, 1 H) | 272.0 |
| 2 | 5-bromo-2-methyl-1-phenyl-1H-indole | 1H NMR (400 MHz, CHLOROFORM-d) δ ppm 2.30 (s, 3 H) 6.35 (s, 1 H) 6.95 (d, J = 8.7 Hz, 1 H) 7.17 (d, J = 8.7 Hz, 1 H) 7.33 (d, J = 7.1 Hz, 2 H) 7.45-7.60 (m, 2 H) 7.54 (d, J = 7.6 Hz, 1 H) 7.69 (d, J = 2.0 Hz, 1 H) | 286.0 |
| 3 | 1-(5-bromo-1H-indol-3-yl)-2-phenylethanone | 1H NMR (400 MHz, DMSO-d6) δ ppm 4.15 (s, 2 H) 7.22 (d, J = 7.1 Hz, 1 H) 7.19 (s, 1 H) 7.26-7.36 (m, 4 H) 7.45 (d, J = 8.7 Hz, 1 H) 8.29 (s, 1 H) 8.56 (s, 1 H) | 314.0 |
| 4 | 5-bromo-3-(2-phenylethyl)-1H-indole | 1H NMR (400 MHz, CHLOROFORM-d) δ ppm 2.96-3.05 (m, 2 H) 3.01 (d, J = 3.1 Hz, 2 H) 6.91 (d, J = 2.0 Hz, 1 H) 7.19-7.30 (m, 7 H) 7.70 (s, 1 H) 7.93 (br. s., 1 H) | 301.1 |

TABLE 11-continued

| Ref. Ex. No | Structure | ¹H-NMR | MS(ESI) [M + H]⁺ |
|---|---|---|---|
| 5 | 5-bromo-3-(2-(pyridin-2-yl)ethyl)-1H-indole | 1H NMR (400 MHz, CHLOROFORM-d) δ ppm 3.11-3.19 (m, 2 H) 3.16 (s, 2 H) 6.92 (d, J = 2.4 Hz, 1 H) 7.08-7.27 (m, 4 H) 7.55 (td, J = 7.7, 2.0 Hz, 1 H) 7.69 (m, 1 H) 8.17 (br. s., 1 H) 8.57 (dd, J = 4.9, 2.0 Hz, 1 H) | 302 (FABMS) |
| 6 | 1-bromo-4-((difluoromethoxy)methyl)benzene | 1H NMR (400 MHz, CHLOROFORM-d) δ ppm 4.85 (s, 2 H) 6.30 (t, J = 72 Hz, 1 H) 7.24 (d, J = 8.1 Hz, 2 H) 7.51 (d, J = 8.5 Hz, 2 H) | — |
| 7 | (5-bromo-1H-indol-3-yl)(phenethyl)methanone | 1H NMR (400 MHz, CHLOROFORM-d) δ ppm 3.05-3.24 (m, 4 H) 7.18-7.34 (m, 6 H) 7.39 (dd, J = 8.5, 2.0 Hz, 1 H) 7.78 (d, J = 3.3 Hz, 1 H) 8.53 (br. s., 1 H) 8.60 (s, 1 H) | 329.9 |
| 8 | 5-bromo-3-(3-phenylpropyl)-1H-indole | 1H NMR (400 MHz, CHLOROFORM-d) δ ppm 2.03 (qd, J = 7.6, 7.5 Hz, 2 H) 2.73 (ddd, J = 15.3, 7.6, 7.5 Hz, 4 H) 6.99 (d, J = 2.0 Hz, 1 H) 7.17-7.32 (m, 7 H) 7.69 (d, J = 2.0 Hz, 1 H) 7.96 (br. s., 1 H) | 314.0 |

TABLE 12

| Ex. No. | Structure | ¹H-NMR | MS(ESI) [M + H]⁺ |
|---|---|---|---|
| 3 | (E)-3-(3-benzoyl-1-phenyl-1H-indol-5-yl)acrylic acid | 1H NMR (400 MHz, DMSO-d6) δ ppm 6.50 (d, J = 15.8 Hz, 1 H) 7.50-7.66 (m, 7 H) 7.75 (d, J = 5.6 Hz, 2 H) 7.72 (d, J = 7.1 Hz, 2 H) 7.92 (d, J = 7.1 Hz, 2 H) 8.20 (s, 1 H) 8.55 (s, 1 H) | 368.1 |

TABLE 12-continued

| Ex. No. | Structure | ¹H-NMR | MS(ESI) [M + H]⁺ |
|---|---|---|---|
| 4 | 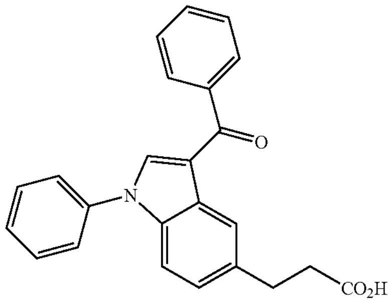 | 1H NMR (400 MHz, CHLOROFORM-d) δ ppm 2.79 (t, J = 7.9 Hz, 2 H) 3.15 (t, J = 7.6 Hz, 2 H) 7.22 (d, J = 8.1 Hz, 1 H) 7.41-7.59 (m, 9 H) 7.74 (s, 1 H) 7.87 (d, J = 7.1 Hz, 2 H) 8.38 (s, 1 H) | 370.1 |
| 7 | 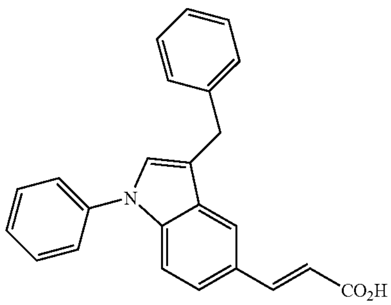 | 1H NMR (400 MHz, DMSO-d6) δ ppm 4.12 (s, 2 H) 6.43 (d, J = 15.8 Hz, 1 H) 7.17 (d, J = 7.6 Hz, 1 H) 7.27 (t, J = 7.6 Hz, 2 H) 7.39 (d, J = 8.1 Hz, 2 H) 7.37 (br. s., 1 H) 7.50-7.60 (m, 7 H) 7.65 (d, J = 15.8 Hz, 1 H) 7.89 (s, 1 H) | 354.1 |
| 8 | 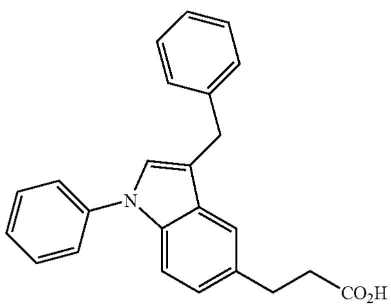 | 1H NMR (400 MHz, CHLOROFORM-d) δ ppm 2.72 (t, J = 7.9 Hz, 2 H) 3.07 (t, J = 7.9 Hz, 2 H) 4.15 (s, 1 H) 7.03 (s, 1 H) 7.08 (d, J = 8.1 Hz, 1 H) 7.19-7.36 (m, 6 H) 7.39-7.52 (m, 6 H) | 356.1 |
| 9 | 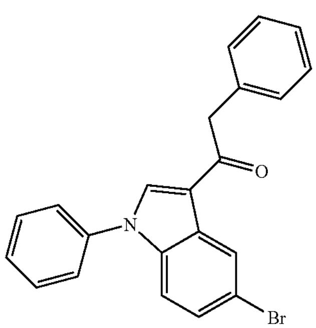 | 1H NMR (400 MHz, CHLOROFORM-d) δ ppm 4.18 (s, 2 H) 7.24-7.62 (m, 12 H) 7.95 (s, 1 H) 8.68 (d, J = 2.0 Hz, 1 H) | 390.0 |
| 11 | 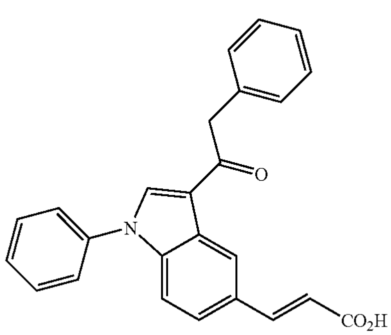 | 1H NMR (400 MHz, MeOH-d4) δ ppm 4.28 (s, 2 H) 6.50 (d, J = 15.8 Hz, 1 H) 7.24 (d, J = 7.1 Hz, 1 H) 7.29-7.40 (m, 4 H) 7.50-7.67 (m, 7 H) 7.79 (d, J = 16.3 Hz, 1 H) 8.52-8.57 (m, 2 H) | 382.1 |

TABLE 12-continued

| Ex. No. | Structure | ¹H-NMR | MS(ESI) [M + H]⁺ |
|---|---|---|---|
| 12 | 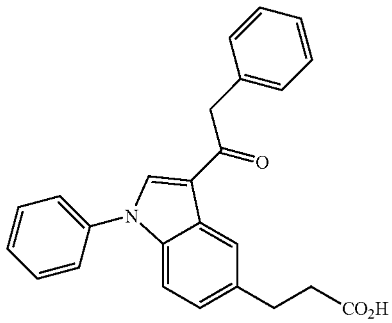 | 1H NMR (400 MHz, MeOH-d4) δ ppm 2.64 (t, J = 7.6 Hz, 2 H) 3.04 (t, J = 7.6 Hz, 2 H) 4.24 (s, 2 H) 7.21 (dd, J = 13.0, 7.9 Hz, 2H) 7.28-7.40 (m, 4 H) 7.41 (s, 1 H) 7.52 (d, J = 7.1 Hz, 1 H) 7.56-7.65 (m, 3 H) 7.60 (d, J = 2.0 Hz, 1 H) 8.22 (s, 1 H) 8.44 (s, 1 H) | 384.1 |
| 13 | 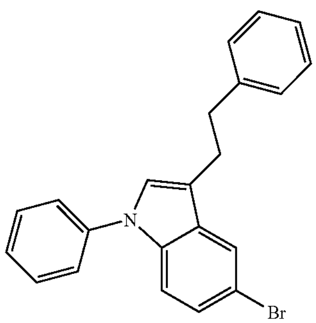 | 1H NMR (400 MHz, CHLOROFORM-d) δ ppm 3.06 (d, J = 10.7 Hz, 1 H) 3.06 (d, J = 3.1 Hz, 1 H) 3.10 (s, 2 H) 7.06 (s, 1 H) 7.21-7.44 (m, 10 H) 7.50 (t, J = 7.9 Hz, 2 H) 7.74 (s, 1 H) | 378.0 |
| 14 | 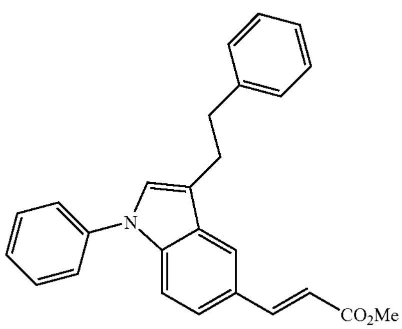 | 1H NMR (400 MHz, CHLOROFORM-d) δ ppm 3.05 (br. s., 2 H) 3.10 (dd, J = 19.8, 7.6 Hz, 2 H) 3.83 (s, 3 H) 6.44 (d, J = 15.8 Hz, 1 H) 7.10 (s, 1 H) 7.21-7.41 (m, 6 H) 7.41-7.55 (m, 6 H) 7.76 (s, 1 H) 7.87 (d, J = 15.8 Hz, 1 H) | 382.1 |

TABLE 13

| Ex. No. | Structure | ¹H-NMR | MS(ESI) [M + H]⁺ |
|---|---|---|---|
| 15 | 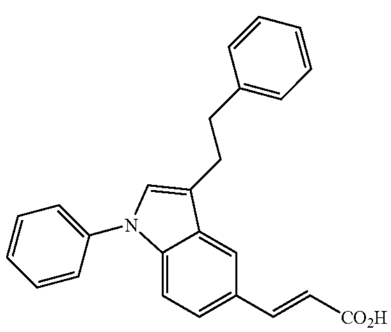 | 1H NMR (400 MHz, MeOH-d4) δ ppm 2.99-3.15 (m, 4 H) 6.40 (d, J = 15.8 Hz, 1 H) 7.12-7.28 (m, 6 H) 7.36 (t, J = 7.4 Hz, 1 H) 7.41-7.55 (m, 6 H) 7.70 (s, 1 H) 7.79 (d, J = 15.8 Hz, 1 H) | 368.1 |

TABLE 13-continued

| Ex. No. | Structure | $^1$H-NMR | MS(ESI) $[M + H]^+$ |
|---|---|---|---|
| 16 | 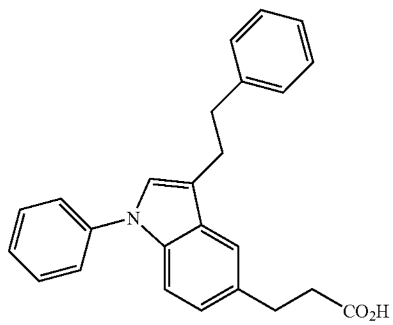 | 1H NMR (400 MHZ, MeOH-d4) δ ppm 2.64 (t, J = 7.9 Hz, 2 H) 3.03 (dd, J = 14.8, 11.7 Hz, 2 H) 3.03 (d, J = 11.2 Hz, 2 H) 3.08 (br. s., 2 H) 7.06 (d, J = 8.7 Hz, 1H) 7.11 (s, 1 H) 7.14-7.33 (m, 6 H) 7.38-7.54 (m, 5 H) 7.47 (dd, J = 18.6, 6.9 Hz, 1 H) | 370.1 |
| 17 | 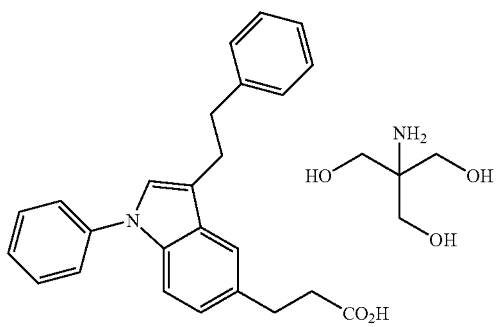 | 1H NMR (400 MHz, MeOH-d4) δ ppm 2.56 (d, J = 8.1 Hz, 1 H) 2.53 (s, 1 H) 2.98-3.11 (m, 5 H) 3.03 (d, J = 7.1 Hz, 1 H) 3.65 (s, 6 H) 7.08 (t, J = 3.3 Hz, 2 H) 7.13-7.32 (m, 6 H) 7.39-7.52 (m, 6 H) | 370.1 |
| 18 | 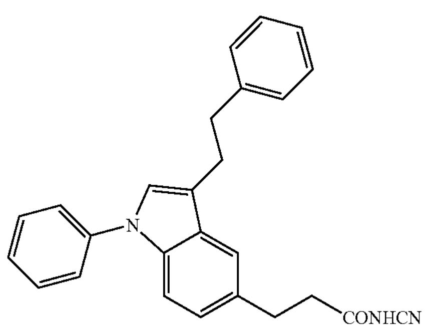 | 1H NMR (400 MHz, CHLOROFORM-d) δ ppm 2.86 (br. s., 2 H) 3.03 (dd, J = 18.6, 6.9 Hz, 1 H) 3.08 (br. s., 5 H) 6.96 (d, J = 8.1 Hz, 1 H) 7.00 (s, 1 H) 7.14-7.30 (m, 6 H) 7.30-7.48 (m, 6 H) | 394.2 |
| 19 | 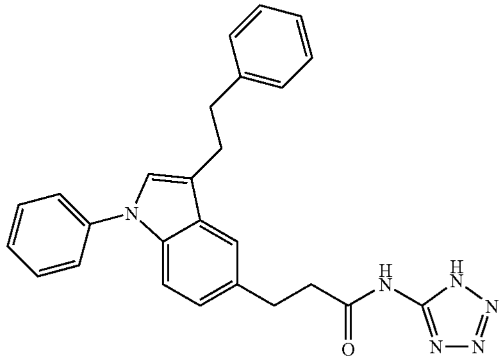 | 1H NMR (400 MHz, DMSO-d6) δ ppm 2.67 (d, J = 2.0 Hz, 2 H) 3.02 (br. s., 4 H) 7.00-7.57 (m, 14 H) 9.20 (br. s., 1 H) 10.43 (br. s., 1 H) | 437.3 |

TABLE 13-continued

| Ex. No. | Structure | ¹H-NMR | MS(ESI) [M + H]⁺ |
|---|---|---|---|
| 21 | 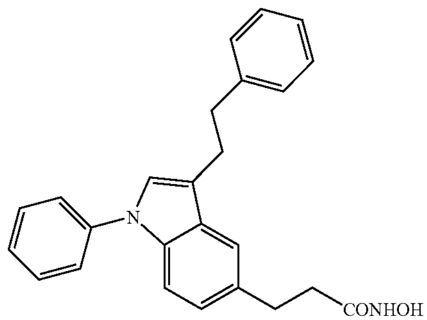 | 1H NMR (400 MHz, DMSO-d6) δ ppm 2.31 (t, J = 7.6 Hz, 2 H) 2.91 (t, J = 7.6 Hz, 2 H) 3.02 (s, 4 H) 7.04 (d, (J = 8.7 Hz, 1 H) 7.20 (t, J = 6.6 Hz, 1 H) 7.27-7.37 (m, 5 H) 7.40-7.58 (m, 7 H) 8.69 (br. s., 1 H) 10.36 (br. s., 1 H) | 385.1 |
| 22 | 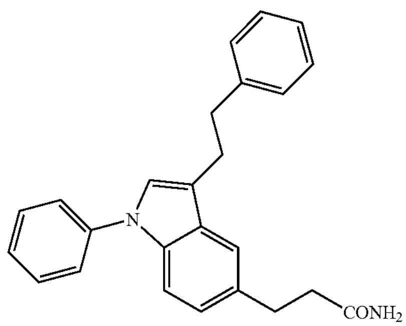 | 1H NMR (400 MHz, CHLOROFORM-d) δ ppm 2.60 (t, J = 7.6 Hz, 2 H) 3.02-3.13 (m, 6 H) 5.30 (br. s., 2 H) 6.98-7.14 (m, 2 H) 7.19-7.34 (m, 6 H) 7.42-7.51 (m, 6 H) | 369.2 |
| 24 | 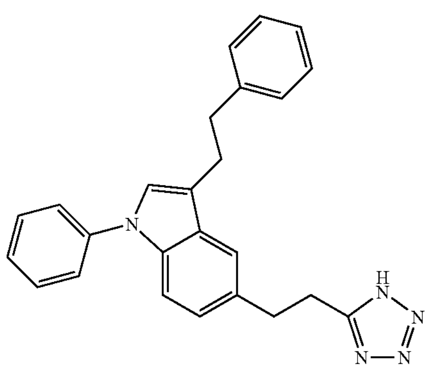 | 1H NMR (400 MHz, CHLOROFORM-d) δ ppm 3.00-3.12 (m, 4 H) 3.20 (t, J = 7.1 Hz, 2 H) 3.38 (t, J = 7.1 Hz, 2 H) 6.98 (d, J = 8.1 Hz, 1 H) 7.12 (s, 1 H) 7.16-7.36 (m, 7 H) 7.41-7.55 (m, 5 H) | 394.2 |
| 25 | 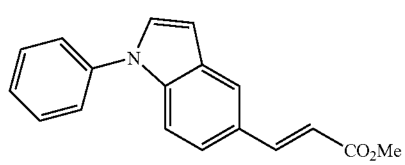 | 1H NMR (400 MHz, CHLOROFORM-d) δ ppm 3.82 (s, 3 H) 6.44 (d, J = 15.8 Hz, 1 H) 6.72 (d, J = 2.5 Hz, 1 H) 7.36-7.57 (m, 6 H) 7.84 (d, J = 2.0 Hz, 1 H) 7.88 (s, 1 H) | 278.1 |

TABLE 14

| Ex. No. | Structure | ¹H-NMR | MS(ESI) [M + H]⁺ |
|---|---|---|---|
| 26 | 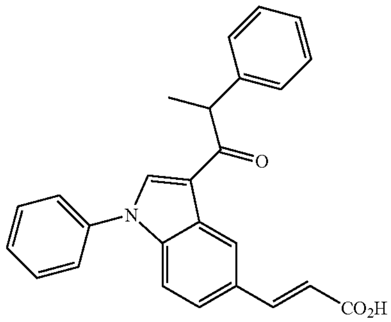 | 1H NMR (400 MHz, MeOH-d4) δ ppm 1.55 (d, J = 7.1 Hz, 3 H) 4.73 (t, J = 6.9 Hz, 1 H) 6.49 (d, J = 15.8 Hz, 1 H) 7.12-7.23 (m, 1 H) 7.29 (t, J = 7.6 Hz, 1 H) 7.40-7.63 (m, 10 H) 7.80 (d, J = 16.3 Hz, 1 H) 8.37 (s, 1 H) 8.59 (s, 1 H) | 396.1 |
| 27 | 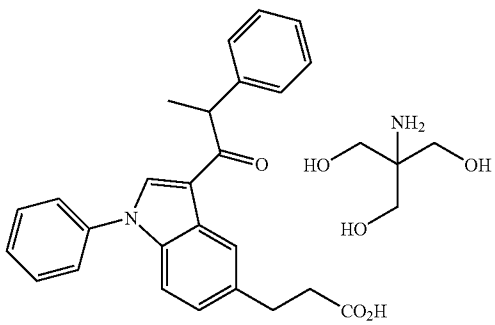 | 1H NMR (400 MHz, MeOH-d4) δ ppm 1.53 (d, J = 7.1 Hz, 3 H) 2.54 (d, J = 8.1 Hz, 1 H) 2.51 (s, 1 H) 3.03 (d, J = 8.1 Hz, 1 H) 3.06 (s, 1 H) 3.60 (s, 6 H) 4.70 (d, J = 7.1 Hz, 1 H) 7.19 (dd, J = 7.1, 4.6 Hz, 1 H) 7.34 (d, J = 8.7 Hz, 1 H) 7.28 (t, J = 7.6 Hz, 1 H) 7.41 (d, J = 7.6 Hz, 1 H) 7.45-7.53 (m, 5 H) 7.59 (t, J = 7.6 Hz, 2 H) 8.21-8.31 (m, 2 H) | 398.1 |
| 28 | 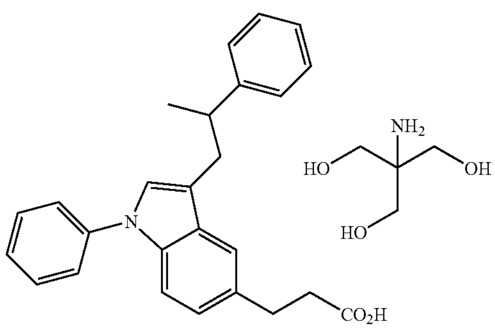 | 1H NMR (400 MHz, MeOH-d4) δ ppm 1.32 (d, J = 6.6 Hz, 3 H) 2.51 (s, 1 H) 2.54 (d, J = 8.1 Hz, 1 H) 3.00 (t, J = 6.9 Hz, 4 H) 3.14 (d, J = 6.6 Hz, 1 H) 3.64 (s, 6 H) 6.89 (s, 1 H) 7.05 (d, J = 9.7 Hz, 2 H) 7.13 (t, J = 6.4 Hz, 2 H) 7.18-7.50 (m, 10 H) | 384.1 |
| 29 | 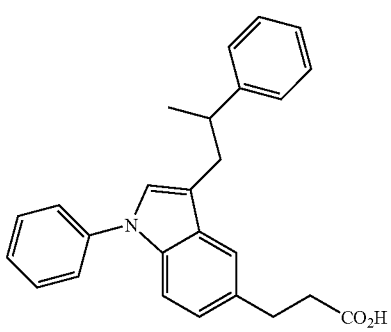 | 1H NMR (400 MHz, CHLOROFORM-d) δ ppm 1.34 (d, J = 6.6 Hz, 3 H) 2.59 (t, J = 7.6 Hz, 2 H) 2.97 (m, 1 H) 3.03-3.18 (m, 4 H) 5.29 (br. s., 2 H) 6.93 (s, 1 H) 7.06 (d, J = 9.7 Hz, 1 H) 7.18-7.34 (m, 6 H) 7.39 (d, J = 7.1 Hz, 1 H) 7.43-7.54 (m, 4 H) 7.46 (d, J = 5.1 Hz, 1 H) | 383.3 |

TABLE 14-continued

| Ex. No. | Structure | ¹H-NMR | MS(ESI) [M + H]⁺ |
|---|---|---|---|
| 33 | 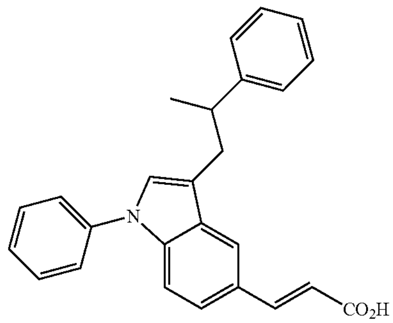 | 1H NMR (400 MHz, CHLOROFORM-d) δ ppm 1.38 (d, J = 7.1 Hz, 3 H) 3.00-3.20 (m, 1 H) 3.10 (d, J = 6.6 Hz, 2 H) 6.43 (d, J = 15.8 Hz, 1 H) 6.96 (s, 1 H) 7.20-7.37 (m, 5 H) 7.44 (d, J = 8.7 Hz, 1 H) 7.39-7.45 (m, 5 H) 7.50 (dd, J = 7.9, 5.9 Hz, 1 H) 7.70 (s, 1 H) 7.92 (d, J = 16.3 Hz, 1 H) | 382.1 |
| 35 | 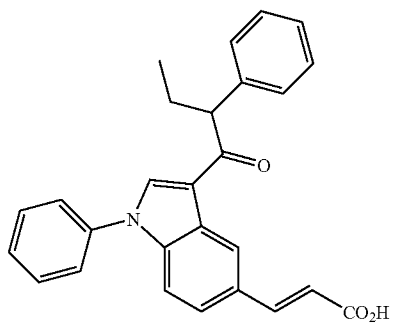 | 1H NMR (400 MHz, CHLOROFORM-d) δ ppm 0.96 (t, J = 7.4 Hz, 3 H) 1.93 (ddd, J = 13.9, 7.1, 6.7 Hz, 1 H) 2.32 (ddd, J = 14.0, 7.4, 7.1 Hz, 1 H) 4.22 (t, J = 7.4 Hz, 1 H) 6.53 (d, J = 15.8 Hz, 1 H) 7.19-7.52 (m, 10 H) 7.60 (s, 1 H) 7.57 (d, J = 8.1 Hz, 1 H) 7.87-7.99 (m, 2 H) 8.78 (s, 1 H) | 410.1 |
| 36 | 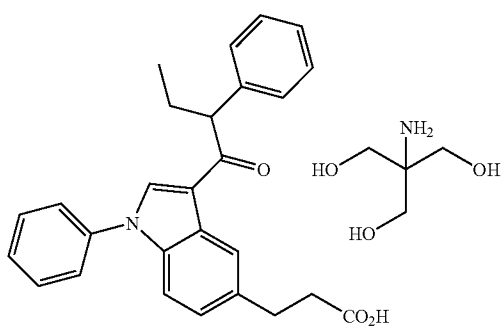 | 1H NMR (400 MHz, MeOH-d4) δ ppm 0.96 (t, J = 7.1 Hz, 3 H) 1.87 (m, 1 H) 2.25 (m, 1 H) 2.55 (t, J = 8.7 Hz, 2 H) 3.05 (t, 2 H) 3.50 (d, J = 7.1 Hz, 1 H) 3.63 (s, 6 H) 4.48 (t, J = 7.4 Hz, 1 H) 7.16-7.64 (m, 11 H) 8.27 (s, 1 H) 8.37 (s, 1 H) | 412.1 |
| 37 | 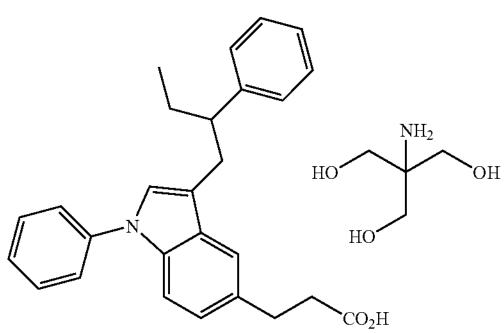 | 1H NMR (400 MHz, MeOH-d4) δ ppm 0.82 (t, J = 7.4 Hz, 3 H) 1.73 (dd, J = 9.7, 7.1 Hz, 1 H) 1.86 (dd, J = 7.4, 4.8 Hz, 1 H) 2.53 (d, J = 8.1 Hz, 2 H) 2.86 (br. s., 1 H) 2.99 (m, J = 10.2 Hz, 3 H) 3.14 (d, J = 6.1 Hz, 1 H) 3.59 (s, 6 H) 6.85 (s, 1 H) 7.05 (d, J = 8.7 Hz, 1 H) 7.12-7.31 (m, 6 H) 7.38 (m, 4 H) 7.47 (t, J = 7.9 Hz, 2 H) | 398.1 |

TABLE 15

| Ex. No. | Structure | ¹H-NMR | MS(ESI) [M + H]⁺ |
|---|---|---|---|
| 39 | 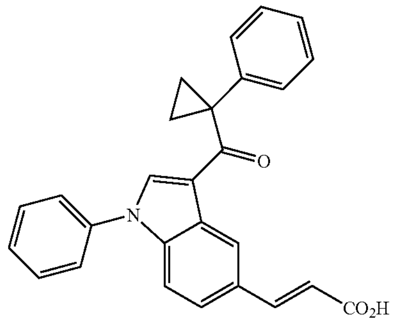 | 1H NMR (400 MHz, MeOH-d4) δ ppm 1.34 (d, J = 10.7 Hz, 1 H) 1.34 (d, J = 3.1 Hz, 1 H) 1.77 (d, J = 10.7 Hz, 1 H) 1.77 (d, J = 3.1 Hz, 1 H) 6.48 (d, J = 15.8 Hz, 1 H) 8.77 (s, 1 H) 7.21 (d, J = 7.1 Hz, 2 H) 7.30-7.53 (m, 9 H) 7.72-7.82 (m, 2 H) 8.61 (s, 1 H) | 408.1 |
| 40 | 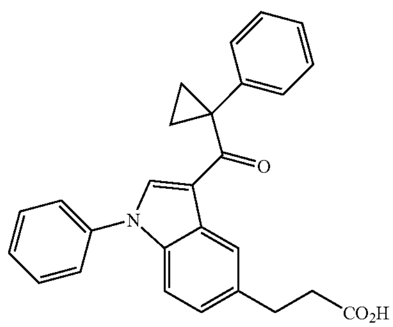 | 1H NMR (400 MHz, CHLOROFORM-d) δ ppm 1.28 (d, J = 10.7 Hz, 1 H) 1.29 (d, J = 3.1 Hz, 1 H) 1.81 (d, J = 10.7 Hz, 1 H) 1.81 (d, J = 3.1 Hz, 1 H) 2.74 (t, J = 7.9 Hz, 2 H) 3.09 (t, J = 7.6 Hz, 2 H) 6.72 (s, 1 H) 7.11-7.15 (m, 3 H) 7.26-7.48 (m, 8 H) 8.39 (s, 1 H) | 410.1 |
| 41 | 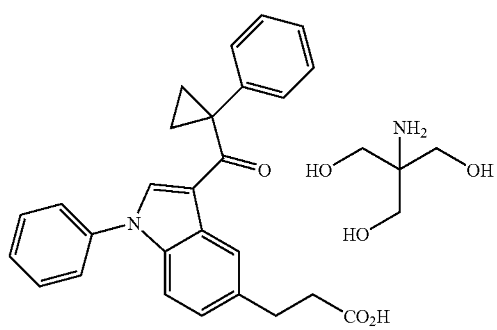 | 1H NMR (400 MHz, MeOH-d4) δ ppm 0.77-0.89 (m, 2 H) 0.89-0.96 (m, 2 H) 2.50 (d, J = 8.1 Hz, 1 H) 2.47 (s, 1 H) 2.97 (s, 1 H) 2.94 (d, J = 8.1 Hz, 1 H) 3.12 (s, 2 H) 3.62 (s, 6 H) 6.92 (s, 1 H) 7.03 (d, J = 8.7 Hz, 2 H) 7.10-7.32 (m, 7 H) 7.39 (d, J = 6.6 Hz, 2 H) 7.36 (s, 1 H) 7.48 (t, J = 7.9 Hz, 2 H) | 396.1 |
| 44 | 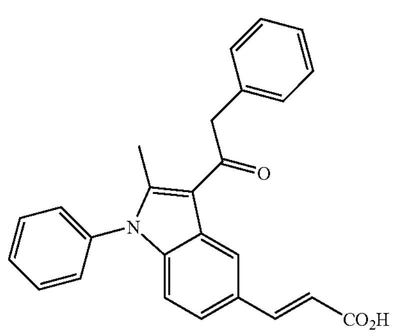 | 1H NMR (400 MHz, MeOH-d4) δ ppm 2.58 (s, 3 H) 4.44 (s, 2 H) 6.45 (d, 1 H) 7.01 (d, J = 8.7 Hz, 1 H) 7.23-7.36 (m, 5 H) 7.44 (d, J = 6.6 Hz, 3 H) 7.64 (m, 3 H) 7.79 (d, J = 16.3 Hz, 1 H) 8.34 (s, 1 H) | 396.0 |

TABLE 15-continued

| Ex. No. | Structure | ¹H-NMR | MS(ESI) [M + H]⁺ |
|---|---|---|---|
| 45 | 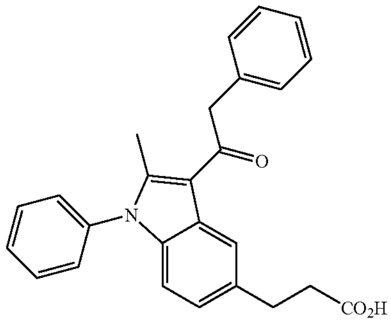 | 1H NMR (400 MHz, CHLOROFORM-d) δ ppm 2.57 (s, 3 H) 2.71 (t, J = 7.9 Hz, 2 H) 3.08 (t, J = 7.6 Hz, 2 H) 4.38 (s, 2 H) 6.92-6.98 (m, 1 H) 6.99-7.08 (m, 1 H) 7.23-7.39 (m, 7 H) 7.47-7.62 (m, 2 H) 7.56 (d, J = 7.1 Hz, 1 H) 7.97 (s, 1 H) | 398.1 |
| 48 | 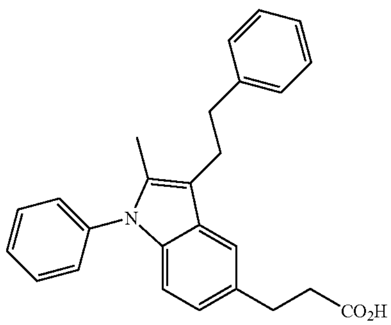 | 1H NMR (400 MHz, CHLOROFORM-d) δ ppm 1.96 (s, 3 H) 2.74 (t, J = 7.9 Hz, 2 H) 2.95 (d, J = 7.6 Hz, 6 H) 3.06 (ddd, J = 16.0, 7.9, 7.6 Hz, 4 H) 6.92-6.98 (m, 1 H) 6.99-7.06 (m, 1 H) 7.16-7.30 (m, 8 H) 7.41 (d, J = 7.1 Hz, 1 H) 7.38 (s, 1 H) 7.50 (t, J = 7.6 Hz, 2 H) | 384.1 |
| 50 | 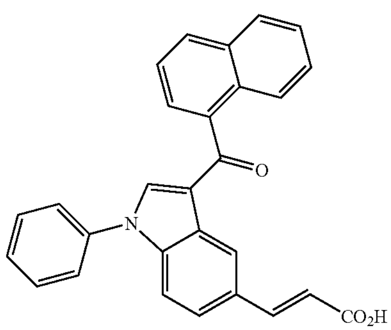 | 1H NMR (400 MHz, DMSO-d6) δ ppm 6.53 (d, J = 15.8 Hz, 1 H) 7.51 (d, J = 7.1 Hz, 1 H) 7.54-7.67 (m, 8 H) 7.78 (d, J = 4.1 Hz, 1 H) 7.75 (br. s., 1 H) 7.87 (d, J = 7.1 Hz, 1 H) 8.05 (d, J = 7.1 Hz, 1 H) 8.01 (s, 1 H) 8.13 (t, J = 7.4 Hz, 2 H) 8.62 (s, 1 H) | 418.1 |
| 51 | 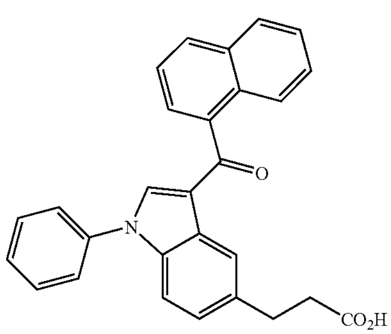 | 1H NMR (400 MHz, CHLOROFORM-d) δ ppm 2.75 (t, J = 7.6 Hz, 2 H) 3.09 (t, J = 7.9 Hz, 2 H) 4.58 (s, 2 H) 6.81 (s, 1 H) 7.11 (d, J = 8.7 Hz, 1 H) 7.35-7.53 (m, 11 H) 7.76 (d, J = 3.6 Hz, 1 H) 7.87 (d, J = 5.1 Hz, 1 H) 8.13 (d, J = 9.7 Hz, 1 H) | 406.1 |

TABLE 15-continued

| Ex. No. | Structure | ¹H-NMR | MS(ESI) [M + H]⁺ |
|---|---|---|---|
| 53 | (naphthyl-C(O)-indole(N-phenyl)-CH=CH-CO₂H) | 1H NMR (400 MHz, DMSO-d6) δ ppm 6.5 (d, J = 15.8 Hz, 1 H) 7.53 (t, J = 7.6 Hz, 1 H) 7.59-7.71 (m, 5 H) 7.76 (d, J = 7.6 Hz, 3 H) 7.95-8.10 (m, 3 H) 7.98 (d, J = 8.7 Hz, 1 H) 8.16 (d, J = 7.6 Hz, 1 H) 8.37 (s, 1 H) 8.59 (s, 2 H) | 418.1 |

TABLE 16

| Ex. No. | Structure | ¹H-NMR | MS(ESI) [M + H]⁺ |
|---|---|---|---|
| 54 | (naphthyl-C(O)-indole(N-phenyl)-CH₂CH₂-CO₂H) | 1H NMR (400 MHz, CHLOROFORM-d) δ ppm 2.70 (t, J = 7.9 Hz, 2 H) 3.05 (t, J = 7.6 Hz, 2 H) 4.30 (s, 2 H) 7.04 (s, 1 H) 7.08 (d, J = 8.7 Hz, 1 H) 7.21-7.32 (m, 1 H) 7.39-7.53 (m, 9 H) 7.73-7.84 (m, 3 H) 7.79 (d, J = 2.5 Hz, 1 H) | 406.1 |
| 56 | (4-Cl-phenyl-CH₂-C(O)-indole(N-phenyl)-CH=CH-CO₂H) | 1H NMR (400 MHz, CHLOROFORM-d) δ ppm 4.18 (s, 2 H) 6.51 (d, J = 15.8 Hz, 1 H) 7.24-7.34 (m, 2 H) 7.30 (d, J = 5.1 Hz, 1 H) 7.43-7.56 (m, 6 H) 7.60 (d, J = 7.1 Hz, 1 H) 7.62 (br. s., 1 H) 7.92 (d, J = 15.8 Hz, 1 H) 7.98 (s, 1 H) 8.70 (s, 1 H) | 416 |
| 57 | (4-Cl-phenyl-CH₂-C(O)-indole(N-phenyl)-CH₂CH₂-CO₂H) | 1H NMR (400 MHz, CHLOROFORM-d) δ ppm 2.74 (t, J = 7.6 Hz, 2 H) 3.10 (t, J = 7.6 Hz, 2 H) 4.16 (s, 2 H) 7.17 (d, J = 8.7 Hz, 1 H) 7.24-7.33 (m, 4 H) 7.38 (d, J = 8.1 Hz, 1 H) 7.49 (d, J = 7.6 Hz, 2 H) 7.46 (br. s., 1 H) 7.56 (d, J = 7.6 Hz, 1 H) 7.59 (br. s., 1 H) 7.95 (s, 1 H) 8.33 (s, 1 H) | 418 |

TABLE 16-continued

| Ex. No. | Structure | ¹H-NMR | MS(ESI) [M + H]⁺ |
|---|---|---|---|
| 58 | 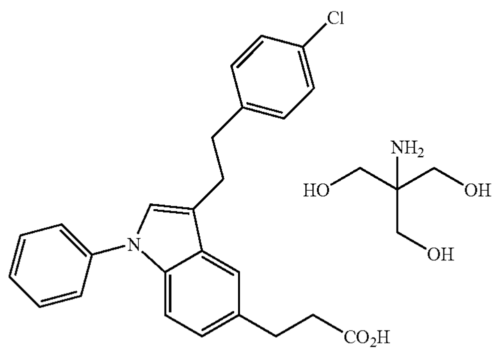 | 1H NMR (400 MHz, CHLOROFORM-d) δ ppm 2.56 (s, 1 H) 2.53 (d, J = 8.1 Hz, 1 H) 2.95-3.13 (m, 5H) 3.02 (d, J = 7.1 Hz, 1 H) 3.62 (s, 6 H) 7.03-7.12 (m, 2 H) 7.15-7.27 (m, 4 H) 7.30 (t, J = 7.4 Hz, 1 H) 7.37-7.56 (m, 6 H) | 404.1 |
| 60 | 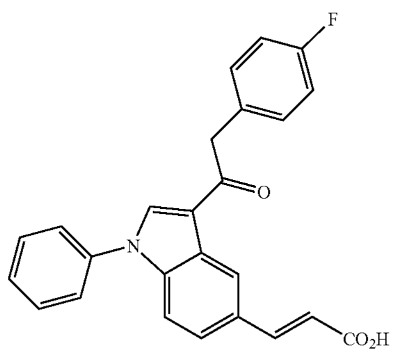 | 1H NMR (400 MHz, CHLOROFORM-d) δ ppm 4.18 (s, 2 H) 6.51 (d, J = 15.8 Hz, 1 H) 7.03 (t, J = 8.7 Hz, 2 H) 7.31 (dd, J = 8.7, 5.6 Hz, 3 H) 7.51 (t, J = 7.4 Hz, 2 H) 7.43-7.56 (m, 4 H) 7.59 (d, J = 7.1 Hz, 1 H) 7.62 (br. s., 1 H) 7.92 (d, J = 15.8 Hz, 1 H) 7.98 (s, 1 H) 8.71 (s, 1 H) | 400.1 |
| 61 | 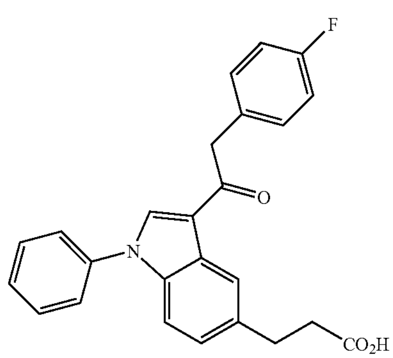 | 1H NMR (400 MHz, CHLOROFORM-d) δ ppm 2.74 (t, J = 7.6 Hz, 2 H) 3.09 (t, J = 7.9 Hz, 2 H) 4.16 (s, 2 H) 7.01 (t, J = 8.7 Hz, 2 H) 7.16 (d, J = 8.1 Hz, 1 H) 7.23-7.40 (m, 3 H) 7.42-7.60 (m, 5 H) 7.95 (s, 1 H) 8.33 (s, 1 H) | 402.1 |
| 62 | 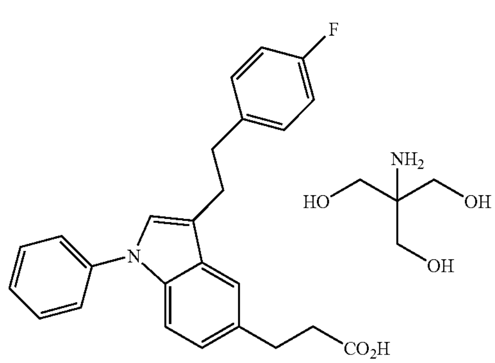 | 1H NMR (400 MHz, MeOH-d4) δ ppm 2.54 (d, J = 8.1 Hz, 1 H) 2.51 (s, 1 H) 2.96-3.09 (m, 6 H) 3.60 (s, 6 H) 6.96 (t, J = 8.9 Hz, 2 H) 7.05-7.12 (m, 2 H) 7.21 (dd, J = 8.65, 5.59 Hz, 2 H) 7.30 (t, J = 7.4 Hz, 1 H) 7.40-7.52 (m, 6 H) | 388.1 |

TABLE 16-continued

| Ex. No. | Structure | ¹H-NMR | MS(ESI) [M + H]⁺ |
|---|---|---|---|
| 64 | 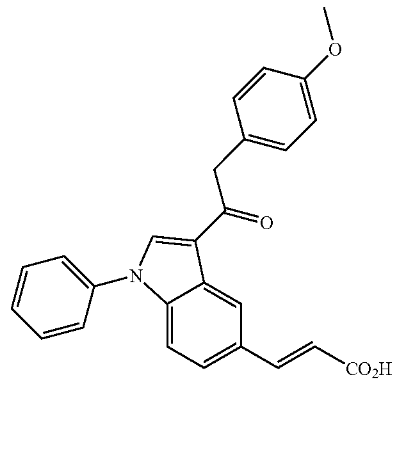 | 1H NMR (400 MHz, CHLOROFORM-d) δ ppm 3.79 (s, 3 H) 4.14 (s, 2 H) 6.51 (d, J = 15.8 Hz, 1 H) 6.88 (d, J = 8.7 Hz, 2 H) 7.28 (s, 2 H) 7.42-7.54 (m, 5 H) 7.61 (br. s, 1 H) 7.58 (d, J = 7.6 Hz, 1 H) 7.92 (d, J = 16.3 Hz, 1 H) 7.97 (s, 1 H) 8.71 (s, 1 H) | 412.1 |
| 65 | 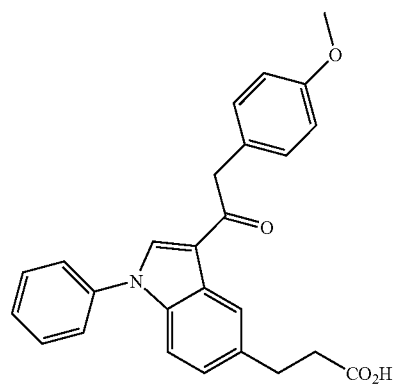 | 1H NMR (400 MHz, CHLOROFORM-d) δ ppm 2.74 (t, J = 7.9 Hz, 2 H) 3.10 (t, J = 7.9 Hz, 2 H) 3.78 (s, 3 H) 4.13 (s, 2 H) 6.87 (d, J = 8.7 Hz, 2 H) 7.16 (d, J = 8.7 Hz, 1 H) 7.27 (br. s., 4 H) 7.38 (d, J = 8.7 Hz, 1 H) 7.48 (d, J = 7.6 Hz, 1 H) 7.46 (br. s., 2 H) 7.56 (d, J = 7.6 Hz, 1 H) 7.58 (br. s., 1 H) 7.94 (s, 1 H) 8.35 (s, 1 H) | 414.1 |

TABLE 17

| Ex. No. | Structure | ¹H-NMR | MS(ESI) [M + H]⁺ |
|---|---|---|---|
| 66 | 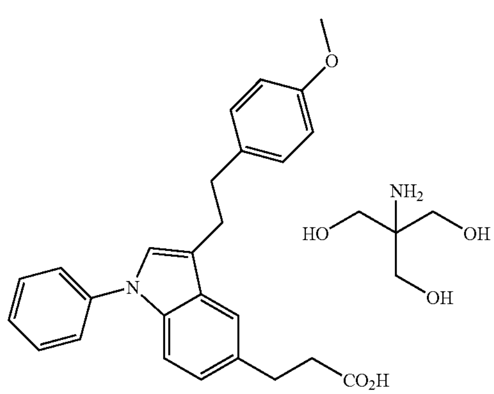 | 1H NMR (400 MHz, MeOH-d4) δ ppm 2.54 (d, J = 8.7 Hz, 1 H) 2.51 (s, 1 H) 3.01 dd, J = 19.3, 3.1 Hz, 1 H) 2.89-3.08 (m, 5 H) 3.61 (s, 6 H) 3.76 (s, 3 H) 6.82 (d, J = 8.7 Hz, 2 H) 7.13 (d, J = 8.7 Hz, 1 H) 7.04-7.15 (m, 3 H) 7.30 (m, 1 H) 7.39-7.53 (m, 6 H) | 400.1 |

TABLE 17-continued

| Ex. No. | Structure | ¹H-NMR | MS(ESI) [M + H]⁺ |
|---|---|---|---|
| 68 | 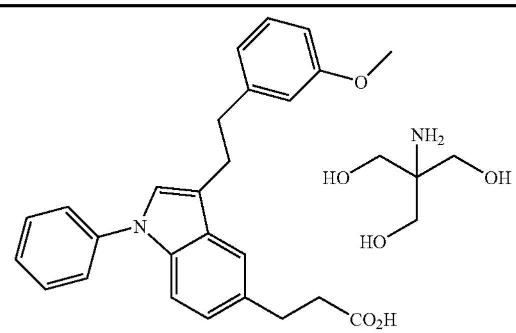 | 1H NMR (400 MHz, MeOH-d4) δ ppm 2.54 (d, J = 8.1 Hz, 1 H) 2.51 (s, 1 H) 2.97-3.10 (m, 6 H) 3.61 (s, 6 H) 3.71 (s, 3 H) 6.70-6.77 (m, 2 H) 6.82 (d, J = 7.6 Hz, 1 H) 7.04-7.11 (m, 2 H) 7.16 (t, J = 8.1 Hz, 1 H) 7.30 (t, J = 7.4 Hz, 1 H) 7.39-7.56 (m, 6 H) | 400.2 |
| 70 | 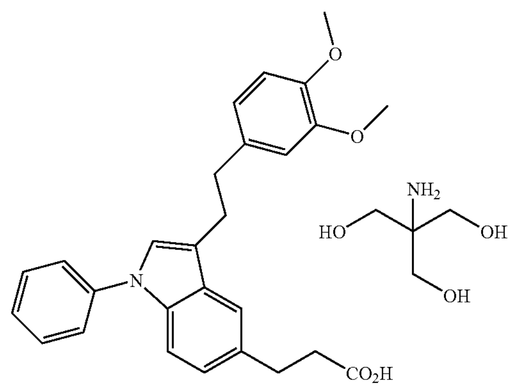 | 1H NMR (400 MHz, MeOH-d4) δ ppm 2.54 (d, J = 8.1 Hz, 1 H) 2.51 (s, 1 H) 2.93-3.08 (m, 6 H) 3.61 (s, 6 H) 3.69 (s, 3 H) 3.79 (s, 3 H) 6.71 (s, 1 H) 6.75-6.81 (m, 1 H) 6.83-6.89 (m, 1 H) 7.04-7.12 (m, 2 H) 7.30 (t, J = 7.1 Hz, 1 H) 7.38-7.54 (m, 6 H) | 430.1 |
| 71 | 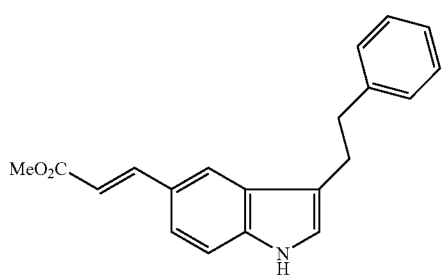 | 1H HMR (400 MHz, CHLOROFORM-d) δ ppm 2.99-3.11 (m, 2 H) 3.05 (dd, J = 18.6, 7.4 Hz, 2 H) 3.81 (s, 3 H) 6.41 (d, J = 15.8 Hz, 1 H) 6.93 (d, J = 2.0 Hz, 1 H) 7.18-7.35 (m, 6 H) 7.38-7.48 (m, 1 H) 7.71 (s, 1 H) 7.84 (d, J = 15.8 Hz, 1 H) 8.02 (br. s., 1 H) | 306.1 |
| 72 | 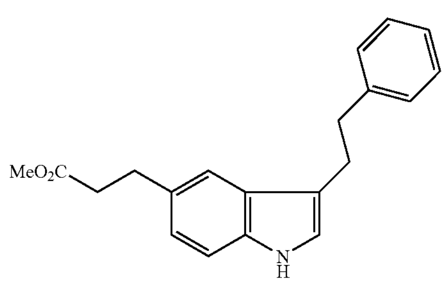 | 1H NMR (400 MHz, CHLOROFORM-d) δ ppm 2.56-2.75 (m, 1 H) 2.69 (d, J = 8.7 Hz, 1 H) 2.98-3.09 (m, 6 H) 3.68 (s, 3 H) 6.91 (d, J = 2.5 Hz, 1 H) 7.04 (d, J = 8.1 Hz, 1 H) 7.18-7.31 (m, 6 H) 7.39 (s, 1 H) 7.84 (br. s., 1 H) | 308.1 |
| 74 | 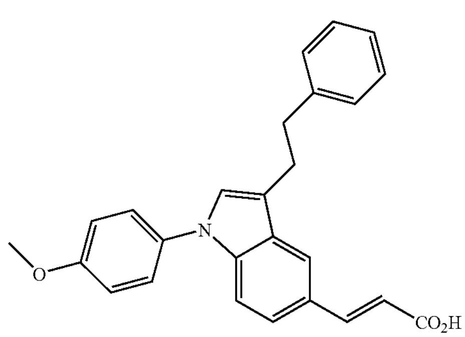 | 1H NMR (400 MHz, CHLOROFORM-d) δ ppm 3.02-3.16 (m, 4 H) 3.88 (s, 3 H) 6.43 (d, J = 15.8 Hz, 1 H) 7.03 (d, J = 4.6 Hz, 2 H) 7.01 (s, 1 H) 7.20-7.36 (m, 7 H) 7.43 (d, J = 5.6 Hz, 1 H) 7.40 (s, 1 H) 7.76 (s, 1 H) 7.94 (d, J = 15.8 Hz, 1 H) | 398.1 |

TABLE 17-continued

| Ex. No. | Structure | ¹H-NMR | MS(ESI) [M + H]⁺ |
|---|---|---|---|
| 77 | 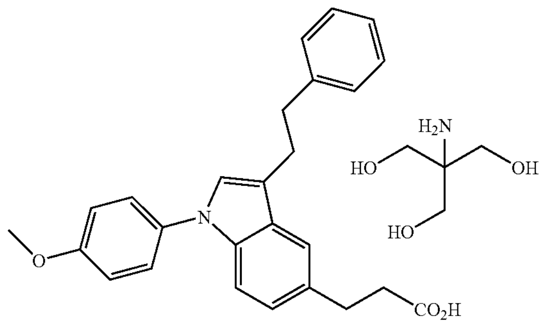 | 1H HMR (400 MHz, MeOH-d4) δ ppm 2.54 (d, J = 8.7 Hz, 1 H) 2.51 (s, 1 H) 2.98-3.13 (m, 6 H) 3.62 (s, 6 H) 3.85 (s, 3 H) 7.05 (d, J = 9.2 Hz, 3 H) 6.99 (s, 1 H) 7.13-7.36 (m, 8 H) 7.42 (s, 1 H) | 400.1 |
| 79 | 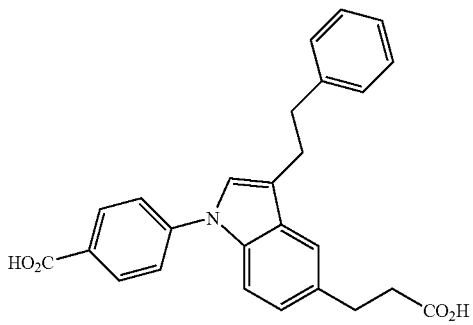 | 1H NMR (400 MHz, MeOH-d4) δ ppm 2.60-2.68 (m, 2H) 2.95-3.12 (m, 6H) 7.08-7.30 (m, 7H) 7.40 (s, 1 H) 7.50-7.62 (m, 3 H) 8.10-8.20 (m, 2 H) | 414.1 |
| 81 | 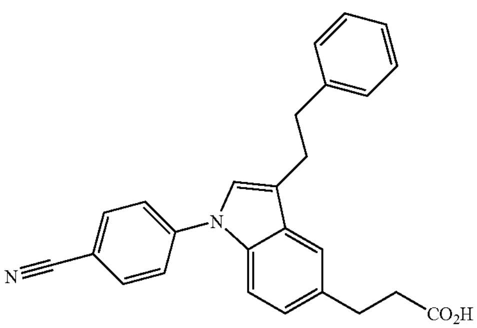 | 1H NMR (400 MHz, MeOH-d4) δ ppm 2.63 (t, J = 7.6 Hz, 2 H) 2.96-3.13 (m, 6 H) 7.10-7.27 (m, 7 H) 7.42 (s, 1 H) 7.56 (d, J = 8.7 Hz, 1 H) 7.66 (d, J = 8.7 Hz, 2 H) 7.84 (d, J = 8.7 Hz, 2 H) | 395.1 |

TABLE 18

| Ex. No. | Structure | ¹H-NMR | MS(ESI) [M + H]⁺ |
|---|---|---|---|
| 83 | 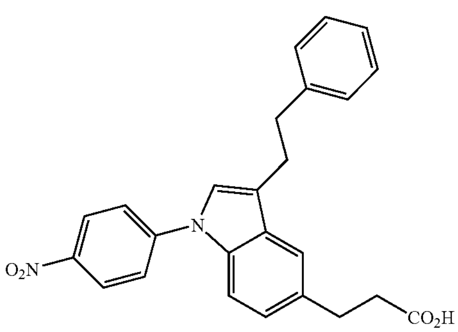 | 1H NMR (400 MHz, DMSO-d6) δ ppm 2.58 (t, J = 7.6 Hz, 2 H) 2.94 (t, J = 7.4 Hz, 2 H) 3.03 (s, 4 H) 7.18 (dd, J = 17.8. 7.6 Hz, 2 H) 7.25-7.35 (m, 4 H) 7.52 (s, 1 H) 7.63 (s, 1 H) 7.66 (d, J = 8.1 Hz, 1 H) 7.85 (d, J = 9.2 Hz, 2 H) 8.38 (d, J = 9.2 Hz, 2 H) | 415.1 |

TABLE 18-continued

| Ex. No. | Structure | ¹H-NMR | MS(ESI) [M + H]⁺ |
|---|---|---|---|
| 85 | 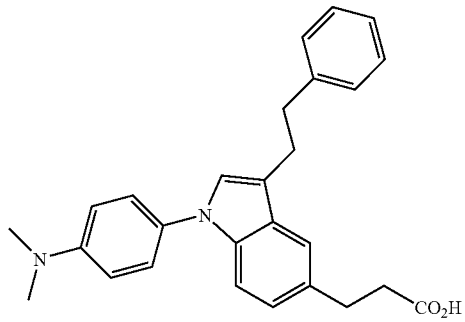 | 1H NMR (400 MHz, CHLOROFORM-d) δ ppm 2.62 (t, J = 7.6 Hz, 2 H) 2.94-3.08 (m, 12 H) 6.88 (d, J = 9.2 Hz, 2 H) 6.98 (s, 1 H) 7.00 (d, J = 8.7 Hz, 1 H) 7.13-7.29 (m, 8 H) 7.37 (s, 1 H) | 413.3 |
| 86 | 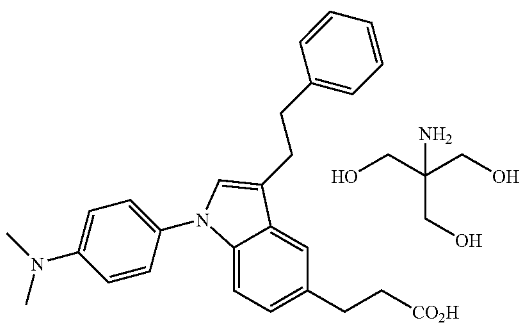 | 1H NMR (400 MHz, MeOH-d4) δ ppm 2.54 (d, J = 5.9 Hz, 1 H) 2.52 (d, J = 8.1 Hz, 1 H) 2.94-3.07 (m, 12 H) 3.60 (s, 6 H) 6.89 (d, J = 9.2 Hz, 1 H) 6.89 (d, J = 4.4 Hz, 1 H) 6.96 (s, 1 H) 7.03 (d, J = 8.4 Hz, 1 H) 7.13-7.28 (m, 8 H) 7.41 (s, 1 H) | 413.3 |
| 88 | 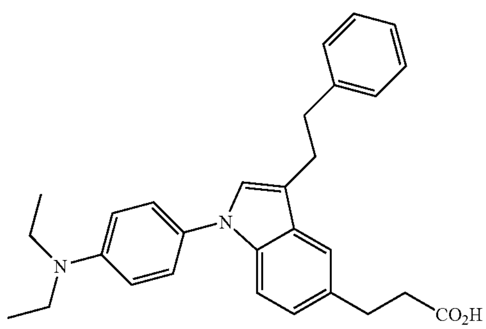 | 1H NMR (400 MHz, CHLOROFORM-d) δ ppm 1.21 (t, J = 7.0 Hz, 6 H) 2.74 (t, J = 7.9 Hz, 2 H) 3.08 (d, J = 19.0 Hz, 4 H) 3.07 (d, J = 7.3 Hz, 2 H) 3.40 (q, J = 7.0 Hz, 4 H) 6.75 (d, J = 9.2 Hz, 2 H) 7.04 (d, J = 8.4 Hz, 1 H) 6.96-7.10 (m, 1 H) 7.18-7.39 (m, 8 H) 7.43 (s, 1 H) | 441.2 |
| 91 | 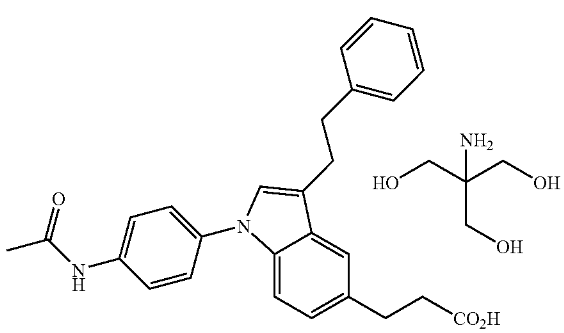 | 1H NMR (400 MHz, MeOH-d4) δ ppm 2.15 (s, 3 H) 2.54 (d, J = 8.1 Hz, 1 H) 2.51 (s, 1 H) 2.98-3.12 (m, 5 H) 3.04 (d, J = 6.1 Hz, 1 H) 3.62 (s, 6 H) 7.04-7.10 (m, 2 H) 7.13-7.28 (m, 4 H) 7.23 (d, J = 4.1 Hz, 1 H) 7.40 (t, J = 12.7 Hz, 1 H) 7.33-7.47 (m, 3 H) 7.68 (d, J = 8.7 Hz, 2 H) | 427.1 |

TABLE 18-continued

| Ex. No. | Structure | ¹H-NMR | MS(ESI) [M + H]⁺ |
|---|---|---|---|
| 93 | 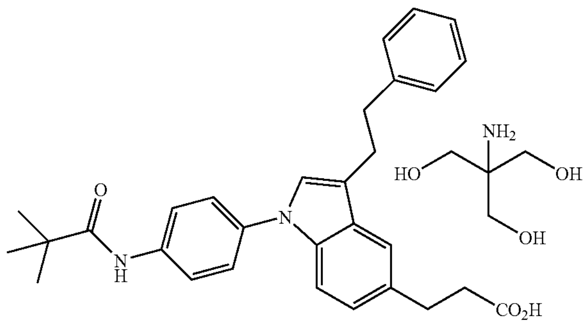 | 1H NMR (400 MHz, MeOH-d4) δ ppm 1.32 (s, 9 H) 2.54 (d, J = 8.7 Hz, 1 H) 2.51 (s, 1 H) 2.95-3.13 (m, 6 H) 3.61 (s, 6 H) 7.04-7.10 (m, 2 H) 7.13-7.28 (m, 5 H) 7.39 (d, J = 8.7 Hz, 3 H) 7.43 (s, 1 H) 7.67 (d, J = 8.7 Hz, 2 H) | 469.2 |
| 95 | 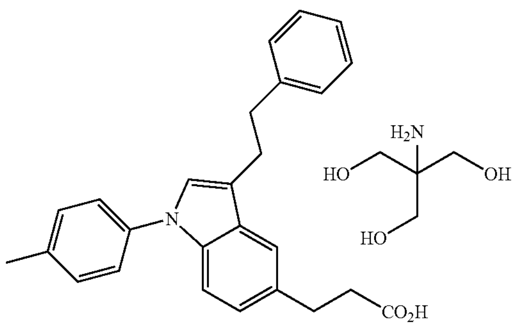 | 1H NMR (400 MHz, MeOH-d4) δ ppm 2.40 (s, 3 H) 2.54 (d, J = 8.1 Hz, 1 H) 2.51 (s, 1 H) 2.98-3.13 (m, 6 H) 3.61 (s, 6 H) 7.04 (s, 1 H) 7.06 (d, J = 10.2 Hz, 2 H) 7.15 (t, J = 7.9 Hz, 1 H) 7.17 (br. s., 1 H) 7.20-7.38 (m, 7H) 7.43 (s, 1 H) | 384.1 |
| 97 | 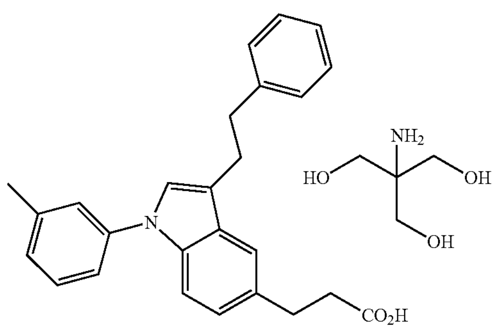 | 1H NMR (400 MHz, MeOH-d4) δ ppm 2.41 (s, 3 H) 2.54 (d, J = 8.7 Hz, 1 H) 2.51 (s, 1 H) 2.98-3.12 (m, 5 H) 3.03 (dd, J = 9.9, 6.9 Hz, 1 H) 3.61 (s, 6 H) 7.05-7.27 (m, 10 H) 7.40 (d, J = 8.1 Hz, 1 H) 7.33-7.42 (m, 1 H) 7.43 (s, 1 H) | 384.2 |
| 99 | 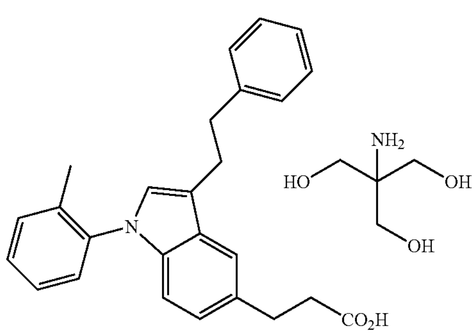 | 1H NMR (400 MHz, MeOH-d4) δ ppm 1.96 (s, 3 H) 2.55 (d, J = 8.1 Hz, 1 H) 2.52 (s, 1 H) 2.99-3.08 (m, 4 H) 3.03 (s, 1 H) 3.09 (br. s., 1 H) 3.62 (s, 6 H) 6.77-6.83 (m, 2 H) 7.01 (d, J = 8.7 Hz, 1 H) 7.11-7.25 (m, 5 H) 7.20 (q, J = 6.6 Hz, 1 H) 7.27-7.38 (m, 3 H) 7.46 (s, 1 H) | 384.2 |

TABLE 19

| Ex. No. | Structure | ¹H-NMR | MS(ESI) [M + H]⁺ |
|---|---|---|---|
| 101 | 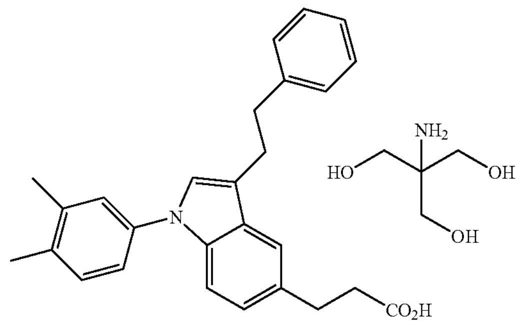 | 1H NMR (400 MHz, MeOH-d4) δ ppm 2.32 (d, J = 6.6 Hz, 6 H) 2.54 (d, J = 8.1 Hz, 1 H) 2.51 (s, 1 H) 2.96-3.14 (m, 6 H) 3.61 (s, 6 H) 7.02 (s, 1 H) 7.06 (d, J = 7.1 Hz, 1 H) 7.11-7.28 (m, 8 H) 7.36 (d, J = 8.7 Hz, 1 H) 7.42 (s, 1 H) | 398.2 |
| 103 | 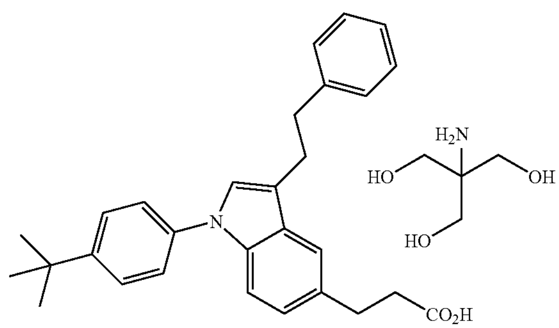 | 1H NMR (400 MHz, MeOH-d4) δ ppm 1.38 (s, 9 H) 2.54 (d, J = 8.1 Hz, 1 H) 2.51 (s, 1 H) 2.97-3.10 (m, 5 H) 3.03 (dd, J = 11.0. 6.9 Hz, 1 H) 3.61 (s, 6 H) 7.03-7.10 (m, 2 H) 7.13-7.28 (m, 4 H) 7.23 (d, J = 2.5 Hz, 1 H) 7.34-7.45 (m, 3 H) 7.37 (d, J = 8.7 Hz, 1 H) 7.54 (d, J = 8.1 Hz, 2 H) | 426.2 |
| 105 | 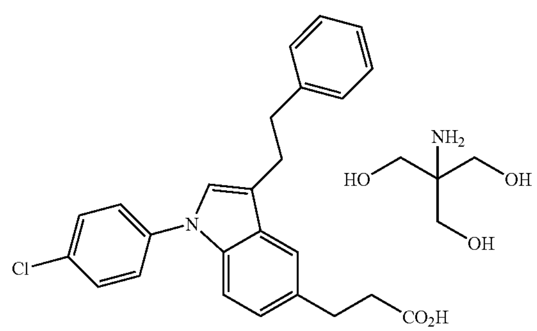 | 1H NMR (400 MHz, MeOH-d4) δ ppm 2.54 (d, J = 8.7 Hz, 1 H) 2.51 (s, 1 H) 2.98-3.09 (m, 6 H) 3.61 (s, 6 H) 7.07-7.27 (m, 7 H) 7.39-7.51 (m, 6 H) | 404.1 |
| 107 | 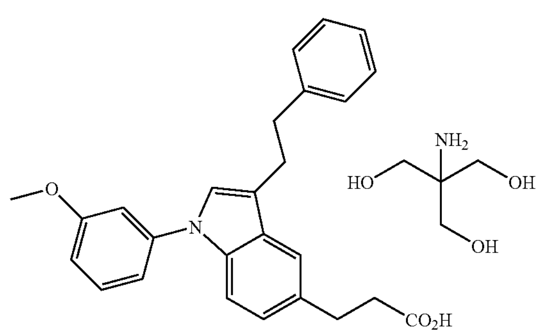 | 1H NMR (400 MHz, MeOH-d4) δ ppm 2.55 (d, J = 8.7 Hz, 1 H) 2.52 (s, 1 H) 2.97-3.10 (m, 6 H) 3.63 (s, 6 H) 3.83 (s, 3 H) 6.86 (d, J = 9.2 Hz, 1 H) 6.95-7.10 (m, 4 H) 7.13-7.27 (m, 5 H) 7.32-7.48 (m, 3 H) | 400.1 |

TABLE 19-continued

| Ex. No. | Structure | ¹H-NMR | MS(ESI) [M + H]⁺ |
|---|---|---|---|
| 109 | 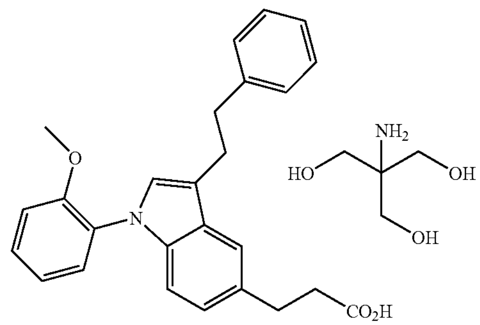 | 1H NMR (400 MHz, MeOH-d4) δ ppm 2.56 (d, J = 8.1 Hz, 1 H) 2.53 (s, 1 H) 2.97-3.09 (m, 6 H) 3.64 (s, 6 H) 3.73 (s, 3 H) 6.91-7.08 (m, 4 H) 7.13-7.29 (m, 7 H) 7.41 (s, 1 H) 7.36 (t, J = 7.1 Hz, 1 H) | 400.2 |
| 112 | 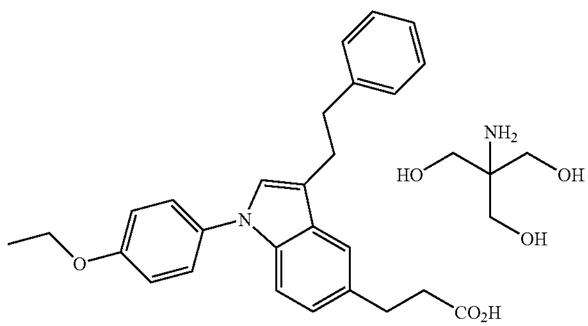 | 1H NMR (400 MHz, MeOH-d4) δ ppm 1.42 (t, J = 6.9 Hz, 3 H) 2.53 (d, J = 8.1 Hz, 1 H) 2.50 (s, 1 H) 2.92-3.10 (m, 6 H) 3.60 (s, 6 H) 4.09 (q, J = 7.0 Hz, 2 H) 6.98-7.07 (m, 3 H) 7.03 (d, J = 8.7 Hz, 1 H) 7.13-7.34 (m, 8 H) 7.42 (s, 1 H) | 414.1 |
| 113 | 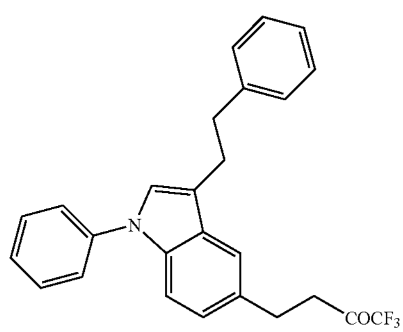 | 1H NMR (400 MHz, CHLOROFORM-d) δ ppm 3.02-3.13 (m, 8 H) 7.04 (d, J = 10.2 Hz, 1 H) 7.09 (s, 1 H) 7.19-7.35 (m, 5 H) 7.37-7.52 (m, 7 H) | 422 (FABMS) |
| 114 | 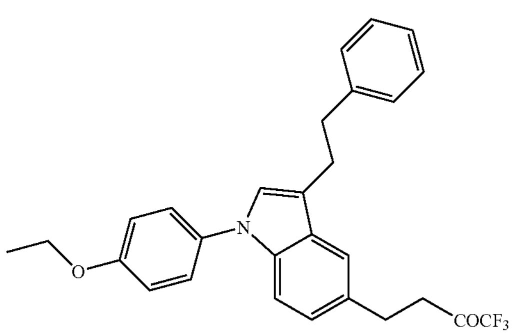 | 1H NMR (400 MHz, CHLOROFORM-d) δ ppm 1.46 (t, J = 7.1 Hz, 3 H) 2.99-3.14 (m, 8 H) 4.09 (q, J = 6.8 Hz, 2 H) 7.01 (d, J = 6.6 Hz, 3 H) 6.98 (s, 1 H) 7.19-7.39 (m, 9 H) | 466 (FABMS) |

TABLE 19-continued

| Ex. No. | Structure | ¹H-NMR | MS(ESI) [M + H]⁺ |
|---|---|---|---|
| 115 | 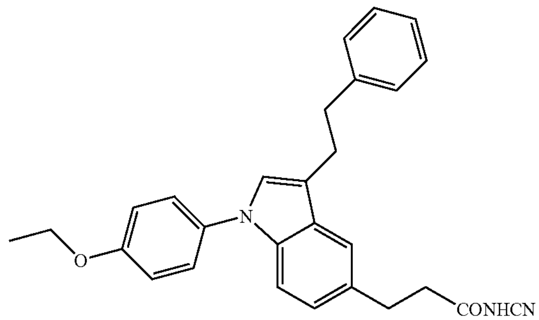 | 1H NMR (400 MHz, MeOH-d4) δ ppm 1.37 (t, J = 7.1 Hz, 3 H) 2.54-2.65 (m, 2H) 2.95-3.10 (m, 6 H) 4.07 (q, J = 6.8 Hz, 2 H) 6.98-7.06 (m, 4 H) 7.10-7.33 (m, 8 H) 7.40 (s, 1 H) | 438.3 |

TABLE 20

| Ex. No. | Structure | ¹H-NMR | MS(ESI) [M + H]⁺ |
|---|---|---|---|
| 116 | 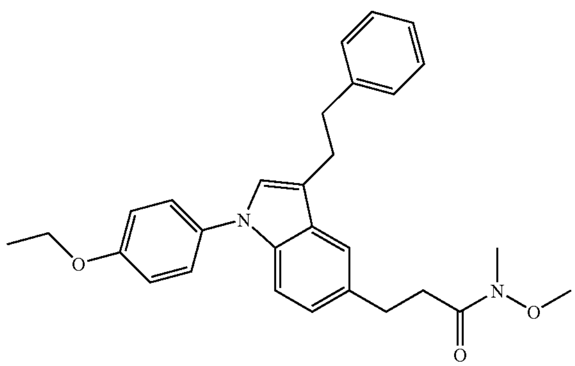 | 1H NMR (400 MHz, CHLOROFORM-d) δ ppm 1.45 (t, J = 7.1 Hz, 3 H) 2.80 (t, J = 7.6 Hz, 2 H) 3.02-3.13 (m, 4 H) 3.07 (d, J = 6.1 Hz, 2 H) 3.19 (s, 3 H) 3.62 (s, 3 H) 4.08 (q, J = 6.8 Hz, 2 H) 6.96-7.03 (m, 2 H) 7.08 (d, J = 8.1 Hz, 1 H) 7.19-7.39 (m, 9 H) 7.47 (s, 1 H) | 457.2 |
| 117 | 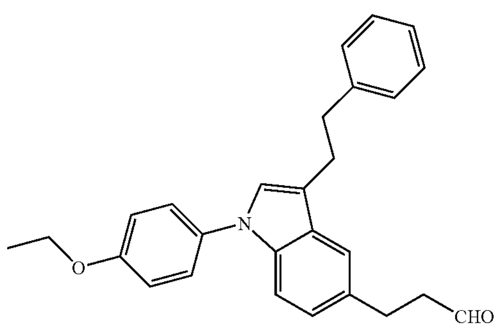 | 1H NMR (400 MHz, CHLOROFORM-d) δ ppm 1.46 (t, J = 7.1 Hz, 3 H) 2.83 (d, J = 15.3 Hz, 1 H) 2.83 (s, 1 H) 3.00-3.13 (m, 4 H) 3.07 (d, J = 7.6 Hz, 2 H) 4.09 (q, J = 7.1 Hz, 2 H) 6.93-7.08 (m, 2 H) 7.01 (d, J = 4.6 Hz, 2 H) 7.19-7.41 (m, 9 H) 9.86 (s, 1 H) | 398.2 |
| 119 | 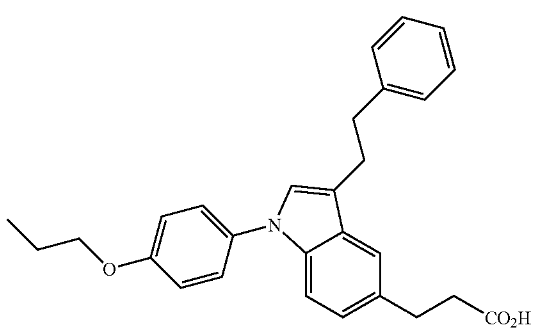 | 1H NMR (400 MHz, CHLOROFORM-d) δ ppm 1.07 (t, J = 7.5 Hz, 3 H) 1.73-1.90 (m, J = 14.1, 7.1, 7.0, 6.9 Hz, 2 H) 2.74 (t, J = 7.9 Hz, 1 H) 2.75 (br. s., 1 H) 3.03-3.12 (m, 4 H) 3.07 (d, J = 5.9 Hz, 2 H) 3.97 (t, J = 6.6 Hz, 2 H) 6.98-7.07 (m, 4 H) 7.19-7.39 (m, 8 H) 7.44 (s, 1 H) | 428.3 |

TABLE 20-continued

| Ex. No. | Structure | ¹H-NMR | MS(ESI) [M + H]⁺ |
|---|---|---|---|
| 121 | 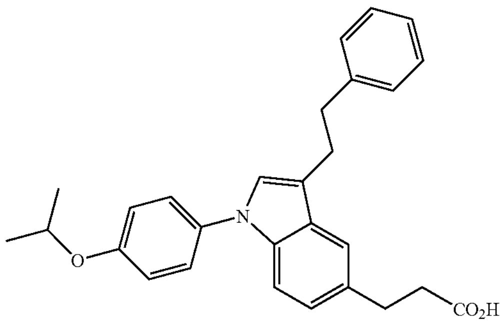 | 1H NMR (400 MHz, CHLOROFORM-d) δ ppm 1.38 (d, J = 6.2 Hz, 6 H) 2.73 (t, J = 7.7 Hz, 2 H) 3.01-3.12 (m, 4 H) 3.07 (d, J = 6.6 Hz, 2 H) 4.58 (dt, J = 12.1, 6.0 Hz, 1 H) 6.95-7.08 (m, 4H) 7.19-7.39 (m, 8 H) 7.43 (s, 1 H) | 428.3 |
| 122 | 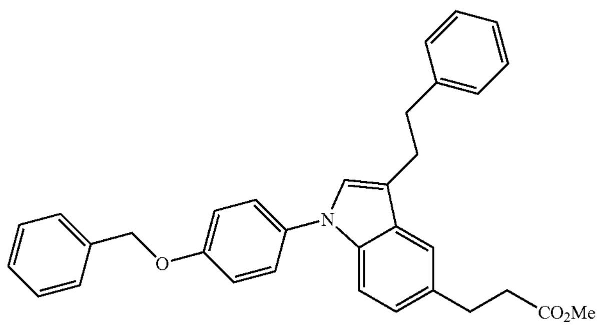 | 1H NMR (400 MHz, CHLOROFORM-d) δ ppm 2.70 (d, J = 8.4 Hz, 1 H) 2.67 (s, 1 H) 3.01-3.09 (m, 6 H) 3.68 (s, 3 H) 5.12 (s, 2 H) 6.99-7.11 (m, 4 H) 7.21-7.43 (m, 12 H) 7.48 (d, J = 1.5 Hz, 1 H) 7.46 (s, 1 H) | 490.2 |
| 123 | 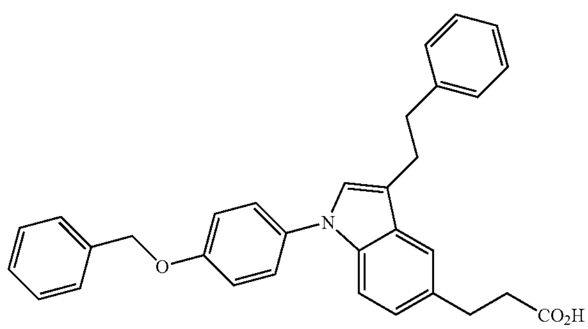 | 1H NMR (400 MHz, CHLOROFORM-d) δ ppm 2.73 (t, J = 7.9 Hz, 2 H) 3.00-3.12 (m, 4 H) 3.07 (t, J = 7.5 Hz, 2 H) 5.11 (s, 2 H) 7.07 (d, J = 9.2 Hz, 2 H) 6.99-7.14 (m, 2 H) 7.23-7.48 (m, 14 H) | 476.1 |
| 124 | 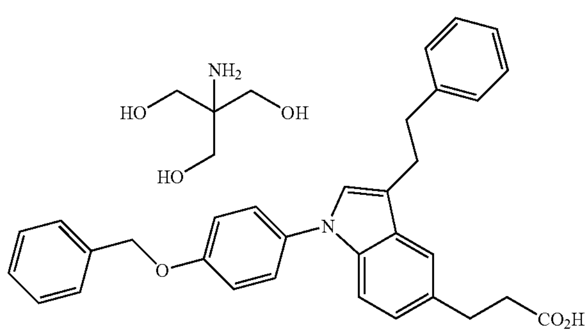 | 1H NMR (400 MHz, MeOH-d4) δ ppm 2.53 (d, J = 6.1 Hz, 1 H) 2.51 (d, J = 8.1 Hz, 1 H) 2.92-3.10 (m, 4 H) 3.01 (dd, J = 17.5, 6.5 Hz, 2 H) 3.61 (s, 6 H) 5.14 (s, 2 H) 6.95-7.50 (m, 18 H) | 476.1 |

TABLE 20-continued

| Ex. No. | Structure | ¹H-NMR | MS(ESI) [M + H]⁺ |
|---|---|---|---|
| 125 | 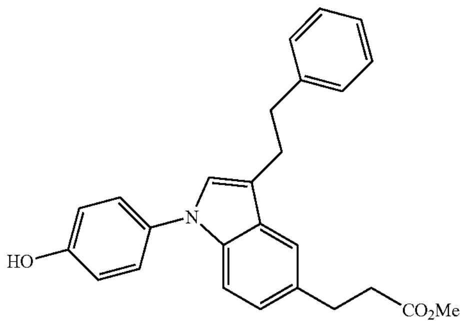 | 1H NMR (400 MHz, CHLOROFORM-d) δ ppm 2.70 (t, J = 7.9 Hz, 2 H) 3.01-3.12 (m, 6 H) 3.69 (s, 3 H) 5.27 (br. s., 1 H) 6.90 (dd, J = 9.0, 2.7 Hz, 1 H) 6.90 (br. s., 1 H) 6.98 (s, 1 H) 7.04 (dd, J = 8.6, 1.7 Hz, 1 H) 7.19-7.36 (m, 8 H) 7.42 (s, 1 H) | 400.1 |
| 126 | 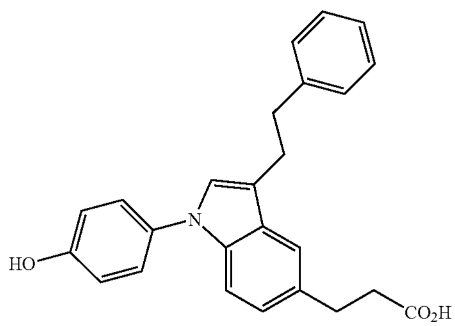 | 1H NMR (400 MHz, MeOH-d4) δ ppm 2.61 (t, J = 7.9 Hz, 2 H) 2.96-3.13 (m, 4 H) 3.01 (dd, J = 16.7, 7.9 Hz, 2 H) 6.79-6.93 (m, 1 H) 6.90 (d, J = 8.8 Hz, 1 H) 7.02 (dd, J = 8.4, 1.5 Hz, 1 H) 6.99 (s, 1 H) 7.13-7.29 (m, 8 H) 7.38 (s, 1 H) | 386.1 |

TABLE 21

| Ex. No. | Structure | ¹H-NMR | MS(ESI) [M + H]⁺ |
|---|---|---|---|
| 128 | 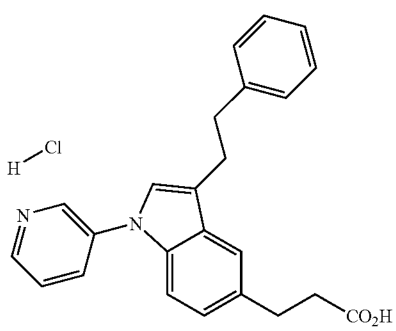 | 1H NMR (400 MHz, DMSO-d6) δ ppm 2.58 (t, J = 7.7 Hz, 2 H) 2.94 (t, J = 7.7 Hz, 2 H) 3.02 (s, 4 H) 7.10-7.24 (m, 2 H) 7.28-7.35 (m, 4 H) 7.47-7.58 (m, 3 H) 7.72 (dd, J = 8.4, 4.8 Hz, 1 H) 8.19 (d, J = 9.5 Hz, 1 H) 8.61 (m, 1 H) 8.90 (d, J = 2.6 Hz, 1 H) | 371.1 |
| 130 | 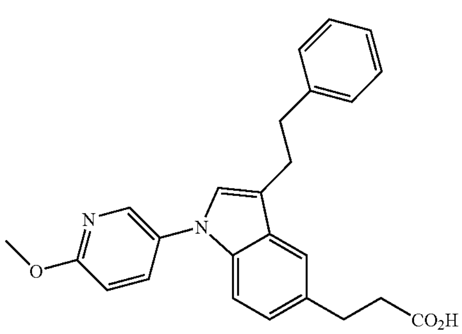 | 1H NMR (400 MHz, CHLOROFORM-d) δ ppm 2.73 (t, J = 7.7 Hz, 2 H) 2.99-3.13 (m, 4 H) 3.08 (t, J = 7.5 Hz, 2 H) 3.99 (s, 3 H) 6.87 (d, J = 8.5 Hz, 1 H) 6.94 (s, 1 H) 7.07 (d, J = 9.7 Hz, 1 H) 7.18-7.35 (m, 8 H) 7.44 (s, 1 H) 7.64 (dd, J = 8.7, 2.6 Hz, 1 H) 8.25 (d, J = 2.4 Hz, 1 H) | 401.1 |

TABLE 21-continued

| Ex. No. | Structure | $^1$H-NMR | MS(ESI) [M + H]$^+$ |
|---|---|---|---|
| 132 | 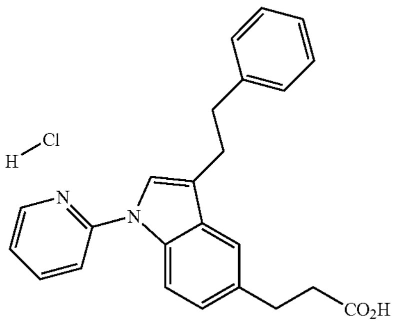 | 1H NMR (400 MHz, DMSO-d6) δ ppm 2.59 (t, J = 7.7 Hz, 2 H) 2.93 (t, J = 7.5 Hz, 2 H) 2.98-3.07 (m, 2 H) 3.03 (s, 2 H) 7.12-7.35 (m, 7 H) 7.47 (d, J = 1.5 Hz, 1 H) 7.68 (d, J = 8.4 Hz, 1 H) 7.83 (s, 1 H) 7.94 (m, 1 H) 8.31 (d, J = 8.4 Hz, 1 H) 8.52 (m, 1 H) | 371.1 |
| 134 | 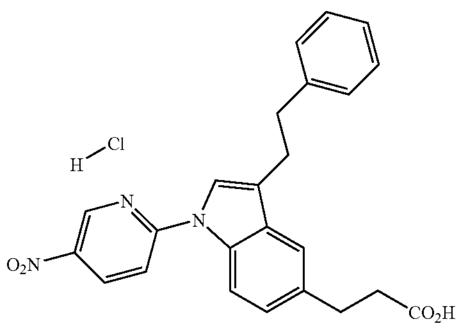 | 1H NMR (400 MHz, DMSO-d6) δ ppm 2.60 (br. s., 1 H) 2.57 (d, J = 8.1 Hz, 1 H) 2.94 (t, J = 7.7 Hz, 2 H) 2.99-3.13 (m, 2 H) 3.03 (d, J = 2.2 Hz, 2 H) 7.21 (dd, J = 6.8, 4.6 Hz, 1 H) 7.18 (br. s., 1 H) 7.25-7.39 (m, 2 H) 7.32 (d, J = 2.6 Hz, 2 H) 7.50 (s, 1 H) 7.94 (d, J = 9.2 Hz, 1 H) 8.02 (s, 1 H) 8.54 (d, J = 8.8 Hz, 1 H) 8.65 (dd, J = 9.2, 2.9 Hz, 1 H) 9.34 (d, J = 2.9 Hz, 1 H) | 416.1 |
| 135 | 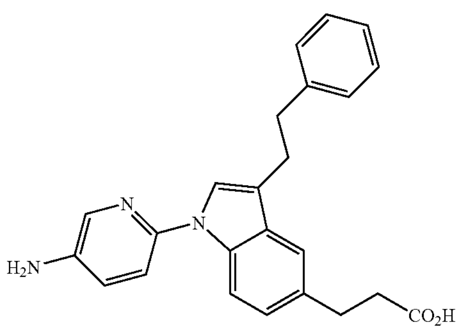 | 1H NMR (400 MHz, MeOH-d4) δ ppm 2.60 (t, J = 7.9 Hz, 2 H) 2.96-3.09 (m, 6 H) 4.56 (s, 2 H) 7.07 (dd, J = 8.5, 1.6 Hz, 1 H) 7.15 (td, J = 6.1, 2.4 Hz, 1 H) 7.21-7.29 (m, 7 H) 7.37 (s, 1 H) 7.68 (d, J = 8.5 Hz, 1 H) 7.93 (d, J = 1.6 Hz, 1 H) | 386.1 |
| 138 | 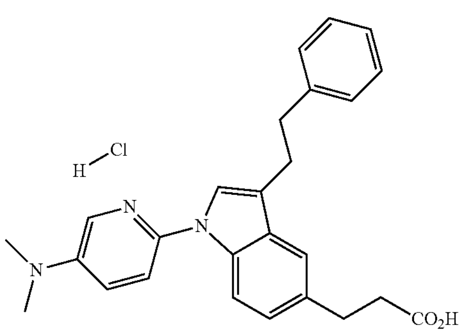 | 1H NMR (400 MHz, MeOH-d4) δ ppm 2.59-2.70 (m, 2 H) 2.98-3.11 (m, 6 H) 3.66 (s, 6 H) 7.05-7.47 (m, 10 H) 7.73 (s, 1 H) 7.98 (s, 1 H) | 414.2 |

TABLE 21-continued

| Ex. No. | Structure | ¹H-NMR | MS(ESI) [M + H]⁺ |
|---|---|---|---|
| 140 | 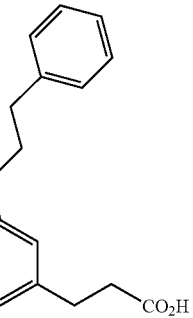 | 1H NMR (400 MHz, CHLOROFORM-d) δ ppm 2.19 (s, 3 H) 2.67 (t, J = 7.5 Hz, 2 H) 2.98-3.15 (m, 6 H) 7.15 (d, J = 8.5 Hz, 1 H) 7.19-7.45 (m, 8 H) 7.96 (d, J = 8.1 Hz, 1 H) 8.31 (dd, J = 8.9, 2.4 Hz, 1 H) 8.47 (d, J = 2.4 Hz, 1 H) | 428.1 |
| 141 | 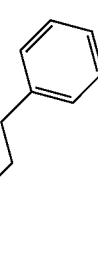 | 1H NMR (400 MHz, CHLOROFORM-d) δ ppm 1.35 (t, J = 7.1 Hz, 3 H) 2.99-3.12 (m, 4 H) 4.27 (q, J = 6.9 Hz, 2 H) 6.41 (d, J = 15.8 Hz, 1 H) 6.93 (d, J = 2.0 Hz, 1 H) 7.18-7.36 (m, 6 H) 7.42 (d, J = 1.6 Hz, 1 H) 7.72 (s, 1 H) 7.84 (d, J = 15.8 Hz, 1 H) 8.01 (br. s., 1 H) | 320.2 |
| 142 | 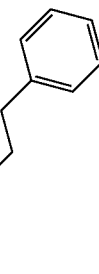 | 1H NMR (400 MHz, CHLOROFORM-d) δ ppm 1.24 (t, J = 7.1 Hz, 3 H) 2.66 (t, J = 8.1 Hz, 2 H) 2.97-3.11 (m, 6 H) 4.14 (q, J = 7.3 Hz, 2 H) 6.90 (d, J = 2.4 Hz, 1 H) 7.04 (d, J = 8.1 Hz, 3 H) 7.17-7.32 (m, 6 H) 7.40 (s, 1 H) 7.84 (br. s., 1 H) | 322.3 |

TABLE 22

| Ex. No. | Structure | ¹H-NMR | MS(ESI) [M + H]⁺ |
|---|---|---|---|
| 144 | 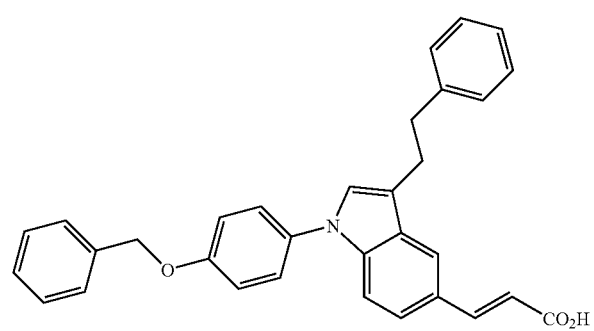 | 1H NMR (400 MHz, CHLOROFORM-d) δ ppm 3.02-3.23 (m, 4H) 5.14 (s, 2 H) 6.43 (d, J = 15.8 Hz, 1 H) 7.03 (s, 1 H) 7.10 (d, J = 8.9 Hz, 2 H) 7.22-7.49 (m, 12 H) 7.43 (d, J = 4.5 Hz, 2 H) 7.77 (s, 1 H) 7.94 (d, J = 15.8 Hz, 1 H) | 474.2 |

TABLE 22-continued

| Ex. No. | Structure | ¹H-NMR | MS(ESI) [M + H]⁺ |
|---|---|---|---|
| 147 | 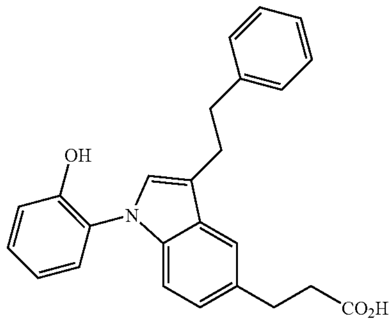 | 1H NMR (400 MHz, CHLOROFORM-d) δ ppm 2.74 (t, J = 7.7 Hz, 2 H) 3.03-3.14 (m, 4 H) 3.08 (d, J = 8.5 Hz, 2H) 6.88 (s, 1 H) 6.98-7.13 (m, 4H) 7.19-7.35 (m, 7 H) 7.48 (s, 1 H) | 386.2 |
| 149 | 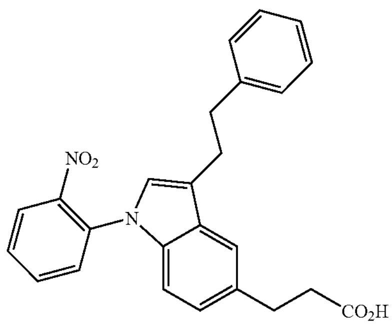 | 1H NMR (400 MHz, CHLOROFORM-d) δ ppm 2.73 (t, J = 7.9 Hz, 2 H) 3.00-3.13 (m, 6 H) 6.85 (s, 1 H) 7.05 (s, 2 H) 7.18-7.35 (m, 5 H) 7.42 (s, 1 H) 7.53 (dd, J = 7.5, 3.0 Hz, 1 H) 7.46-7.59 (m, 1 H) 7.66-7.78 (m, 1 H) 7.98-8.07 (m, 1 H) | 415.1 |
| 151 | 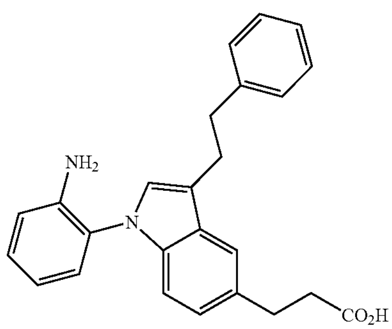 | 1H NMR (400 MHz, CHLOROFORM-d) δ ppm 2.73 (t, J = 7.7 Hz, 2 H) 2.99-3.16 (m, 4 H) 3.07 (d, J = 8.1 Hz, 2 H) 6.79-6.91 (m, 3 H) 7.04 (s, 2 H) 7.12-7.31 (m, 7 H) 7.46 (s, 1 H) | 385.2 |
| 153 | 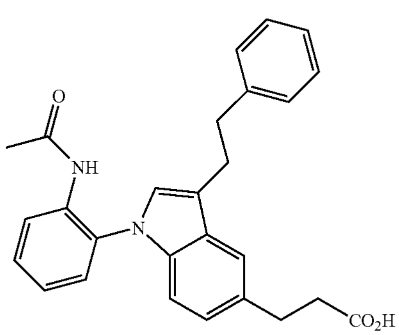 | 1H NMR (400 MHz, DMSO-d6) δ ppm 1.87 (s, 3 H) 2.74 (t, J = 7.9 Hz, 2 H) 3.01-3.19 (m, 6 H) 6.80-6.91 (m, 1 H) 6.87 (s, 1 H) 6.98 (t, J = 7.7 Hz, 1 H) 7.07 (d, J = 8.1 Hz, 1 H) 7.17-7.35 (m, 6 H) 7.36-7.53 (m, 2H) 8.42 (br. s., 1 H) | 427.2 |

TABLE 22-continued

| Ex. No. | Structure | $^1$H-NMR | MS(ESI) [M + H]$^+$ |
|---|---|---|---|
| 155 | 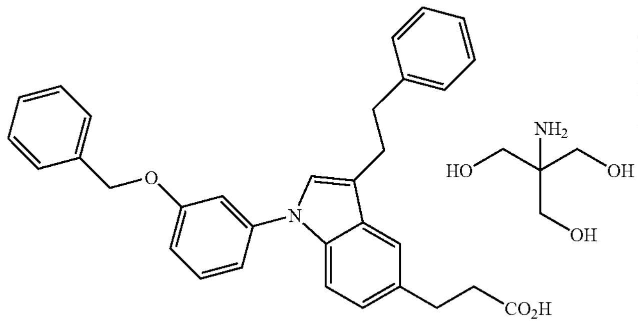 | 1H NMR (400 MHz, MeOH-d4) δ ppm 2.54 (d, J = 7.7 Hz, 2 H) 2.94-3.10 (m, 6 H) 3.60 (s, 6 H) 5.16 (s, 2 H) 6.95 (br. s., 1 H) 7.04 (d, J = 7.7 Hz, 2 H) 7.00 (br. s., 3 H) 7.15 (br. s., 1 H) 7.19-7.49 (m, 11 H) | 476.2 |
| 157 | 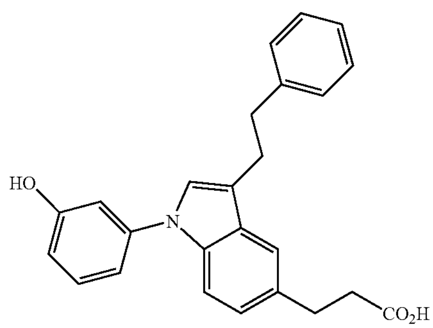 | 1H NMR (400 MHz, CHLOROFORM-d) δ ppm 2.73 (t, J = 7.7 Hz, 2 H) 3.01-3.11 (m, 4 H) 3.06 (d, J = 5.3 Hz, 2 H) 6.76 (dd, J = 7.9, 2.2 Hz, 1 H) 6.93 (t, J = 2.2 Hz, 1 H) 7.00-7.09 (m, 3 H) 7.19-7.34 (m, 6 H) 7.42 (s, 1 H) 7.51 (d, J = 8.5 Hz, 1 H) | 386.2 |
| 159 | 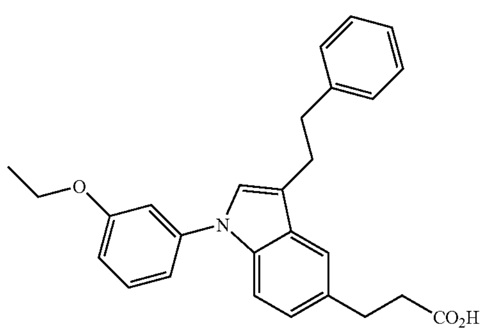 | 1H NMR (400 MHz, CHLOROFORM-d) δ ppm 1.44 (t, J = 6.9 Hz, 3 H) 2.74 (t, J = 7.9 Hz, 2 H) 3.02-3.12 (m, 4 H) 3.07 (d, J = 8.9 Hz, 2 H) 4.07 (q, J = 7.0 Hz, 2 H) 6.84 (m, 1 H) 6.96-7.12 (m, 4 H) 7.19-7.38 (m, 6 H) 7.43 (s, 1 H) 7.52 (d, J = 8.5 Hz, 1 H) | 414.2 |
| 161 | 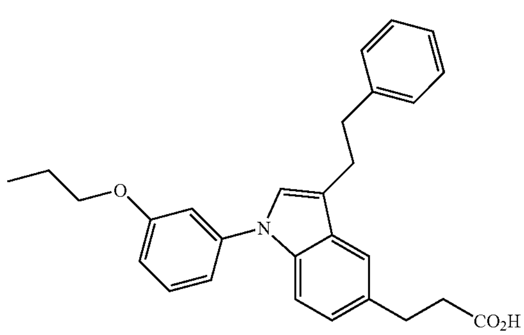 | 1H NMR (400 MHz, CHLOROFORM-d) δ ppm 1.06 (t, J = 7.5 Hz, 3 H) 1.84 (q, J = 6.9 Hz, 2 H) 2.74 (t, J = 7.9 Hz, 2 H) 3.02-3.12 (m, 4 H) 3.07 (d, J = 5.3 Hz, 2 H) 3.96 (t, J = 6.5 Hz, 2 H) 6.84 (dd, J = 8.3, 1.8 Hz, 1 H) 6.96-7.10 (m, 4 H) 7.19-7.38 (m, 6 H) 7.43 (s, 1 H) 7.52 (d, J = 8.5 Hz, 1 H) | 428.3 |

TABLE 23

| Ex. No. | Structure | ¹H-NMR | MS(ESI) [M + H]⁺ |
|---|---|---|---|
| 163 | 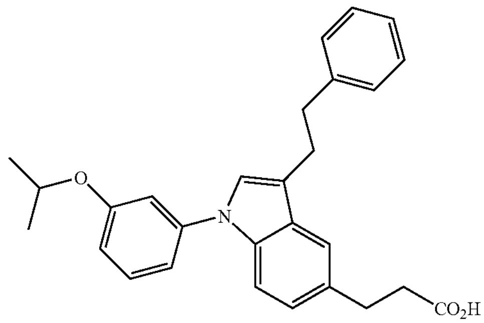 | 1H NMR (400 MHz, CHLOROFORM-d) δ ppm 1.37 (d, J = 6.1 Hz, 6 H) 2.73 (t, J = 7.7 Hz, 2 H) 3.02-3.11 (m, 4 H) 3.07 (d, J = 5.3 Hz, 2 H) 4.58 (dt, J = 12.2, 6.1 Hz, 1 H) 6.83 (dd, J = 7.9, 2.2 Hz, 1 H) 6.96 (t, J = 2.0 Hz, 1 H) 7.00 (d, J = 8.1 Hz, 1 H) 7.04-7.10 (m, 2 H) 7.19-7.37 (m, 6 H) 7.43 (s, 1 H) 7.51 (d, J = 8.1 Hz, 1 H) | 428.3 |
| 165 | 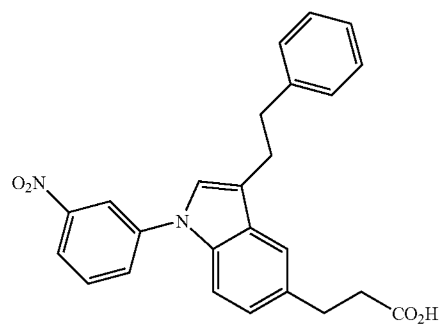 | 1H NMR (400 MHz, CHLOROFORM-d) δ ppm 2.75 (t, J = 7.9 Hz, 2 H) 3.03-3.18 (m, 6 H) 7.08 (s, 1 H) 7.13-7.16 (m, 1 H) 7.19-7.37 (m, 5 H) 7.45 (s, 1 H) 7.51 (d, J = 8.5 Hz, 1 H) 7.66 (t, J = 8.1 Hz, 1 H) 7.80 (d, J = 9.3 Hz, 1 H) 8.14 (d, J = 7.3 Hz, 1 H) 8.31 (t, J = 2.2 Hz, 1 H) | 415.1 |
| 167 | 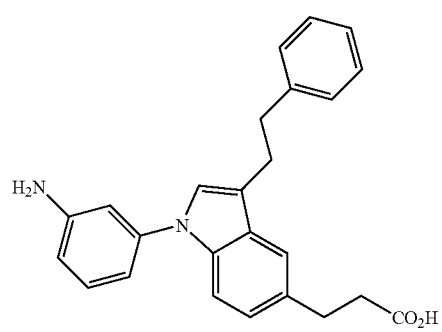 | 1H NMR (400 MHz, MeOH-d4) δ ppm 2.65 (t, J = 7.9 Hz, 2 H) 2.99-3.12 (m, 6 H) 6.67 (d, J = 8.9 Hz, 1 H) 6.82 (t, J = 2.0 Hz, 1 H) 6.75-6.85 (m, 1 H) 7.06 (s, 1 H) 7.04 (d, J = 1.6 Hz, 1 H) 7.15-7.29 (m, 6 H) 7.40 (s, 1 H) 7.49 (d, J = 8.5 Hz, 1 H) 7.73 (s, 2 H) | 385.2 |
| 169 | 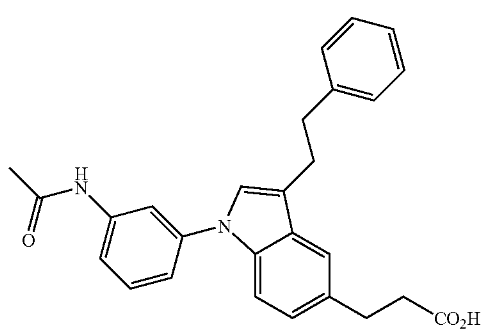 | 1H NMR (400 MHz, MeOH-d4) δ ppm 2.15 (s, 3 H) 2.62 (t, J = 7.7 Hz, 2 H) 2.98-3.15 (m, 6 H) 7.07 (d, J = 8.5 Hz, 1 H) 7.13-7.29 (m, 7 H) 7.38-7.47 (m, 2 H) 7.40 (d, J = 5.3 Hz, 1 H) 7.51 (d, J = 8.5 Hz, 1 H) 7.86 (d, J = 2.0 Hz, 1 H) | 427.2 |

TABLE 23-continued

| Ex. No. | Structure | ¹H-NMR | MS(ESI) [M + H]⁺ |
|---|---|---|---|
| 171 | 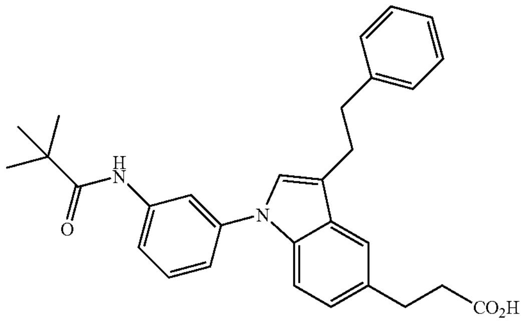 | 1H NMR (400 MHz, MeOH-d4) δ ppm 1.32 (s, 9 H) 2.61 (t, J = 7.9 Hz, 2 H) 2.96-3.17 (m, 6 H) 7.09 (d, J = 8.5 Hz, 1 H) 7.13-7.31 (m, 8 H) 7.35-7.49 (m, 1 H) 7.43 (d, J = 1.6 Hz, 1 H) 7.53 (d, J = 8.1 Hz, 1 H) 7.83 (s, 1 H) | 469.2 |
| 173 | 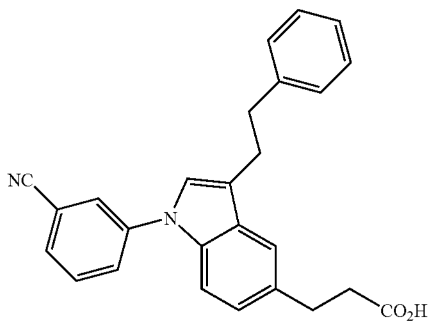 | 1H NMR (400 MHz, MeOH-d4) δ ppm 2.63 (t, J = 7.7 Hz, 2 H) 3.00-3.14 (m, 6 H) 7.11-7.28 (m, 7 H) 7.48 (d, J = 8.5 Hz, 1 H) 7.42 (s, 1 H) 7.58-7.74 (m, 2 H) 7.79-7.89 (m, 2 H) | 395.2 |
| 175 | 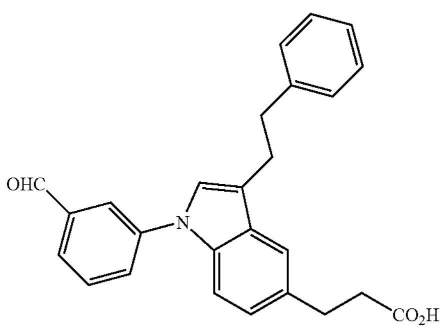 | 1H NMR (400 MHz, CHLOROFORM-d) δ ppm 2.74 (t, J = 7.9 Hz, 2 H) 3.00-3.18 (m, 4 H) 3.09 (t, J = 7.3 Hz, 2 H) 7.06-7.16 (m, 2 H) 7.19-7.37 (m, 5 H) 7.45 (s, 1 H) 7.50 (d, J = 8.1 Hz, 1 H) 7.64-7.77 (m, 1 H) 7.67 (d, J = 7.7 Hz, 1 H) 7.81 (d, J = 7.30 Hz, 1 H) 7.96 (s, 1 H) 10.08 (s, 1 H) | 398.2 |
| 177 | 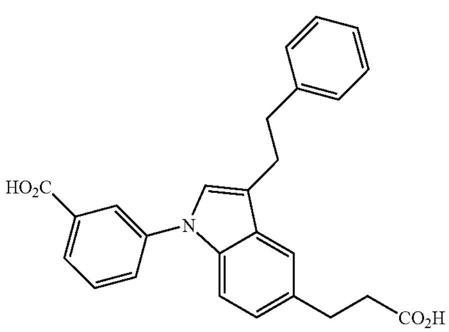 | 1H NMR (400 MHz, MeOH-d4) δ ppm 2.64 (t, J = 7.7 Hz, 2 H) 2.97-3.14 (m, 6 H) 7.08-7.28 (m, 7 H) 7.46 (d, J = 8.5 Hz, 1 H) 7.41 (s, 1 H) 7.56-7.70 (m, 1 H) 7.60 (t, J = 7.9 Hz, 1 H) 7.95 (d, J = 7.7 Hz, 1 H) 8.08 (d, J = 2.0 Hz, 1 H) | 414.2 |

TABLE 23-continued

| Ex. No. | Structure | $^1$H-NMR | MS(ESI) [M + H]$^+$ |
|---|---|---|---|
| 179 | 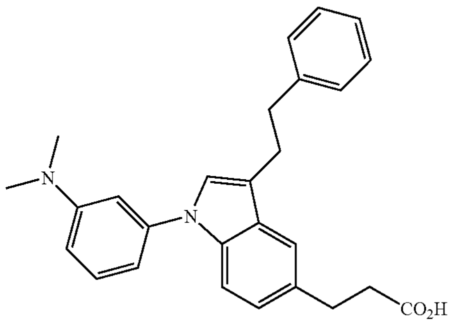 | 1H NMR (400 MHz, CHLOROFORM-d) δ ppm 2.74 (t, J = 7.9 Hz, 2 H) 2.97-3.13 (m, 6 H) 6.67 (dd, J = 8.5, 2.4 Hz, 1 H) 6.73-6.80 (m, 2 H) 7.04-7.11 (m, 2 H) 7.18-7.34 (m, 6 H) 7.43 (s, 1 H) 7.53 (d, J = 8.5 Hz, 1 H) | 413.3 |

TABLE 24

| Ex. No. | Structure | $^1$H-NMR | MS(ESI) [M + H]$^+$ |
|---|---|---|---|
| 181 | 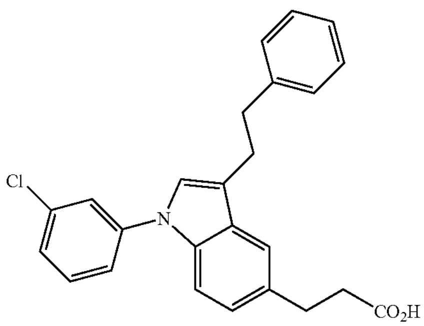 | 1H NMR (400 MHz, CHLOROFORM-d) δ ppm 2.73 (t, J = 7.9 Hz, 2 H) 3.08 (d, J = 4.1 Hz, 2 H) 3.00-3.20 (m, 4 H) 7.03 (s, 1 H) 7.10 (d, J = 8.5 Hz, 1 H) 7.21-7.50 (m, 9 H) 7.44 (d, J = 7.7 Hz, 2 H) | 404.1 |
| 183 | 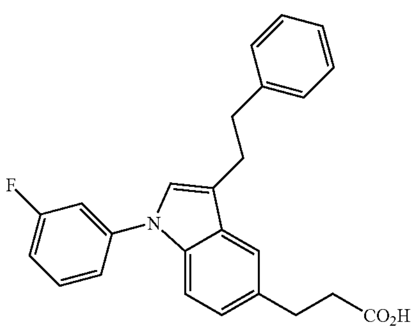 | 1H NMR (400 MHz, CHLOROFORM-d) δ ppm 2.74 (t, J = 7.7 Hz, 2 H) 2.99-3.20 (m, 4 H) 3.08 (d, J = 5.7 Hz, 2 H) 6.98-7.07 (m, 2 H) 7.11 (d, J = 8.5 Hz, 1 H) 7.15-7.35 (m, 6 H) 7.37-7.58 (m, 4 H) | 388.2 |
| 185 | 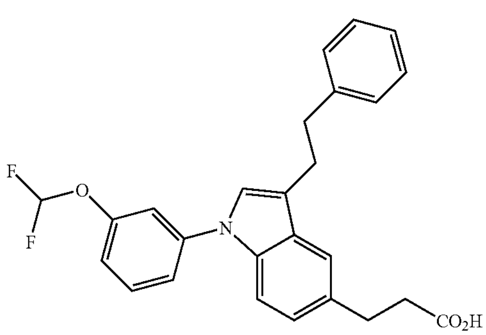 | 1H NMR (400 MHz, CHLOROFORM-d) δ ppm 2.73 (t, J = 7.9 Hz, 2 H) 2.99-3.15 (m, 6 H) 6.57 (t, J = 72 Hz, 2 H) 7.04 (s, 1 H) 7.08 (dd, J = 16.0, 1.8 Hz, 1 H) 7.08 (s, 1 H) 7.19-7.35 (m, 7 H) 7.47 (dd, J = 14.0, 8.3 Hz, 1 H) 7.41-7.54 (m, 2 H) | 436.1 |

TABLE 24-continued

| Ex. No. | Structure | ¹H-NMR | MS(ESI) [M + H]⁺ |
|---|---|---|---|
| 186 | 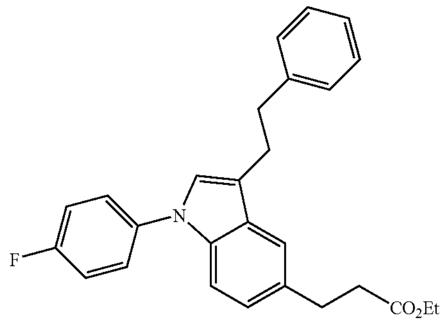 | 1H NMR (400 MHz, CHLOROFORM-d) δ ppm 1.25 (t, J = 7.1 Hz, 3 H) 2.68 (t, J = 8.5 Hz, 2 H) 2.98-3.12 (m, 6 H) 4.14 (q, J = 6.9 Hz, 2 H) 7.00 (s, 1 H) 7.08 (d, J = 9.7 Hz, 1 H) 7.13-7.33 (m, 6 H) 7.35-7.46 (m, 3 H) 7.38 (dd, J = 6.5, 2.0 Hz, 1 H) 7.58 (dd, J = 8.5, 5.3 Hz, 1 H) | 416.2 |
| 187 | 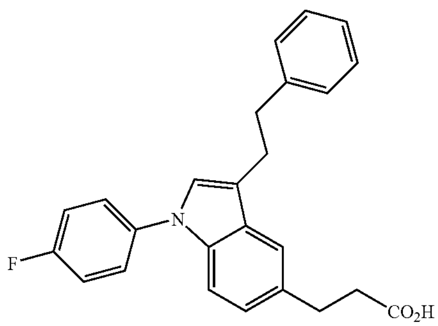 | 1H NMR (400 MHz, CHLOROFORM-d) δ ppm 2.74 (t, J = 7.7 Hz, 2 H) 3.05 (br. s., 1 H) 3.05-3.15 (m, 3 H) 3.07 (d, J = 8.1 Hz, 2 H) 7.00 (s, 1 H) 7.08 (d, J = 8.5 Hz, 1 H) 7.15-7.34 (m, 7 H) 7.37-7.45 (m, 2 H) 7.39 (d, J = 8.5 Hz, 2 H) | 388.1 |
| 188 | 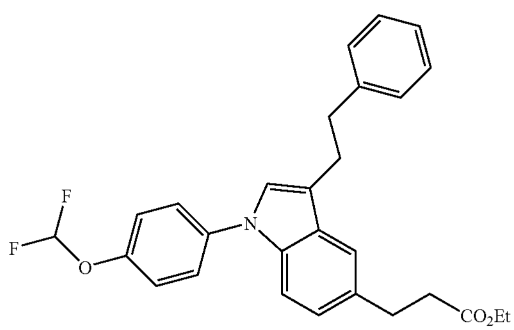 | 1H NMR (400 MHz, CHLOROFORM-d) δ ppm 1.25 (t, J = 7.1 Hz, 3 H) 2.68 (t, J = 7.7 Hz, 2 H) 3.01-3.12 (m, 6 H) 4.15 (q, J = 6.9 Hz, 2 H) 6.55 (t, J = 72 Hz, 1 H) 7.01 (s, 1 H) 7.08 (dd, J = 8.5, 1.6 Hz, 1 H) 7.19-7.33 (m, 7 H) 7.43 (d, J = 8.9 Hz, 2 H) 7.38-7.52 (m, 2 H) | 464.2 |
| 189 | 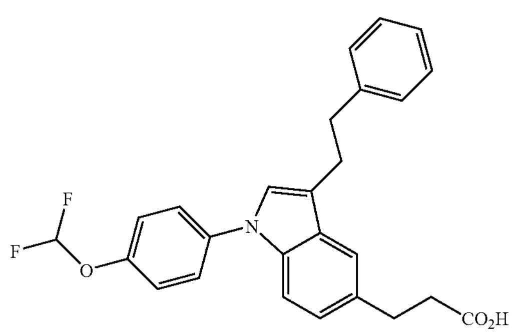 | 1H NMR (400 MHz, CHLOROFORM-d) δ ppm 2.73 (t, J = 7.7 Hz, 2 H) 3.00-3.12 (m, 4 H) 3.07 (d, J = 7.3 Hz, 2 H) 6.55 (t, J = 72 Hz, 1 H) 7.01 (s, 1 H) 7.08 (dd, J = 8.5, 1.6 Hz, 1 H) 7.19-7.33 (m, 7 H) 7.42 (d, J = 8.9 Hz, 4 H) | 436.2 |

TABLE 24-continued
| Ex. No. | Structure | ¹H-NMR | MS(ESI) [M + H]⁺ |
|---|---|---|---|
| 190 | 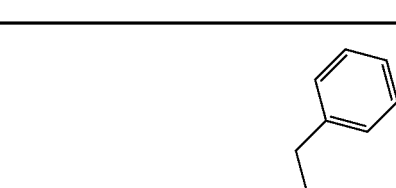 | 1H NMR (400 MHz, MeOH-d4) δ ppm 2.54 (d, J = 8.1 Hz, 1 H) 2.50 (s, 1 H) 2.97-3.16 (m, 6 H) 3.62 (s, 6 H) 6.86 (t, J = 72 Hz, 1 H) 7.04-7.18 (m, 3 H) 7.20-7.32 (m, 6 H) 7.48 (d, J = 8.5 Hz, 2 H) 7.34-7.53 (m, 2 H) | 436.2 |
| 191 | 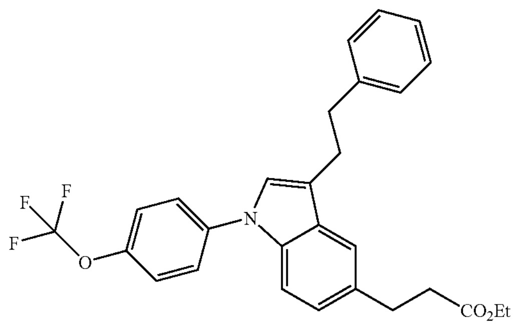 | 1H NMR (400 MHz, CHLOROFORM-d) δ ppm 1.25 (t, J = 7.1 Hz, 3 H) 2.68 (t, J = 7.9 Hz, 2 H) 3.00-3.12 (m, 6 H) 4.15 (q, J = 7.3 Hz, 2 H) 7.01 (s, 1 H) 7.09 (dd, J = 8.5, 1.6 Hz, 1 H) 7.19-7.37 (m, 7 H) 7.39-7.52 (m, 4 H) | 482.2 |
TABLE 25
| Ex. No. | Structure | ¹H-NMR | MS(ESI) [M + H]⁺ |
|---|---|---|---|
| 192 | 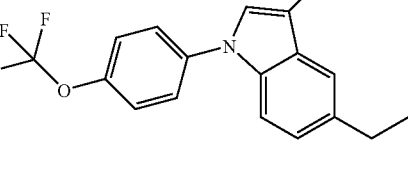 | 1H NMR (400 MHz, CHLOROFORM-d) δ ppm 2.74 (t, J = 7.9 Hz, 2 H) 2.98-3.15 (m, 6H) 7.02 (s, 1 H) 7.10 (d, J = 1.6 Hz, 1 H) 7.18-7.38 (m, 7 H) 7.42-7.52 (m, 2 H) 7.45 (t, J = 4.1 Hz, 2 H) | 454.1 |
| 193 | 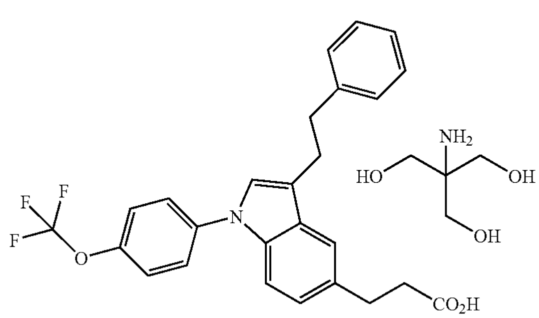 | 1H NMR (400 MHz, MeOH-d4) δ ppm 2.54 (d, J = 8.5 Hz, 1 H) 2.52 (d, J = 9.7 Hz, 1 H) 2.99-3.10 (m, 6 H) 3.62 (s, 6 H) 7.09-7.27 (m, 7 H) 7.41 (s, 2 H) 7.43 (dd, J = 8.3, 3.0 Hz, 2 H) 7.55 (d, J = 8.9 Hz, 1 H) 7.55 (t, J = 5.1 Hz, 1 H) | 454.2 |

TABLE 25-continued

| Ex. No. | Structure | ¹H-NMR | MS(ESI) [M + H]⁺ |
|---|---|---|---|
| 196 | 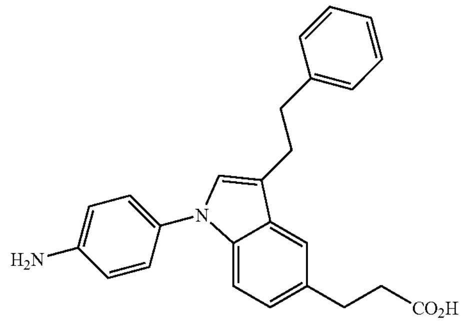 | 1H NMR (400 MHz, MeOH-d4) δ ppm 2.61 (t, J = 7.7 Hz, 2 H) 3.01 (dd, J = 15.6, 7.5 Hz, 2 H) 3.05 (s, 4 H) 5.49 (s, 2H) 6.83 (d, J = 8.5 Hz, 1 H) 6.82 (s, 1 H) 6.97 (s, 1 H) 7.00 (dd, J = 8.5, 1.6 Hz, 1 H) 7.12-7.27 (m, 8 H) 7.37 (s, 1 H) | 385.1 |
| 197 | 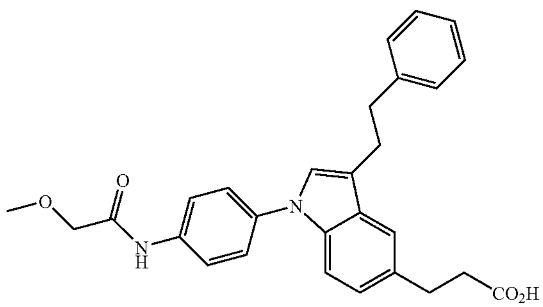 | 1H NMR (400 MHz, MeOH-d4) δ ppm 2.62 (t, J = 7.7 Hz, 2 H) 2.99-3.13 (m, 6 H) 3.51 (s, 3 H) 4.07 (s, 2 H) 7.09 (s, 1 H) 7.06 (dd, J = 8.3, 1.8 Hz, 1 H) 7.14-7.27 (m, 5 H) 7.39-7.45 (m, 2 H) 7.40 (d, J = 5.3 Hz, 2 H) 7.75 (d, J = 8.9 Hz, 1 H) 7.73-7.78 (m, 1 H) | 457.2 |
| 199 | 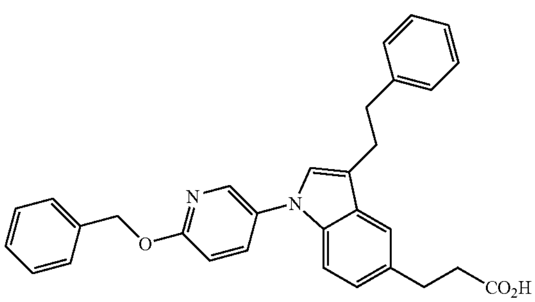 | 1H NMR (400 MHz, MeOH-d4) δ ppm 2.59 (t, J = 7.7 Hz, 2 H) 2.94-3.11 (m, 4 H) 3.00 (d, J = 5.7 Hz, 2 H) 5.26 (s, 2 H) 6.71 (d, J = 9.3 Hz, 1 H) 6.94 (s, 1 H) 6.99-7.08 (m, 1 H) 7.10-7.28 (m, 6 H) 7.30-7.44 (m, 6 H) 7.66 (dd, J = 9.7, 2.8 Hz, 1 H) 7.84-7.90 (m, 1 H) | 477.2 |
| 201 | 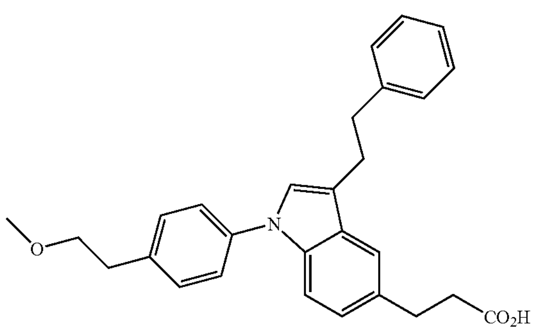 | 1H NMR (400 MHz, CHLOROFORM-d) δ ppm 2.74 (t, J = 7.9 Hz, 2 H) 2.94 (t, J = 6.9 Hz, 2 H) 3.00-3.15 (m, 4 H) 3.07 (d, J = 7.3 Hz, 2 H) 3.39 (s, 3 H) 3.66 (t, J = 6.9 Hz, 2 H) 6.98-7.14 (m, 1 H) 7.06 (d, J = 8.5 Hz, 1 H) 7.19-7.39 (m, 9 H) 7.48 (s, 1 H) 7.45 (d, J = 8.5 Hz, 1 H) | 428.3 |
| 203 | 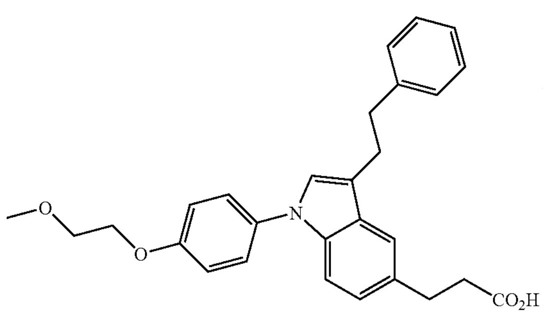 | 1H NMR (400 MHz, MeOH-d4) δ ppm 2.62 (t, J = 7.7 Hz, 2 H) 2.98-3.09 (m, 6 H) 3.44 (s, 3 H) 3.78 (d, J = 4.5 Hz, 1 H) 3.77 (d, J = 6.5 Hz, 1 H) 4.18 (s, 1 H) 4.16 (d, J = 4.5 Hz, 1 H) 7.01-7.10 (m, 4 H) 7.13-7.36 (m, 6 H) 7.38 (s, 1 H) | 444.2 |

TABLE 25-continued

| Ex. No. | Structure | ¹H-NMR | MS(ESI) [M + H]⁺ |
|---|---|---|---|
| 205 | 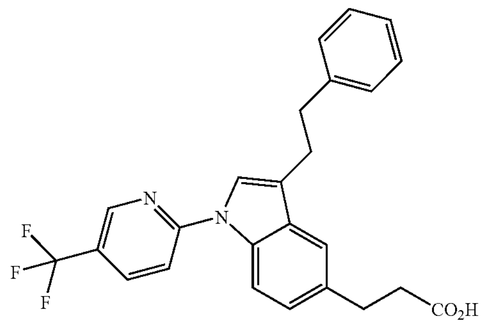 | 1H NMR (400 MHz, CHLOROFORM-d) δ ppm 2.74 (t, J = 7.7 Hz, 2 H) 3.00-3.19 (m, 6 H) 7.15-7.46 (m, 9 H) 7.97 (br. s., 1 H) 8.29 (d, J = 8.1 Hz, 1 H) 8.76 (br. s., 1 H) | 439.1 |
| 207 | 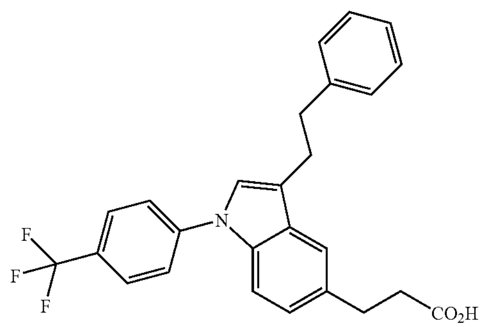 | 1H NMR (400 MHz, CHLOROFORM-d) δ ppm 2.74 (t, J = 7.7 Hz, 2 H) 3.05-3.15 (m, 6 H) 7.07 (s, 1 H) 7.11 (d, J = 9.3 Hz, 1 H) 7.19-7.38 (m, 5 H) 7.44 (s, 1 H) 7.56 (d, J = 8.5 Hz, 1 H) 7.48-7.63 (m, 2 H) 7.74 (d, J = 8.1 Hz, 2 H) | 438.2 |

TABLE 26

| Ex. No. | Structure | ¹H-NMR | MS(ESI) [M + H]⁺ |
|---|---|---|---|
| 209 | 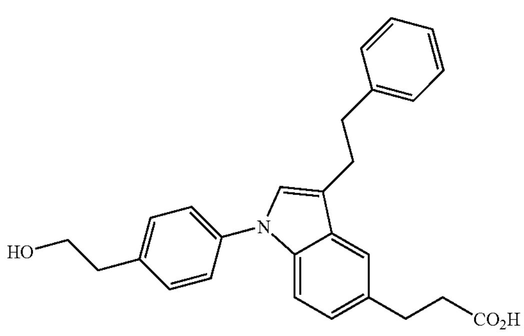 | 1H NMR (400 MHz, DMSO-d6) δ ppm 2.74 (t, J = 7.7 Hz, 2 H) 2.94 (t, J = 6.5 Hz, 2 H) 2.99-3.13 (m, 4 H) 3.07 (d, J = 6.9 Hz, 2 H) 3.93 (t, J = 6.5 Hz, 2 H) 7.05 (s, 1 H) 7.08 (d, J = 8.5 Hz, 1 H) 7.20-7.40 (m, 9 H) 7.48 (s, 1 H) 7.45 (d, J = 8.5 Hz, 1 H) | 414.2 |
| 211 | 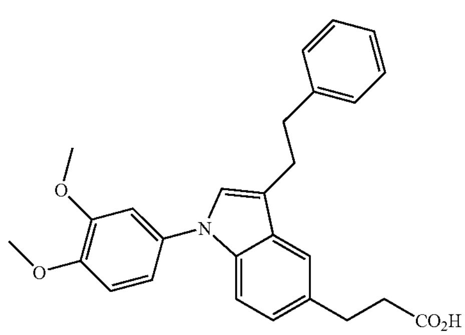 | 1H NMR (400 MHz, CHLOROFORM-d) δ ppm 2.74 (t, J = 7.9 Hz, 2 H) 3.00-3.21 (m, 6 H) 3.90 (s, 3 H) 3.94 (s, 3 H) 6.91-7.13 (m, 5 H) 7.17-7.36 (m, 5 H) 7.39 (s, 1 H) 7.43 (d, J = 10.6 Hz, 1 H) | 430.2 |

TABLE 26-continued

| Ex. No. | Structure | ¹H-NMR | MS(ESI) [M + H]⁺ |
|---|---|---|---|
| 213 | 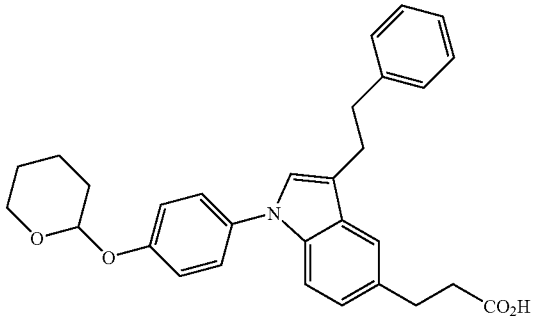 | 1H NMR (400 MHz, MeOH-d4) δ ppm 1.56-1.78 (m, 3 H) 1.81-1.95 (m, 1 H) 1.87 (td, J = 8.4, 4.7 Hz, 1 H) 1.97-2.07 (m, 1 H) 2.62 (t, J = 7.9 Hz, 2 H) 2.95-3.12 (m, 6 H) 3.63 (d, J = 11.0 Hz, 1 H) 3.88-4.00 (m, 1 H) 5.47 (t, J = 3.3 Hz, 1 H) 7.05 (d, J = 1.6 Hz, 1 H) 7.03 (s, 1 H) 7.12-7.29 (m, 8 H) 7.34 (d, J = 8.9 Hz, 1 H) 7.33 (d, J = 8.5 Hz, 1 H) 7.39 (s, 1 H) | 470.2 |
| 214 | 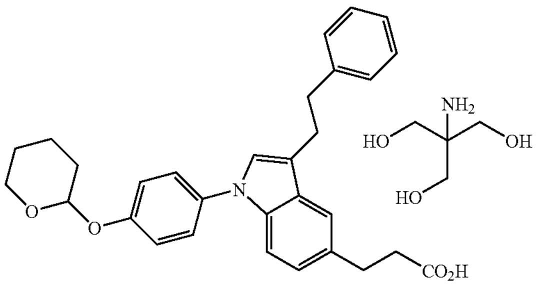 | 1H NMR (400 MHz, MeOH-d4) δ ppm 1.58-1.76 (m, 3 H) 1.81-1.94 (m, 2 H) 2.02 (d, J = 17.9 Hz, 1 H) 2.02 (dd, J = 5.7, 3.7 Hz, 1 H) 2.53 (d, J = 8.5 Hz, 1 H) 2.50 (s, 1 H) 2.97-3.09 (m, 6 H) 3.59-3.67 (m, 1 H) 3.62 (s, 6 H) 3.93 (ddd, J = 11.5, 9.0, 3.0 Hz, 1 H) 5.47 (t, J = 3.5 Hz, 1 H) 7.01 (s, 1 H) 7.06 (dd, J = 8.5, 1.6 Hz, 1 H) 7.14-7.36 (m, 10 H) 7.43 (s, 1 H) | 470.2 |
| 215 | 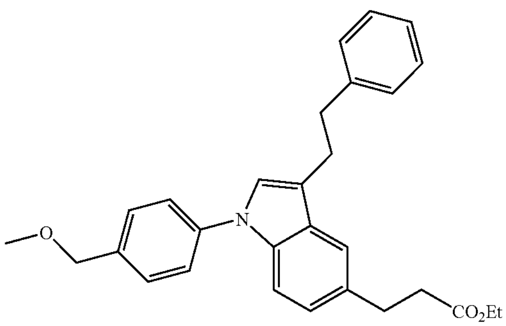 | 1H NMR (400 MHz, DMSO-d6) δ ppm 1.25 (t, J = 7.1 Hz, 3 H) 2.68 (t, J = 7.9 Hz, 2 H) 3.02-3.12 (m, 4 H) 3.07 (d, J = 4.1 Hz, 2 H) 3.44 (s, 3 H) 4.15 (q, J = 7.2 Hz, 2 H) 4.51 (s, 2 H) 7.00-7.11 (m, 2 H) 7.20-7.33 (m, 5 H) 7.41-7.52 (m, 4 H) 7.44 (d, J = 4.5 Hz, 2 H) | 442.3 |
| 216 | 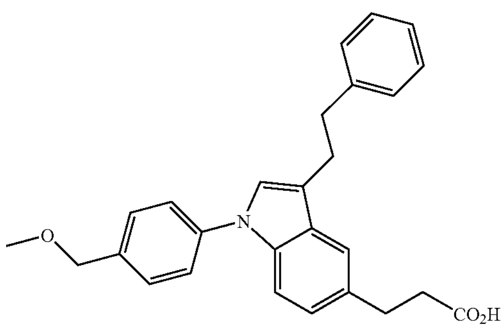 | 1H NMR (400 MHz, CHLOROFORM-d) δ ppm 2.73 (t, J = 7.9 Hz, 2 H) 3.00-3.14 (m, 4 H) 3.07 (d, J = 6.9 Hz, 2 H) 3.44 (s, 3 H) 4.51 (s, 2 H) 6.99-7.11 (m, 2 H) 7.19-7.33 (m, 5 H) 7.40-7.50 (m, 4 H) 7.44 (d, J = 5.3 Hz, 2 H) | 414.2 |
| 217 | 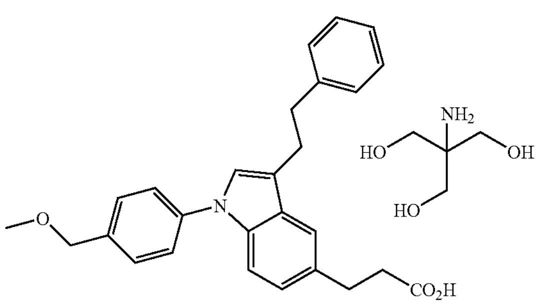 | 1H NMR (400 MHz, MeOH-d4) δ ppm 2.53 (d, J = 8.1 Hz, 1 H) 2.52 (d, J = 10.6 Hz, 1 H) 2.98-3.10 (m, 6 H) 3.41 (s, 3 H) 3.61 (s, 6 H) 4.51 (s, 2 H) 7.07 (d, J = 1.6 Hz, 1 H) 7.09 (s, 1 H) 7.13-7.18 (m, 1 H) 7.21-7.28 (m, 2 H) 7.23 (d, J = 2.4 Hz, 2 H) 7.41-7.50 (m, 4 H) 7.46 (d, J = 6.5 Hz, 2 H) | 414.2 |

TABLE 26-continued

| Ex. No. | Structure | $^1$H-NMR | MS(ESI) [M + H]$^+$ |
|---|---|---|---|
| 219 | 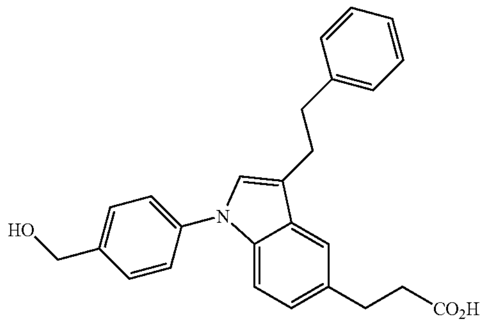 | 1H NMR (400 MHz, CHLOROFORM-d) δ ppm 2.73 (t, J = 7.7 Hz, 2 H) 3.05-3.15 (m, 6 H) 4.76 (s, 2 H) 6.97-7.15 (m, 2 H) 7.17-7.38 (m, 6 H) 7.38-7.61 (m, 5 H) | 400.2 |
| 220 | 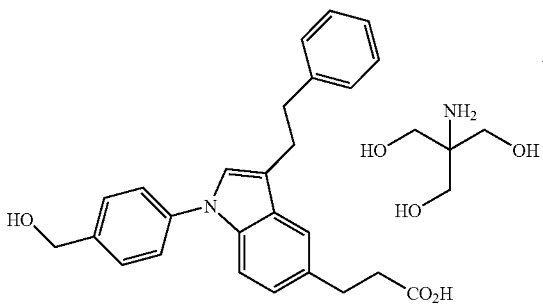 | 1H NMR (400 MHz, MeOH-d4) δ ppm 2.53 (d, J = 8.5 Hz, 1 H) 2.50 (s, 1 H) 2.98-3.10 (m, 6 H) 3.62 (s, 6 H) 4.64 (s, 2 H) 7.06-7.10 (m, 2 H) 7.13-7.30 (m, 3 H) 7.23 (d, J = 2.4 Hz, 2 H) 7.40-7.52 (m, 6 H) | 400.2 |

TABLE 27

| Ex. No. | Structure | $^1$H-NMR | MS(ESI) [M + H]$^+$ |
|---|---|---|---|
| 222 | 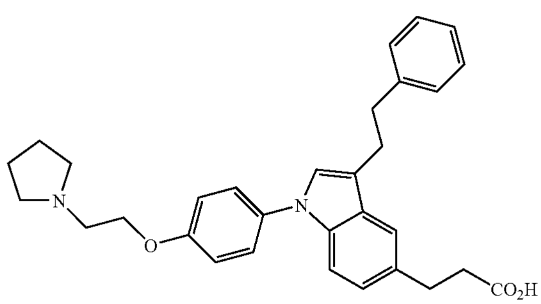 | 1H NMR (400 MHz, CHLOROFORM-d) δ ppm 1.79-1.96 (m, 4 H) 2.63-2.71 (m, 2 H) 2.80-3.10 (m, 12 H) 3.96 (t, J = 5.5 Hz, 2 H) 6.60-6.65 (m, 1 H) 6.64 (d, J = 8.5 Hz, 1 H) 6.80 (br. s., 1 H) 6.95-7.10 (m, 1 H) 7.03 (d, J = 8.1 Hz, 2 H) 7.10-7.31 (m, 6 H) 7.47 (br. s., 1 H) | 483.4 |
| 223 | 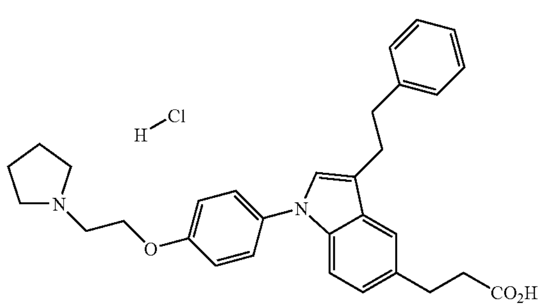 | 1H NMR (400 MHz, DMSO-d6) δ ppm 1.92 (br. s., 4 H) 2.57 (t, J = 7.5 Hz, 2 H) 2.92 (t, J = 7.5 Hz, 2 H) 3.01 (s, 4 H) 3.44-3.60 (br. s., 2 H) 4.36 (br. s., 2 H) 7.05 (d, J = 8.1 Hz, 1 H) 7.20 (d, J = 6.5 Hz, 1 H) 7.17 (d, J = 8.5 Hz, 2 H) 7.26-7.37 (m, 4 H) 7.31 (t, J = 5.5 Hz, 2 H) 7.42-7.51 (m, 3 H) | 483.3 |

TABLE 27-continued

| Ex. No. | Structure | ¹H-NMR | MS(ESI) [M + H]⁺ |
|---|---|---|---|
| 225 | 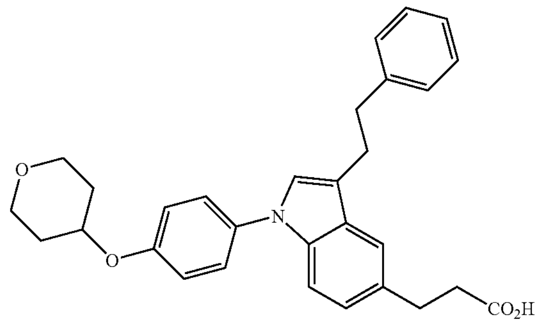 | 1H NMR (400 MHz, MeOH-d4) δ ppm 1.71-1.80 (m, 2 H) 2.07 (t, J = 12.4 Hz, 1 H) 2.07 (ddd, J = 13.5, 1.8, 1.7 Hz, 1 H) 2.62 (t, J = 7.7 Hz, 2 H) 2.98-3.09 (m, 4 H) 3.02 (dd, J = 17.3, 7.5 Hz, 2 H) 3.61 (ddd, J = 11.7, 8.6, 2.8 Hz, 2 H) 3.95-4.04 (m, 2 H) 4.55-4.64 (m, 1 H) 7.02-7.11 (m, 4 H) 7.13-7.27 (m, 5 H) 7.30-7.40 (m, 2 H) 7.34 (d, J = 8.9 Hz, 2 H) | 470.2 |
| 226 | 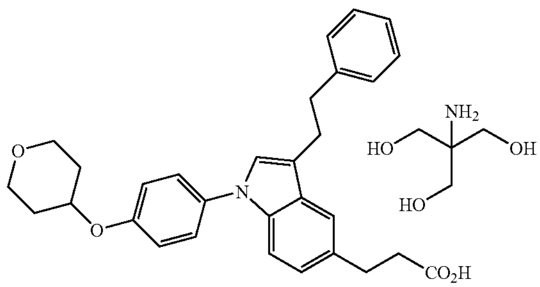 | 1H NMR (400 MHz, MeOH-d4) δ ppm 1.66-1.84 (m, 2 H) 2.02-2.13 (m, 2 H) 2.53 (d, J = 8.1 Hz, 1 H) 2.52 (d, J = 10.2 Hz, 1 H) 2.98-3.12 (m, 6 H) 3.56-3.71 (m, 2 H) 3.61 (s, 6 H) 3.98 (dd, J = 17.0, 4.06 Hz, 1 H) 3.98 (br. s., 1 H) 4.55-4.70 (m, 1 H) 7.00-7.37 (m, 12 H) 7.43 (s, 1 H) | 470.2 |
| 227 | 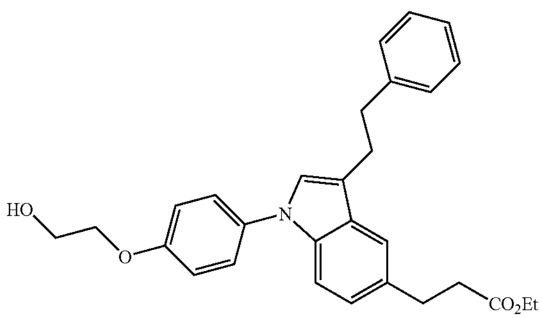 | 1H NMR (400 MHz, CHLOROFORM-d) δ ppm 1.25 (t, J = 7.1 Hz, 3 H) 2.69 (d, J = 8.1 Hz, 1 H) 2.66 (s, 1 H) 3.00-3.14 (m, 6 H) 4.00 (br. s., 1 H) 4.01 (d, J = 4.9 Hz, 1 H) 4.15 (q, J = 6.9 Hz, 2 H) 4.14 (d, J = 4.9 Hz, 2 H) 6.88-7.06 (m, 2 H) 7.03 (d, J = 8.9 Hz, 1 H) 7.07 (d, J = 1.6 Hz, 1 H) 7.20-7.39 (m, 8 H) 7.44 (s, 1 H) | 458.2 |
| 228 | 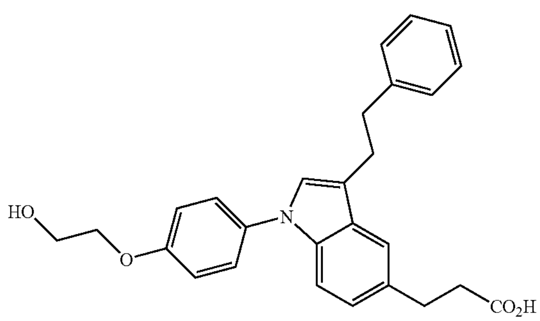 | 1H NMR (400 MHz, CHLOROFORM-d) δ ppm 2.74 (t, J = 7.9 Hz, 2 H) 3.02-3.12 (m, 6 H) 4.01 (d, J = 4.5 Hz, 1 H) 4.00 (s, 1 H) 4.16 (s, 1 H) 4.14 (d, J = 5.3 Hz, 1 H) 6.99-7.11 (m, 4 H) 7.19-7.39 (m, 8 H) 7.44 (s, 1 H) | 430.2 |
| 229 | 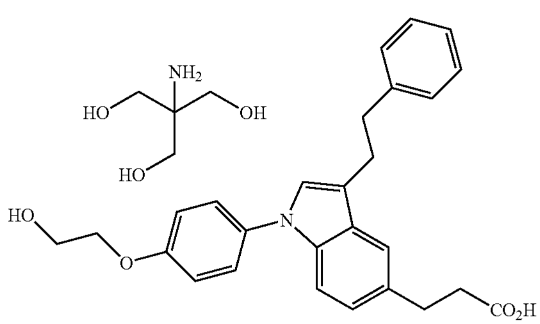 | 1H NMR (400 MHz, MeOH-d4) δ ppm 2.53 (d, J = 8.1 Hz, 1 H) 2.52 (d, J = 10.2 Hz, 1 H) 2.97-3.09 (m, 6 H) 3.62 (s, 6 H) 3.91 (d, J = 4.9 Hz, 1 H) 3.89 (s, 1 H) 4.11 (s, 1 H) 4.10 (d, J = 4.9 Hz, 1 H) 7.00-7.18 (m, 5 H) 7.20-7.36 (m, 7 H) 7.42 (s, 1 H) | 430.2 |

TABLE 27-continued
| Ex. No. | Structure | ¹H-NMR | MS(ESI) [M + H]⁺ |
|---|---|---|---|
| 230 | 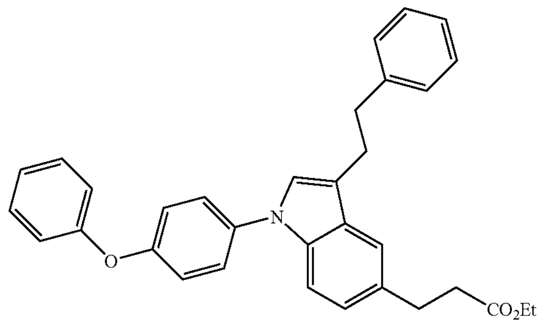 | 1H NMR (400 MHz, CHLOROFORM-d) δ ppm 1.26 (t, J = 7.1 Hz, 3 H) 2.69 (d, J = 8.5 Hz, 1 H) 2.66 (s, 1 H) 3.01-3.15 (m, 6 H) 4.15 (q, J = 7.3 Hz, 2 H) 6.99-7.45 (m, 18 H) | 490.2 |
| 231 | 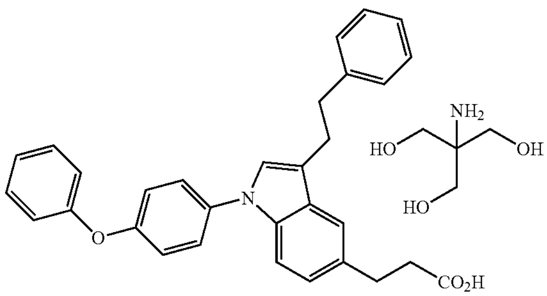 | 1H NMR (400 MHz, MeOH-d4) δ ppm 2.51 (d, J = 10.2 Hz, 1 H) 2.53 (d, J = 8.5 Hz, 1 H) 2.98-3.10 (m, 6 H) 3.61 (s, 6 H) 7.04-7.27 (m, 12 H) 7.34-7.48 (m, 6 H) | 462.3 |
TABLE 28
| Ex. No. | Structure | ¹H-NMR | MS(ESI) [M + H]⁺ |
|---|---|---|---|
| 233 | 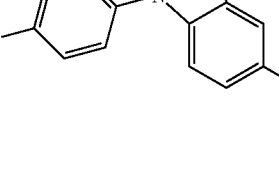 | 1H NMR (400 MHz, DMSO-d6) δ ppm 2.54 (d, J = 8.5 Hz, 1 H) 2.51 (s, 1 H) 2.96-3.09 (m, 4 H) 3.02 (t, J = 6.1 Hz, 2 H) 3.61 (s, 6 H) 4.29 (s, 4 H) 6.84-7.00 (m, 4 H) 7.05 (dd, J = 8.5, 1.6 Hz, 1 H) 7.12-7.27 (m, 5 H) 7.32 (d, J = 8.1 Hz, 1 H) 7.41 (d, J = 1.6 Hz, 1 H) | 428.3 |
| 235 | 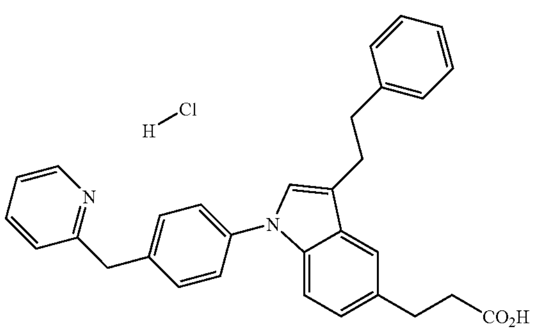 | 1H NMR (400 MHz, DMSO-d6) δ ppm 2.57 (t, J = 7.7 Hz, 2 H) 2.90 (br. s., 1 H) 2.93 (d, J = 8.5 Hz, 1 H) 3.00 (s, 4 H) 4.33 (br. s., 2 H) 7.03-7.57 (m, 13 H) 7.63 (br. s., 1 H) 7.70 (br. s., 1 H) 8.18 (br. s., 1 H) 8.72 (br. s., 1 H) | 461.1 |

TABLE 28-continued

| Ex. No. | Structure | ¹H-NMR | MS(ESI) [M + H]⁺ |
|---|---|---|---|
| 237 | 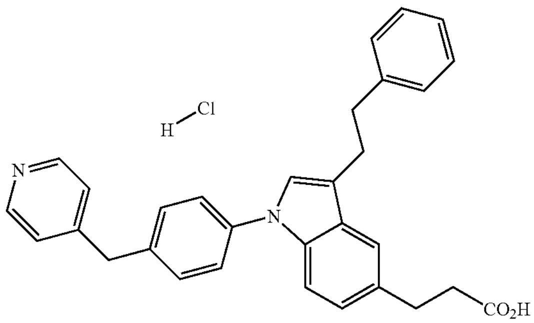 | 1H NMR (400 MHz, DMSO-d6) δ ppm 2.57 (d, J = 7.7 Hz, 2 H) 2.90-3.00 (m, 1 H) 3.01 (s, 4 H) 4.25 (s, 2 H) 7.06 (d, J = 8.5 Hz, 1 H) 7.31 (s, 2 H) 7.30 (d, J = 3.7 Hz, 2 H) 7.36-7.55 (m, 8 H) 7.79 (br. s., 2 H) 8.73 (d, J = 5.7 Hz, 2 H) | 461.2 |
| 239 | 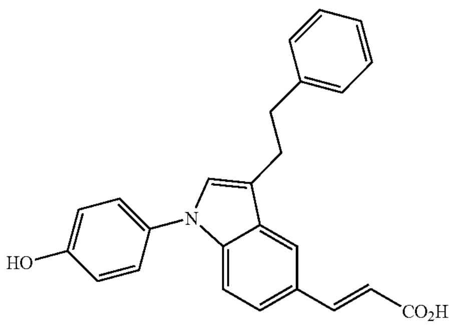 | 1H NMR (400 MHz, MeOH-d4) δ ppm 3.00-3.15 (m, 4 H) 6.39 (d, J = 15.8 Hz, 1 H) 6.85-6.95 (m, 1 H) 6.93 (d, J = 8.9 Hz, 1 H) 7.07 (s, 1 H) 7.14-7.27 (m, 7 H) 7.33-7.39 (m, 1 H) 7.42-7.47 (m, 1 H) 7.69 (s, 1 H) 7.78 (d, J = 15.8 Hz, 1 H) | 384.1 |
| 243 | 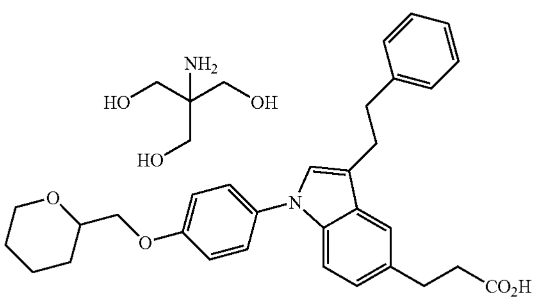 | 1H NMR (400 MHz, MeOH-d4) δ ppm 1.45-1.75 (m, 5 H) 1.90-1.96 (m, 1 H) 2.54 (d, J = 8.5 Hz, 1 H) 2.51 (s, 1 H) 2.97-3.09 (m, 4 H) 3.03 (t, J = 6.5 Hz, 2 H) 3.53 (td, J = 11.0, 3.3 Hz, 1 H) 3.62 (s, 6 H) 3.67-3.80 (m, 1 H) 3.94-4.04 (m, 1 H) 3.98 (d, J = 6.5 Hz, 2 H) 6.99 (s, 1 H) 7.06 (d, J = 8.9 Hz, 2 H) 7.02-7.08 (m, 1 H) 7.13-7.34 (m, 8 H) 7.42 (s, 1 H) | 484.2 |
| 245 | 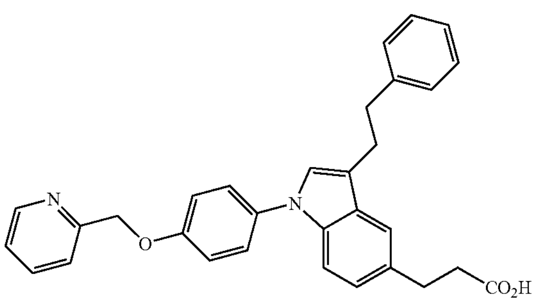 | 1H NMR (400 MHz, MeOH-d4) δ ppm 2.61 (t, J = 7.7 Hz, 2 H) 2.96-3.18 (m, 6 H) 5.24 (s, 2 H) 7.05 (d, J = 1.6 Hz, 1 H) 7.03 (s, 1 H) 7.13-7.28 (m, 7 H) 7.31-7.42 (m, 5 H) 7.65 (d, J = 8.1 Hz, 1 H) 7.90 (td, J = 7.7, 1.6 Hz, 1 H) 8.56 (d, J = 4.5 Hz, 1 H) | 477.2 |
| 246 | 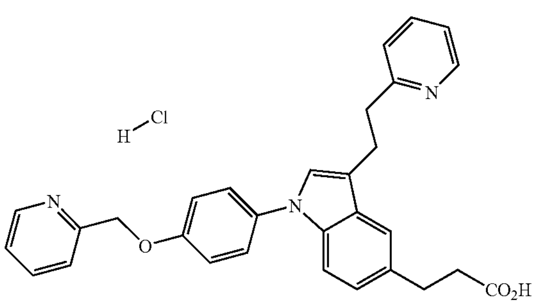 | 1H NMR (400 MHz, DMSO-d6) δ ppm 2.57 (t, J = 7.7 Hz, 2 H) 2.92 (t, J = 7.5 Hz, 2 H) 3.00 (s, 4 H) 5.36 (s, 2 H) 7.04 (d, J = 8.5 Hz, 1 H) 7.17-7.36 (m, 8 H) 7.46 (d, J = 8.9 Hz, 3 H) 7.58-7.61 (m, 1 H) 7.77 (d, J = 7.7 Hz, 1 H) 8.12 (t, J = 7.9 Hz, 1 H) 8.73 (d, J = 4.9 Hz, 1 H) | 477.2 |

TABLE 28-continued

| Ex. No. | Structure | ¹H-NMR | MS(ESI) [M + H]⁺ |
|---|---|---|---|
| 248 | 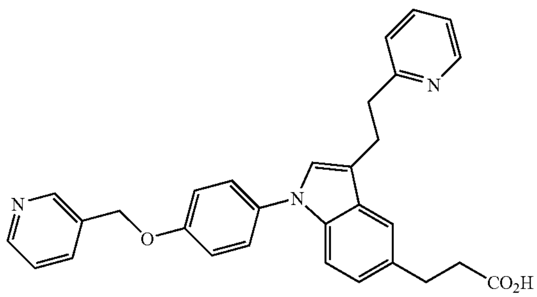 | 1H NMR (400 MHz, CHLOROFORM-d) δ ppm 2.68 (d, J = 8.5 Hz, 1 H) 2.65 (s, 1 H) 2.97-3.15 (m, 4 H) 3.07 (d, J = 4.5 Hz, 2 H) 5.15 (s, 2 H) 7.01 (s, 1 H) 7.08 (d, J = 8.9 Hz, 3 H) 7.21-7.43 (m, 8 H) 7.45 (s, 1 H) 7.87 (d, J = 7.7 Hz, 1 H) 8.57 (d, J = 4.9 Hz, 1 H) 8.68 (s, 1 H) | 477.2 |
| 249 | 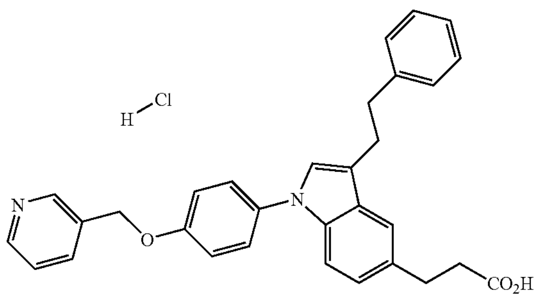 | 1H NMR (400 MHz, DMSO-d6) δ ppm 2.57 (t, J = 7.5 Hz, 2 H) 2.92 (t, J = 7.5 Hz, 2 H) 3.01 (s, 4 H) 5.31 (s, 2 H) 7.05 (d, J = 8.12 Hz, 1 H) 7.18-7.36 (m, 7 H) 7.32 (t, J = 7.1 Hz, 1 H) 7.46 (d, J = 8.5 Hz, 3 H) 7.75 (br. s., 1 H) 7.78 (d, J = 5.3 Hz, 1 H) 8.27 (d, J = 7.3 Hz, 1 H) 8.74 (d, J = 4.5 Hz, 1 H) 8.88 (s, 1 H) | 477.2 |

TABLE 29

| Ex. No. | Structure | ¹H-NMR | MS(ESI) [M + H]⁺ |
|---|---|---|---|
| 251 | 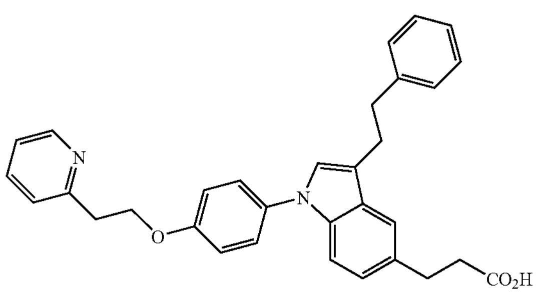 | 1H NMR (400 MHz, MeOH-d4) δ ppm 2.60 (t, J = 7.7 Hz, 2 H) 3.03 (d, J = 7.3 Hz, 2 H) 2.97-3.17 (m, 6 H) 4.40 (t, J = 6.5 Hz, 2 H) 6.99-7.10 (m, 4 H) 7.14-7.35 (m, 9 H) 7.38 (s, 1 H) 7.46 (d, J = 8.1 Hz, 1 H) 7.80 (td, J = 7.7, 1.6 Hz, 1 H) 8.50 (s, 1 H) | 491.2 |
| 253 | 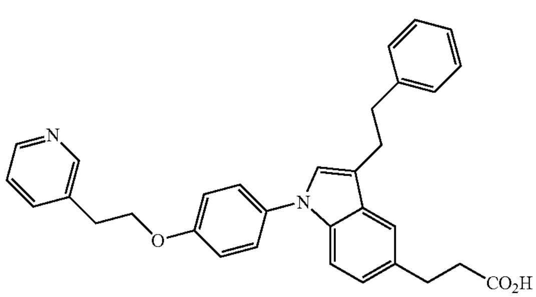 | 1H NMR (400 MHz, CHLOROFORM-d) δ ppm 2.73 (t, J = 7.9 Hz, 2 H) 2.99-3.17 (m, 8 H) 4.23 (t, J = 6.5 Hz, 2 H) 6.87-7.01 (m, 3 H) 7.05 (d, J = 8.5 Hz, 1 H) 7.18-7.36 (m, 9 H) 7.43 (s, 1 H) 7.67 (d, J = 8.1 Hz, 1 H) 8.51 (d, J = 3.3 Hz, 1 H) 8.59 (s, 1 H) | 491.2 |

TABLE 29-continued

| Ex. No. | Structure | ¹H-NMR | MS(ESI) [M + H]⁺ |
|---|---|---|---|
| 255 | 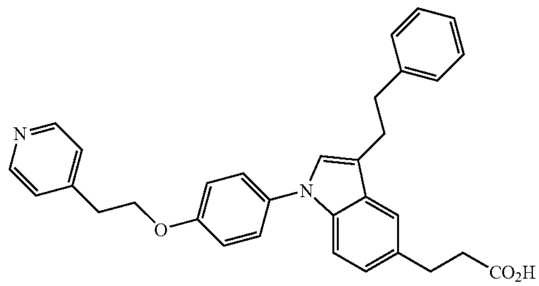 | 1H NMR (400 MHz, MeOH-d4) δ ppm 2.60 (t, J = 7.7 Hz, 2 H) 2.97-3.10 (m, 6H) 3.18 (t, J = 6.1 Hz, 2 H) 4.33 (t, J = 6.3 Hz, 2 H) 7.01-7.10 (m, 3 H) 7.12-7.48 (m, 13 H) 8.47 (s, 1 H) | 491.2 |
| 257 | 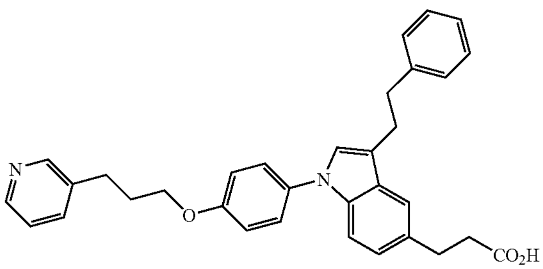 | 1H NMR (400 MHz, MeOH-d4) δ ppm 2.07-2.20 (m, 2 H) 2.62 (t, J = 7.7 Hz, 2 H) 2.92 (s, 1 H) 2.89 (d, J = 8.1 Hz, 1 H) 2.97-3.10 (m, 6 H) 4.04 (t, J = 6.1 Hz, 2 H) 7.02-7.09 (m, 4 H) 7.14-7.27 (m, 5 H) 7.30-7.42 (m, 5 H) 7.77 (d, J = 7.7 Hz, 1 H) 8.38 (br. s., 1 H) 8.44 (s, 1 H) | 505.2 |
| 258 | 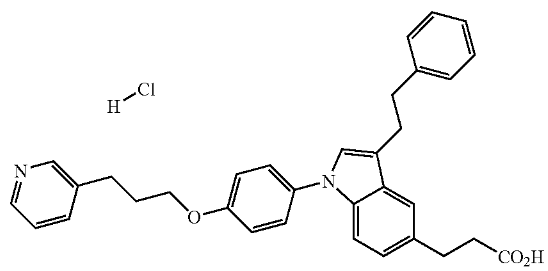 | 1H NMR (400 MHz, CHLOROFORM-d) δ ppm 1.17-1.39 (m, 2 H) 2.15-2.30 (m, 2 H) 2.73 (t, J = 7.7 Hz, 2 H) 2.95-3.15 (m, 6 H) 4.06 (br. s., 2 H) 6.91-7.12 (m, 3 H) 7.00 (s, 1 H) 7.19-7.39 (m, 8 H) 7.44 (s, 1 H) 7.78 (br. s., 1 H) 8.21 (br. s., 1 H) 8.63 (br. s., 1 H) 8.70 (br. s., 1 H) | 505.2 |
| 260 | 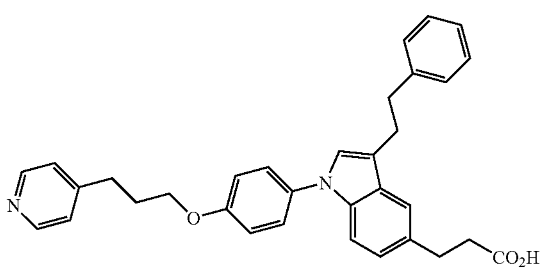 | 1H NMR (400 MHz, MeOH-d4) δ ppm 2.14-2.22 (m, 1 H) 2.17 (dd, J = 9.1, 6.3 Hz, 1 H) 2.63 (t, J = 7.9 Hz, 2 H) 2.93 (s, 1 H) 2.91 (d, J = 8.1 Hz, 1 H) 2.99-3.14 (m, 4 H) 3.03 (d, J = 6.9 Hz, 2 H) 4.05 (t, J = 6.1 Hz, 2 H) 7.00-7.08 (m, 4 H) 7.15-7.36 (m, 10 H) 7.40 (s, 1 H) 8.43 (d, J = 4.9 Hz, 2 H) | 505.2 |
| 263 | 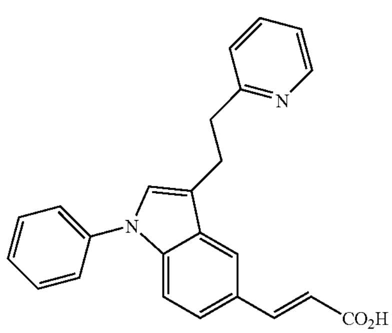 | 1H NMR (400 MHz, MeOH-d4) δ ppm 3.19-3.27 (m, 4 H) 6.44 (d, J = 16.2 Hz, 1 H) 7.24-7.40 (m, 4 H) 7.45-7.57 (m, 6 H) 7.69-7.81 (m, 3 H) 8.48 (d, J = 4.5 Hz, 1 H) | 369.1 |

TABLE 29-continued

| Ex. No. | Structure | ¹H-NMR | MS(ESI) [M + H]⁺ |
|---|---|---|---|
| 264 | 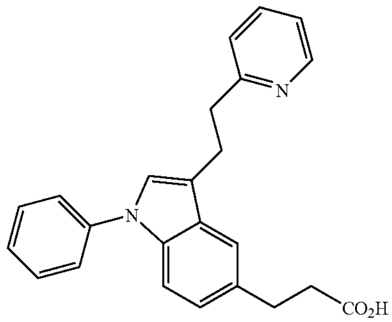 | 1H NMR (400 MHz, MeOH-d4) δ ppm 2.62 (t, J = 7.9 Hz, 2 H) 3.00 (t, J = 7.7 Hz, 2 H) 3.20 (d, J = 17.9 Hz, 2 H) 3.20 (s, 2 H) 7.04-7.07 (m, 1 H) 7.15 (s, 1 H) 7.20-7.34 (m, 3 H) 7.39-7.53 (m, 6 H) 7.71 (td, J = 7.7, 2.0 Hz, 1 H) 8.46 (d, J = 4.1 Hz, 1 H) | 371.1 |
| 267 | 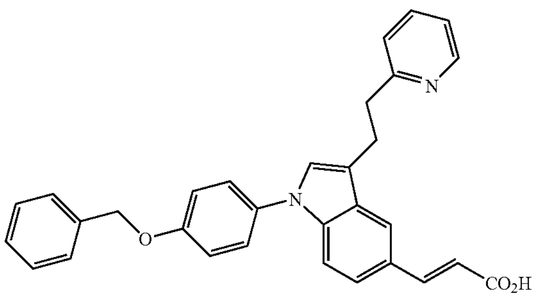 | 1H NMR (400 MHz, CHLOROFORM-d) δ ppm 3.23 (s, 4 H) 5.14 (s, 2 H) 6.42 (d, J = 15.8 Hz, 1 H) 7.05-7.21 (m, 5 H) 7.31-7.49 (m, 9 H) 7.63 (td, J = 7.7, 2.0 Hz, 1 H) 7.78 (s, 1 H) 7.84 (d, J = 15.8 Hz, 1 H) 8.53 (d, J = 4.5 Hz, 1 H) | 475.2 |

TABLE 30

| Ex. No. | Structure | ¹H-NMR | MS(ESI) [M + H]⁺ |
|---|---|---|---|
| 268 | 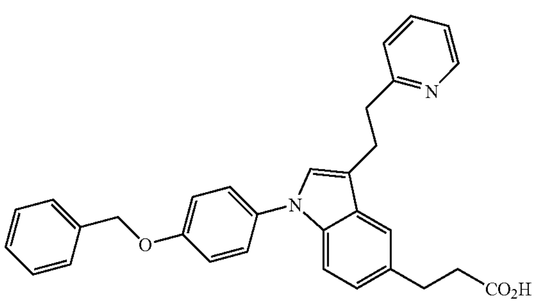 | 1H NMR (400 MHz, CHLOROFORM-d) δ ppm 2.67 (t, J = 7.7 Hz, 2 H) 3.06 (t. J = 7.7 Hz, 2 H) 3.16-3.27 (m, 4 H) 5.12 (s, 2 H) 7.00-7.14 (m, 2 H) 7.08 (d, J = 8.9 Hz, 2 H) 7.14-7.25 (m, 1 H) 7.17 (d, J = 7.3 Hz, 1 H) 7.29-7.49 (m, 9 H) 7.63 (td, J = 7.7, 1.6 Hz, 1 H) 8.51 (d, J = 4.9 Hz, 1 H) | 477.2 |
| 269 | 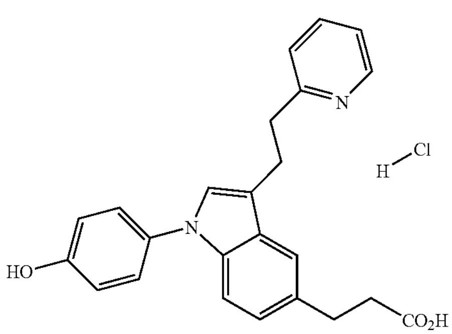 | 1H NMR (400 MHz, DMSO-d6) δ ppm 2.53-2.62 (m, 2 H) 2.99 (t, J = 7.5 Hz, 2 H) 3.47 (t, J = 7.3 Hz, 2 H) 6.92 (d, J = 8.1 Hz, 1 H) 7.03 (d, J = 8.1 Hz, 1 H) 7.11 (s, 1 H) 7.20 (d, J = 8.5 Hz, 1 H) 7.31 (d, J = 8.5 Hz, 1 H) 7.39 (s, 1 H) 7.76 (d, J = 7.3 Hz, 1 H) 7.88 (s, 2 H) 8.28 (br. s., 1 H) 8.72 (d, J = 5.3 Hz, 1 H) 9.36 (br. s., 1 H) | 387.1 |

TABLE 30-continued

| Ex. No. | Structure | ¹H-NMR | MS(ESI) [M + H]⁺ |
|---|---|---|---|
| 271 | 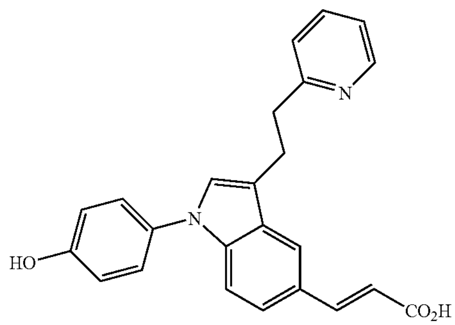 | 1H NMR (400 MHz, CHLOROFORM-d) δ ppm 3.23 (s, 4 H) 6.44 (s, J = 15.8 Hz, 1 H) 6.94 (d, J = 8.9 Hz, 2 H) 7.08 (s, 1 H) 7.25 (d, J = 8.5 Hz, 4 H) 7.35-7.46 (m, 7 H) 7.68-7.78 (m, 2 H) 8.48 (br. s., 1 H) | 385.1 |
| 275 | 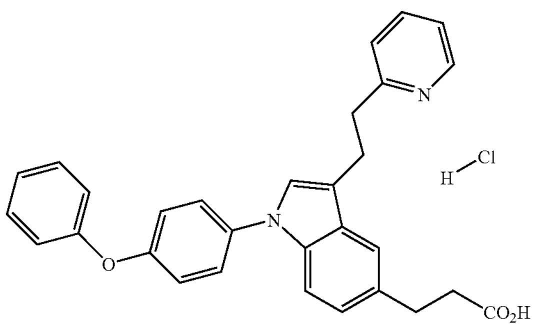 | 1H NMR (400 MHz, DMSO-d6) δ ppm 2.57 (t, J = 7.7 Hz, 2 H) 2.92 (t, J = 7.7 Hz, 2 H) 3.20 (br. s., 1 H) 3.23 (d, J = 7.7 Hz, 1 H) 3.60 (t, J = 6.3 Hz, 2 H) 7.10 (d, J = 8.9 Hz, 1 H) 7.07 (m, 2 H) 7.14-7.25 (m, 2 H) 7.17 (d, J = 8.1 Hz, 1 H) 7.39-7.57 (m, 7 H) 7.77 (br. s., 1 H) 7.89 (d, J = 7.7 Hz, 1 H) 8.35 (br. s., 1 H) 8.76 (d, J = 5.7 Hz, 1 H) | 463.3 |
| 277 | 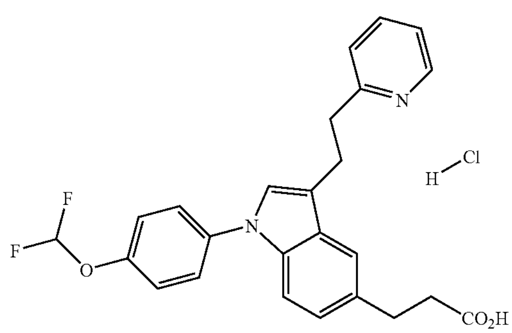 | 1H NMR (400 MHz, DMSO-d6) δ ppm 2.56-2.61 (m, 2 H) 2.97 (t, J = 7.5 Hz, 2 H) 3.61 (s, 2 H) 7.07 (d, J = 8.5 Hz, 1 H) 7.04 (t, J = 72 Hz, 1 H) 7.31 (d, J = 8.9 Hz, 2 H) 7.16-7.34 (m, 1 H) 7.40 (s, 1 H) 7.42 (d, J = 3.3 Hz, 1 H) 7.50 (d, J = 8.9 Hz, 2 H) 7.68 (br. s., 1 H) 7.79 (br. s., 1 H) 8.25 (br. s., 1 H) 8.73 (d, J = 5.3 Hz, 1 H) | 437.1 |
| 279 | 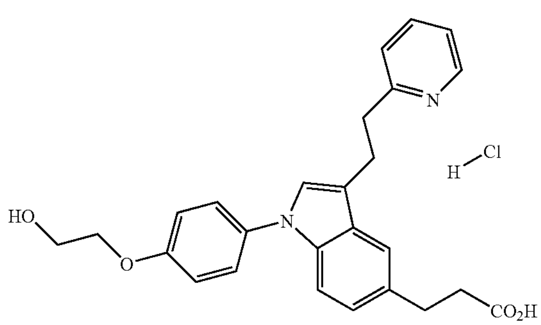 | 1H NMR (400 MHz, DMSO-d6) δ ppm 2.96 (br. s., 2 H) 3.22 (br. s., 2 H) 3.82 (br. s., 2 H) 4.11 (br. s., 2 H) 7.00-7.60 (m, 8 H) 7.84 (br. s., 1 H) 7.95 (br. s., 1 H) 8.39 (br. s., 1 H) 8.82 (br. s., 1 H) | 431.2 |

TABLE 30-continued

| Ex. No. | Structure | ¹H-NMR | MS(ESI) [M + H]⁺ |
|---|---|---|---|
| 281 | 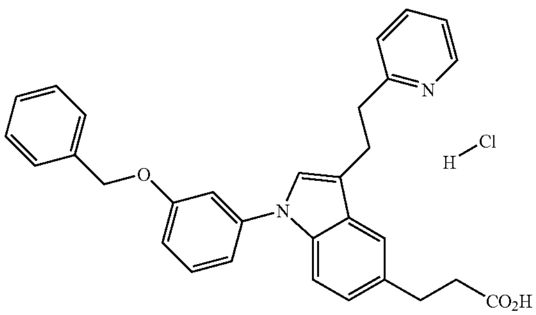 | 1H NMR (400 MHz, DMSO-d6) δ ppm 2.56 (d, J = 7.7 Hz, 1 H) 2.59 (br. s., 1 H) 2.91 (d, J = 6.9 Hz, 2 H) 3.21 (br. s., 2 H) 5.21 (s, 2 H) 6.98-7.30 (m, 3 H) 7.06 (dd, J = 14.2, 8.1 Hz, 2 H) 7.32-7.54 (m, 8 H) 7.69 (br. s., 1 H) 7.82 (br. s., 1 H) 8.27 (br. s., 1 H) 8.74 (br. s., 1 H) | 477.1 |
| 282 | 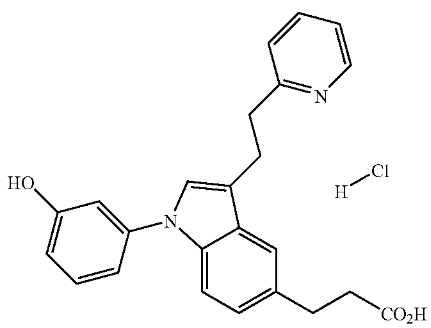 | 1H NMR (400 MHz, DMSO-d6) δ ppm 2.58 (t, J = 7.7 Hz, 2 H) 2.92 (t, J = 7.7 Hz, 2 H) 3.21 (br. s., 1 H) 3.23 (d, J = 7.3 Hz, 1 H) 3.60 (t, J = 6.7 Hz, 1 H) 3.58 (d, J = 8.9 Hz, 1 H) 6.76 (d, J = 8.1 Hz, 1 H) 6.87-7.00 (m, 2 H) 7.08 (d, J = 8.5 Hz, 1 H) 7.32 (t, J = 7.9 Hz, 1 H) 7.37-7.51 (m, 3 H) 7.82 (br. s., 1 H) 7.93 (d, J = 7.7 Hz, 1 H) 8.40 (br. s., 1 H) 8.78 (d, J = 5.3 Hz, 1 H) 9.85 (br. s., 1 H) | 387.1 |

TABLE 31

| Ex. No. | Structure | ¹H-NMR | MS(ESI) [M + H]⁺ |
|---|---|---|---|
| 284 | 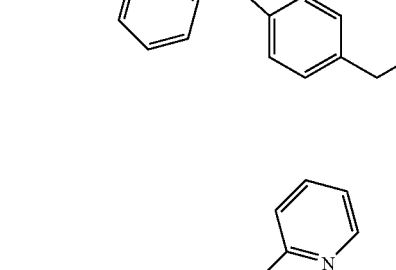 | 1H NMR (400 MHz, DMSO-d6) δ ppm 2.30 (t, J = 7.9 Hz, 2 H) 2.90 (t, J = 7.9 Hz, 2 H) 3.00 (s, 4 H) 6.91 (d, J = 8.5 Hz, 2 H) 6.99 (d, J = 8.9 Hz, 1 H) 7.17-7.34 (m, 9 H) 7.42 (s, 1 H) 8.73 (br. s., 1 H) 10.37 (br. s., 1 H) | 401.2 |
| 286 | 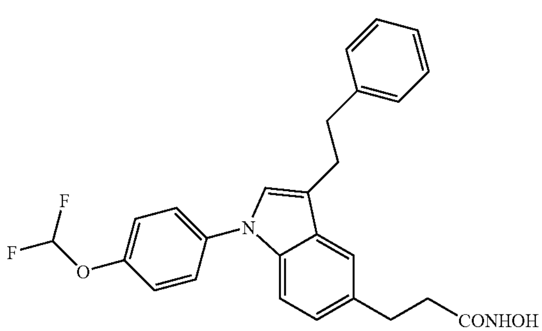 | 1H NMR (400 MHz, CHLOROFORM-d) δ ppm 2.53 (t, J = 7.3 Hz, 2 H) 3.01-3.19 (m, 4 H) 3.09 (d, J = 8.1 Hz, 2 H) 6.56 (t, J = 72 Hz, 1 H) 6.99-7.16 (m, 2 H) 7.20-7.36 (m, 7 H) 7.42 (d, J = 8.5 Hz, 4 H) 7.92 (br. s., 1 H) | 451.1 |

TABLE 31-continued

| Ex. No. | Structure | ¹H-NMR | MS(ESI) [M + H]⁺ |
|---|---|---|---|
| 288 | 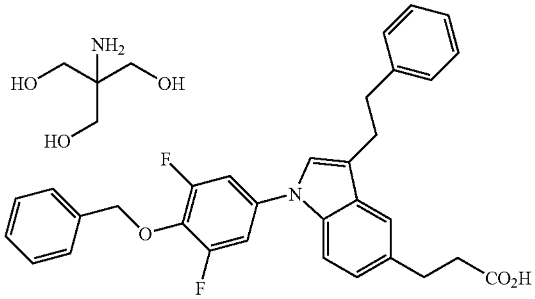 | 1H NMR (400 MHz, MeOH-d4) δ ppm 2.53 (d, J = 8.5 Hz, 1 H) 2.50 (s, 1 H) 2.96-3.09 (m, 6 H) 3.61 (s, 6 H) 5.18 (s, 2 H) 7.05-7.27 (m, 9 H) 7.31-7.49 (m, 7 H) | 512.1 |
| 289 | 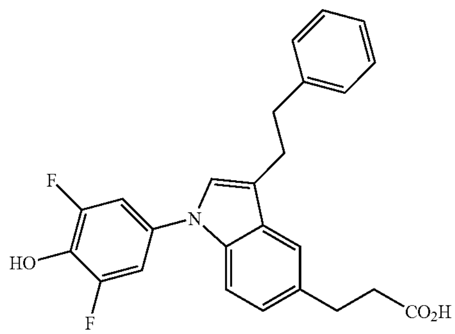 | 1H NMR (400 MHz, MeOH-d4) δ ppm 2.62 (t, J = 7.7 Hz, 2 H) 2.97-3.09 (m, 4 H) 3.01 (d, J = 7.3 Hz, 2 H) 7.01-7.10 (m, 4 H) 7.14-7.27 (m, 5 H) 7.39 (d, J = 8.1 Hz, 1 H) 7.39 (s, 1 H) | 422.0 |
| 291 | 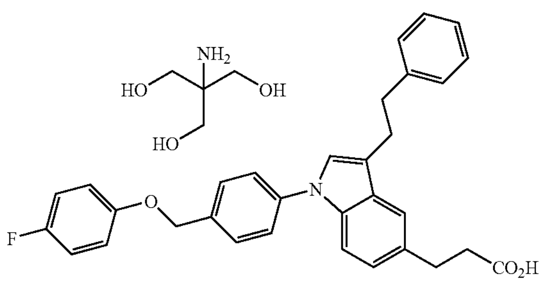 | 1H NMR (400 MHz, MeOH-d4) δ ppm 2.55 (d, J = 8.1 Hz, 1 H) 2.51 (s, 1 H) 2.98-3.11 (m, 6 H) 3.63 (s, 6 H) 5.09 (s, 2 H) 6.98-7.11 (m, 6 H) 7.12-7.28 (m, 5 H) 7.40-7.49 (m, 4 H) 7.56 (d, J = 8.5 Hz, 2 H) | 494.2 |
| 293 | 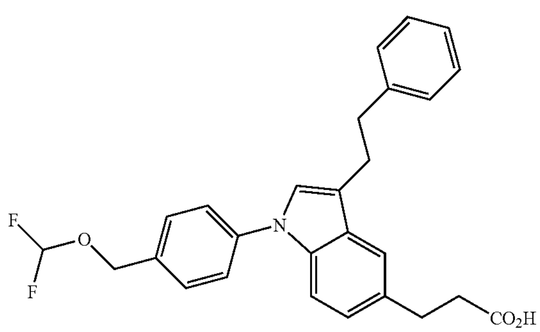 | 1H NMR (400 MHz, CHLOROFORM-d) δ ppm 2.73 (t, J = 7.7 Hz, 2 H) 3.07 (d, J = 7.3 Hz, 2 H) 3.09 (br. s., 4 H) 4.94 (s, 2 H) 6.34 (t, J = 72 Hz, 1 H) 7.05 (s, 1 H) 7.07 (d, J = 8.9 Hz, 2 H) 7.17-7.38 (m, 4 H) 7.38-7.58 (m, 6 H) | 450.0 |
| 295 | 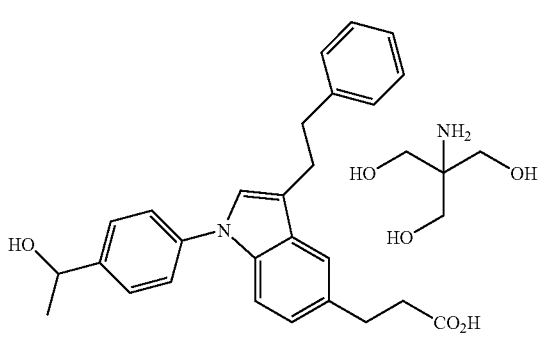 | 1H NMR (400 MHz, MeOH-d4) δ ppm 1.49 (d, J = 6.5 Hz, 3 H) 2.54 (d, J = 8.1 Hz, 1 H) 2.52 (d, J = 9.7 Hz, 1 H) 2.98-3.17 (m, 4 H) 3.03 (dd, J = 11.2, 6.7 Hz, 2 H) 3.61 (s, 6 H) 7.05-7.12 (m, 2 H) 7.13-7.31 (m, 3 H) 7.23 (d, J = 2.4 Hz, 2 H) 7.43 (t, J = 4.7 Hz, 2 H) 7.40 (d, J = 4.9 Hz, 2 H) 7.51 (d, J = 8.5 Hz, 2 H) | 414.1 |

TABLE 31-continued

| Ex. No. | Structure | ¹H-NMR | MS(ESI) [M + H]⁺ |
|---|---|---|---|
| 297 | 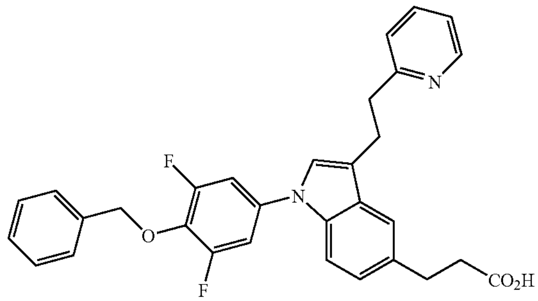 | 1H NMR (400 MHz, CHLOROFORM-d) δ ppm 2.78 (t, J = 7.3 Hz, 2 H) 3.16 (d, J = 7.7 Hz, 2 H) 2.99-3.18 (m, 2 H) 3.19 (br. s., 2 H) 5.19 (s, 2 H) 6.87-7.04 (m, 3 H) 7.12 (d, J = 7.7 Hz, 1 H) 7.17-7.29 (m, 2 H) 7.30-7.52 (m, 6 H) 7.56-7.74 (m, 2 H) 8.66 (d, J = 4.1 Hz, 1 H) | 513.1 |
| 298 | 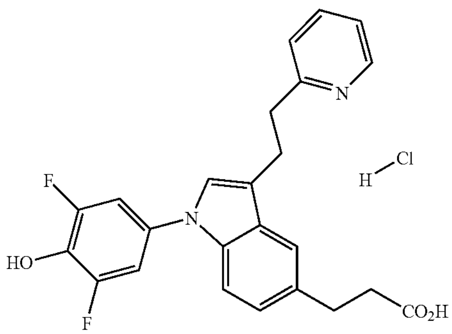 | 1H NMR (400 MHz, DMSO-d6) δ ppm 2.57 (t, J = 7.7 Hz, 2 H) 2.91 (t, J = 7.5 Hz, 2 H) 3.19 (t, J = 7.7 Hz, 1 H) 7.27 (d, J = 8.9 Hz, 1 H) 7.45 (d, J = 2.8 Hz, 1 H) 7.42 (d, J = 4.1 Hz, 2 H) 7.77 (br. s., 1 H) 7.89 (br. s., 1 H) 8.34 (br. s., 1 H) 8.76 (d, J = 5.3 Hz, 1 H) 10.36 (br. s., 1 H) | 423.0 |

TABLE 32

| Ex. No. | Structure | ¹H-NMR | MS(ESI) [M + H]⁺ |
|---|---|---|---|
| 300 | 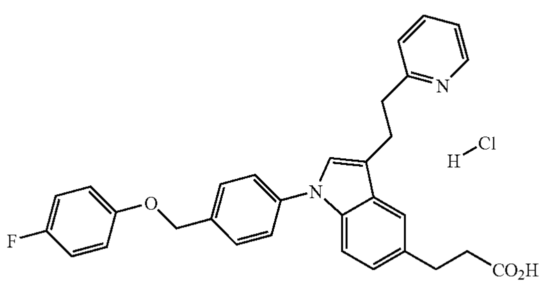 | 1H NMR (400 MHz, DMSO-d6) δ ppm 2.57 (t, J = 7.7 Hz, 1 H) 2.54 (s, 1 H) 2.92 (t, J = 7.7 Hz, 2 H) 3.21 (t, J = 7.5 Hz, 4 H) 5.15 (s, 2 H) 7.04-7.18 (m, 5 H) 7.40-7.56 (m, 3 H) 7.46 (d, J = 2.8 Hz, 2 H) 7.60-7.66 (m, 2 H) 7.70 (br. s., 1 H) 7.82 (br. s., 1 H) 8.25 (br. s., 1 H) 8.73 (d, J = 5.3 Hz, 1 H) | 495.1 |
| 302 | 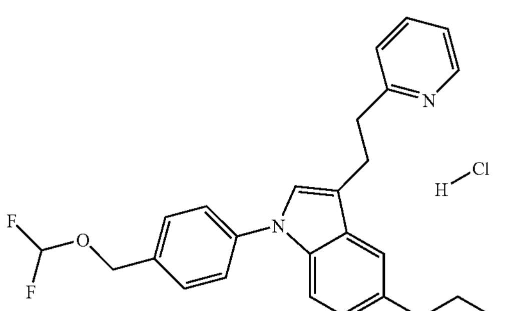 | 1H NMR (400 MHz, DMSO-d6) δ ppm 2.60 (br. s., 1 H) 2.57 (d, J = 8.1 Hz, 1 H) 2.92 (t, J = 7.3 Hz, 2 H) 3.24 (d, J = 6.9 Hz, 2 H) 4.99 (s, 2 H) 6.84 (t, J = 72 Hz, 1 H) 7.09 (d, J = 8.9 Hz, 1 H) 7.48 (d, J = 4.9 Hz, 2 H) 7.47 (br. s., 1 H) 7.56 (m, 4 H) 7.78 (d, J = 6.9 Hz, 1 H) 7.91 (br. s., 1 H) 8.36 (br. s., 1 H) 8.77 (d, J = 4.9 Hz, 1 H) | 451.1 |

TABLE 32-continued
| Ex. No. | Structure | ¹H-NMR | MS(ESI) [M + H]⁺ |
|---|---|---|---|
| 304 | 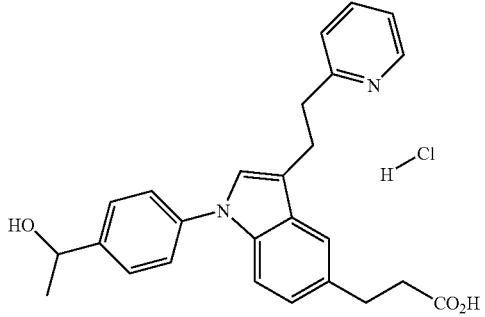 | 1H NMR (400 MHz, DMSO-d6) d ppm 1.37 (d, J = 6.5 Hz, 3 H) 2.57 (t, J = 7.7 Hz, 2 H) 2.92 (t, J = 7.5 Hz, 2 H) 3.18 (br. s., 1 H) 3.21 (d, J = 8.1 Hz, 1 H) 4.79 (q, J = 6.2 Hz, 1 H) 7.07 (d, J = 7.3 Hz, 1 H) 7.39-7.55 (m, 7 H) 7.68 (br. s., 1 H) 7.82 (br. s., 1 H) 8.26 (br. s., 1 H) 8.73 (d, J = 5.3 Hz, 1 H) | 415.1 |
| 306 | 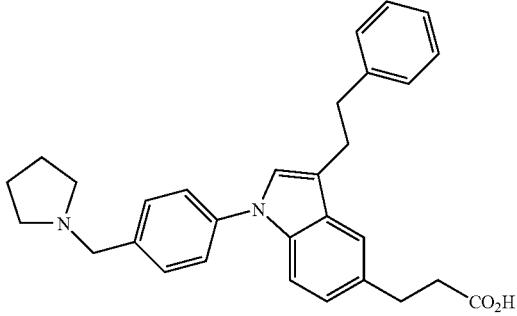 | 1H NMR (400 MHz, CHLOROFORM-d) δ ppm 1.85-1.92 (m, 4 H) 2.74-2.87 (m, 6 H) 2.99-3.11 (m, 4 H) 3.13-3.18 (m, 2 H) 3.80 (s, 2 H) 6.45 (d, J = 8.3 Hz 2 H) 6.71 (s, 1 H) 6.79 (d, J = 8.3 Hz 2 H) 7.17-7.31 (m, 7 H) 7.66 (s, 1 H) | 453 (FABMS) |
| 308 | 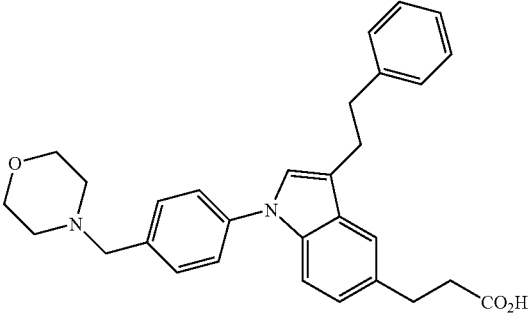 | 1H NMR (400 MHz, CHLOROFORM-d) δ ppm 2.55 (br. s., 4 H) 2.76 (t, J = 7.3 Hz 2 H) 2.99-3.15 (m, 6 H) 3.54 (s, 2 H) 3.73 (t, J = 4.5 Hz, 4 H) 6.91 (s, 1 H) 6.96 (d, J = 8.3 Hz, 2 H) 7.09-7.31 (m, 9 H) 7.39 (d, J = 8.3 Hz, 1 H) 7.52 (s, 1 H) | 469.2 |
| 310 | 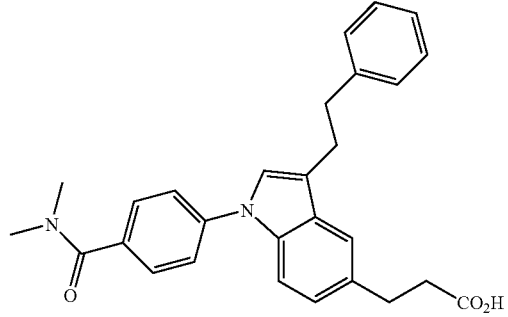 | 1H NMR (400 MHz, CHLOROFORM-d) δ ppm 2.74 (t, J = 7.4 Hz, 2 H) 2.97-3.20 (m, 12 H) 7.07 (s, 1 H) 7.09 (d, J = 8.5 Hz, 1 H) 7.18-7.33 (m, 5 H) 7.39-7.59 (m, 6 H) | 441.2 |

TABLE 32-continued
| Ex. No. | Structure | ¹H-NMR | MS(ESI) [M + H]⁺ |
|---|---|---|---|
| 312 | 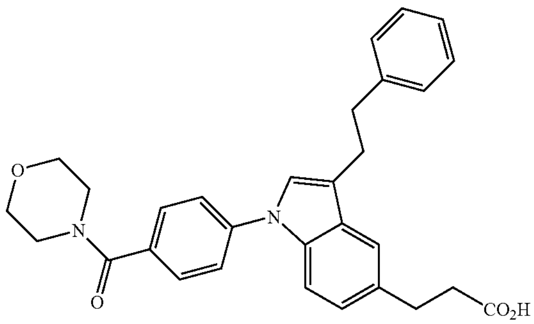 | 1H NMR (400 MHz, CHLOROFORM-d) δ ppm 2.74 (t, J = 7.5 Hz, 2 H) 3.02-3.14 (m, 6 H) 3.46-3.89 (m, 8 H) 7.06 (s, 1 H) 7.10 (dd, J = 1.7, 8.6 Hz, 1 H) 7.19-7.34 (m, 5 H) 7.44 (d, J = 1.1 Hz 1 H) 7.48-7.58 (m, 5 H) | 483.3 |
| 314 | 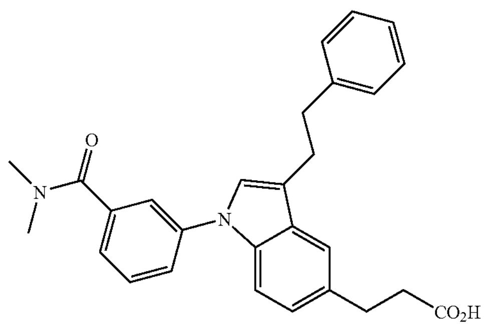 | 1H NMR (400 MHz, CHLOROFORM-d) δ ppm 2.72 (t, J = 7.8 Hz, 2 H) 3.02-3.19 (m, 12 H) 7.03-7.10 (m, 2 H) 7.18-7.38 (m, 6 H) 7.42 (s, 1 H) 7.47-7.60 (m, 4 H) | 441.2 |
| 316 | 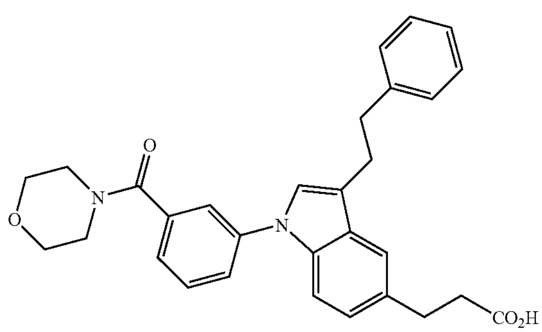 | 1H NMR (400 MHz, CHLOROFORM-d) δ ppm 2.73 (t, J = 7.8 Hz, 2 H) 3.02-3.15 (m, 6 H) 3.43-3.91 (m, 8 H) 7.05-7.13 (m, 2 H) 7.21-7.37 (m, 6 H) 7.44-7.59 (m, 5 H) | 483.3 |
TABLE 33
| Ex. No. | Structure | ¹H-NMR | MS(ESI) [M + H]⁺ |
|---|---|---|---|
| 318 | 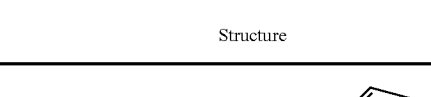 | 1H NMR (400 MHz, CHLOROFORM-d) δ ppm 2.74 (t, J = 7.7 Hz, 2 H) 2.78 (s 6 H) 3.02-3.14 (m, 6 H) 7.09 (s, 1 H) 7.13 (dd, J = 1.6, 8.5 Hz, 1 H) 7.19-7.36 (m, 5 H) 7.44 (d, J = 1.1 Hz 1H) 7.56 (d, J = 8.4 Hz, 1 H) 7.61 (d, J = 8.7 Hz, 2 H) 7.89 (d, J = 8.7 Hz 2 H) | 477.2 |

TABLE 33-continued

| Ex. No. | Structure | ¹H-NMR | MS(ESI) [M + H]⁺ |
|---|---|---|---|
| 320 | 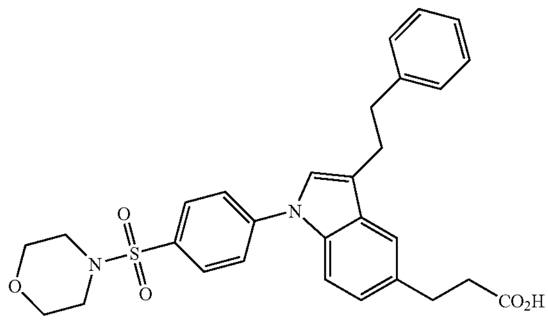 | 1H NMR (400 MHz, CHLOROFORM-d) δ ppm 2.74 (t, J = 7.7 Hz, 2 H) 2.98-3.14 (m, 10 H) 3.73-3.82 (m, 4 H) 7.08 (s, 1 H) 7.13 (dd, J = 1.7, 8.6 Hz, 1 H) 7.20-7.35 (m, 5 H) 7.44 (d, J = 1.2 Hz 1 H) 7.56 (d, J = 8.5 Hz, 1 H) 7.61 (d, J = 8.6 Hz, 2 H) 7.86 (d, J = 8.6 Hz 2 H) | 519.2 |
| 322 | 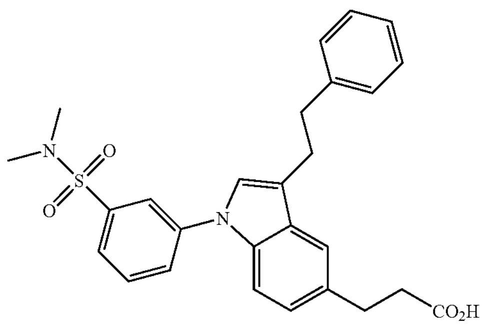 | 1H NMR (400 MHz, CHLOROFORM-d) δ ppm 2.71-2.81 (m, 8 H) 3.03-3.14 (m, 6 H) 7.08 (s, 1 H) 7.12 (dd, J = 1.4, 8.5 Hz, 1 H) 7.21-7.36 (m, 5 H) 7.44 (s, 1 H) 7.50 (d, J = 8.5 Hz, 1 H) 7.65-7.74 (m, 3 H) 7.85 (d, J = 1.4 Hz 1 H) | 477.1 |
| 324 | 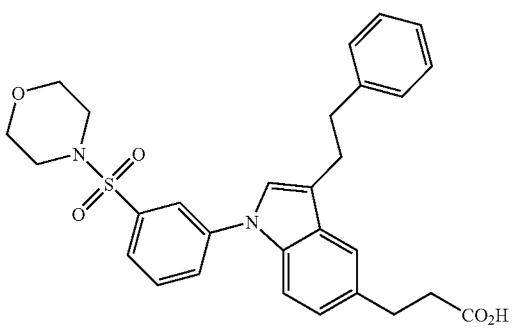 | 1H NMR (400 MHz, CHLOROFORM-d) δ ppm 2.74 (t, J = 7.5 Hz, 2 H) 2.98-3.15 (m, 10 H) 3.74-3.82 (m, 4 H) 7.07 (s, 1 H) 7.12 (dd, J = 1.6, 8.5 Hz, 1 H) 7.19-7.35 (m, 5 H) 7.44 (d, J = 1.0 Hz 1 H) 7.49 (d, J = 8.5 Hz, 1 H) 7.64-7.79 (m, 3 H) 7.82-7.85 (m, 1 H) | 519.2 |
| 326 | 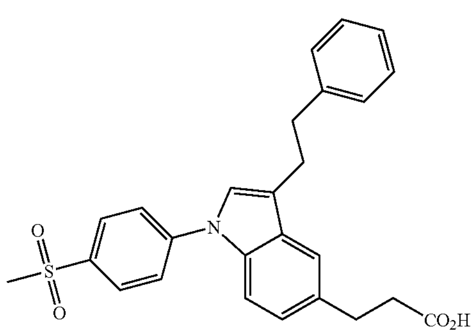 | 1H NMR (400 MHz, CHLOROFORM-d) δ ppm 2.74 (t, J = 7.6 Hz, 2 H) 3.02-3.15 (m, 6 H) 3.12 (s, 3 H) 7.08 (s, 1 H) 7.12-7.16 (m, 1 H) 7.19-7.34 (m, 5 H) 7.44 (s, 1 H) 7.56 (d, J = 8.5 Hz, 1 H) 7.64 (d, J = 8.5 Hz, 2 H) 8.05 (d, J = 8.5 Hz 2 H) | 448.2 |

TABLE 33-continued

| Ex. No. | Structure | ¹H-NMR | MS(ESI) [M + H]⁺ |
|---|---|---|---|
| 328 | 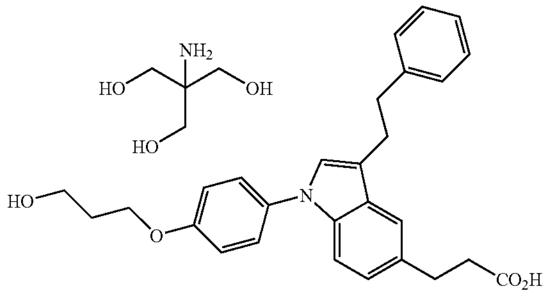 | 1H NMR (400 MHz, MeOH-d4) δ ppm 1.97-2.06 (m, 2 H) 2.50-2.56 (m, 2 H) 2.98-3.11 (m, 6 H) 3.62 (s, 6 H) 3.77 (t, J = 6.2 Hz 2 H) 4.13 (t, J = 6.3 Hz 2H) 6.99 (s, 1 H) 7.03-7.08 (m, 3 H) 7.14-7.20 (m, 1 H) 7.22-7.34 (m, 7 H) 7.43 (s, 1 H) | 447.2 |

TABLE 34

| Ex. No. | Structure | ¹H-NMR | MS(ESI) [M + H]⁺ |
|---|---|---|---|
| 329 | 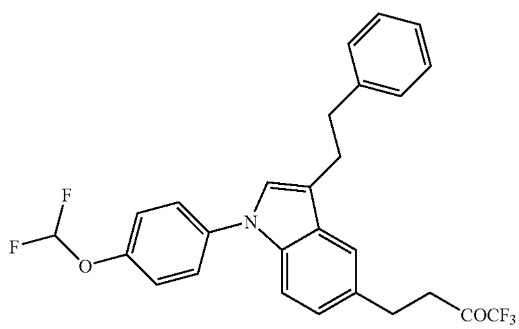 | 1H NMR (400 MHz, CHLOROFORM-d) δ ppm 2.98-3.19 (m, 8 H) 6.56 (t, 1 H) 6.99-7.15 (m, 2 H) 7.06 (d, J = 8.1 Hz, 1 H) 7.19-7.36 (m, 6 H) 7.42 (t, J = 9.5 Hz, 4 H) | — |
| 330 | 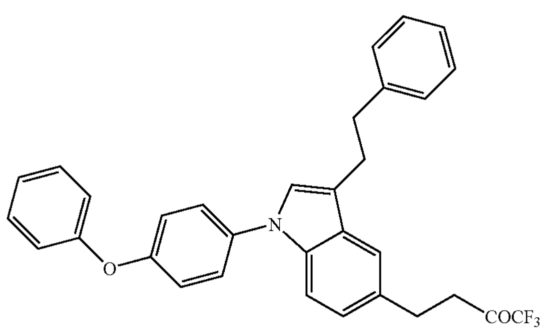 | 1H NMR (400 MHz, CHLOROFORM-d) δ ppm 3.00-3.15 (m, 8 H) 7.03-7.17 (m, 9 H) 7.21-7.33 (m, 3 H) 7.36-7.42 (m, 6 H) | — |
| 331 | 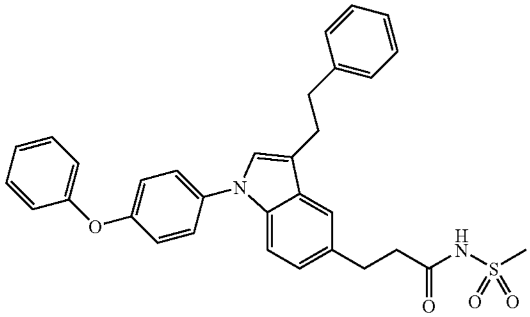 | 1H NMR (400 MHz, CHLOROFORM-d) δ ppm 2.68 (t, J = 7.3 Hz, 2 H) 3.12 (t, J = 7.5 Hz, 4 H) 3.07 (d, J = 5.7 Hz, 2 H) 3.21 (s, 3 H) 7.03-7.17 (m, 9 H) 7.21-7.34 (m, 3 H) 7.36-7.46 (m, 6 H) | 539.2 |

TABLE 34-continued

| Ex. No. | Structure | ¹H-NMR | MS(ESI) [M + H]⁺ |
|---|---|---|---|
| 332 | 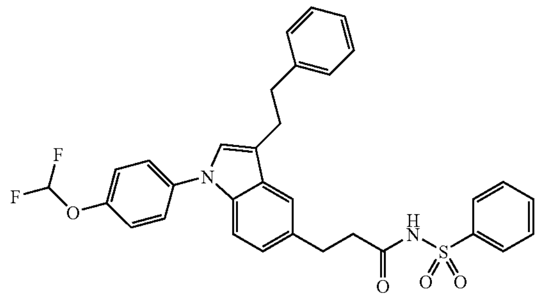 | 1H NMR (400 MHz, CHLOROFORM-d) δ ppm 2.61 (t, J = 7.5 Hz, 2 H) 2.96-3.09 (m, 6 H) 6.57 (t, 1 H) 6.93 (dd, J = 8.3, 1.8 Hz, 2 H) 7.03 (s, 1 H) 7.10 (s, 1 H) 7.20-7.36 (m, 6 H) 7.39-7.52 (m, 4 H) 7.59 (t, J = 7.3 Hz, 1 H) 7.79 (br. s., 1 H) 7.99 (d, J = 7.3 Hz, 2 H) | 575.0 |
| 333 | 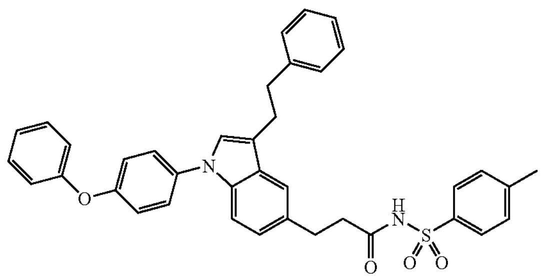 | 1H NMR (400 MHz, CHLOROFORM-d) δ ppm 2.40 (s, 3 H) 2.60 (t, J = 7.7 Hz, 2 H) 2.95-3.10 (m, 6 H) 6.91 (dd, J = 8.5, 1.6 Hz, 1 H) 7.03-7.20 (m, 8 H) 7.21-7.41 (m, 10 H) 7.74 (s, 1 H) 7.86 (d, J = 8.5 Hz, 2 H) | 615.2 |
| 334 | 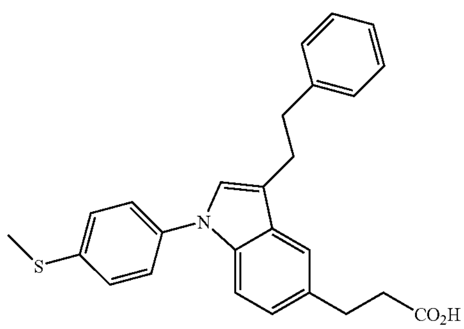 | 1H NMR (400 MHz, CHLOROFORM-d) δ ppm 2.51 (br. s., 3 H) 2.73 (br. s., 2 H) 3.02 (br. s., 6 H) 6.99 (br. d., J = 8.5 Hz, 2 H) 7.26 (br. s., 11 H) | 416.0 |
| 335 | 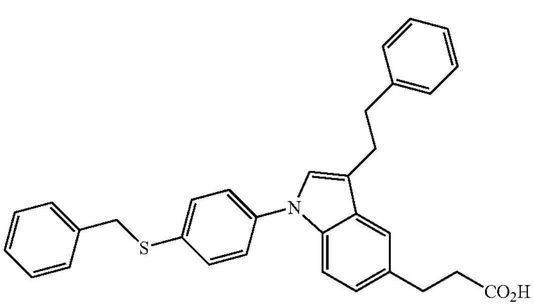 | 1H NMR (400 MHz, CHLOROFORM-d) δ ppm 2.74 (t, J = 7.7 Hz, 2 H) 3.00-3.12 (m, 4 H) 3.07 (d, J = 6.1 Hz, 2 H) 4.14 (s, 2 H) 7.03 (s, 1 H) 7.08 (d, J = 7.3 Hz, 1 H) 7.20-7.35 (m, 12 H) 7.43 (t, J = 8.7 Hz, 3 H) 7.39 (s, 1 H) | 492.0 |

TABLE 35

| Ex. No. | Structure | ¹H-NMR | MS(ESI) [M + H]⁺ |
|---|---|---|---|
| 336 | 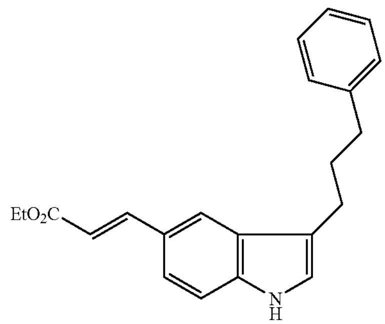 | 1H NMR (400 MHz, CHLOROFORM-d) δ ppm 1.35 (t, J = 7.1 Hz, 3 H) 2.02-2.10 (m, J = 7.7, 7.7, 7.7, 7.7 Hz, 2 H) 2.70-2.84 (m, 2 H) 2.76 (d, J = 13.0 Hz, 2 H) 4.27 (q, J = 6.9 Hz, 2 H) 6.41 (d, J = 15.8 Hz, 1 H), 7.01 (s, 1 H), 7.18-7.44 (m, 7 H), 7.72 (s, 1 H), 7.84 (d, J = 15.8 Hz, 1 H), 8.04 (br. s., 1 H) | 334.2 |
| 337 | 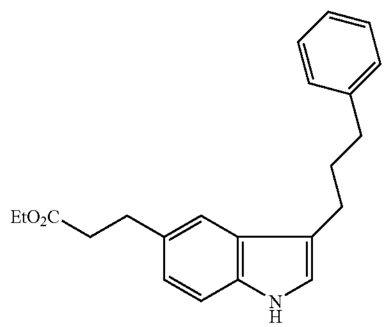 | 1H NMR (400 MHz, CHLOROFORM-d) δ ppm 1.24 (t, J = 7.3 Hz, 3 H) 2.00-2.10 (m, 2 H) 2.64-2.81 (m, 6 H) 3.07 (s, 1 H) 3.04 (d, J = 8.1 Hz, 1 H) 4.13 (q, J = 6.9 Hz, 2 H) 6.96-7.06 (m, 2 H), 7.17-7.31 (m, 6 H) 7.38 (s, 1 H), 7.86 (br. s., 1 H) | 336.2 |
| 338 | 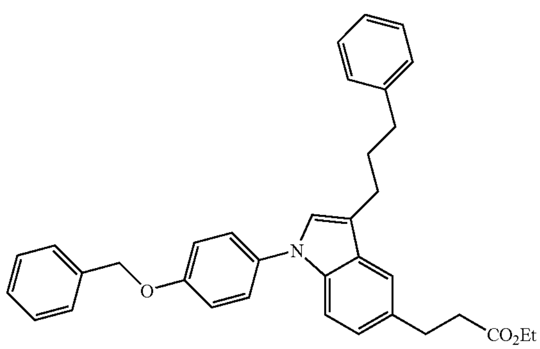 | 1H NMR (400 MHz, CHLOROFORM-d) δ ppm 1.25 (t, J = 7.1 Hz, 3 H) 2.02-2.13 (m, 2 H) 2.65-2.84 (m, 6 H) 3.03-3.09 (m, 2 H) 4.14 (q, J = 6.9 Hz, 2 H) 5.12 (s, 2 H) 6.97-7.14 (m, 4 H) 7.19-7.50 (m, 14 H) | 518.1 |
| 339 | 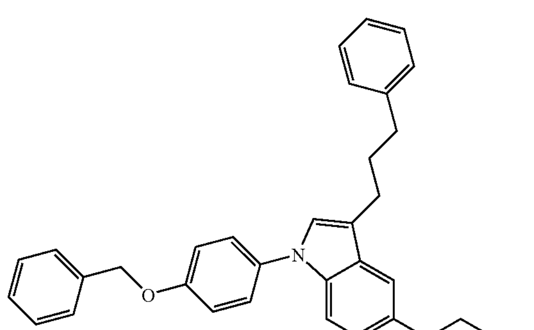 | 1H NMR (400 MHz, CHLOROFORM-d) δ ppm 2.05-2.15 (m, 2 H) 2.72-2.84 (m, 6 H) 3.05-3.15 (m, 2 H) 5.12 (s, 2 H) 7.02-7.15 (m, 4 H) 7.21-7.50 (m, 14 H) | 490.1 |

TABLE 35-continued

| Ex. No. | Structure | ¹H-NMR | MS(ESI) [M + H]⁺ |
|---|---|---|---|
| 340 | 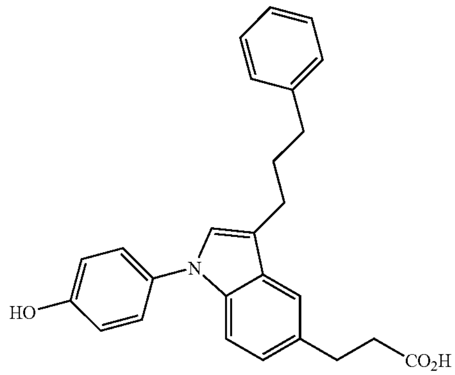 | 1H NMR (400 MHz, DMSO-d6) δ ppm 1.99-2.13 (m, 2 H) 2.70-2.78 (m, 2 H) 2.74 (t, J = 7.7 Hz, 2 H) 2.81 (t, J = 7.3 Hz, 2 H) 3.05-3.12 (m, 2 H) 7.03-7.50 (m, 13 H) | 400.1 |
| 341 | 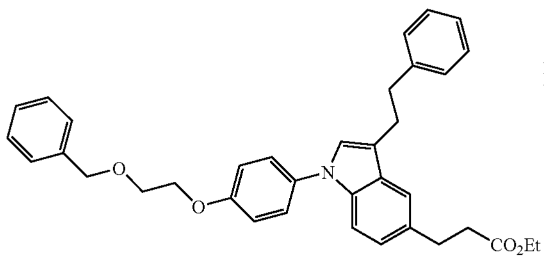 | 1H NMR (400 MHz, CHLOROFORM-d) δ ppm 1.20-1.30 (t, 3 H) 2.65-2.75 (m, 2 H) 2.99-3.13 (m, 4 H) 3.82-3.92 (m, 1 H) 3.86 (d, J = 4.9 Hz, 1 H) 4.09-4.24 (m, 4 H) 4.63-4.71 (s, 2 H) 6.96-7.10 (m, 3 H) 7.20-7.60 (m, 15 H) | 548.1 |
| 342 | 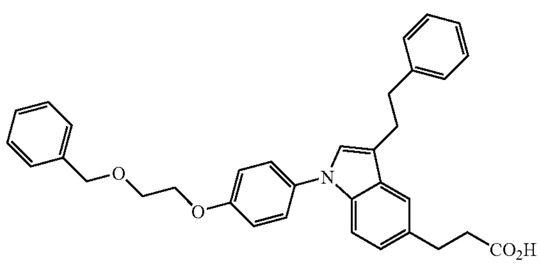 | 1H NMR (400 MHz, CHLOROFORM-d) δ ppm 2.74 (t, J = 8.1 Hz, 2 H) 3.02-3.13 (m, 4 H) 3.07 (d, J = 5.7 Hz, 2 H) 3.87 (t, J = 4.1 Hz, 2 H) 4.21 (t, J = 4.1 Hz, 2 H) 4.66 (s, 2 H) 6.99-7.11 (m, 2 H) 7.03 (d, J = 8.9 Hz, 2 H) 7.19-7.40 (m, 14 H) | 520.2 |

TABLE 36

| Ex. No. | Structure | ¹H-NMR | MS(ESI) [M + H]⁺ |
|---|---|---|---|
| 343 | 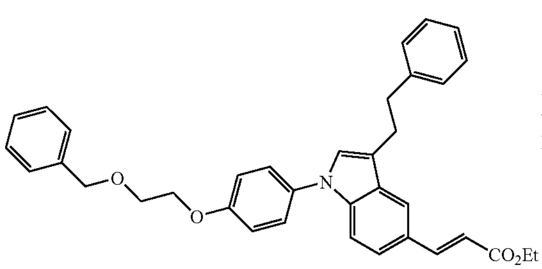 | 1H NMR (400 MHz, CHLOROFORM-d) δ ppm 1.35 (t, J = 7.1 Hz, 3 H) 3.02-3.14 (m, 4 H) 3.87 (d, J = 3.7 Hz, 1 H) 3.89 (br. s., 1 H) 4.16-4.23 (m, 2 H) 4.27 (q, J = 7.1 Hz, 2 H) 4.65 (s, 2 H) 6.42 (d, J = 15.8 Hz, 1 H) 6.92-7.08 (m, 2 H) 7.03 (d, J = 5.7 Hz, 2 H) 7.22-7.41 (m, 13 H) 7.75 (s, 1 H) 7.84 (d, J = 15.9 Hz, 1 H) | 546.2 |

TABLE 36-continued

| Ex. No. | Structure | ¹H-NMR | MS(ESI) [M + H]⁺ |
|---|---|---|---|
| 344 | 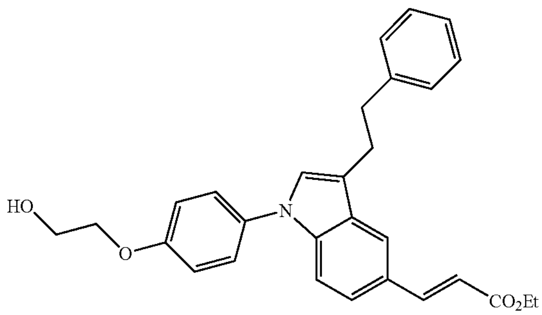 | 1H NMR (400 MHz, CHLOROFORM-d) δ ppm 1.35 (t, J = 7.1 Hz, 3 H) 3.09 (dd, J = 19.3, 7.9 Hz, 2 H) 3.02-3.15 (m, 2 H) 4.02 (ddd, J = 6.3, 4.7, 4.5 Hz, 2 H) 4.14-4.19 (m, 2 H) 4.28 (q, J = 7.1 Hz, 2H) 6.42 (d, J = 15.9 Hz, 1H) 7.01-7.06 (m, 1 H) 7.05 (d, J = 8.9 Hz, 2 H) 7.20-7.42 (m, 9 H) 7.75 (s, 1 H) 7.85 (d, J = 15.9 Hz, 1 H) | 456.1 |
| 345 | 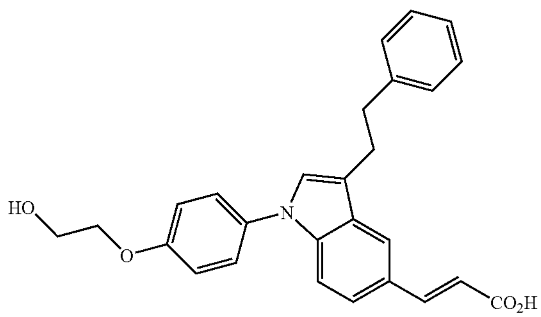 | 1H NMR (400 MHz, CHLOROFORM-d) δ ppm 3.04-3.16 (m, 4 H) 4.03 (d, J = 4.9 Hz, 2 H) 4.02 (s, 1 H) 4.18 (s, 1 H) 4.16 (d, J = 4.9 Hz, 2 H) 6.43 (d, J = 15.9 Hz, 1 H) 7.06 (d, J = 8.9 Hz, 2 H) 7.03-7.09 (m, 1 H) 7.22-7.47 (m, 8 H) 7.44 (d, J = 6.1 Hz, 1 H) 7.92 (d, J = 15.9 Hz, 1 H) | 428.1 |
| 346 | 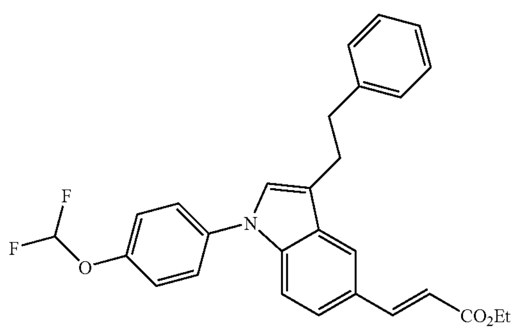 | 1H NMR (400 MHz, CHLOROFORM-d) δ ppm 1.36 (t, J = 7.3 Hz, 3 H) 3.00-3.15 (m, 4 H) 4.28 (q, J = 7.3 Hz, 2 H) 6.43 (d, J = 15.9 Hz, 1 H) 6.57 (t, J = 73.4 Hz, 1 H) 7.03 (s, 1 H) 7.06 (d, J = 8.9 Hz, 1 H) 7.16-7.36 (m, 6 H) 7.40-7.52 (m, 4 H), 7.76 (s, 1 H) 7.84 (d, J = 15.9 Hz, 1 H) | 462.1 |
| 347 | 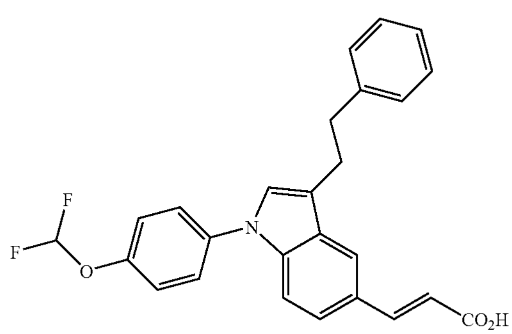 | 1H NMR (400 MHz, CHLOROFORM-d) δ ppm 3.03-3.18 (m, 4 H) 6.44 (d, J = 15.9 Hz, 1 H) 6.57 (t, J = 73.4 Hz, 1 H) 7.04 (s, 1 H) 7.21-7.33 (m, 7 H) 7.41-7.49 (m, 4 H) 7.76 (s, 1 H), 7.92 (d, 15.9 Hz, 1 H) | 434.0 |

TABLE 36-continued

| Ex. No. | Structure | $^1$H-NMR | MS(ESI) [M + H]$^+$ |
|---|---|---|---|
| 348 | 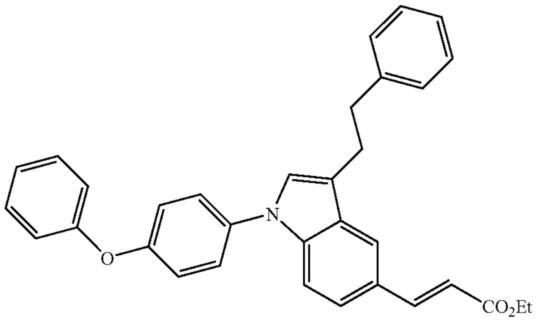 | 1H NMR (400 MHz, CHLOROFORM-d) δ ppm 1.36 (t, J = 7.1 Hz, 3 H) 3.00-3.15 (m, 4 H) 4.28 (q, J = 7.1 Hz, 2 H) 6.43 (d, J = 15.9 Hz, 1 H) 7.04-7.50 (m, 17 H) 7.76 (s, 1 H) 7.85 (d, J = 15.9 Hz, 1 H) | 488.1 |
| 349 | 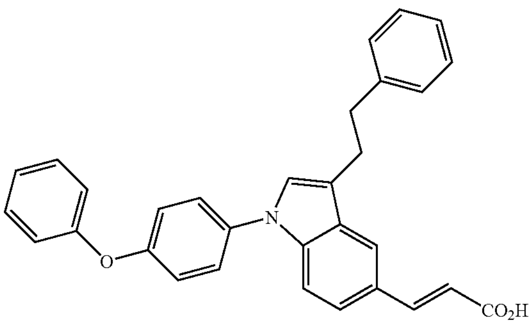 | 1H NMR (400 MHz, CHLOROFORM-d) δ ppm 3.01-3.19 (m, 4 H) 6.44 (d, J = 15.8 Hz, 1 H) 7.02-7.50 (m, 17 H) 7.77 (s, 1 H) 7.94 (d, J = 15.8 Hz, 1 H) | 460.1 |

TABLE 37

| Ex. No. | Structure | $^1$H-NMR | MS(ESI) [M + H]$^+$ |
|---|---|---|---|
| 350 | 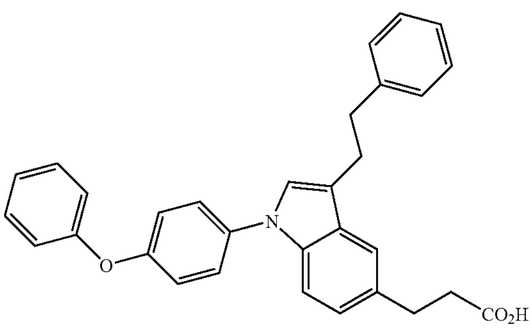 | 1H NMR (400 MHz, CHLOROFORM-d) δ ppm 2.74 (t, J = 8.1 Hz, 2 H) 3.01-3.17 (m, 6 H) 7.01-7.46 (m, 16 H) 7.37 (d, J = 6.5 Hz, 2 H) | 462.2 |
| 351 | 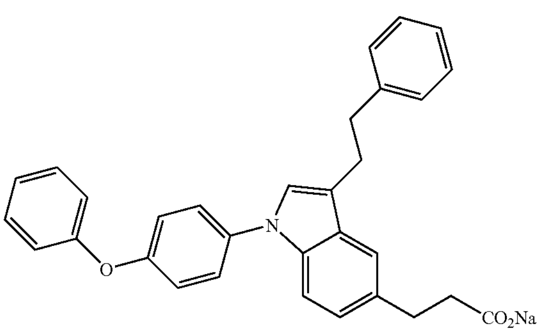 | 1H NMR (400 MHz, MeOD) δ ppm 2.47-2.54 (m, 2 H) 2.98-3.12 (m, 4 H) 3.03 (dd, J = 11.8, 5.3 Hz, 2 H) 7.04-7.27 (m, 12 H) 7.35-7.45 (m, 6 H) | 484.0 |

TABLE 37-continued

| Ex. No. | Structure | ¹H-NMR | MS(ESI) [M + H]⁺ |
|---|---|---|---|
| 352 | (structure: 1-(4-phenoxyphenyl)-3-(2-phenylethyl)-1H-indole-5-propanoic acid, ½ Zn salt) | 1H NMR (400 MHz, MeOD/DMSO-d6(3:2)) δ ppm 2.52 (t, J = 7.9 Hz, 2 H) 2.98 (t, J = 7.9 Hz, 2 H) 3.02-3.08 (br. s., 4 H) 7.05-7.20 (m, 7 H) 7.23-7.31 (m, 5 H) 7.38-7.51 (m, 6 H) | 462.1 |
| 353 | (structure with ½ piperazine) | 1H NMR (400 MHz, MeOD) δ ppm 2.57 (t, J = 8.5 Hz, 2 H) 2.98-3.10 (m, 6 H) 3.03 (s, 8 H) 7.04-7.17 (m, 8 H) 7.20-7.27 (m, 2 H) 7.23 (d, J = 4.1 Hz, 2 H) 7.36-7.45 (m, 6 H) | 462.1 |
| 354 | (structure with ½ N,N'-dibenzylethylenediamine) | 1H NMR (400 MHz, MeOD) δ ppm 2.57 (t, J = 8.5 Hz, 2 H) 2.93 (s, 2 H) 3.03 (m, 6 H) 3.92 (s, 2 H) 7.02-7.47 (m, 23 H) | 462.1 |
| 355 | (structure with L-arginine) | 1H NMR (400 MHz, DMSO-d6) δ ppm 1.46-1.70 (m, 4 H) 2.37 (t, J = 7.7 Hz, 2 H) 2.88 (t, J = 7.7 Hz, 2 H) 2.99-3.16 (m, 4 H) 3.01 (s, 4 H) 7.04-7.21 (m, 7 H) 7.27-7.47 (m, 9 H) 7.53 (d, J = 8.9 Hz, 1 H) 7.53 (d, J = 4.5 Hz, 1 H) | 462.1 |

| Ex. No. | Structure | ¹H-NMR | MS(ESI) [M + H]⁺ |
|---|---|---|---|
| 356 | 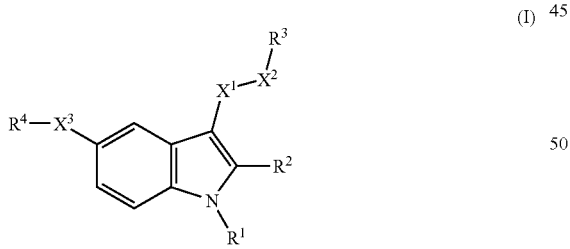 | 1H NMR (400 MHz, MeOH-d4) δ ppm 2.51 (d, J = 10.2 Hz, 1 H) 2.53 (d, J = 8.5 Hz, 1 H) 2.98-3.10 (m, 6 H) 3.61 (s, 6 H) 7.04-7.27 (m, 12 H) 7.34-7.48 (m, 6 H) | 462.3 |

INDUSTRIAL APPLICABILITY

As shown in the above Experimental Examples, the compounds according to the present invention exhibit activity inhibiting cPLA$_2$ enzymes, exhibit activity inhibiting the production of various types of lipid mediators positioned downstream in the metabolic cascade and have anti-inflammatory action. Therefore, the compounds of the present invention are useful for the prevention or treatment of diseases involving cPLA$_2$, that is, diseases in which the increase in amount of expression of cPLA$_2$ enzymes or increase in activity of the enzymes is involved in the exacerbation of the condition and diseases in which the increase in amount of lipid mediators produced based on the cPLA$_2$ enzyme activity and change of balance. Specifically, the present compounds are useful for the prevention or treatment of rheumatoid arthritis, osteoarthritis, dysmenorrhea, acute pain, bronchial asthma and other asthma, allergic rhinitis, chronic and acute airway inflammation, chronic obstructive pulmonary disease, acute lung injury, multiple sclerosis, cerebral ischemia/reperfusion injury, dermatitis, ulticaria, eczema, prurigo, pancreatitis, psoriasis, inflammatory colitis, food allergy, allergic colitis, osteoporosis and atherosclerosis.

The invention claimed is:

1. A compound, or its salt, represented by the formula (I):

(I)

wherein R$^1$ indicates (1) a C$_6$ to C$_{14}$ aromatic hydrocarbon group, (2) a 5- to 10-membered aromatic heterocyclic group including one to four hetero atoms selected from nitrogen atoms, sulfur atoms and oxygen atoms, other than carbon atoms or (3) a bicyclic or tricyclic condensed polycyclic group formed by the condensation the above aromatic heterocyclic group and the above C$_6$ to C$_{14}$ aromatic hydrocarbon cyclic ring, where said group (1) to (3) of R$^1$ may be optionally substituted with one to five groups selected from (i) a halogen atom, (ii) a nitro, (iii) a cyano, (iv) a C$_1$ to C$_6$ alkyl unsubstituted or substituted with one to three groups selected from a halogen atom, a C$_1$ to C$_6$ alkoxy unsubstituted or substituted with one to three halogen atoms, a C$_1$ to C$_7$ acyloxy, a hydroxyl, a 5- to 6-membered heterocyclic unsubstituted or substituted with one to three halogen atoms, a 5- to 6-membered heterocyclic oxy unsubstituted or substituted with one to three halogen atoms, a C$_6$ to C$_{14}$ aromatic hydrocarbon unsubstituted or substituted with one to three halogen atoms and a C$_6$ to C$_{14}$ aromatic hydrocarbon oxy unsubstituted or substituted with one to three halogen atoms, (v) a C$_2$ to C$_6$ alkenyl unsubstituted or substituted with one to three halogen atoms, (vi) a C$_2$ to C$_6$ alkynyl unsubstituted or substituted with one to three halogen atoms, (vii) a C$_3$ to C$_6$ cycloalkyl, (viii) a hydroxyl, (ix) a C$_1$ to C$_6$ alkoxy unsubstituted or substituted with one to three groups selected from a halogen atom, a C$_1$ to C$_6$ alkoxy unsubstituted or substituted with one to three halogen atoms, a C$_7$ to C$_{16}$ aralkyloxy, a hydroxyl, a mono- or di-C$_1$ to C$_6$ alkylamino, a carbamoyl, a mono- or di-C$_1$ to C$_6$ alkylcarbamoyl, a mono- or di-C$_7$ to C$_{16}$ aralkylcarbamoyl, a carboxyl, a C$_1$ to C$_6$ alkoxycarbonyl, a C$_1$ to C$_6$ acyloxy, a 5- to 6-membered heterocyclic unsubstituted or substituted with one to three halogen atoms, a 5- to 6-membered heterocyclic oxy unsubstituted or substituted with one to three halogen atoms, a C$_6$ to C$_{14}$ aromatic hydrocarbon unsubstituted or substituted with one to three halogen atoms and a C$_6$ to C$_{14}$ aromatic hydrocarbon oxy unsubstituted or substituted with one to three halogen atoms, (x) a C$_6$ to C$_{14}$ aromatic hydrocarbon oxy unsubstituted or substituted with one to three groups selected from a halogen atom, a C$_1$ to C$_6$ alkyl, a C$_1$ to C$_6$ alkoxy, and a hydroxyl, (xi) a 5- to 6-membered heterocyclic oxy unsubstituted or substituted with one to three halogen atoms, (xii) a C$_1$ to C$_5$ alkylenedioxy, (xiii) a C$_1$ to C$_6$ alkylthio unsubstituted or substituted with one to three groups selected from a halogen atom, a C$_1$ to C$_6$ alkoxy, a hydroxyl, a mono- or di-C$_1$ to C$_6$ alkylamino, a carbamoyl, a mono- or di-C$_1$ to C$_6$ alkylcarbamoyl, a mono- or di-C$_7$ to C$_{16}$ aralkylcarbamoyl, a carboxyl, a C$_1$ to C$_6$ alkoxycarbonyl, a C$_1$ to C$_6$ acyloxy, a 5- to 6-membered heterocyclic unsubstituted or substituted with one to three halogen atoms, a 5- to 6-membered heterocyclic oxy unsubstituted or substituted with one to three halogen atoms, a C$_6$ to C$_{14}$ aromatic hydrocarbon unsubstituted or substituted with one to three halogen atoms and a C$_6$ to C$_{14}$ aromatic hydrocarbon oxy unsubstituted or substituted with one to three halogen atoms, (xiv) a 5- to 6-membered heterocyclic thio unsubstituted or substituted with one to three halogen atoms, (xv) an amino, (xvi) a mono-$C_1$ to $C_6$ alkylamino, (xvii) a di-$C_1$ to $C_6$ alkylamino, (xviii) a 5- to 6-membered cyclic amino, (xix) a $C_1$ to $C_6$ acyl, (xx) a carboxyl, (xxi) a $C_1$ to $C_6$ alkoxycarbonyl, (xxii) a carbamoyl, (xxiii) a thiocarbamoyl, (xxiv) a mono-$C_1$ to $C_6$ alkylcarbamoyl, (xxv) a di-$C_1$ to $C_6$ alkylcarbamoyl, (xxvi) a 5- to 6-membered heterocyclic carbonyl unsubstituted or substituted with one to three halogen atoms, (xxvii) a sulfo, (xxviii) a $C_1$ to $C_6$ alkylsulfonyl, (xxix) a $C_1$ to $C_6$ acylamino unsubstituted or substituted with a $C_1$ to $C_6$ alkoxy, (xxx) a $C_1$ to $C_6$ alkoxycarbonylamino, (xxxi) an aminosulfonyl, (xxxii) a mono- or di-$C_1$ to $C_6$ alkylaminosulfonyl and (xxxiii) a 5- to 6-membered heterocyclic sulfonyl unsubstituted or substituted with one to three halogen atoms and $R^2$ indicates (1) a hydrogen atom, (2) a $C_1$ to $C_6$ alkyl, (3) a $C_3$ to $C_6$ cycloalkyl group and (4) a halogen atom, $R^3$ indicates (1) a $C_6$ to $C_{14}$ aromatic hydrocarbon group or (2) a 5- to 10-membered aromatic heterocyclic group including one to four hetero atoms selected from nitrogen atoms, sulfur atoms and oxygen atoms, other than carbon atoms, where the groups (1) to (2) of said $R^3$ may be optionally substituted with one to five groups selected from (i) a halogen atom, (ii) a $C_1$ to $C_6$ alkyl unsubstituted or substituted with one to three halogen atoms, (iii) a $C_3$ to $C_6$ cycloalkyl, (iv) a hydroxyl, (v) a $C_1$ to $C_6$ alkoxy unsubstituted or substituted with one to three halogen atoms, (vi) a $C_1$ to $C_5$ alkylenedioxy, (vii) a $C_1$ to $C_6$ alkylthio unsubstituted or substituted with one to three halogen atoms, (viii) an amino, (ix) a mono-$C_1$ to $C_6$ alkylamino and (x) a di-$C_1$ to $C_6$ alkylamino, $R^4$ indicates (1) —$CO_2R^5$ where $R^5$ indicates a hydrogen atom, a $C_1$ to $C_6$ alkyl or a $C_7$ to $C_{16}$ aralkyl, (2) —COC$(R^6)_3$ where $R^6$ indicates a halogen atom, (3) —$CONR^7R^8$ where $R^7$ and $R^8$ may be the same or different and indicate a hydrogen atom, a hydroxyl, a $C_1$ to $C_6$ alkyl, a $C_7$ to $C_{16}$ aralkyl, a $C_1$ to $C_6$ alkoxy, a $C_7$ to $C_{16}$ aralkyloxy, a cyano, or a tetrazole, (4) —CHO, (5) —$CONHSO_2R^9$ where $R^9$ indicates a hydrogen atom, a $C_1$ to $C_6$ alkyl, a phenyl unsubstituted or substituted with one to three $C_1$ to $C_3$ alkyls or a $C_7$ to $C_{16}$ aralkyl, (6) a cyano, (7) a tetrazole, (8) an isoxazole, (9) an isothiazole or (10) a hydroxythiadiazole, $X^1$ indicates (1) a carbonyl group or (2) methylene, $X^2$ indicates (1) a straight-chain, branched or cyclic $C_1$ to $C_6$ alkylene or (2) a connecting bond, and $X^3$ indicates (1) a straight-chain or branched $C_1$ to $C_6$ alkylene, (2) a straight-chain or branched $C_2$ to $C_6$ alkenylene, or (3) a straight-chain or branched $C_2$ to $C_6$ alkynylene.

2. A compound, or its salt as claimed in claim 1, wherein $R^1$ is (1) a $C_6$ to $C_{14}$ aromatic hydrocarbon group or (2) a 5- to 6-membered aromatic heterocyclic group including one to four hetero atoms selected from nitrogen atoms, sulfur atoms, and oxygen atoms, other than carbon atoms.

3. A compound, or its salt as claimed in claim 2, wherein the aromatic hydrocarbon group or aromatic heterocyclic group of $R^1$ is unsubstituted or substituted with one to three groups selected from (i) a halogen atom, (ii) a nitro, (iii) a cyano, (iv) a $C_1$ to $C_6$ alkyl unsubstituted or substituted with one to three groups selected from a halogen atom, a $C_1$ to $C_6$ alkoxy unsubstituted or substituted with one to three halogen atoms, a $C_1$ to $C_7$ acyloxy, a hydroxyl, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (v) a $C_2$ to $C_6$ alkenyl unsubstituted or substituted with one to three halogen atoms, (vi) a $C_2$ to $C_6$ alkynyl unsubstituted or substituted with one to three halogen atoms, (vii) a $C_3$ to $C_6$ cycloalkyl, (viii) a hydroxyl, (ix) a $C_1$ to $C_6$ alkoxy unsubstituted or substituted with one to three groups selected from a halogen atom, a $C_1$ to $C_6$ alkoxy unsubstituted or substituted with one to three halogen atoms, a $C_7$ to $C_{16}$ aralkyloxy, a hydroxyl, a mono- or di-$C_1$ to $C_6$ alkylamino, a carbamoyl, a mono- or di-$C_1$ to $C_6$ alkylcarbamoyl, a mono- or di-$C_7$ to $C_{16}$ aralkylcarbamoyl, a carboxyl, a $C_1$ to $C_6$ alkoxycarbonyl, a $C_1$ to $C_6$ acyloxy, a 5- to 6-membered heterocyclic unsubstituted or substituted with one to three halogen atoms, a 5- to 6-membered heterocyclic oxy unsubstituted or substituted with one to three halogen atoms, a $C_6$ to $C_{14}$ aromatic hydrocarbon unsubstituted or substituted with one to three halogen atoms and a $C_6$ to $C_{14}$ aromatic hydrocarbon oxy unsubstituted or substituted with one to three halogen atoms, (x) a $C_6$ to $C_{14}$ aromatic hydrocarbon oxy unsubstituted or substituted with one to three groups selected from a halogen atom, a $C_1$ to $C_6$ alkyl, a $C_1$ to $C_6$ alkoxy and a hydroxyl, (xi) a 5- to 6-membered heterocyclic oxy unsubstituted or substituted with one to three halogen atoms, (xii) a $C_1$ to $C_5$ alkylenedioxy, (xv) an amino, (xvi) a mono-$C_1$ to $C_6$ alkylamino, (xvii) a di-$C_1$ to $C_6$ alkylamino, (xviii) a 5- to 6-membered cyclic amino, (xix) a $C_1$ to $C_6$ acyl, (xx) a carboxyl, (xxi) a $C_1$ to $C_6$ alkoxycarbonyl, (xxii) a carbamoyl, (xxiv) a mono-$C_1$ to $C_6$ alkylcarbamoyl, (xxv) a di-$C_1$ to $C_6$ alkylcarbamoyl, (xxvi) a 5- to 6-membered heterocyclic carbonyl unsubstituted or substituted with one to three halogen atoms, (xxvii) a sulfo, (xxviii) a $C_1$ to $C_6$ alkylsulfonyl, (xxix) a $C_1$ to $C_6$ acylamino unsubstituted or substituted with a $C_1$ to $C_6$ alkoxy, (xxx) a $C_1$ to $C_6$ alkoxycarbonylamino, (xxxi) an aminosulfonyl, (xxxii) a mono- or di-$C_1$ to $C_6$ alkylaminosulfonyl and (xxxiii) a 5- to 6-membered heterocyclic sulfonyl unsubstituted or substituted with one to three halogen atoms.

4. A compound, or its salt as claimed in claim 1, wherein $R^2$ is (1) a hydrogen atom or (2) a $C_1$ to $C_6$ alkyl.

5. A compound, or its salt as claimed in claim 1, wherein $R^3$ indicates (1) a $C_6$ to $C_{14}$ aromatic hydrocarbon group or (2) a 5- to 6-membered aromatic heterocyclic group including one to four hetero atoms selected from nitrogen atoms, sulfur atoms and oxygen atoms, other than carbon atoms, where the groups (1) to (2) of said $R^3$ may be optionally substituted with one to three groups selected from (i) a halogen atom, (ii) a $C_1$ to $C_6$ alkyl unsubstituted or substituted with one to three halogen atoms, (iii) a hydroxyl and (iv) a $C_1$ to $C_6$ alkoxy unsubstituted or substituted with one to three halogen atoms.

6. A compound, or its salt as claimed in claim 1, wherein $R^4$ is (1) —$CO_2R^5$ where $R^5$ indicates a hydrogen atom or a $C_1$ to $C_4$ alkyl or a $C_7$ to $C_8$ aralkyl, (2) —COC$(R^6)_3$ where $R^6$ indicates a fluorine atom, a chlorine atom, or a bromine atom, (3) —$CONR^7R^8$ where one of $R^7$ and $R^8$ is a hydrogen atom and the other is a hydrogen atom, a hydroxyl, a $C_1$ to $C_4$ alkyl, a $C_7$ to $C_8$ aralkyl, a $C_1$ to $C_4$ alkoxy, a $C_7$ to $C_8$ aralkyloxy, a cyano or a tetrazole, (4) —CHO, (6) a cyano, or (7) a tetrazole.

7. A compound, or its salt as claimed in claim 6, wherein $R^4$ is —$CO_2R^5$ where $R^5$ indicates a hydrogen atom, a $C_1$ to $C_4$ alkyl or a $C_7$ to $C_8$ aralkyl.

8. A compound, or its salt as claimed in claim 1, wherein $X^2$ is (1) a straight-chain $C_1$ to $C_6$ alkylene or (2) a connecting bond.

9. A compound, or its salt as claimed in claim 1, wherein $X^3$ is (1) a straight-chain $C_1$ to $C_6$ alkylene or (2) a straight-chain $C_2$ to $C_6$ alkenylene.

10. A compound, or its salt as claimed in claim 1, which is at least one member selected from the group of:

3-[1-phenyl-3-(2-phenylethyl)-1H-indol-5-yl]propanoic acid,

3-{1-[4-(benzyloxy)phenyl]-3-(2-phenylethyl)-1H-indol-5-yl}propanoic acid,

3-[1-(4-hydroxyphenyl)-3-(2-phenylethyl)-1H-indol-5-yl]propanoic acid,

3-[1-(4-fluorophenyl)-3-(2-phenylethyl)-1H-indol-5-yl]propanoic acid,

3-{1-[4-(difluoromethoxy)phenyl]-3-(2-phenylethyl)-1H-indol-5-yl}propanoic acid, 3-{3-(2-phenylethyl)-1-[4-(trifluoromethoxy)phenyl]-1H-indol-5-yl}propanoic acid, 3-{1-[4-(methoxymethyl)phenyl]-3-(2-phenylethyl)-1H-indol-5-yl}propanoic acid, 3-{1-[4-(2-hydroxyethoxy)phenyl]-3-(2-phenylethyl)-1H-indol-5-yl}propanoic acid, 3-[1-(4-phenoxyphenyl)-3-(2-phenylethyl)-1H-indol-5-yl]propanoic acid and (2E)-3-[1-(4-phenoxyphenyl)-3-(2-phenylethyl)-1H-indol-5-yl]propenoic acid and their salts.

11. A salt of a compound, as claimed in claim 1, wherein said salt is sodium 3-[1-(4-phenoxyphenyl)-3-(2-phenylethyl)-1H-indol-5-yl]propanoate, 3-[1-(4-phenoxyphenyl)-3-(2-phenylethyl)-1H-indol-5-yl]propanoic acid 2-amino-2-(hydroxymethyl)propane-1,3-diol salt and/or 3-[1-(4-phenoxyphenyl)-3-(2-phenylethyl)-1H-indol-5-yl] propanoic acid L-arginine salt.

12. A cPLA$_2$ inhibitor comprising, as an active ingredient, a compound or its salt according to claim 1.

13. An inhibitor of arachidonic acid production comprising, as an active ingredient, a compound or its salt according to claim 1.

14. An inhibitor of prostanoid production comprising, as an active ingredient, a compound or its salt according to claim 1.

15. An inhibitor of prostaglandin production comprising, as an active ingredient, a compound or its salt according to claim 1.

16. An inhibitor of leukotriene production comprising, as an active ingredient, a compound or its salt according to claim 1.

17. An inhibitor of prostaglandin E$_2$ production comprising, as an active ingredient, a compound or its salt according to claim 1.

18. An inhibitor of prostaglandin D$_2$ production comprising, as an active ingredient, a compound or its salt according to claim 1.

19. An inhibitor of thromboxane A$_2$ or B$_2$ production comprising, as an active ingredient, a compound or its salt according to claim 1.

20. An inhibitor of cysteinyl leukotriene production comprising, as an active ingredient, a compound or its salt according to claim 1.

21. An inhibitor of leukotriene B$_4$ production comprising, as an active ingredient, a compound or its salt according to claim 1.

22. An inhibitor of platelet activating factor (PAF) production comprising, as an active ingredient, a compound or its salt according to claim 1.

23. A pharmaceutical composition comprising, as an active ingredient, a compound or its pharmacologically acceptable salt according to claim 1.

24. A method for producing a compound, or a salt thereof, having the formula (I):

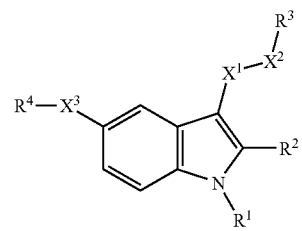

(I)

wherein $R^1$, $R^2$, $R^3$, $R^4$, $X^1$, $X^2$ and $X^3$ are as defined in claim 1 comprising reacting a compound (II), or a salt thereof, having the formula (II):

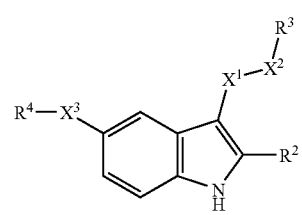

(II)

wherein $R^2$, $R^3$, $R^4$, $X^1$, $X^2$ and $X^3$ are as defined in claim 1 with a compound, or its salt, having the formula (III):

$R^1$—$Y^1$ (III)

wherein $R^1$ is as defined in claim 1 and $Y^1$ is a halogen atom or a triflate and, if necessary, removing the protective groups and/or reducing the same.

25. A method for producing a compound, or its salt, having the formula (I):

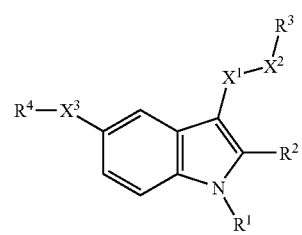

(I)

wherein $R^1$, $R^2$, $R^3$, $R^4$, $X^1$, $X^2$ and $X^3$ are as defined in claim 1 comprising reacting a compound (IV), or its salt, having the formula (IV):

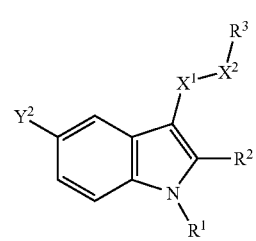

(IV)

wherein $R^1$, $R^2$, $R^3$, $X^1$ and $X^2$ are as defined in claim 1 and $Y^2$ is a halogen atom with a compound (V), or its salt, having the formula (V):

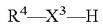    (V)

wherein $R^4$ and $X^3$ are as defined in claim 1 and, if necessary, removing the protective groups and/or reducing the same.

26. A method for producing a compound, or its salt, having the formula (I):

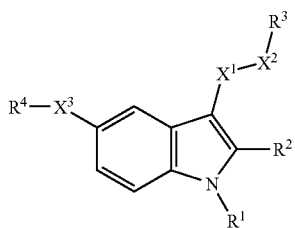    (I)

wherein $R^1$, $R^2$, $R^3$, $R^4$, $X^1$, $X^2$ and $X^3$ are as defined in claim 1 comprising reacting a compound, or its salt, having the formula (VI):

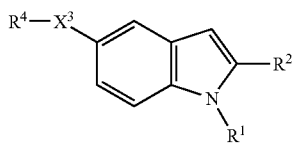    (VI)

wherein $R^1$, $R^2$, $R^4$ and $X^3$ are as defined in claim 1
with a compound having the formula (VII):

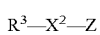    (VII)

wherein $R^3$ and $X^2$ is as defined in claim 1, Z is a halocarbonyl group or (1H-1,2,3-benzotriazol-1-yl)carbonyl group or a compound, a salt thereof, having the formula (VIII):

    (VIII)

wherein $R^{3a}$ is a 5- to 10-membered aromatic heterocyclic group including one to four hetero atoms selected from nitrogen atoms, sulfur atoms and oxygen atoms, other than carbon atoms, and may be optionally substituted with one to five groups selected from (i) a halogen atom, (ii) a $C_1$ to $C_6$ alkyl unsubstituted or substituted with one to three halogen atoms, (iii) a $C_3$ to $C_6$ cycloalkyl, (iv) a hydroxyl, (v) a $C_1$ to $C_6$ alkoxy unsubstituted or substituted with one to three halogen atoms, (vi) a $C_1$ to $C_5$ alkylenedioxy, (vii) a $C_1$ to $C_6$ alkylthio unsubstituted or substituted with one to three halogen atoms, (viii) an amino, (ix) a mono-$C_1$ to $C_6$ alkylamino and (x) a di-$C_1$ to $C_6$ alkylamino and, if necessary, removing the protective groups and/or reducing the same.

27. A compound, or its salt, having the formula (II):

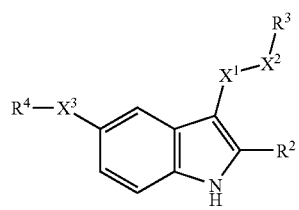    (II)

wherein $R^2$, $R^3$, $R^4$, $X^1$, $X^2$ and $X^3$ are as defined in claim 1, provided that the following compounds are removed:
(i) a compound where $R^2$ is a hydrogen atom or a methyl, $R^3$ is an unsubstituted pyridyl, $R^4$ is $COOR^5$ where $R^5$ is hydrogen, t-butyl or benzyl, $X^1$ is methylene, $X^2$ is a connecting bond, $X^3$ is $C_2$ alkenylene or $C_3$ alkylene;
(ii) a compound where $R^2$ is methyl, $R^3$ is unsubstituted imidazole, $R^4$ is $COOR^5$ where $R^5$ is benzyl, $X^1$ is methylene, $X^2$ is a connecting bond, $X^3$ is $C_2$ alkylene; and
(iii) a compound where $R^2$ is a hydrogen atom, $R^3$ is phenyl, $R^4$ is $COOR^5$ where $R^5$ is a hydrogen atom, $X^1$ is methylene, $X^2$ is $C_1$ alkylene, $X^3$ is $C_1$ alkylene.

28. A compound, or its salt, having the formula (IV):

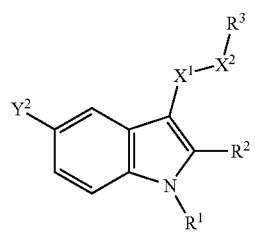    (IV)

wherein $R^1$, $R^2$, $R^3$, $X^1$ and $X^2$ are as defined in claim 1 and $Y^2$ is a halogen atom.

29. A compound, or its salt, having the formula (VI):

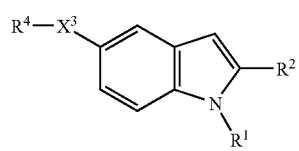    (VI)

wherein $R^1$, $R^2$, $R^4$ and $X^3$ are as defined in claim 1, provided that the following compounds are removed:
a compound where $R^1$ is 4-fluorophenyl, $R^2$ is a hydrogen atom, $R^4$ is cyano or tetrazol, $X^3$ is $C_1$ alkylene;
(ii) a compound where $R^1$ is unsubstituted 3-pyridyl, $R^2$ is a hydrogen atom, $R^4$ is $COOR^5$ where $R^5$ is a hydrogen atom or $C_2$ alkyl, $X^3$ is $C_2$ alkenylene.

30. A pharmaceutical composition for treating an inflammatory disease or an allergic disease selected from the group consisting of asthma, allergic rhinitis, chronic and acute airway inflammation, chronic obstructive pulmonary disease, acute lung injury, pulmonary fibrosis, rheumatoid arthritis, osteoarthritis, acute pain, multiple sclerosis, cerebral ischemia or reperfusion injury, dermatitis, urticaria, eczema, prurigo, pancreatitis, psoriasis, inflammatory colitis, food allergy, allergic colitis, osteoporosis, atherosclerosis, bronchial asthma, and dysmenorrheal, comprising a compound or its pharmacologically acceptable salt according to claim 1.

* * * * *